United States Patent
Meffre et al.

(10) Patent No.: US 11,311,543 B2
(45) Date of Patent: Apr. 26, 2022

(54) COMPOSITIONS AND METHODS FOR INHIBITING PTPN22

(71) Applicant: YALE UNIVERSITY, New Haven, CT (US)

(72) Inventors: Eric Meffre, New Haven, CT (US); Jean-Nicolas Schickel, New Haven, CT (US)

(73) Assignee: Yale University, New Haven, CT (US)

( * ) Notice: Subject to any disclaimer, the term of this patent is extended or adjusted under 35 U.S.C. 154(b) by 185 days.

(21) Appl. No.: 16/304,807

(22) PCT Filed: May 26, 2017

(86) PCT No.: PCT/US2017/034720
§ 371 (c)(1),
(2) Date: Nov. 27, 2018

(87) PCT Pub. No.: WO2017/205765
PCT Pub. Date: Nov. 30, 2017

(65) Prior Publication Data
US 2020/0316070 A1 Oct. 8, 2020

Related U.S. Application Data

(60) Provisional application No. 62/342,250, filed on May 27, 2016.

(51) Int. Cl.
| | |
|---|---|
| A61K 31/515 | (2006.01) |
| A61P 37/00 | (2006.01) |
| A61K 31/7105 | (2006.01) |
| C12N 15/113 | (2010.01) |
| A61K 45/06 | (2006.01) |

(52) U.S. Cl.
CPC ........ *A61K 31/515* (2013.01); *A61K 31/7105* (2013.01); *A61P 37/00* (2018.01); *C12N 15/113* (2013.01); *A61K 45/06* (2013.01); *C12N 2310/14* (2013.01); *C12N 2310/531* (2013.01)

(58) Field of Classification Search
CPC .. A61K 31/515; A61K 31/7105; A61K 45/06; A61P 37/00
USPC ........................................................ 514/270
See application file for complete search history.

(56) References Cited

U.S. PATENT DOCUMENTS

| | | |
|---|---|---|
| 2005/0221354 A1 | 10/2005 | Mounts |
| 2010/0210836 A1 | 8/2010 | Bottini |
| 2014/0275220 A1 | 9/2014 | Thum |

FOREIGN PATENT DOCUMENTS

WO   WO 2007/002587   * 1/2007

OTHER PUBLICATIONS

Draborg et al. Review Article: Epstein-Barr virus and systemic lupus erythematosus. Clinical and Developmental Immunology, vol. 2012, pp. 10.*
Dorwald (Side Reactions in Organic Synthesis: A Guide to Successful Synthesis Design, Weinheim: WILEY-VCH Verlag GmbH & Co. KGaA, 2005, Preface).*
Lea & Lee. The association between the PTPN22 C1858T polymorphism and systemic lupus erythematosus: a meta-analysis update. Lupus, 2011, 20, 51-57.*
He et al., Small molecule tools for functional interrogation of protein tyrosine phosphatases FEBS J., 2013,, vol. 280, No. 2, pp. 731-750.
Arechiga et al., Cutting edge: The PTPN22 allelic variant associated with autoimmunity impairs B cell signaling. J. Immunol. 2009, 182:3343-3347.
Bottini and Peterson, Tyrosine phosphatase PTPN22: Multifunctional regulator of immune signaling, development, and disease. Annu. Rev. Immunol. 2014, 32:83-119.
Cantaert et al., Activation-induced cytidine deaminase expression in human B cell precursors is essential for central B cell tolerance. Immunity. 2015, 43:884-895.
Chamberlain et al., Rituximab does not reset defective early B cell tolerance checkpoints. J. Clin. Invest. 2016, 126:282-287.
Corbett et al., J. Mol. Biol. 1997, 270:587-597.
Dai et al., A disease-associated PTPN22 variant promotes systemic autoimmunity in murine models. J. Clin. Invest. 2013, 123:2024-2036.
Edwards et al., Efficacy of B-cell-targeted therapy with rituximab in patients with rheumatoid arthritis. N. Engl. J. Med. 2004, 350:2572-2581.
Grimaldi et al., B cell selection and susceptibility to autoimmunity. J. Immunol. 2005, 174:1775-1781.
Hauser et al., B-cell depletion with rituximab in relapsing-remitting multiple sclerosis. N. Engl. J. Med. 2008, 358:676-688.
Kalscheuer et al., A model for personalized in vivo analysis of human immune responsiveness. Sci. Transl. Med. 2012, 4:125ra30.
Meffre, The establishment of early B cell tolerance in humans: Lessons from primary immunodeficiency diseases. Ann. N. Y. Acad. Sci. 2011, 1246:1-10.
Meyers et al., Activation-induced cytidine deaminase (AID) is required for B-cell tolerance in humans. Proc. Natl. Acad. Sci. U.S.A. 2011, 108:11554-11559.
Ng et al., Bruton's tyrosine kinase is essential for human B cell tolerance. J. Exp. Med. 2004, 200:927-934.
Orrú et al., A loss-of-function variant of PTPN22 is associated with reduced risk of systemic lupus erythematosus. Hum. Mol. Genet. 2009, 18:569-579.
Pescovitz et al., Rituximab, B-lymphocyte depletion, and preservation of β-cell function. N. Engl. J. Med. 2009, 361:2143-2152.
Rieck et al., Genetic variation in PTPN22 corresponds to altered function of T and B lymphocytes. J. Immunol. 2007, 179:4704-4710.
Rodriguez-Rodriguez et al., The PTPN22 R263Q polymorphism is a risk factor for rheumatoid arthritis in Caucasian case-control samples. Arthritis Rheum. 2011, 63:365-372.

(Continued)

*Primary Examiner* — Yevgeny Valenrod
(74) *Attorney, Agent, or Firm* — Riverside Law LLP

(57) ABSTRACT

The present invention provides compositions and methods for inhibiting PTPN22 for restoring human central B-cell tolerance or for treating or preventing an autoimmune disease or disorder.

8 Claims, 68 Drawing Sheets

Specification includes a Sequence Listing.

(56) References Cited

OTHER PUBLICATIONS

Rongvaux et al., Development and function of human innate immune cells in a humanized mouse model. Nat. Biotechnol. 2014, 32:364 372.

Ruer-Laventie et al., Overexpression of Fkbp11, a feature of lupus B cells, leads to B cell tolerance breakdown and initiates plasma cell differentiation. Immun. Inflamm. Dis. 2015, 3:265-279.

Salmond et al., The tyrosine phosphatase PTPN22 discriminates weak self peptides from strong agonist TCR signals. Nat. Immunol. 2014, 15:875-883.

Samuels et al., Impaired early B cell tolerance in patients with rheumatoid arthritis. J. Exp. Med. 2005, 201:1659-1667.

Schickel et al., Carabin deficiency in B cells increases BCR-TLR9 costimulation-induced autoimmunity. EMBO Mol. Med. 2012, 4:1261-1275.

Shultz et al., Human lymphoid and myeloid cell development in NOD/LtSz-scid IL2Rγnull mice engrafted with mobilized human hematopoietic stem cells. J. Immunol. 2005, 174:6477-6489.

Tiller et al., Efficient generation of monoclonal antibodies from single human B cells by single cell RT-PCR and expression vector cloning. J. Immunol. Methods. 2008, 329:112-124.

Vang et al., LYP inhibits T-cell activation when dissociated from CSK. Nat. Chem. Biol. 2012, 8:437-446.

Wardemann et al., Predominant autoantibody production by early human B cell precursors. Science. 2003, 301:1374-1377.

Yurasov et al., Defective B cell tolerance checkpoints in systemic lupus erythematosus. J. Exp. Med. 2005, 201:703-711.

Gregersen and Olsson, Recent advances in the genetics of autoimmune disease. Annu Rev. Immunol., 2009, 27:363.

Ishikawa et al., Development of functional human blood and immune systems in NOD/SCID/IL2 receptor {gamma} chain(null) mice. Blood, 2005, 106:1565.

Stanford et al., Discovery of a novel series of inhibitors of lymphoid tyrosine phosphatase with activity in human T cells. J Med Chem, 2011, 54:1640.

Zennou et al., HIV-1 genome nuclear import is mediated by a central DNA flap. Cell. 2000, 101(2):173-85.

* cited by examiner

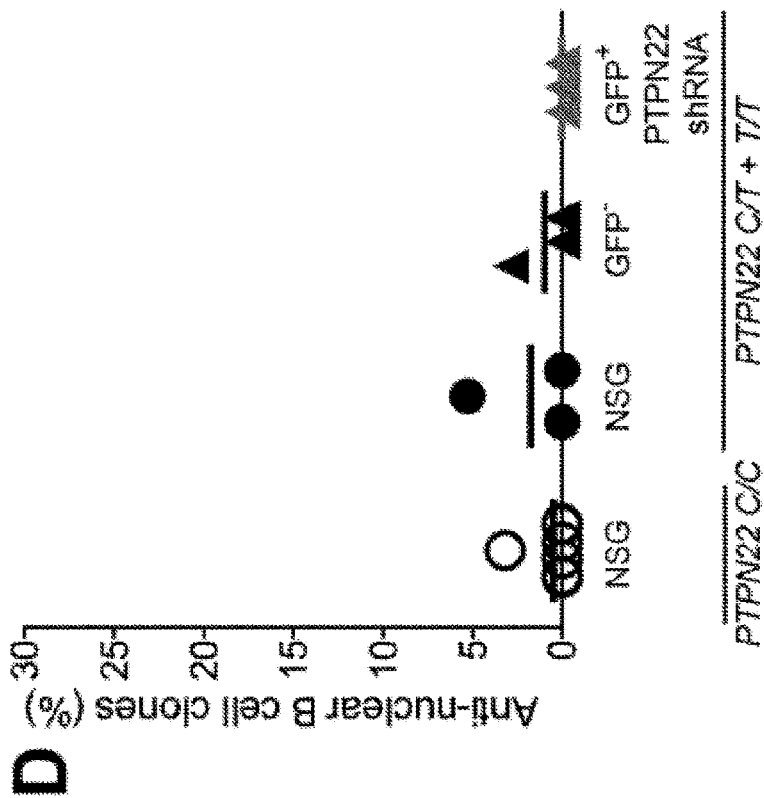
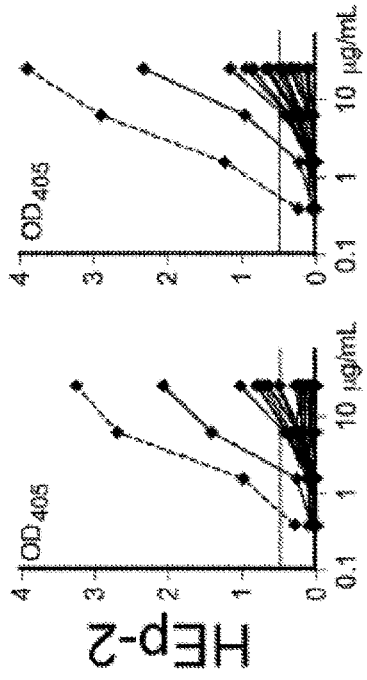
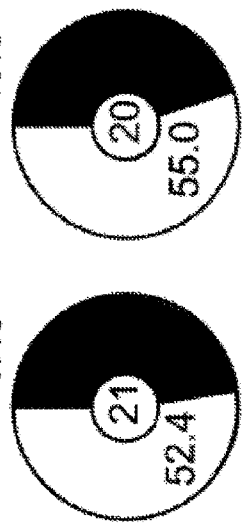
Figures 10C – 10D

Repertoire and reactivity of antibodies from new emigrant B cells of Mouse #1

| Ig | Heavy Chain | | | | | | Light Chain | | | | | Reactivity | | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM1-K2 | 1-3 | 1-7 | 2 | 4 | DLELYFDY | 4 | 9 | 3-20 | 1 | QQYGSSPT | 43 | 8 | - | - | - |
| neM1-K5 | 4-30-2 | 3-10 | 2 | 4 | ISGSYYNY | 5 | 8 | 1-39 | 1 | QQSYSTPWT | 44 | 9 | - | + | - |
| neM1-K8 | 4-59 | 3-9 | 2 | 4 | SPPFDWIYYFDY | 6 | 12 | 3-20 | 1 | QQYGSSPWT | 45 | 9 | - | - | - |
| neM1-K9 | 3-73 | 4-23 | 2 | 4 | RYGGNYYFDY | 7 | 10 | 3-11 | 4 | QQRSNWPLT | 46 | 9 | - | + | - |
| neM1-K1 | 3-15 | 1-26 | 1 | 3 | QTEWELDAFDI | 8 | 11 | 3-20 | 4 | QQYGSSPPLT | 47 | 10 | - | - | - |
| neM1-K11 | 3-74 | 3-10 | 2 | 6 | DPGKGYYGSGSYYYYGMDV | 9 | 20 | 1-6 | 2 | LQDYNYPYT | 48 | 9 | - | - | - |
| neM1-K16 | 4-30-2 | / | / | 3 | TNEPNAFDI | 10 | 9 | 2-28 | 4 | MQALQTPLT | 49 | 9 | - | - | - |
| neM1-K22 | 4-4 | 3-22 | 2 | 3 | DRADYYDSSGYYYAFDI | 11 | 17 | 1-17 | 4 | LQHNSYPPT | 50 | 9 | - | - | - |
| neM1-K23 | 3-7 | 1-26 | 2 | 6 | NRPPGAINYYGMDV | 12 | 14 | 3-11 | 1 | QQRSNWPWT | 51 | 9 | - | - | - |
| neM1-K25 | 4-34 | 1-26 | 3 | 4 | GGGATEY | 13 | 7 | 1-17 | 1 | LQHNSYLWT | 52 | 9 | - | - | - |
| neM1-K32 | 4-59 | / | / | 3 | THPQSDAFDI | 14 | 10 | 2-30 | 4 | MQGTHWPLT | 53 | 9 | - | + | - |
| neM1-K33# | 3-7 | 3-10 | 3 | 3 | ILGGITMVRGAEDAFDI | 15 | 17 | 3-20 | 1 | QQYGSSPRT | 54 | 9 | | | |
| neM1-K37 | 3-30 | 3-10 | 1 | 4 | EKGWFGELEGLAIDY | 16 | 15 | 3-15 | 1 | QQYNNWPQT | 55 | 9 | - | - | - |
| neM1-K38 | 4-34 | 7-27 | 2 | 2 | GLTGDSGTDWYFDL | 17 | 14 | 1-39 | 4 | QQSYSTPLT | 56 | 9 | - | - | - |
| neM1-K4 | 4-39 | 6-13 | 2 | 4 | HPYSSSFDY | 18 | 9 | 3-20 | 2 | QQYGSSYT | 57 | 8 | - | - | - |
| neM1-K42 | 3-33 | 3-10 | 2 | 6 | DPRLGSGSYYYYGMDV | 19 | 16 | 1-39 | 3 | QQSYSTPFT | 58 | 9 | - | + | - |
| neM1-K43# | 4-30-4 | 7-27 | 2 | 4 | NKLNWGLDY | 20 | 9 | 1-5 | 1 | QQYNSYSPWT | 59 | 10 | | | |
| neM1-K45 | 4-4 | 7-27 | 2 | 5 | GWGFGNWFDP | 21 | 10 | 3-20 | 2 | QQYGSSPPYT | 60 | 10 | - | - | - |
| neM1-K46 | 4-59 | / | / | 4 | SFSRLASFDY | 22 | 10 | 3-20 | 1 | QQYGSSLGT | 61 | 9 | - | - | - |
| neM1-K48 | 4-59 | / | / | 4 | VGGRGGDFDY | 23 | 10 | 1-33 | 3 | QQYDNLPRVT | 62 | 10 | - | - | - |

RF, reading frame; # antibody failed to be expressed
- non reactive; +, reactive
c, diffuse cytoplasmic staining; N, nuclear staining, F, cytoplasmic fibers; V, vesicles

Figure 11

| Ig | Heavy Chain | | | | | | | Light Chain | | | | | | Reactivity | | |
|---|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM1-L1 | 3-30 | 6-13 | 2 | 4 | SGSSWYYFDY | 24 | 10 | 2-14 | 2 | SSYTSSSTV | 63 | 9 | - | - | - |
| neM1-L3 | 1-69 | / | / | 4 | VMAVYYFDY | 25 | 9 | 1-40 | 1 | QSYDSSLSGYV | 64 | 11 | + | + | - |
| neM1-L6 | 3-30-3 | 3-16 | 2 | 4 | GPSRGGEVFDY | 26 | 11 | 3-21 | 3 | QVWDSSSDQNWV | 65 | 12 | - | - | - |
| neM1-L7 | 5-51 | 3-22 | 2 | 4 | LRIPDYDSSGYYFDY | 27 | 15 | 2-8 | 3 | SSYAGSNNLV | 66 | 10 | - | - | - |
| neM1-L12 | 4-4 | / | / | 4 | GSIPSDYYFDY | 28 | 11 | 3-25 | 2 | QSADSSGTYPV | 67 | 11 | - | - | - |
| neM1-L13# | 1-69 | 6-13 | 2 | 5 | TIYSSSWYWFDP | 29 | 12 | 5-37 | 2 | MIWPSNAYVV | 68 | 10 | - | - | - |
| neM1-L14 | 3-30 | 3-22 | 2 | 2 | DYYDSSGYYYWYFDL | 30 | 15 | 1-44 | 2 | AAWDDSLNGPV | 69 | 11 | - | + | - |
| neM1-L24 | 3-13 | 6-13 | 2 | 3 | GGRDSSWYIAFDI | 31 | 13 | 2-23 | 1 | CSYAGSSTYV | 70 | 10 | - | - | - |
| neM1-L26 | 1-3 | 7-27 | 2 | 5 | GQTTNLGMGPNWFDP | 32 | 15 | 1-40 | 2 | QSYDSSLSGVV | 71 | 11 | - | + | - |
| neM1-L27 | 3-23 | 2-15 | 2 | 3 | DPLSRYCSGGSCYSGAFDI | 33 | 19 | 1-44 | 2 | AAWDDSLNGHVV | 72 | 12 | - | - | - |
| neM1-L28 | 1-18 | 6-19 | 3 | 4 | GIAVAGYFDY | 34 | 10 | 2-8 | 2 | SSYAGSNNLV | 66 | 10 | - | - | - |
| neM1-L3 | 3-7 | / | / | 4 | DRLGSFDY | 35 | 8 | 1-47 | 3 | AAWDDSLSGWV | 73 | 11 | - | - | - |
| neM1-L31 | 3-33 | 3-9 | 2 | 4 | DAALRYFDWLLDY | 36 | 13 | 2-14 | 1 | SSYTSSSTLV | 74 | 10 | - | - | - |
| neM1-L34 | 3-7 | / | / | 1 | DLVGIRATDY | 37 | 10 | 1-51 | 1 | GTWDSSLSAYV | 75 | 11 | - | + | - |
| neM1-L35 | 3-30 | 6-13 | 3 | 4 | DVNAAAGNRAYFQH | 38 | 14 | 3-21 | 2 | QVWDSSSDHYV | 76 | 11 | - | - | - |
| neM1-L36 | 3-30 | 1-26 | 2 | 4 | DGDSGSYFDY | 39 | 10 | 2-23 | 2 | CSYAGSSTYVV | 70 | 11 | - | - | - |
| neM1-L39 | 3-30-3 | 7-27 | 1 | 3 | VCSPELGQWIDI | 40 | 12 | 3-21 | 2 | QVWDSSSDHVV | 77 | 11 | - | + | - |
| neM1-L41 | 3-15 | 3-16 | 2 | 3 | DWGTRAFDI | 41 | 9 | 1-51 | 3 | GTWDSSLSAGV | 78 | 11 | - | - | - |
| neM1-H4 | 3-64 | 6-19 | 3 | 4 | GIVAVAGNLDY | 42 | 11 | | | | - | | | | |

RF, reading frame: # antibody failed to be expressed
-, non reactive; +, reactive
c, diffuse cytoplasmic staining; N, nuclear staining, F, cytoplasmic fibers; V, vesicles

Figure 11 (cont'd)

Repertoire and reactivity of antibodies from new emigrant B cells of Mouse #2

| Ig | Heavy Chain | | | | | | Light Chain | | | | | Reactivity | | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM2-K04# | 3-33 | 3-16 | 1 | 3 | PRPRGEPLLNWSWAFDI | 79 | 17 | 1-5 | 1 | QHYNPYSRT | 115 | 9 | | |
| neM2-K08 | 3-33 | 1-26 | 3 | 4 | AEEGVGGSYFDY | 80 | 12 | 2-24 | 1 | MQATQFPWT | 116 | 9 | - | - |
| neM2-K10 | 4-31 | 3-22 | 2 | 3 | NPAREYYYDSSGYYGYAFDI | 81 | 20 | 4-1 | 2 | QQYYSTPFMY T | 117 | 11 | - | - |
| neM2-K12 | 3-11 | 2-2 | 3 | 4 | ARERGVVVPAAIVGDY | 82 | 16 | 4-1 | 2 | QQYYSAPQT | 118 | 9 | - | - |
| neM2-K13 | 4-34 | 2-8 | 2 | 4 | GQQDNAPHTPLYY | 83 | 13 | 2-28 | 2 | MQALQTPT | 119 | 8 | - | - |
| neM2-K14 | 3-9 | 6-6 | 2 | 3 | GTHTSSGAFDI | 84 | 12 | 4-1 | 4 | QQYYSTPLT | 120 | 9 | - | - |
| neM2-K15 | 3-7 | 2-2 | 3 | 3 | VSHIVVPAAIRGGDAFDI | 85 | 19 | 4-1 | 3 | QQYYSTPCT | 121 | 9 | + | + |
| neM2-K16 | 3-15 | 1-26 | 3 | 4 | DPVGACVFDY | 86 | 10 | 3-20 | 4 | QQYGSSPLT | 122 | 9 | - | - |
| neM2-K18 | 3-23 | 3-22 | 2 | 3 | TVDYYDSSGYYYSAFDI | 87 | 17 | 3-20 | 3 | QQYGSSPPT | 123 | 9 | - | - |
| neM2-K24 | 3-21 | 2-8 | 2 | 4 | GGDDSRSPNGGYCLDY | 88 | 16 | 2-29 | 2 | MQGIHLRYT | 124 | 9 | - | - |
| neM2-K25 | 3-11 | 1-26 | 3 | 4 | EGPGIVGVHHPYFDY | 89 | 15 | 1-39 | 1 | QQSYSTPWT | 44 | 9 | - | - |
| neM2-K26 | 1-2 | 3-3 | 3 | 5 | GSIGVGGSLYGNWFDP | 90 | 16 | 1-16 | 4 | QQYNSYPLT | 125 | 9 | - | - |
| neM2-K27 | 4-39 | 7-27 | 3 | 4 | RGLGIVHYFDY | 91 | 11 | 3-11 | 4 | QQRINWLT | 126 | 8 | - | - |
| neM2-K29 | 1-2 | 6-13 | 3 | 3 | LWGGIKPGIAAAGTAFDI | 92 | 18 | 3-20 | 1 | QQYGSSPRT | 54 | 9 | - | - |
| neM2-K30 | 1-46 | 4-23 | 2 | 4 | ARLAEHYQRYGGNSGPFDY | 93 | 19 | 3-20 | 1 | QQYGSSPGT | 127 | 9 | - | + |
| neM2-K35# | 4-34 | 3-10 | 3 | 5 | RGKLTMDRGNWFDP | 94 | 14 | 2-28 | 2 | MQALQTPT | 119 | 8 | - | + | N |
| neM2-K38 | 3-49 | 3-10 | 2 | 4 | DHLIGSGSYFDY | 95 | 12 | 3-20 | 2 | QQYGSSPQT | 128 | 9 | - | + |
| neM2-K41 | 3-49 | 6-13 | 3 | 4 | DPLEGKSIAAAGPWDFDY | 96 | 18 | 2-30 | 2 | MQGTHWPPY T | 129 | 10 | - | + |

RF, reading frame; # antibody failed to be expressed
-, non reactive; +, reactive
c, diffuse cytoplasmic staining; N, nuclear staining; F, cytoplasmic fibers; V, vesicles

Figure 12

| Ig | Heavy Chain | | | | | | Light Chain | | | | | Reactivity | |
|---|---|---|---|---|---|---|---|---|---|---|---|---|---|
| | VH | D | RF | JH | CDR3 (aa) | SEQ ID NO | Length | Vk | Jk | CDR3 (aa) | SEQ ID NO | Length | Poly | HEp-2 Staining |
| neM2-K48# | | | | | | -- | | 1-39 | 2 | QQSYSTPYT | 130 | 9 | | |
| neM2-L01 | 3-48 | 6-19 | 3 | 4 | GIAVAGESVDY | 97 | 11 | 1-44 | 3 | AWDDSLNGPV | 131 | 10 | - | - |
| neM2-L2 | 1-2 | 1-26 | 2 | 4 | LRDSGSSYFDY | 98 | 11 | 2-18 | 2 | SSYTSSSNVV | 132 | 10 | - | - |
| neM2-L04 | 3-33 | 3-16 | 1 | 3 | PRPRGEPLLNWSWAFDI | 79 | 17 | 2-8 | 2 | SSYAGSNNLV | 66 | 10 | - | - |
| neM2-L05# | 3-53 | 6-13 | 2 | 4 | AGYSSSWSAFDY | 99 | 12 | 1-51 | 2 | TWDSSLSAVV | 133 | 10 | - | - |
| neM2-L07 | 1-46 | 6-13 | 3 | 6 | DKAAAGTDYYYGMDV | 100 | 15 | 6-57 | 2 | QSYDSSNHVV | 134 | 10 | - | - |
| neM2-L09 | 3-9 | 6-13 | 2 | 5 | DRAGYSSSDWFDP | 101 | 13 | 1-40 | 2 | QSYDSSLSGSV | 135 | 11 | - | - |
| neM2-L17 | 3-33 | 6-13 | 3 | 4 | DTAAAGLQSRYYFDY | 102 | 15 | 2-11 | 1 | CSYAGSYTYV | 136 | 10 | - | - |
| neM2-L19 | 3-30 | 4-17 | 2 | 4 | DPCSDYGDSYFDY | 103 | 13 | 1-40 | 2 | YDSSLSGSVV | 137 | 10 | + | + |
| neM2-L22 | 3-9 | 6-13 | 3 | 4 | DMAAAGPYYFDY | 104 | 12 | 2-14 | 2 | SSYTSSSTFGV | 138 | 11 | - | - |
| neM2-L23 | 3-15 | 6-19 | 3 | 4 | VHARIAVAARNDY | 105 | 13 | 2-14 | 2 | SSFTSITYVV | 139 | 10 | - | - |
| neM2-L28 | 4-59 | 5-24 | 2 | 1 | DGGDGYKYGYFQH | 106 | 13 | 1-44 | 3 | AWDDSLNGVV | 140 | 10 | - | - |
| neM2-L31 | 3-23 | 1-26 | 3 | 4 | VWGATTMGGHYFDY | 107 | 14 | 2-14 | 2 | SSYTSSSTFVV | 141 | 11 | - | - |
| neM2-L33 | 4-34 | 3-10 | 3 | 5 | RGKLTMDRGNWFDP | 94 | 14 | 2-23 | 1 | AGSSTFHYV | 142 | 9 | - | + |
| neM2-L40 | 3-7 | 6-19 | 3 | 4 | DVRIAVAGFDY | 108 | 11 | 3-1 | 2 | QAWDSSTVV | 143 | 9 | - | + |
| neM2-L42 | 3-11 | 7-27 | 1 | 2 | RQLGLSIEYWYFDL | 109 | 14 | 9-49 | 3 | GADHGSGSNFVWV | 144 | 13 | - | + |
| neM2-L44 | 3-9 | 6-19 | 2 | 5 | ALGRYSSGWTGWFDP | 110 | 15 | 1-51 | 3 | GTWDSSLSAPWV | 145 | 12 | - | - |
| neM2-L47# | 3-23 | 1-26 | 2 | 2 | GGGSPWGWYFDL | 111 | 12 | 2-8 | 1 | SSYAGSNNFYV | 146 | 11 | | |
| neM2-L32# | | | | | | -- | | 2-8 | 1 | SSYAGSNNYV | -- | 10 | | |
| neM2-H37 | 1-69 | 2-2 | 2 | 4 | ASHHRNTYCSSTSCFDY | 112 | 17 | | | | -- | | | |
| neM2-H46 | 3-23 | 1-26 | 3 | 4 | VWGATTMGGHYFDY | 107 | 14 | | | | -- | | | |
| neM2-H06 | 4-34 | 6-19 | 2 | 4 | GGMVDSSGWYYFDY | 113 | 14 | | | | -- | | | |
| neM2-H20 | 3-33 | 3-22 | 2 | 4 | DISLYYDSSGYSAGVFDY | 114 | 19 | | | | -- | | | |

RF, reading frame; # antibody failed to be expressed
-, non reactive; +, reactive
c, diffuse cytoplasmic staining; N, nuclear staining, F, cytoplasmic fibers; V, vesicles

Figure 12 (cont'd)

Repertoire and reactivity of antibodies from new emigrant B cells of Mouse #3

| Ig | Heavy Chain | | | | | | | Light Chain | | | | | Reactivity | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM3 K02 | 4-39 | / | / | 2 | PRGRYWYFDL | 147 | 10 | 1-33 | 2 | QQHDNLPYT | 180 | 9 | - | - |
| neM3 K03 | 4-34 | 6-19 | 2 | 4 | GLGVSGWFDY | 148 | 10 | 3-20 | 3 | QQYGSSPFT | 181 | 9 | - | - |
| neM3 K08 | 5-a | / | / | 6 | HQARPYYYGMDV | 149 | 13 | 3-20 | 2 | QQYGSSPKT | 182 | 9 | - | - |
| neM3 K09 | 4-59 | 7-27 | 3 | 3 | VSGDAFDI | 150 | 8 | 1-9 | 4 | QQLNSYPLT | 183 | 9 | - | - |
| neM3 K11 | 1-69 | 7-27 | 2 | 5 | ANWGSYNWFDP | 151 | 11 | 3-11 | 4 | QQRSNWPT | 184 | 8 | - | - |
| neM3 K15 | 4-59 | 7-27 | 2 | 2 | DLSWGPYWYFDL | 152 | 12 | 3-15 | 3 | QQYNNWPFT | 185 | 9 | - | - |
| neM3 K16 | 4-39 | 6-13 | 2 | 3 | QPGQYSSSWYAFDI | 153 | 14 | 1-33 | 3 | QQYDNLPIFT | 186 | 10 | - | - |
| neM3 K18 | 1-18 | 1-7 | 3 | 4 | DRWAGITGTTPFDY | 154 | 14 | 3-15 | 3 | QQYNNWPPFT | 187 | 10 | - | - |
| neM3 K21 | 3-23 | 5-12 | 2 | 4 | YSGYDFTYYFDY | 155 | 12 | 1-8 | 3 | QQYSFPFT | 188 | 9 | - | + |
| neM3 K22 | 4-61 | 6-19 | 2 | 4 | RDSAYSSGFDY | 156 | 11 | 2-28 | 4 | MQALQTPLT | 49 | 9 | - | - |
| neM3 K27 | 4-39 | / | / | 4 | AVFIDY | 157 | 6 | 3-15 | 2 | QQYNNWPYT | 189 | 9 | + | + |
| neM3 K30 | 3-23 | 7-27 | 1 | 4 | DPPELGMGESGFDY | 158 | 14 | 1-5 | 1 | QQYNSYSRT | 190 | 9 | - | - |
| neM3 K32 | 4-61 | 4-4 | 2 | 4 | DLGSNYDY | 159 | 8 | 3-10 | 1 | QQYGSSPQT | 128 | 9 | - | - |
| neM3 K33 | 3-23 | 6-13 | 2 | 4 | DPRSSWYFDY | 160 | 10 | 1-39 | 3 | QQSYSTPFT | 58 | 9 | - | - |
| neM3 K34 | 3-30 | 6-13 | 3 | 2 | DRIAAAGTWYFDL | 161 | 13 | 1-33 | 4 | QQYDNLPPLT | 191 | 10 | - | - |
| neM3 K37 | 3-33 | / | / | 4 | GAGYYFDY | 162 | 8 | 3-11 | 1 | QQRSNWRGT | 192 | 9 | - | + |
| neM3 K38 | 3-30 | 7-27 | 2 | 4 | DSSAHEPSWGYFDY | 163 | 14 | 3-15 | 4 | QQYNNWPLT | 193 | 9 | - | - |
| neM3 K40 | 1-3 | 6-13 | 2 | 4 | DLGADSSSWTFDY | 164 | 13 | 3-15 | 2 | QQYNNWPMYT | 194 | 10 | - | + |
| neM3 K41 | 3-30 | / | / | 5 | GHPKGNWFDP | 165 | 10 | 3-20 | 2 | QQYGSSRYT | 195 | 9 | - | + |
| neM3 K42# | 4-59 | 3-10 | 1 | 4 | APRFGELYFDY | 166 | 11 | 3-15 | 1 | QQYNNWWT | 196 | 8 | | |
| neM3 K46# | 1-69 | 1-26 | 3 | 4 | AVGATVDFDY | 167 | 10 | 3-11 | 4 | QQRSNWLT | 197 | 8 | | |

Figure 13

| Ig | Heavy Chain | | | | | | | | Light Chain | | | | | | Reactivity | |
|---|---|---|---|---|---|---|---|---|---|---|---|---|---|---|---|---|
| | VH | D | RF | JH | CDR3 (aa) | SEQ ID NO | Length | | Vκ | Jκ | CDR3 (aa) | SEQ ID NO | Length | Poly | HEp-2 | Staining |
| neM3 L4# | 4-59 | 5-5 | 2 | 4 | QPGYSYGFDY | 168 | 10 | | 2-11 | 2 | CSYAGSYVV | 198 | 9 | | | |
| neM3 L12# | 3-11 | 1-26 | 1 | 5 | DGWELYHWFDP | 169 | 11 | | 2-23 | 2 | CSYAGRV | 199 | 7 | | | |
| neM3 L17# | 4-59 | 3-22 | 2 | 4 | GRDTTKASYYDSSGYYY | 170 | 17 | | 3-21 | 1 | QVWDSSSDHYV | 76 | 11 | | | |
| neM3 L19 | 1-24 | 1-14 | 2 | 3 | VLYPGNAFDI | 171 | 10 | | 1-47 | 1 | AAWDDSLSGYV | 200 | 11 | - | - | - |
| neM3 L24 | 4-39 | 1-26 | 2 | 4 | NSGSYYFDY | 172 | 9 | | 2-23 | 1 | CSYAGSSTYV | 70 | 10 | - | - | - |
| neM3 L25# | 1-69 | 1-26 | 2 | 4 | DSSAYSGSYYYFDY | 173 | 14 | | 1-51 | 2 | GTWDSSLSAVV | 201 | 11 | | | |
| neM3 L31# | 5-51 | 6-13 | 2 | 4 | RGSSSWGYFDY | 174 | 11 | | 1-51 | 1 | GTWDSSLSV | 202 | 9 | | | |
| neM3 L7 | | | | | | -- | | | 9-49 | 1 | GADHGSGSNFVYV | 203 | 13 | | | |
| neM3 L10 | | | | | | -- | | | 3-21 | 2 | QVWDSSSDHVV | 77 | 11 | | | |
| neM3 L29 | | | | | | -- | | | 3-1 | 1 | QAWDSSTYV | 204 | 9 | | | |
| neM3 L36 | | | | | | -- | | | 3-25 | 1 | QSADSSGTYGV | 205 | 11 | | | |
| neM3 L43 | | | | | | -- | | | 2-23 | 2 | CSYAGSSTLV | 206 | 10 | | | |
| neM3 K13 | 4-31 | 6-13 | 3 | 6 | DLAGTNYYYGMDV | 175 | 13 | | | | | -- | | | | |
| neM3 L20 | 1-69 | 6-19 | 2 | 1 | HYSSRAEYFQH | 176 | 11 | | | | | -- | | | | |
| neM3 L26 | 5-51 | 4-4 | 2 | 4 | RRDYSNYDY | 177 | 9 | | | | | -- | | | | |
| neM3 L45 | 5-51 | 3-10 | 2 | 6 | ANGSGSYYNYYYGMDV | 178 | 16 | | | | | -- | | | | |
| neM3 K47 | 3-33 | 4-4 | 2 | 4 | GTAHSNYSGFDY | 179 | 12 | | | | | -- | | | | |

RF, reading frame; #, antibody failed to be expressed
-, non reactive; +, reactive
c, diffuse cytoplasmic staining; N, nuclear staining; F, cytoplasmic fibers; V, vesicles

Figure 13 (cont'd)

Repertoire and reactivity of antibodies from new emigrant B cells of Mouse #4

| Ig | Heavy Chain | | | | | | | Light Chain | | | | | Reactivity | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM4-K49 | 4-59 | 3-10 | 2 | 5 | QGVTSAYNWFDP | 207 | 12 | 1-39 | 2 | QQSYSTPRYT | 230 | 10 | - | - |
| neM4-K61 | 1-2 | / | / | 4 | DGPAGVGVGFDY | 208 | 12 | 1-39 | 4 | RQSYSTPRLT | 231 | 10 | - | - |
| neM4-K62 | 1-2 | 1-20 | 3 | 3 | GFSASTGTTDAFDI | 209 | 15 | 3-11 | 1 | QQRSNWPPWT | 232 | 10 | - | + |
| neM4-K66# | 3-49 | 3-9 | 1 | 5 | DFQPWGYFDWPLNWFDP | 210 | 17 | 3-20 | 1 | QQYGSSPRT | 54 | 9 | | |
| neM4-K72 | 3-7 | 6-13 | 3 | 6 | VRRGGAAAGIVDWYYYGMDV | 211 | 21 | 1-39 | 4 | QQSYSTPLT | 56 | 9 | - | - |
| neM4-K74 | 1-46 | 6-6 | 2 | 4 | RRYSSSFDY | 212 | 9 | 3-20 | 1 | QQYGSSPT | 43 | 8 | - | - |
| neM4-K75 | 1-2 | 2-2 | 3 | 5 | ANIVVPAAMYNWFDP | 213 | 16 | 1-9 | 4 | QQLNSYPLT | 183 | 9 | - | + |
| neM4-K77 | 3-30 | 6-13 | 3 | 4 | VRGGIAAAGFLAGENGSFDY | 214 | 20 | 2-28 | 3 | MQALLTQFT | 233 | 9 | - | - |
| neM4-K79 | 3-30 | 3-9 | 2 | 5 | DWADYDILTGSQSGPYWFDP | 215 | 20 | 1-8 | 1 | QQYYSPQT | 234 | 9 | - | - |
| neM4-K81# | 1-3 | 4-11 | 3 | 5 | NPTTITTIIWFNP | 216 | 13 | 1D-8 | 4 | QQYYSFPLT | 235 | 9 | | |
| neM4-K83 | 3-21 | 6-6 | 3 | 4 | VPGSIAARPNLFDY | 217 | 14 | 1-17 | 2 | LQHNSYPVT | 236 | 9 | + | + |
| neM4-K85 | 4-61 | 3-22 | 2 | 6 | GPGYYDSSGPYYGMDV | 218 | 17 | 1-9 | 4 | QQLNSYPPT | 237 | 9 | - | - |
| neM4-K88 | 3-23 | 2-2 | 2 | 2 | VGCSSTSCYEDFDL | 219 | 14 | 1-39 | 2 | QQSYSTPYT | 130 | 9 | - | - |
| neM4-K90 | 3-48 | / | / | 4 | DRNSVDY | 220 | 7 | 3-15 | 1 | QQYNNWPPWT | 238 | 10 | - | - |
| neM4-L52 | 3-33 | 6-6 | 2 | 4 | DPDLRYSSSSSFDY | 221 | 14 | 2-23 | 1 | CSYAGSSTPNYV | 239 | 13 | - | - |
| neM4-L53 | 3-30 | / | / | 6 | LHAPNLYYMDV | 222 | 11 | 1-51 | 3 | GTWDSSLSAGV | 78 | 11 | - | - |
| neM4-L54 | 3-30 | 2-2 | 2 | 4 | DCLGTWRYCSSTSCSVGADY | 223 | 20 | 1-44 | 2 | AAWDDSLNGVV | 240 | 11 | + | + |
| neM4-L55 | 3-30 | 6-13 | 3 | 5 | DKGSAAADNWFDP | 224 | 13 | 3-21 | 1 | QVWDSSSDHYV | 76 | 11 | - | - |
| neM4-L58 | 4-59 | 6-19 | 1 | 4 | MKRLGIDY | 225 | 9 | 3-21 | 1 | QVWDSSSDHYV | 76 | 11 | - | - |
| neM4-L63 | 3-30 | 6-13 | 3 | 6 | SYEGIAADKNYYYGMDV | 226 | 19 | 6-57 | 2 | QSYDSSNQV | 241 | 9 | - | - |
| neM4-L67 | 3-21 | 2-2 | 3 | 5 | APRGVPAANWFDP | 227 | 13 | 2-14 | 3 | SSYTRSSTLV | 242 | 10 | - | - |
| neM4-L76# | 4-34 | 2-2 | 3 | 3 | ACERDIVVPAVNGAFDI | 228 | 18 | 2-14 | 2 | SSYTSSSTRV | 243 | 10 | | |
| neM4-L78# | 3-23 | 2-15 | 3 | 3 | DLNKTSLAAAGDRDAFDI | 229 | 18 | 1-51 | 2 | GTWDSSLSAGV | 78 | 11 | | |
| neM4-L89# | 3-48 | / | / | 4 | DRNSVDY | 220 | 7 | 1-51 | 2 | GTWDSSLSAGVV | 244 | 12 | | |

RF, reading frame; # antibody failed to be expressed
- non reactive; +, reactive
c, diffuse cytoplasmic staining; N, nuclear staining, F, cytoplasmic fibers; V, vesicles

Figure 14

Repertoire and reactivity of antibodies from new emigrant B cells of Mouse #5

| Ig | Heavy Chain | | | | | | | | Light Chain | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM5-H08 | 3-74 | / | / | 3 | EGSLNHDAFDI | 245 | 11 | 3-15 | 1 | QQYNNWPPWT | 238 | 10 | - | - | - |
| neM5-H12 | 1-2 | 6-19 | 3 | 4 | GSTENRIAVAGRPGVGADY | 246 | 19 | 3-20 | 4 | QQYGSSPMQS | 277 | 10 | - | - | - |
| neM5-H17 | 3-33 | 3-10 | 2 | 4 | GPSSGVPFAFDY | 247 | 12 | 1-5 | 1 | QQYNSYSRT | 190 | 9 | - | - | - |
| neM5-H19 | 4-39 | 1-26 | 2 | 4 | RWTGGSYGY | 248 | 9 | 1-39 | 3 | QQSYSTPFT | 58 | 9 | - | - | - |
| neM5-H21# | 5-10 | 5-5 | 2 | 4 | LVREERYSYGLTNRDDY | 249 | 17 | 3-20 | 2 | QQYGSSPPNT | 278 | 10 | | - | - |
| neM5-H34 | 3-33 | 6-13 | 2 | 5 | VDNSSSPYNWFDP | 250 | 13 | 1-39 | 3 | QQSYSTPFT | 58 | 9 | - | - | - |
| neM5-H35 | 4-61 | 4-23 | 3 | 2 | RTVVGKKGDWYFDL | 251 | 14 | 3-20 | 4 | QQYGSSLT | 279 | 8 | - | - | - |
| neM5-H37 | 3-15 | 2-8 | 2 | 6 | EAYCTGGVCYTGVLGYYYYMDV | 252 | 23 | 1-39 | 1 | QQSYSTPTRGMT | 281 | 12 | - | + | - |
| neM5-H38 | 3-33 | 1-7 | 3 | 4 | DTGITGTFDY | 253 | 10 | 1-17 | 2 | LQHNSYPYT | 282 | 9 | - | - | - |
| neM5-H45 | 4-59 | 3-22 | 2 | 4 | GRAQDSSGPNPLDY | 254 | 14 | 3-11 | 4 | QQRSNWPLT | 46 | 9 | - | - | - |
| neM5-H46 | 3-48 | 3-9 | 2 | 4 | DLHDYDILTGYYIFDY | 255 | 16 | 1-39 | 1 | QQSYSTPWT | 44 | 9 | - | - | - |
| neM5-H01 | 4-34 | 6-6 | 2 | 6 | GFKWSGRNSSSSLNYYYMDV | 256 | 21 | 3-25 | 2 | QSADSSGTYVV | 283 | 11 | - | + | - |
| neM5-H03 | 4-34 | 7-27 | 1 | 4 | GPRLGTARKPFDY | 257 | 13 | 9-49 | 3 | GADHGSGSNFVWV | 144 | 13 | - | + | - |
| neM5-H04 | 3-30 | 7-27 | 1 | 4 | LGSDYKPFDY | 258 | 10 | 1-51 | 1 | GTWDSSLSAYV | 75 | 11 | - | - | - |
| neM5-H05 | 6-19 | / | / | 4 | VEGLSVVGLPY | 259 | 11 | 1-47 | 2 | AWDDSLSGVV | 284 | 10 | - | - | - |
| neM5-H06# | 3-30-3 | 3-10 | 2 | 6 | DRGSGSYLTYYYYGMDV | 260 | 18 | 2-14 | 1 | SSYTSSSTYV | 285 | 10 | - | - | - |
| neM5-H07 | 3-23 | / | / | 4 | DELPIDDESERFDY | 261 | 15 | 1-44 | 2 | AAWDDSLNGVV | 240 | 11 | - | + | - |
| neM5-H09 | 3-48 | 5-12 | 2 | 4 | SKTDVADHLPRYSGYDPGNY | 262 | 20 | 1-44 | 3 | AAWDDSLNGWV | 286 | 11 | - | - | - |
| neM5-H11 | 4-34 | 4-17 | 2 | 4 | APGDSTRMVDY | 263 | 11 | 1-44 | 2 | AAWDDSLNGRV | 287 | 11 | - | - | - |
| neM5-H13# | 5-51 | 2-2 | 2 | 6 | WYANLGYCSSTSCYTAGMDV | 264 | 20 | 2-11 | 1 | CSYAGSSYV | 288 | 9 | - | - | - |
| neM5-H15 | 3-21 | 6-6 | 2 | 4 | DLDEYSSSVPFDY | 265 | 13 | 2-8 | 1 | SSYAGSNNYV | 289 | 10 | - | - | - |
| neM5-H23# | 4-31 | 2-15 | 3 | 3 | QIVVVDAIRDAFDI | 266 | 15 | 1-47 | 2 | AAWDDSLSGVV | 290 | 11 | - | - | - |
| neM5-H24# | 3-15 | 6-13 | 2 | 3 | SDSSSWGAFDI | 267 | 11 | 1-40 | 2 | QSYDSSLSGSV | 135 | 11 | - | - | - |
| neM5-H25 | 3-15 | 3-16 | 2 | 4 | DVWGSYRYLDY | 268 | 11 | 1-44 | 3 | AAWDDSLNGPV | 69 | 11 | - | + | - |
| neM5-H26 | 3-15 | 1-20 | 3 | 4 | GWITGTSPDFDY | 269 | 12 | 2-14 | 1 | SSYTSSSTLYV | 291 | 11 | - | - | - |
| neM5-H27 | 4-34 | 4-17 | 2 | 4 | GDLHGDLDY | 270 | 9 | 6-57 | 2 | QSYDSNVV | 292 | 8 | - | - | - |
| neM5-H28 | 1-2 | 6-19 | 2 | 6 | GGSGWSPPNYYYYMDV | 271 | 16 | 2-23 | 2 | CSYAGSSTYVV | 289 | 11 | - | - | - |
| neM5-H31 | 3-30-3 | 2-2 | 3 | 4 | DPVVVPAAMWGTFDY | 272 | 15 | 3-1 | 1 | QAWDSSTNYV | 293 | 10 | - | + | - |
| neM5-H41 | 3-23 | / | / | 3 | GAPRGAFDI | 273 | 9 | 3-21 | 3 | QVWDSSSDHRV | 294 | 11 | - | + | - |
| neM5-H43 | 1-46 | 3-16 | 2 | 5 | ERDYVWGSYRYTGPWFDP | 274 | 18 | 2-11 | 1 | CSYAGSYTYV | 136 | 10 | + | + | - |
| neM5-H48 | 3-7 | 6-13 | 3 | 4 | GRYGAIAAAGTVLDY | 275 | 15 | 2-23 | 2 | CSYAGSSSVV | 295 | 10 | - | - | - |
| neM5-H33 | 3-49 | 2-15 | 3 | 4 | QDIDIVVVAATPRGIDY | 276 | 18 | | | | | | | | |

Figure 15

Repertoire and reactivity of antibodies from new emigrant B cells of Mouse #6

| Ig | Heavy Chain | | | | | | | Light Chain | | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM6-K1 | 5-51 | 6-13 | 3 | 5 | GIAAAGTWFDP | 296 | 11 | 3-15 | 4 | QQYNNWPPLT | 330 | 10 | - | - | - |
| neM6-K2 | 1-3 | 3-22 | 2 | 4 | DPFRRFGGYYDSSGYYDY | 297 | 18 | 3-15 | 2 | QQYNNWPPYT | 331 | 10 | - | - | - |
| neM6-K3 | 6-1 | 6-13 | 3 | 5 | GIAAAGTPYWFDP | 298 | 13 | 1-39 | 1 | QQSYSTRTF | 332 | 9 | - | - | - |
| neM6-K4 | 3-15 | 4-23 | 3 | 4 | GAAVVTPY | 299 | 8 | 3-20 | 1 | QQYGSSPWT | 45 | 9 | - | - | - |
| neM6-K13 | 3-23 | 3-22 | 2 | 6 | EKDYYDSSGRTSNYYYYGMDV | 300 | 21 | 1-39 | 3 | QQSYSTPFT | 58 | 9 | - | - | - |
| neM6-K17 | 4-34 | 7-27 | 2 | 6 | RMTANWDYYYGMDV | 301 | 15 | 3-20 | 4 | QQYGSSPLT | 122 | 9 | - | - | - |
| neM6-K18 | 3-7 | 1-1 | 2 | 5 | DAKYNWNDGRS WFDP | 302 | 16 | 1D-8 | 2 | QQYYSFPYT | 333 | 9 | - | - | - |
| neM6-K22 | 1-3 | 6-13 | 3 | 3 | DSSIAAAGTSDAFDI | 303 | 15 | 1-5 | 2 | QQYNSYSYT | 334 | 9 | - | - | - |
| neM6-K29# | 1-3 | 4-11 | 3 | 5 | DRTTVTTINWFDP | 304 | 13 | 1-17 | 4 | LQHNSYPLT | 335 | 9 | - | - | - |
| neM6-K37# | 3-21 | 3-22 | 3 | 4 | SKINSPVTMIVVGAKGFDY | 305 | 19 | 3-15 | 3 | QQYNNWPFT | 185 | 9 | - | - | - |
| neM6-K38 | 4-34 | 3-16 | 2 | 6 | VRMLGDYDVHYYYGMDV | 306 | 18 | 3-11 | 2 | QQRSNWPRYT | 336 | 10 | - | - | + |
| neM6-K39 | 3-7 | / | / | 4 | DTPAGRSY | 307 | 8 | 1-17 | 2 | LQHNSYPYT | 282 | 9 | - | - | + |
| neM6-K41 | 3-49 | 6-6 | 2 | 4 | PHSSSSDYFDY | 308 | 11 | 1D-8 | 3 | QQYSFPPFT | 337 | 10 | - | - | - |
| neM6-K12# | | | | | | | | 1-5 | 1 | QQYNSYSTFG | 338 | 10 | - | - | - |
| neM6-K15# | | | | | | | | 3-15 | 3 | QQYNNWPFT | 185 | 9 | - | - | + |
| neM6-A6 | 3-30 | 2-2 | 3 | 3 | VLTVVPAADDAFDI | 309 | 14 | 3-21 | 2 | QVWDSSSDHVV | 77 | 11 | - | - | - |
| neM6-A8 | 4-30 | 5-5 | 3 | 4 | IIVDTIFDY | 310 | 9 | 2-23 | 2 | CSYAGSSTLV | 206 | 10 | - | - | + |
| neM6-A11 | 3-11 | / | / | 4 | DPKGIGY | 311 | 8 | 1-51 | 2 | GTWDSSLSAVV | 201 | 11 | - | - | - |
| neM6-A16# | 1-69 | 7-27 | 3 | 2 | DRTQLGNTGTYWYFDL | 312 | 17 | 2-11 | 3 | CSYAGSYTWV | 339 | 10 | - | - | - |
| neM6-A20 | 1-3 | 6-19 | 2 | 6 | ERVRRLAVAGPYYYYGMDV | 313 | 20 | 1-40 | 1 | QSYDSSLSGYV | 64 | 11 | - | + | + |
| neM6-A24 | 3-23 | 6-13 | 2 | 6 | KGSSSQYYYYGMDV | 314 | 16 | 2-14 | 2 | SSYTSSSTVV | 340 | 10 | - | - | - |
| neM6-A25 | 3-30 | 6-13 | 2 | 6 | YGYSSSWYYYYGMDV | 315 | 16 | 2-8 | 2 | SSYAGSNNLV | 66 | 10 | - | - | - |
| neM6-A27 | 3-9 | 3-10 | 2 | 4 | ALYYGSGSYFDY | 316 | 13 | 2-14 | 2 | SSYTSSSTHVV | 341 | 11 | - | + | - |
| neM6-A32 | 4-30 | 3-10 | 3 | 4 | LRARGVIDY | 317 | 9 | 3-1 | 3 | QAWDSSTAV | 342 | 10 | - | - | - |

Figure 16

| Ig | Heavy Chain | | | | | | | | Light Chain | | | | | | Reactivity | |
|---|---|---|---|---|---|---|---|---|---|---|---|---|---|---|---|---|
| | VH | D | RF | JH | CDR3 (aa) | SEQ ID NO | Length | Vk | Jk | CDR3 (aa) | SEQ ID NO | Length | Poly | HEp-2 | Staining |
| neM6-λ33 | 3-15 | 6-13 | 2 | 3 | GGSSSSWFDAFDI | 318 | 13 | 2-8 | 1 | SSYAGSNNYV | 289 | 10 | - | - | - |
| neM6-λ36 | 1-2 | 6-6 | 2 | 3 | NSSSSAFDI | 319 | 9 | 2-23 | 3 | CSYAGSST | 343 | 8 | - | - | - |
| neM6-λ19 | | | | | | - | | 3-10 | 2 | YSTDSSGNHRV | 344 | 11 | | | |
| neM6-λ28 | | | | | | - | | 3-21 | 1 | QVWDSSSDHYV | 76 | 11 | | | |
| neM6-λ31 | | | | | | - | | 1-40 | 3 | QSYDSSLSGWV | 345 | 11 | | | ? |
| neM6-λ26 | | | | | | - | | 1-47 | 3 | AAWDDSLSGWV | 73 | 11 | | | ? |
| neM6-H34 | 4-30 | 2-15 | 2 | 6 | YCSGGSCYGMDV | 3 | 12 | | | | - | | | | |
| neM6-H36 | 1-2 | 6-6 | 2 | 3 | NSSSSAFDI | 319 | 9 | | | | - | | | | |
| neM6-H40 | 3-23 | / | / | 4 | SFSGGDYDY | 320 | 9 | | | | - | | | | |
| neM6-H43 | 4-59 | 3-9 | 2 | 4 | HPGTYDILTGYYFDY | 321 | 15 | | | | - | | | | |
| neM6-H10 | 4-39 | 3-10 | 3 | 4 | RRVVRGVMIFDY | 322 | 12 | | | | - | | | | |
| neM6-H14 | 3-15 | 3-10 | 2 | 4 | DDYYGSGSPYY | 323 | 11 | | | | - | | | | |
| neM6-H35 | 3-7 | 4-23 | 2 | 5 | DNRDHDYGGNSPWFDP | 324 | 16 | | | | - | | | | |
| neM6-H45 | 3-23 | 3-10 | 2 | 5 | DKEMYYYGSGSYYWFDP | 325 | 17 | | | | - | | | | |
| neM6-H46 | 3-30 | 3-10 | 1 | 4 | EDDPLWFGDY | 326 | 10 | | | | - | | | | |
| neM6-H48 | 4-39 | 1-26 | 1 | 4 | QFAGWELRKQYKNFDY | 327 | 16 | | | | - | | | | |
| neM6-H9 | 3-48 | 3-10 | 2 | 4 | LISGYYFDY | 328 | 11 | | | | - | | | | |
| neM6-H42 | 4-61 | 6-13 | 2 | 4 | GAGYSSSWYYFDY | 329 | 13 | | | | - | | | | |
| neM6-H40 | 3-23 | / | / | 4 | SFSGGDYDY | 320 | 9 | | | | - | | | | |

Figure 16 (cont'd)

Repertoire and reactivity of antibodies from new emigrant B cells of Mouse #7

| Ig | Heavy Chain | | | | | | Light Chain | | | | | Reactivity | |
|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM7-κ1 | 1-18 | 7-27 | 2 | 3 | GWAGNWGLGSDAFDI | 346 | 15 | 1-5 | 1 | QQYNSYWT | 374 | 8 | | |
| neM7-κ2 | 3-21 | 3-9 | 2 | 4 | CDILTGYYLFDY | 347 | 12 | 3-11 | 4 | QQRSNWPLT | 46 | 9 | - | + |
| neM7-κ3 | 3-30 | 6-13 | 3 | 4 | SIAAAVHYFDY | 348 | 11 | 3-15 | 2 | QQYNNRPPYP | 375 | 10 | - | + |
| neM7-κ4 | 3-48 | 7-27 | 2 | 4 | GRGGNWGSTQPGYYFDY | 349 | 17 | 1-8 | 2 | QQYYSFPYT | 333 | 9 | - | - |
| neM7-κ5 | 1-2 | / | / | 3 | GPIVAWADAFDI | 350 | 12 | 3-20 | 2 | QQYGSSPYT | 376 | 9 | - | - |
| neM7-κ7 | 3-15 | 3-10 | 1 | 4 | VNPSFGDQDFDY | 351 | 12 | 1-8 | 3 | QQYYSPFT | 377 | 9 | - | - |
| neM7-κ9 | 3-33 | 5-5 | 1 | 4 | GRGWIQLWTDLYYFDY | 352 | 16 | 1-5 | 2 | QQYNSYSPYT | 378 | 10 | + | + |
| neM7-κ11 | 3-7 | 3-10 | 1 | 1 | DYRGGFGELLYFQH | 353 | 14 | 3-11 | 2 | QQRSNWPPYT | 379 | 10 | - | - |
| neM7-κ18 | 3-33 | 6-13 | 3 | 4 | VKGIAAAGSFDY | 354 | 12 | 1-8 | 2 | QQYYSPYT | 380 | 9 | - | + |
| neM7-κ22 | 4-38 | 3-10 | 2 | 1 | PQKRYYYGSGSYDEYFQH | 355 | 18 | 3-11 | 4 | QQRSNSLT | 381 | 8 | - | + | C |
| neM7-κ25 | 3-11 | 1-26 | 2 | 4 | GGRSGSYFDY | 356 | 10 | 3-20 | 1 | QQYGSSPPGT | 382 | 10 | - | - |
| neM7-κ26 | 4-38 | 6-19 | 3 | 4 | HAAVAGTPYYFDY | 357 | 13 | 3-15 | 1 | QQYNNWPPTCT | 383 | 11 | - | - |
| neM7-κ28 | 1-3 | 3-10 | 2 | 4 | GGSGSYYNLFDY | 358 | 12 | 3-15 | 4 | QQYNNWPPLT | 330 | 10 | - | - |
| neM7-κ31 | 4-59 | 3-10 | 3 | 3 | VAMVRGVISAFDI | 359 | 13 | 3-20 | 2 | QQYGSSPPY | 384 | 9 | - | - |
| neM7-κ33# | 3-49 | 3-22 | 2 | 6 | DRYYYDSSGYYYYYMDV | 360 | 19 | 1-8 | 2 | QQYYSFPRT | 385 | 9 | - | - |
| neM7-κ34 | 4-38 | / | / | 4 | RGKYFDY | 361 | 8 | 3-15 | 2 | QQYNNWPPYT | 331 | 10 | - | + |
| neM7-κ37 | 4-38 | 4-17 | 2 | 4 | NYGDYVGFDY | 362 | 10 | 1-12 | 4 | QQANSFPPLT | 386 | 10 | - | - |
| neM7-κ38# | 4-39 | 5-12 | 2 | 4 | HIGGAGYSGPFDY | 363 | 13 | 3-20 | 4 | QQYGSFLT | 387 | 8 | - | - |
| neM7-κ42 | 4-61 | 3-10 | 2 | 4 | DSDYYGSGSYFDY | 364 | 13 | 3-11 | 5 | QQRSNWPLT | 46 | 9 | - | - |
| neM7-λ10 | 1-46 | 2-2 | 2 | 5 | RYCSSTSCWFDP | 365 | 12 | 6-57 | 2 | QSYDSSNQV | 241 | 9 | - | - |
| neM7-λ14 | 3-30 | 3-10 | 2 | 3 | GGRKYYGSGSYYDLDAFDI | 366 | 19 | 2-14 | 3 | SSYTSSSTWV | 388 | 10 | - | - |
| neM7-λ19 | 4-34 | / | / | 4 | LGLKGLGPYFDY | 367 | 12 | 2-23 | 3 | CSYAGSSTKV | 389 | 10 | - | - |
| neM7-λ20 | 4-38 | 2-2 | 2 | 5 | RYCSSTSCYVNWFDP | 368 | 15 | 1-40 | 3 | QSYDSSLSGSV | 135 | 11 | - | - |
| neM7-λ21 | 3-30 | 6-19 | 2 | 4 | SYSSGWFDY | 369 | 9 | 2-14 | 3 | SSYTSSSTYWV | 390 | 11 | - | - |
| neM7-λ24 | 4-59 | 1-26 | 1 | 3 | RSEWEPEGVDAFDI | 370 | 14 | 3-21 | 2 | QVWDSSDHVV | 391 | 10 | - | - |
| neM7-λ29# | 4-34 | 3-10 | 2 | 4 | NPYYYGSGRPPFDY | 371 | 14 | 1-47 | | SLSGPDGTGTKVTVL | 392 | 28 | - | - |
| neM7-λ32 | 3-7 | 3-10 | 2 | 4 | VGYGSGSYFDY | 372 | 11 | 3-10 | 3 | YSTDSSGNQGV | 393 | 11 | - | - |
| neM7-λ38 | 4-39 | 5-12 | 2 | 4 | HIGGAGYSGPFDY | 363 | 13 | 1-47 | 2 | AAWDDSLSGVV | 290 | 11 | - | - |
| neM7-λ41# | 5-51 | 6-13 | 2 | 4 | HRDHSSSWDTLGYFDY | 373 | 16 | 2-23 | 3 | CSYAGSSTWV | 394 | 10 | - | - |

Figure 17

Repertoire and reactivity of antibodies from new emigrant B cells of Mouse #8

| Ig | Heavy Chain | | | | | | Light Chain | | | | | Reactivity | |
|---|---|---|---|---|---|---|---|---|---|---|---|---|---|
| | VH | D | RFJH | JH | CDR3 (aa) | SEQ ID NO | Length | Vκ | Jκ | CDR3 (aa) | SEQ ID NO | Length | Poly | HEp-2 Staining |
| neM8-K01 | 4-34 | 3-10 | 1 | 4 | GQLHVLLWFGELLSSHIFDY | 395 | 20 | 2-28 | 4 | MQALQTPLT | 49 | 9 | | |
| neM8-K02 | 3-23 | 3-22 | 2 | 4 | RSDYDSSGYPISVDY | 396 | 15 | 1-16 | 3 | QQYNSYPFT | 420 | 9 | - | + |
| neM8-K10 | 4-4 | 3-10 | 2 | 6 | VGDPKDYYYGSGGNYYYYGMDV | 397 | 23 | 3-20 | 3 | QQYGSSPPVFT | 421 | 11 | - | - |
| neM8-K13# | 5-51 | 5-12 | 3 | 6 | HVVATTNLASYYYYGMDV | 398 | 18 | 3-15 | 2 | QQYNNWPLYT | 422 | 10 | - | - |
| neM8-K15# | 4-59 | 2-8 | 2 | 2 | STGYWYFDL | 399 | 10 | 3-11 | 3 | QQRSNWPFT | 423 | 9 | | |
| neM8-K18# | 3-30 | 4-23 | 3 | 6 | VFSRSVVTYYYGMDV | 400 | 17 | 2-28 | 1 | MQALQTPPT | 424 | 9 | | |
| neM8-K20 | 3-30-3 | 3-10 | 2 | 5 | YYGSGSLSD | 401 | 9 | 3-20 | 3 | QQYGSSPFT | 181 | 9 | - | - |
| neM8-K25 | 3-11 | 5-5 | 3 | 4 | ETTRGDIAMVTPCNY | 402 | 15 | 1-12 | 3 | QQANSFPFT | 425 | 9 | - | - |
| neM8-K26# | 1-46 | 3-9 | 2 | 3 | DLCRGGGYDILTHDAFDI | 403 | 18 | 3-20 | 2 | QQYGSSPLYT | 426 | 10 | + | + |
| neM8-K27# | 4-34 | 2-2 | 2 | 6 | DRYCSSTSCYSYYYYGMDV | 404 | 19 | 3-20 | 5 | QQYGSSPPIT | 427 | 10 | | |
| neM8-K29 | 4-34 | 4-4 | 2 | 4 | VAKEDDYSKLKVYYFDY | 405 | 17 | 1-8 | 1 | QQYSFPWT | 428 | 9 | - | - |
| neM8-K35 | 3-30-3 | / | / | 6 | VSTAGMDV | 406 | 8 | 3-20 | 3 | QQYGSSPHT | 429 | 9 | - | + |
| neM8-K41 | 4-34 | / | / | 4 | ADFIDY | 407 | 6 | 3-11 | 3 | QQRSTWVT | 430 | 8 | - | - |
| neM8-K42# | 5-51 | 6-13 | 3 | 2 | HRIAAAGTWYFDL | 408 | 13 | 1-5 | 1 | QQYNSYSQT | 431 | 9 | - | - |
| neM8-K43 | 3-64 | / | / | 6 | RMTGMDV | 409 | 7 | 1-17 | 3 | LQHNSYPFT | 432 | 9 | | + |
| neM8-K44 | 3-48 | 4-17 | 2 | 5 | DPPPYGDYDGWFDP | 410 | 14 | 1-8 | 4 | QQYSYPPL | 433 | 9 | - | - |
| neM8-K45 | 4-34 | 6-13 | 2 | 4 | GLSSSPYYFDY | 411 | 11 | 3-20 | 4 | QQYGSSLT | 279 | 8 | - | - |
| neM8-K47 | 3-23 | / | / | 4 | DFLYFDY | 412 | 8 | 3-15 | 2 | QQYNNWPPYT | 331 | 10 | - | - |
| neM8-K48# | 3-30 | 2-15 | 2 | 4 | IGYCSGGSCYSQGDYFDY | 413 | 18 | 2-30 | 5 | MQGTHWPIT | 434 | 9 | - | + |
| neM8-L07 | 1-3 | / | / | 4 | EEGY | 414 | 4 | 3-25 | 1 | QSADSSGTYV | 435 | 0 | - | - |
| neM8-L19# | 5-51 | 5-5 | 2 | 4 | PRRGTAMAFGYSGPYYFDY | 415 | 20 | 2-14 | 3 | SSYTSSSTQV | 436 | 0 | - | - |
| neM8-L21 | 4-34 | 4-17 | 2 | 4 | SPYGDSLPIDY | 416 | 11 | 2-8 | 2 | SSYAGSNNLV | 66 | 0 | | |
| neM8-L23# | 1-69 | 2-15 | 2 | 6 | DGYCSGGSCYAPYYYYGMDV | 417 | 20 | 7-43 | 2 | LLYYGGAVV | 437 | 0 | | |
| neM8-L30 | 3-7 | 3-22 | 3 | 4 | DQSVTMIVVIWPEYYFDY | 418 | 19 | 1-40 | 3 | QSYDSSLSGSV | 135 | 11 | + | + |
| neM8-L38 | 3-11 | 1-7 | 2 | 6 | ASGWNYYYGMDV | 419 | 13 | 1-47 | 3 | AWDDSLSGPV | 438 | 0 | + | + |
| neM8-L42 | 5-51 | 6-13 | 3 | 2 | HRIAAAGTWYFDL | 408 | 13 | 2-14 | 2 | SSYTSSSTLV | 74 | 10 | - | + |
| neM8-L09 | | | | | | --- | | 2-14 | 1 | SSYTSSSTYV | 285 | 10 | | |

Figure 18

Repertoire and reactivity of antibodies from new emigrant B cells of Mouse #9

| Ig | Heavy Chain | | | | | | Light Chain | | | | | Reactivity | |
|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM9-K01 | 4-61 | 2-21 | 2 | 4 | VGCGGDCPLDY | 439 | 11 | 3-15 | 4 | QQYNNWPPLT | 330 | 10 | - | + |
| neM9-K07# | 3-48 | 3-10 | 2 | 6 | LKAVRGVYYYMDV | 440 | 14 | 1-39 | 1 | QQSYSTPPWT | 463 | 10 | | |
| neM9-K08 | 3-23 | 2-2 | 2 | 3 | DQGGYCSSTSCPDAFDI | 441 | 17 | 1-16 | 2 | QQYNSYPYT | 464 | 9 | - | - |
| neM9-K13 | 3-30-3 | 6-6 | 3 | 4 | DGADTGSIASSSGYFDY | 442 | 17 | 3-20 | 4 | QQYGSSPLT | 122 | 9 | - | - |
| neM9-K15 | 3-30 | / | / | 2 | ATGDRGNWYFDL | 443 | 12 | 3-20 | 4 | QQYGSSPPLT | 47 | 10 | + | + |
| neM9-K17 | 3-33 | 3-10 | 2 | 4 | GVSEYGSGSYYFDY | 444 | 14 | 3-20 | 4 | QQYGSSSPLT | 465 | 10 | + | + |
| neM9-K22 | 3-49 | 2-8 | 2 | 4 | DPTLLYCTNGVCHSFDY | 445 | 17 | 3-20 | 1 | QQYGSSPRT | 54 | 9 | + | + |
| neM9-K26 | 3-48 | 6-19 | 1 | 4 | ESTTQWLDLDY | 446 | 11 | 1-16 | 4 | QQNSYPLT | 466 | 8 | - | + |
| neM9-K30 | 1-69 | 7-27 | 3 | 3 | GGTGAQGFAFDI | 447 | 12 | 1-17 | 4 | LQHNSYPLT | 335 | 9 | + | + |
| neM9-K31 | 4-34 | / | / | 4 | GDRHYFDY | 448 | 8 | 1-39 | 1 | QQSYSTPPWT | 463 | 10 | - | - |
| neM9-K32 | 3-11 | 7-27 | 1 | 4 | QPLGKGLDFD | 449 | 10 | 1-17 | 1 | LQHNSYPWT | 467 | 9 | - | - |
| neM9-K34 | 4-59 | 6-13 | 3 | 4 | GGIAAAGSLGHGY | 450 | 13 | 3-20 | 1 | QQYGSSPWT | 468 | 9 | - | + |
| neM9-K35 | 3-30-3 | 3-22 | 2 | 4 | EASLPYDSSGRVGEATDY | 451 | 18 | 3-20 | 1 | QQYGSSPTWT | 469 | 10 | - | - |
| neM9-K39 | 3-30-3 | / | / | 3 | DCVSGAFDI | 452 | 9 | 3-15 | 4 | QQYNNWPPLT | 330 | 10 | - | - |
| neM9-K42 | 4-34 | 6-6 | 2 | 4 | GNPTPTYSSSYYFDY | 453 | 15 | 2-28 | 2 | MQALQTPQT | 470 | 9 | - | - |
| neM9-K43 | 3-21 | 1-26 | 2 | 4 | NSGSYHLFDY | 454 | 10 | 2-30 | 4 | MQGTHWPPLT | 471 | 10 | - | - |
| neM9-K44# | 3-23 | 7-27 | 2 | 4 | DRDWGFIDY | 455 | 9 | 3-20 | 1 | QQYGSSPTWT | 469 | 10 | | |
| neM9-L06 | 4-34 | / | / | 4 | PLGFDY | 456 | 6 | 1-51 | 3 | GTWDSSLSAV | 472 | 10 | - | - |
| neM9-L11 | 3-33 | 6-13 | 3 | 4 | PLAAAGLY | 457 | 8 | 1-51 | 2 | GTWDSSLSVV | 473 | 10 | + | N |
| neM9-L12# | 3-11 | 1-26 | 2 | 3 | DHGYSGSYYAFDI | 458 | 13 | 1-44 | 2 | AAWDDSLNGVV | 240 | 11 | | |
| neM9-L24 | 3-15 | 7-27 | 3 | 4 | DPPLSRTGGSDY | 459 | 12 | 2-14 | 2 | SSYTSSSTLNVV | 474 | 12 | - | - |
| neM9-L29 | 3-33 | 6-13 | 3 | 4 | PLAAAGLY | 457 | 8 | 3-1 | 2 | QAWDSSTAHVV | 475 | 11 | - | + |
| neM9-L45 | 3-30 | 7-27 | 1 | 4 | VALSPAAELGMRPFDY | 460 | 16 | 2-14 | 2 | SSYTSSSTLVV | 74 | 11 | | |
| neM9-L48 | 4-38-2 | 2-8 | 3 | 4 | SCLSQMVYAFDY | 461 | 12 | 1-47 | 3 | AAWDDSLSGRV | 476 | 11 | | |
| neM9-H38 | 1-18 | / | / | 2 | DQDPRPSYFDL | 462 | 11 | | | | -- | | | |

Figure 19

Repertoire and reactivity of antibodies from new emigrant B cells of Mouse #10

| Ig | Heavy Chain | | | | | | | Light Chain | | | | | Reactivity | |
|---|---|---|---|---|---|---|---|---|---|---|---|---|---|---|
|  | VH | D | RF | JH | CDR3 (aa) | SEQ ID NO | Length | Vκ | Jκ | CDR3 (aa) | SEQ ID NO | Length | Poly | HEp-2 Staining |
| neM10-K03# | 4-34 | 7-27 | 1 | 2 | ASLGNDRNWYFDL | 477 | 13 | 1-37 | 4 | QRTYNAP | 514 | 7 | | |
| neM10-K04# | 5-51 | 6-13 | 3 | 6 | LPGIAAAGASYYYYYMDV | 478 | 19 | 3-20 | 4 | QQYGSSPLT | 122 | 9 | | |
| neM10-K07 | 3-15 | / | / | 3 | DRWGAFDI | 479 | 8 | 1-8 | 4 | QQYYSYPLT | 515 | 9 | - | - |
| neM10-K11 | 3-9 | 6-13 | 2 | 4 | GYSSSWYFDY | 480 | 10 | 1-8 | 4 | QQYYSYHGT | 516 | 10 | - | - |
| neM10-K14 | 3-21 | 7-27 | 2 | 3 | HWGSGAFDI | 481 | 9 | 3-11 | 3 | QQRSNWPPFT | 517 | 9 | - | - |
| neM10-H17 | 3-15 | 6-19 | 2 | 4 | DFPYSTYYFDY | 482 | 11 | 1-8 | 2 | QQYSTYPYS | 518 | 9 | + | + |
| neM10-K19 | 1-2 | 7-27 | 3 | 4 | DTGTGAGDRFDY | 483 | 12 | 3-20 | 4 | QQYGSSRLT | 519 | 9 | - | - |
| neM10-K20 | 4-34 | 7-27 | 1 | 2 | GGVQLGMVKGWYFDL | 484 | 15 | 1-8 | 4 | QQYYSYPLT | 515 | 9 | + | + |
| neM10-K21 | 1-2 | 1-7 | 2 | 4 | ASYNWNYYFDY | 485 | 11 | 3-11 | 1 | QQRSTWPPWT | 520 | 10 | + | + |
| neM10-K23 | 4-39 | 6-6 | 2 | 5 | RSSSYWFDP | 486 | 9 | 1-39 | 3 | QQSYSTPFT | 58 | 9 | - | + |
| neM10-K24 | 3-7 | 2-2 | 2 | 1 | GKDCSSTSCYLSEYFQH | 487 | 17 | 1-12 | 1 | QQANSFPQT | 521 | 9 | - | - |
| neM10-K25 | 3-33 | / | / | 4 | DSNGGSYYFDY | 488 | 11 | 1-27 | 2 | QKYNSAPRD | 522 | 9 | + | - |
| neM10-K26 | 3-33 | 6-13 | 1 | 3 | GSSMSDPQLVSTDAFDI | 489 | 17 | 2-30 | 4 | MQGTHWPLT | 53 | 9 | + | - |
| neM10-K31 | 4-31 | 5-5 | 3 | 4 | EWRNTAMVDY | 490 | 10 | 1-39 | 2 | QQSYSTPPYT | 523 | 10 | - | - |
| neM10-K32 | 3-53 | 1-26 | 2 | 4 | ASRASSGYYFDY | 491 | 13 | 3-20 | 4 | QQYGSSPLT | 47 | 10 | - | + |
| neM10-K35 | 3-23 | 6-13 | 3 | 4 | DQSFKAAAGPIDY | 492 | 13 | 1D-8 | 1 | QQYYSFPRT | 385 | 9 | - | + |
| neM10-K37 | 3-23 | 6-13 | 2 | 4 | DRLGGYSSSWYFDY | 493 | 14 | 1D-12 | 2 | QQANSFPPYT | 524 | 10 | - | - |
| neM10-K39# | 1-18 | 7-27 | 3 | 4 | ITGDHHYFDY | 494 | 10 | 1D-8 | 4 | QQYYSFPLT | 235 | 9 | + | - |
| neM10-K42 | 4-34 | 3-10 | 2 | 4 | SRYYGSGSYYYYFDY | 495 | 15 | 1-8 | 2 | QQYYSYPYT | 380 | 9 | + | + |

Figure 20

| Ig | Heavy Chain | | | | | | Light Chain | | | | | | Reactivity | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM10-K43 | 3-23 | / | / | 4 | RPGAGDY | 496 | 7 | 1-39 | 4 | QQSYSTPLT | 56 | 9 | + | - |
| neM10-K45 | 3-30-3 | 7-27 | 1 | 4 | DRGQLGIFDY | 497 | 10 | 3-15 | 2 | QQYNNWPYS | 525 | 9 | - | + |
| neM10-K47 | 5-51 | 2-21 | 2 | 4 | LVDFSGVGSGVCGGDCYFDY | 498 | 20 | 3-15 | 4 | QQYNNWPPLT | 330 | 10 | - | - |
| neM10-L01# | 1-2 | / | / | 6 | DLVGRQTEYYYYGMDV | 499 | 17 | 1-47 | 2 | AAWDDSLSGVV | 290 | 11 | - | - |
| neM10-L09 | 4-61 | 2-15 | 2 | 3 | RYCSGGSCYSAFDI | 500 | 14 | 3-1 | 2 | QAWDSSTAHVV | 475 | 11 | - | - |
| neM10-L12 | 4-59 | 3-10 | 2 | 4 | TAYGSGSYYIDY | 501 | 12 | 3-25 | 1 | QSADSSGTYV | 435 | 10 | + | + |
| neM10-L16 | 3-11 | 2-8 | 2 | 4 | EATNGVCFDY | 502 | 10 | 1-44 | 2 | AAWDDSLNGPV | 69 | 11 | - | - |
| neM10-L18# | 4-59 | 6-13 | 2 | 4 | DRSWGSNYFDY | 503 | 11 | 1-47 | 2 | AAWDDSLSGPV | 526 | 11 | - | - |
| neM10-L29 | 3-30-3 | 3-10 | 3 | 3 | VMVRGVNAFDI | 504 | 11 | 1-40 | 2 | QSYDSSLSGVV | 71 | 11 | - | + |
| neM10-L30 | 3-23 | 4-17 | 2 | 4 | ERTSYGDYFDY | 505 | 11 | 2-11 | 3 | CSYAGSYTWV | 339 | 10 | - | + |
| neM10-L34 | 3-7 | 1-26 | 2 | 4 | DSGSYYYFDY | 506 | 10 | 2-23 | 1 | CSYAGSSTYV | 70 | 10 | + | + |
| neM10-L38 | 3-11 | 3-22 | 2 | 3 | WDYYDSSGYYAFDI | 507 | 14 | 2-18 | 2 | SSYTSSSTLV | 74 | 10 | - | - |
| neM10-H02 | 3-23 | 1-7 | 3 | 3 | IITGENAFDI | 508 | 10 | | | | | | | |
| neM10-H06 | 4-34 | 6-6 | 1 | 4 | EGQLVGDYFDY | 509 | 11 | | | | | | | |
| neM10-H17 | 3-15 | 6-19 | 2 | 4 | DFPYSTYYFDY | 482 | 11 | | | | | | | |
| neM10-H27 | 3-48 | 3-10 | 2 | 4 | TYYYGSGSRYYFDY | 510 | 14 | | | | | | | |
| neM10-H36 | 4-38-2 | 6-13 | 1 | 2 | GGEQQLVSWYFDL | 511 | 13 | | | | | | | |
| neM10-H40 | 1-2 | 6-13 | 2 | 4 | GGSSSWYYFDY | 512 | 11 | | | | | | | |
| neM10-H41 | 1-2 | / | / | 4 | ERWGDY | 513 | 6 | | | | | | | |

Figure 20 (cont'd)

Repertoire and reactivity of antibodies from new emigrant B cells of Mouse #11 GFP-

| Ig | Heavy Chain | | | | | | | Light Chain | | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP-M11-K53 | 4-4 | 6-19 | 2 | 4 | VLSSGHFDY | 527 | 9 | 1-8 | 4 | QQYYSYPLT | 515 | 9 | - | - | - |
| neGFP-M11-K58# | 4-59 | 1-26 | 2 | 3 | EEEGGSYAFDI | 528 | 11 | 1-33 | 3 | QQYDNLP | 545 | 7 | | | |
| neGFP-M11-K61 | 4-34 | 2-2 | 2 | 4 | RYCSSTSCYYFDY | 529 | 13 | 3-15 | 3 | QQYNNWPFT | 185 | 9 | - | - | - |
| neGFP-M11-K63 | 4-39 | 3-22 | 2 | 5 | RDLNYYDSSGYYSWFDP | 530 | 17 | 1-39 | 1 | QQSYSTPPWT | 463 | 10 | - | - | - |
| neGFP-M11-K67# | 3-30-3 | 6-13 | 3 | 1 | DPQRIAAAGPFQH | 531 | 13 | 1-5 | 1 | QQYNSYSRT | 190 | 9 | | | |
| neGFP-M11-K68 | 3-48 | / | / | 2 | DSQLGRGYFDL | 532 | 11 | 3-15 | 1 | QQYNNWPPWT | 238 | 10 | - | - | - |
| neGFP-M11-K73 | 4-4 | 4-11 | 2 | 4 | GSSNRNTNDY | 533 | 10 | 3-20 | 2 | QQYGSSYS | 546 | 8 | - | - | - |
| neGFP-M11-K78 | 4-34 | / | / | 4 | GVAANRLRSPGLDY | 534 | 14 | 3-20 | 4 | QQYGSSPPT | 123 | 9 | - | + | - |
| neGFP-M11-K80 | 4-34 | 6-19 | 2 | 4 | PYSSGWYFDY | 535 | 10 | 3-11 | 1 | QQRSNWLYT | 547 | 9 | - | - | - |
| neGFP-M11-K64 | | | | | | -- | | 1-17 | 2 | LQHNSYPQYS | 548 | 10 | | | |
| neGFP-M11-K75 | | | | | | -- | | 3-20 | 2 | QQYGSSPPYS | 549 | 10 | | | |
| neGFP-M11-L59 | 4-34 | 1-26 | 2 | 4 | HLPVRYSGSYPSSDY | 536 | 15 | 1-36 | 1 | AAWDDSLSGSYV | 550 | 12 | - | - | - |
| neGFP-M11-L62 | 4-61 | 7-27 | 2 | 4 | IRPTTNWGFTKYYFDY | 537 | 16 | 2-14 | 2 | SSYTSSSTLV | 74 | 10 | + | + | - |
| neGFP-M11-L66 | 3-11 | / | / | 4 | GVAGLGY | 538 | 7 | 2-14 | 1 | SSYTSSSTYV | 285 | 10 | - | - | - |
| neGFP-M11-L70 | 3-7 | / | / | 3 | AAFDI | 539 | 5 | 1-51 | 1 | GTWDSSLSAYV | 75 | 11 | - | + | - |
| neGFP-M11-L76 | 4-34 | 4-17 | 2 | 3 | VPHYGDYHDAFDI | 540 | 13 | 1-47 | 3 | AAWDDSLSGRV | 476 | 11 | - | + | - |
| neGFP-M11-L77 | 3-11 | 3-10 | 3 | 3 | VKANRGAEDAFDI | 541 | 13 | 2-14 | 3 | SSYTSSSTWV | 388 | 10 | - | - | - |
| neGFP-M11-L81 | 4-59 | 3-22 | 2 | 3 | SHASSGYYAFDI | 542 | 12 | 2-23 | 1 | CSYAGSSTYV | 70 | 10 | - | - | - |
| neGFP-M11-L91 | 4-39 | 3-10 | 2 | 4 | LIRVFDYYGSGSAFDY | 543 | 16 | 1-44 | 2 | AAWDDSLNGHVV | 72 | 12 | - | - | - |
| neGFP-M11-L94 | 3-30-3 | / | / | 4 | DPPLFDY | 544 | 7 | 2-14 | 3 | SSYTSSSTLV | 74 | 10 | - | - | - |

Figure 21

Repertoire and reactivity of antibodies from new emigrant B cells of Mouse #11 GFP+ PTPN22 620W expression

| Ig | Heavy Chain | | | | | | | | Light Chain | | | | | Reactivity | | |
|---|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP+M11-K7 | 3-23D | 6-13 | 3 | 4 | DRGIAAAGTFDY | 551 | 12 | 1-39 | 2 | QQSYSTRYS | 569 | 9 | - | - | - |
| neGFP+M11-K8 | 3-7 | 3-3 | 3 | 6 | GRFTADYYYMDV | 552 | 13 | 3-15 | 3 | QQYNNWPT | 570 | 8 | - | - | - |
| neGFP+M11-K10 | 4-39 | 3-3 | 1 | 4 | AEGDLLEWLSIGCFDY | 553 | 16 | 1-27 | 4 | QKYNSALLT | 571 | 9 | - | + | - |
| neGFP+M11-K19 | 3-74 | 7-27 | / | 3 | AEYFLGDWHHDAFDI | 554 | 15 | 1-12 | 3 | QQANSFPFT | 425 | 9 | - | - | - |
| neGFP+M11-K24 | 3-23D | 6-13 | 3 | 4 | DRGIAAAGTFDY | 551 | 12 | 1-39 | 1 | QQSYSTPWT | 44 | 9 | - | - | - |
| neGFP+M11-K25 | 4-61 | 2-21 | 3 | 4 | ATVVTAQYYFDY | 555 | 13 | 1-39 | 2 | QQSYSTPYT | 130 | 9 | + | + | - |
| neGFP+M11-K29 | 3-23D | 6-19 | 2 | 3 | RGWGHAFDI | 556 | 9 | 1-33 | 2 | QQYDNLPPRGTA | 572 | 12 | + | - | - |
| neGFP+M11-K38 | 1-2 | 6-13 | 2 | 4 | HSWYYFDY | 557 | 8 | 3-11 | 1 | QQRSNWWT | 573 | 8 | + | + | - |
| neGFP+M11-K47 | 3-30 | 2-21 | 2 | 3 | KSPPYCGGDCYSRDDAFDI | 558 | 19 | 3-20 | 5 | QQYGSSVT | 574 | 8 | - | - | - |
| neGFP+M11-L2 | 3-21 | 2-15 | 1 | 4 | DERGIGWYFDY | 559 | 11 | 2-23 | 1 | CSYAGSSTYV | 70 | 10 | - | + | N |
| neGFP+M11-L4 | 1-2 | 6-6 | 3 | 3 | VRGIAARRPDAFDI | 560 | 14 | 3-21 | 3 | QVWDSSSDHPV | 575 | 11 | - | - | - |
| neGFP+M11-L6 | 3-11 | 4-17 | 2 | 4 | RDYGDYGRGGPRWYFDY | 561 | 17 | 3-21 | 1 | QVWDSSSDHYV | 76 | 11 | - | - | - |
| neGFP+M11-L12 | 3-33 | 4-11 | 2 | 4 | NDYSNYGAFDY | 562 | 11 | 1-40 | 3 | QSYDSSLSGWV | 345 | 11 | - | + | - |
| neGFP+M11-L13 | 3-21 | 3-22 | 3 | 3 | GRVTMIVVDAFDI | 563 | 13 | 1-51 | 2 | GTWDSSLSAVV | 201 | 11 | - | + | - |
| neGFP+M11-L14 | 1-69 | 6-6 | 3 | 5 | EGASIAARPYNWFDP | 564 | 15 | 1-47 | 3 | AAWDDSLSGWV | 73 | 11 | + | + | - |
| neGFP+M11-L18 | 3-73 | 3-22 | 2 | 4 | SPGYYDSSGYYGY | 565 | 13 | 2-11 | 3 | CSYAGSYTWV | 339 | 10 | + | + | N |
| neGFP+M11-L32 | 3-30 | 6-6 | 1 | 6 | GEQLSDFDYYYGMDV | 566 | 16 | 3-1 | 1 | QAWDSSTAYV | 576 | 10 | - | - | - |
| neGFP+M11-L44 | 4-30 | 3-3 | 3 | 4 | ERITIFGVAGSFDY | 567 | 14 | 2-23 | 2 | CSYAGSSTLV | 206 | 10 | + | + | - |
| neGFP+M11-L48 | 3-33 | 7-27 | 3 | 4 | EGTITGPGYFDY | 568 | 14 | 3-25 | 3 | QSADSSGTYWV | 577 | 11 | - | - | - |

Figure 22

Repertoire and reactivity of antibodies from new emigrant B cells of Mouse #12 GFP-

| Ig | HEAVY CHAIN | | | | | | | | LIGHT CHAIN | | | | | REACTIVITY | | |
|---|---|---|---|---|---|---|---|---|---|---|---|---|---|---|---|---|
| | VH | D | RF | JH | (-) | CDR3 (aa) | SEQ ID NO | (+) | Length | Vκ | Jκ | CDR3(aa) | SEQ ID NO | Length | Poly | HEp-2 | Staining |
| neGFP-M12-k02 | 3-53 | 4-11 | 3 | 5 | 1 | GWSTVTNWFDP | 578 | 0 | 11 | 1-39 | 3 | QQSYSTPFT | 58 | 9 | + | + | - |
| neGFP-M12-k07 | 3-33 | 6-13 | 1 | 4 | 3 | PALHEQQLDYYFDY | 579 | 1 | 14 | 3-15 | 1 | QQYNNWPRWT | 606 | 10 | - | - | - |
| neGFP-M12-k16 | 1-3 | 6-13 | 3 | 5 | 2 | DCGIAAAGNWFDP | 580 | 0 | 13 | 1-8 | 3 | QQYYSYPFT | 377 | 9 | - | + | - |
| neGFP-M12-k19# | 1-69 | 7-27 | 3 | 4 | 2 | VVETGVENY | 581 | 0 | 9 | 3-11 | 1 | QQRRNWPPWT | 607 | 10 | | | |
| neGFP-M12-k20 | 4-34 | / | / | 3 | 1 | GRIPFDI | 582 | 1 | 7 | 3-20 | 4 | QQYGSPPGT | 608 | 9 | - | - | - |
| neGFP-M12-k24 | 1-3 | / | / | 4 | 1 | AGMAFDY | 583 | 0 | 7 | 1-5 | 1 | QQYNSYSWT | 609 | 9 | - | + | - |
| neGFP-M12-k25 | 4-39 | 7-27 | 3 | 4 | 1 | PGTGTNIDY | 584 | 0 | 9 | 3-15 | 1 | QQYNNWPRT | 610 | 9 | + | + | - |
| neGFP-M12-k26 | 4-34 | 7-27 | 1 | 4 | 2 | SRHARKELGLLDY | 585 | 3 | 13 | 1-5 | 2 | QQYNSYST | 611 | 8 | - | - | - |
| neGFP-M12-k29 | 4-34 | 7-27 | 3 | 3 | 3 | ARTRTGHRDDAFDI | 586 | 4 | 14 | 4-1 | 1 | QQYYSTPWT | 612 | 9 | - | - | - |
| neGFP-M12-k30 | 4-61 | 3-9 | 2 | 3 | 2 | LGGFLTGYYNDAFDI | 587 | 0 | 15 | 1-5 | 2 | QQYNSYPYT | 464 | 9 | - | - | - |
| neGFP-M12-k32 | 6-1 | 2-21 | 2 | 4 | 3 | DGYCGGDCYSVDY | 588 | 0 | 13 | 2-30 | 1 | MQGTHWPWT | 613 | 9 | - | - | - |
| neGFP-M12-k33 | 3-15 | 4-17 | 2 | 4 | 3 | VGEDPRDY | 589 | 1 | 8 | 3-20 | 2 | QQYGSSPPYT | 60 | 10 | - | - | - |
| neGFP-M12-k37 | 1-18 | 7-27 | 1 | 6 | 2 | DLGMVGMDV | 590 | 0 | 9 | 3-20 | 1 | QQYGSSRT | 614 | 8 | - | - | - |
| neGFP-M12-k40 | 6-1 | 7-27 | 2 | 4 | 2 | GRGPPAGDFDY | 591 | 1 | 11 | 2-30 | 1 | MQGTHWPWT | 613 | 9 | - | - | - |
| neGFP-M12-k44 | 4-34 | 5-5 | 2 | 3 | 1 | VQSGYSYGYAFDI | 592 | 0 | 13 | 3-20 | 4 | QQYGSSPPT | 123 | 9 | - | - | - |
| neGFP-M12-k45# | 4-31 | 6-13 | 3 | 4 | 2 | DHGIAAAGTFDY | 593 | 1 | 12 | 1-39 | 1 | QQSYSTPRT | 615 | 9 | | | |
| neGFP-M12-k46 | 4-61 | 4-23 | 2 | 4 | 2 | DYGGNSVGYFDY | 594 | 0 | 12 | 3-20 | 1 | QQYGSSPWT | 468 | 9 | - | - | - |
| neGFP-M12-L04 | 3-11 | 3-22 | 2 | 4 | 3 | GRDYDSSGYYFDY | 595 | 1 | 14 | 2-18 | 2 | SSYTSSSTLV | 74 | 10 | - | - | - |
| neGFP-M12-L05 | 3-11 | 1-7 | 3 | 5 | 3 | DWGDITGTNWFDP | 596 | 0 | 13 | 2-23 | 2 | CSYAGSSTFVV | 616 | 11 | - | - | - |
| neGFP-M12-L10# | 3-48 | 3-10 | 2 | 4 | 3 | DKPFDYYGSGSYYNYFDY | 597 | 1 | 18 | 2-8 | 2 | SSYAGSNNLV | 66 | 10 | | | |
| neGFP-M12-L12# | 1-3 | 1-26 | 3 | 3 | 2 | SKLTPDAFDI | 598 | 1 | 10 | 2-14 | 3 | SSYTSSSTWV | 388 | 10 | - | - | - |
| neGFP-M12-L14 | 3-15 | 3-3 | 3 | 4 | 2 | DPGITFGVVIDY | 599 | 0 | 13 | 2-14 | 2 | SSYTSSSTLV | 74 | 10 | - | - | - |
| neGFP-M12-L15 | 1-2 | 6-6 | 2 | 2 | 3 | DLKREAGWYFDL | 600 | 2 | 12 | 3-1 | 2 | QAWDSSTVV | 143 | 9 | - | + | - |
| neGFP-M12-L18 | 3-33 | 6-13 | 2 | 4 | 1 | TGGYSSSWYFDY | 601 | 0 | 12 | 2-14 | 2 | SSYTSSSTPYVV | 617 | 12 | - | - | - |
| neGFP-M12-L28# | 3-33 | 6-13 | 3 | 3 | 4 | DRRIAAADDAFDI | 602 | 2 | 13 | 1-44 | 1 | AAWDDSLNGPYV | 618 | 12 | | | |
| neGFP-M12-L39 | 1-69 | 6-19 | 2 | 4 | 2 | DHSSGWYYFDY | 603 | | 11 | 3-1 | 1 | QAWDSSTNYV | 293 | 10 | - | - | - |
| neGFP-M12-L42 | 5-51 | 7-27 | 2 | 2 | 2 | IPGDWYFDL | 604 | 0 | 9 | 2-11 | 3 | CSYAGSYTWV | 339 | 10 | - | - | - |
| neGFP-M12-L47 | 3-23 | 7-27 | 1 | 4 | 1 | EELGIDY | 605 | 0 | 7 | 1-47 | 3 | AAWDDSLSGWV | 73 | 11 | - | - | - |

Figure 23

Repertoire and reactivity of antibodies from new emigrant B cells of Mouse #12 GFP+ PTPN22 620W expression

| Ig | Heavy Chain | | | | | | | Light Chain | | | | | Reactivity | | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP+M12-K49 | 4-38-2 | / | / | 4 | DGRTFFDY | 619 | 8 | 3-11 | 2 | QQRSNWPPYT | 379 | 10 | + | + | N |
| neGFP+M12-K50 | 4-34 | 6-13 | 2 | 3 | TGYSSSWYRAFDI | 620 | 13 | 3-15 | 3 | QQYNNWPPGGP | 645 | 11 | + | + | - |
| neGFP+M12-K53 | 3-33 | / | / | 6 | DYYYGMDV | 621 | 9 | 3-20 | 3 | QQYGSSPT | 43 | 8 | - | + | - |
| neGFP+M12-K55 | 4-39 | 7-27 | 3 | 2 | AELGGGVWYFDL | 622 | 12 | 1-5 | 1 | QQYNSYWT | 374 | 8 | + | + | - |
| neGFP+M12-K56 | 1-69 | / | / | 5 | VGPRRDWFDP | 623 | 10 | 3-11 | 4 | QQRSNWLT | 197 | 8 | + | - | - |
| neGFP+M12-K58 | 1-69 | / | / | 4 | RGIGGLDY | 624 | 8 | 1-5 | 2 | DYNYPYT | 646 | 7 | - | - | - |
| neGFP+M12-K60 | 3-23 | / | / | 4 | VGKAPDEKLTHYYFDY | 625 | 16 | 1-5 | 4 | QQYNSYSLT | 647 | 9 | - | + | - |
| neGFP+M12-K63 | 4-4 | 7-27 | 3 | 3 | SVLLPGDQRHDAFDI | 626 | 15 | 2-30 | 1 | MQGTHWPPTVRT | 648 | 12 | - | + | - |
| neGFP+M12-K65 | 1-69 | 1-26 | 2 | 4 | VSGSYYYFDY | 627 | 10 | 3-20 | 2 | QQYGSSPRYT | 649 | 10 | + | + | - |
| neGFP+M12-K68 | 4-59 | / | / | 2 | DGDWYFDL | 628 | 8 | 1-NL1 | 3 | QQYYSTPFT | 650 | 9 | - | + | - |
| neGFP+M12-K70 | 3-33 | / | / | 4 | DLGRFDY | 629 | 7 | 1-39 | 2 | QQSYSTPQYT | 651 | 10 | - | + | - |
| neGFP+M12-K71 | 3-48 | 7-27 | 3 | 4 | GATGDSFDY | 630 | 9 | 1D-8 | 1 | QQYSFPWT | 428 | 9 | - | - | - |
| neGFP+M12-K81 | 3-21 | / | / | 4 | DSWPSYYFDY | 631 | 10 | 3-15 | 3 | QQYNNWPFT | 185 | 9 | - | + | - |
| neGFP+M12-K91 | 4-39 | / | / | 3 | HSTEKKNDAFDI | 632 | 12 | 2-28 | 4 | MQALQTPLS | 652 | 9 | - | + | - |
| neGFP+M12-K92# | 1-69 | 5-5 | 2 | 5 | YLLGYSYGVWFDP | 633 | 13 | 3-20 | 4 | QQYGSSPLT | 122 | 9 | - | - | - |
| neGFP+M12-K95 | 3-64D | 7-27 | 3 | 3 | DRQLTGDLHDAFDI | 634 | 14 | 1-5 | 1 | QQYNSYWGT | 653 | 9 | - | - | - |
| neGFP+M12-L57 | 4-39 | / | / | 4 | LGADRGWYFDY | 635 | 11 | 3-21 | 3 | QVWDSSSDHWV | 654 | 11 | - | + | - |
| neGFP+M12-L61# | 3-30 | 3-10 | 2 | 4 | ERLQSYVGSGSYYFDY | 636 | 16 | 2-11 | 1 | CSYAGSYTWV | 339 | 10 | - | - | - |
| neGFP+M12-L69# | 4-34 | 2-2 | 2 | 1 | AGLGYCSSTSCYAEYFQH | 637 | 18 | 2-23 | 7 | CSYAGSSTGHAV | 655 | 12 | - | - | - |
| neGFP+M12-L80 | 1-69 | 6-6 | 2 | 5 | NDSSNWFDP | 638 | 9 | 2-23 | 1 | CSYAGSYV | 656 | 8 | - | - | - |
| neGFP+M12-L82 | 4-34 | 4-11 | 3 | 4 | GGRMTVTDYFDY | 639 | 13 | 1-44 | 3 | AAWDDSLNGWV | 286 | 11 | - | - | - |
| neGFP+M12-L83 | 3-53 | 3-16 | 3 | 2 | DQFGDRTLHFDL | 640 | 12 | 3-21 | 2 | QVWDSSSDHPV | 575 | 11 | - | - | - |
| neGFP+M12-L84# | 4-34 | 6-13 | 3 | 4 | RQTAAAFDY | 641 | 9 | 2-23 | 1 | CSYAGSSTYV | 70 | 10 | - | - | - |
| neGFP+M12-L85 | 4-39 | 7-27 | 2 | 2 | RVLGIGRYFDL | 642 | 11 | 3-21 | 1 | QVWDSSSDLVV | 657 | 11 | - | - | - |
| neGFP+M12-L86 | 3-49 | 7-27 | 3 | 4 | DLETGDLGFDY | 643 | 11 | 2-23 | 2 | CSYAGSSTVV | 658 | 10 | - | - | - |
| neGFP+M12-L92 | | | | | see kappa | -- | | 2-14 | 2 | SSYTSSSTVV | 340 | 10 | + | - | - |
| neGFP+M12-L96 | 4-61 | 6-6 | 2 | 5 | EGFHERWDSSSSNWFDP | 644 | 17 | 2-23 | 3 | CSYAGSSTWV | 394 | 10 | - | - | - |

Figure 24

Repertoire and reactivity of antibodies from new emigrant B cells of Mouse #13 GFP-

| Ig | Heavy Chain | | | | | | | Light Chain | | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP-M13-K03 | 3-15 | 2-15 | 2 | 6 | DPPYCSGGSCYYYGMDV | 659 | 17 | 2-30 | 1 | MQGTHWPRT | 679 | 9 | - | - | - |
| neGFP-M13-K04 | 3-15 | / | / | 4 | DNSNYFDY | 660 | 8 | 2-24 | 2 | MQATQFPYT | 680 | 9 | - | - | - |
| neGFP-M13-K06# | 4-34 | 6-6 | 2 | 4 | GGEYSSSYFDY | 661 | 11 | 1-9 | 3 | QQLNSYPT | 681 | 8 | | | |
| neGFP-M13-K11 | 1-3 | / | / | 3 | VGTGNDAFDI | 662 | 10 | 3-15 | 1 | QQYNNWPPWT | 238 | 10 | - | + | - |
| neGFP-M13-K13 | 4-61 | 6-6 | 1 | 4 | VVEGQLVDY | 663 | 9 | 3-15 | 2 | QQYNNWPLYT | 422 | 10 | + | + | - |
| neGFP-M13-K16 | 3-20 | / | / | 4 | RWKGYYFDY | 664 | 9 | 3-11 | 3 | QQRSNWPPFT | 517 | 10 | - | + | - |
| neGFP-M13-K18 | 3-13 | 6-6 | 2 | 2 | GEYSSSDWYFDL | 665 | 12 | 1-17 | 2 | LQHNSYPHT | 682 | 9 | - | - | - |
| neGFP-M13-K20 | 3-15 | 1-26 | 2 | 4 | GWRVFSGSYYFDY | 666 | 13 | 1-9 | 3 | QQLNSYPFT | 683 | 9 | - | - | - |
| neGFP-M13-K25 | 4-4 | / | / | 4 | DGFQYYYYY | 667 | 10 | 3-20 | 3 | QQYGSSPFT | 181 | 9 | - | - | - |
| neGFP-M13-K27 | 3-11 | 1-26 | 3 | 4 | DGVGATDY | 668 | 8 | 1-5 | 2 | QQYNSYSYT | 334 | 9 | - | - | - |
| neGFP-M13-K32# | 3-7 | 1-1 | 1 | 2 | VQLGIVRWYFDL | 669 | 12 | 3-20 | 3 | QQYGSSPHNVVTEFT | 684 | 15 | | | |
| neGFP-M13-K39# | 4-59 | 6-19 | 2 | 4 | GGSGWYYFDY | 670 | 10 | 3-11 | 4 | QQRSNWPPLT | 685 | 10 | | | |
| neGFP-M13-K40 | 3-30 | 1-26 | 2 | 4 | DGHSGSYFDY | 671 | 10 | 1-17 | 2 | LQHNSYPYT | 282 | 9 | - | - | - |
| neGFP-M13-L02 | 3-33 | 5-24 | 2 | 4 | DWDGYNDY | 672 | 8 | 1-47 | 1 | AAWDDSLSGYV | 200 | 11 | - | - | - |
| neGFP-M13-L09 | 5-51 | 7-27 | 3 | 4 | HEDSGLTGDHYFDY | 673 | 14 | 2-14 | 1 | SSYTSSSTLV | 74 | 10 | - | - | - |
| neGFP-M13-L14# | 3-30 | 7-27 | 3 | 2 | QSRLGTWYFDL | 674 | 11 | 2-14 | 2 | SSYTSSSTLV | 74 | 10 | - | - | - |
| neGFP-M13-L17 | 3-33 | 6-13 | 3 | 4 | EESIAAAGTDY | 675 | 11 | 2-23 | 2 | CSYAGSSTFVV | 616 | 11 | - | - | - |
| neGFP-M13-L28 | 3-7 | 6-13 | 2 | 4 | DPGYSSSWFDY | 676 | 11 | 2-23 | 2 | CSYAGSHVV | 686 | 9 | - | - | - |
| neGFP-M13-L30 | 3-15 | 6-13 | 3 | 4 | AIAAAGNY | 677 | 8 | 2-23 | 3 | CSYAGSSTWV | 394 | 10 | - | - | - |
| neGFP-M13-L46 | 3-30 | 4-11 | 2 | 4 | ARHDYSNYFDY | 678 | 11 | 2-14 | 1 | SSYTSSSTYV | 285 | 10 | - | + | + |

Figure 25

Repertoire and reactivity of antibodies from new emigrant B cells of Mouse #13 GFP+ PTPN22 620W expression

| Ig | Heavy Chain | | | | | | | Light Chain | | | | | | Reactivity | | |
|---|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP+M13-K49 | 4-39 | 6-6 | 2 | 4 | RGYSSSFDY | 687 | 9 | 1-5 | 1 | QQYNSYSWT | 609 | 9 | - | - | - |
| neGFP+M13-K54# | 3-11 | 1-26 | 2 | 4 | EAQSGSYYY | 688 | 9 | 3-15 | 1 | QQYNNWPRT | 610 | 9 | | + | |
| neGFP+M13-K56 | 3-11 | 3-10 | 2 | 2 | REGSGSYYNWYFDL | 689 | 14 | 1-39 | 2 | QQSYSTPYT | 130 | 9 | - | - | - |
| neGFP+M13-K59 | 3-7 | 3-22 | 2 | 3 | DRGYDSSGYYSDAFDI | 690 | 16 | 1-NL1 | 2 | QQYYSTPRT | 709 | 9 | - | + | - |
| neGFP+M13-K60 | 1-46 | 7-27 | 2 | 3 | QNWGDAFDI | 691 | 9 | 1-17 | 3 | LQHNSYPFT | 432 | 9 | + | - | - |
| neGFP+M13-K62# | 2-15 | 2-15 | 2 | 4 | GSCSGGSCYFDY | 692 | 12 | 4-1 | 2 | QQYYSTPPT | 710 | 9 | | | |
| neGFP+M13-K64# | 3-30 | 7-27 | 3 | 6 | DRTGDLHYYYGMDV | 693 | 14 | 3-20 | 2 | QQYGSSPYT | 376 | 9 | - | - | - |
| neGFP+M13-K66 | 3-23 | 3-10 | 1 | 5 | DEGFGENNWFDP | 694 | 12 | 1-39 | 2 | QQSYSTPYT | 130 | 9 | + | - | - |
| neGFP+M13-K74# | 4-4 | 7-27 | 2 | 4 | RNWGVSGY | 695 | 8 | 1D-8 | 4 | QQYYSFPLT | 235 | 9 | - | - | - |
| neGFP+M13-K77 | 4-4 | 5-5 | 1 | 3 | VPGIQLWLKGAFDI | 696 | 14 | 3-20 | 1 | QQYGSSRT | 614 | 8 | - | - | - |
| neGFP+M13-K90 | 3-33 | / | / | 4 | APPVLGENYYFDY | 697 | 14 | 3-20 | 4 | QQYGSSPLT | 122 | 9 | - | + | - |
| neGFP+M13-K91 | 4-31 | 7-27 | 3 | 4 | GVVTGDFDY | 698 | 9 | 1-16 | 5 | QQYNSYPIT | 711 | 9 | - | - | N |
| neGFP+M13-L50# | 3-33 | 6-6 | 2 | 2 | ARDSSSWYFDL | 699 | 12 | 6-57 | 7 | QPYDSSNHAV | 712 | 10 | - | - | - |
| neGFP+M13-L52 | 3-15 | 1-26 | 2 | 2 | NHYSGSYNYWYFDL | 700 | 14 | 1-51 | 1 | GTWDSSLSAYV | 75 | 11 | - | + | - |
| neGFP+M13-L53 | 3-30-3 | 6-6 | 3 | 2 | ERGRTIAARYFDL | 701 | 13 | 2-14 | 1 | SSYTSSSTLV | 74 | 10 | - | - | - |
| neGFP+M13-L61 | 3-23 | / | / | 4 | DLILVLA | 702 | 7 | 2-23 | 3 | CSYAGSRV | 713 | 8 | - | + | - |
| neGFP+M13-L63 | 4-39 | 4-11 | 2 | 2 | PPWFDDYSNYWYFDL | 703 | 15 | 3-1 | 2 | QAWDSSTAV | 342 | 9 | + | + | - |
| neGFP+M13-L65 | 3-53 | / | / | 2 | GLRDGAAWYFDL | 704 | 12 | 2-23 | 3 | CSYAGSSTWV | 394 | 10 | - | + | - |
| neGFP+M13-L72# | 3-53 | 3-10 | 3 | 2 | ASWPGVWYFDL | 705 | 11 | 2-23 | 3 | CSYAGSYTWA | 714 | 10 | - | - | - |
| neGFP+M13-L73 | 5-10-1 | 6-13 | 3 | 1 | LVRIAAAGTEYFQH | 706 | 14 | 2-14 | 3 | SSYTSSSTLV | 74 | 10 | - | + | - |
| neGFP+M13-L88 | 4-34 | 4-17 | 2 | 2 | GNDYGDYWYFDL | 707 | 12 | 2-23 | 3 | CSYAGSHWV | 715 | 9 | - | + | - |
| neGFP+M13-L93 | 4-23 | 4-23 | 2 | 6 | GSGVYGGNYYYYGMDV | 708 | 16 | 2-14 | 3 | SSYTSSSTGWV | 716 | 11 | - | + | - |

Figure 26

Repertoire and reactivity of antibodies from new emigrant B cells of Mouse #14 GFP+ PTPN22 WT expression

| Ig | HEAVY CHAIN | | | | | | | | | LIGHT CHAIN | | | | | REACTIVITY | |
|---|---|---|---|---|---|---|---|---|---|---|---|---|---|---|---|---|
| | VH | D | RF | JH | (-) | CDR3 (aa) | SEQ ID NO | (+) | Length | Vκ | Jκ | CDR3(aa) | SEQ ID NO | Length | Poly | HEp-2 | Staining |
| neGFP+M14-K12 | 4-34 | 3-22 | 3 | 6 | 1 | LVVIKSYYYYGMDV | 717 | 1 | 14 | 1-9 | 4 | QQLNSYPLT | 183 | 9 | - | + | - |
| neGFP+M14-K20 | 3-48 | 3-22 | 2 | 2 | 4 | DGTDYYDSSGYYWYFDL | 718 | 0 | 17 | 3-20 | 4 | QQYGSSPLT | 122 | 9 | - | + | - |
| neGFP+M14-K21 | 3-21 | 4-17 | 2 | 4 | 2 | ANYGDYFDY | 719 | 0 | 9 | 3-15 | 4 | QQYNWPLT | 193 | 9 | - | - | - |
| neGFP+M14-K27 | 3-23 | 3-10 | 2 | 4 | 1 | LIVREMATLYGSGSYQNYY | 720 | 1 | 19 | 1-5 | 4 | QQYNSYPLT | 125 | 9 | - | - | - |
| neGFP+M14-K29 | 1-69 | 6-13 | 2 | 5 | 1 | NGVYSSSWYWFDP | 721 | 0 | 13 | 4-1 | 2 | QQYYSTPPYT | 740 | 10 | + | - | - |
| neGFP+M14-K30 | 3-30 | 4-17 | 2 | 4 | 3 | DVYGDYFDY | 722 | 0 | 9 | 1-39 | 2 | QQSYSTPYT | 130 | 9 | - | - | - |
| neGFP+M14-K33 | 1-3 | 1-26 | 3 | 4 | 2 | DLGVSGSYYFDY | 723 | 0 | 12 | 3-20 | 4 | QQYGSSLT | 279 | 8 | - | - | - |
| neGFP+M14-L01 | 3-15 | 6-19 | 3 | 4 | 1 | GTHYFDY | 724 | 1 | 7 | 3-27 | 2 | YSAADNNLV | 741 | 9 | - | - | - |
| neGFP+M14-L02 | 3-30-3 | 6-13 | 3 | 4 | 2 | EKAGTHYFDY | 725 | 2 | 10 | 2-18 | 1 | SSYTSSSTYV | 285 | 10 | - | + | - |
| neGFP+M14-L07 | 3-30 | 1-26 | 2 | 4 | 3 | DDSGSYLIDY | 726 | 0 | 10 | 1-44 | 3 | AAWDDSLNGL | 742 | 10 | - | - | - |
| neGFP+M14-L08# | 3-30-3 | 6-13 | 3 | 6 | 1 | NVAAAGTYPSAVFYYYYGMDV | 727 | 0 | 21 | 3-25 | 1 | QSADSSGTYV | 435 | 10 | | | |
| neGFP+M14-L09# | 3-7 | 3-22 | 2 | 4 | 1 | GHSSGYYHYFDY | 728 | 2 | 12 | 2-14 | 2 | SSYTSSSTGV | 743 | 10 | - | - | - |
| neGFP+M14-L11 | 4-4 | 4-17 | 2 | 4 | 5 | GTDDYGDNRERNYFDY | 729 | 2 | 16 | 2-14 | 2 | SSYTSSSTP | 744 | 9 | - | - | + |
| neGFP+M14-L13 | 4-59 | 7-27 | 3 | 4 | 2 | QGKITGEGNFDY | 730 | 1 | 12 | 2-18 | 2 | SSYTSSSTLVV | 74 | 11 | - | - | - |
| neGFP+M14-L14 | 4-39 | 3-22 | 2 | 5 | 3 | HERYYYDSSGYYNWFDP | 731 | 2 | 17 | 1-51 | 3 | GTWDSSLSVNWV | 745 | 12 | - | - | - |
| neGFP+M14-L24# | 1-3 | 3-3 | 2 | 4 | 3 | TDTVRTDYDFWSGYSY | 732 | 1 | 16 | 2-14 | 2 | SSYTSSSVV | 746 | 9 | | | |
| neGFP+M14-L25# | 1-3 | 2-15 | 2 | 4 | 2 | NSIDCSGGSCYFDY | 733 | 0 | 14 | 1-40 | 1 | QSYDSSLSGSV | 135 | 11 | | | |
| neGFP+M14-L31 | 3-30-3 | 6-13 | 3 | 4 | 2 | EKAGTHYFDY | 725 | 2 | 10 | 2-18 | 2 | SSYTSSSTFE | 747 | 10 | - | - | - |
| neGFP+M14-L39 | 4-34 | 2-2 | 3 | 4 | 1 | RLHRGSTSCYDY | 734 | 3 | 12 | 2-14 | 2 | SSYTSSSTVV | 340 | 10 | - | + | - |
| neGFP+M14-L40 | 3-23 | 6-6 | 2 | 4 | 2 | RLLTSSCDSGFDY | 735 | 1 | 13 | 1-40 | 1 | QSYDSSLSGFYV | 748 | 12 | - | - | - |
| neGFP+M14-L45# | 4-34 | 6-13 | 3 | 3 | 3 | GIAAADDAFDI | 736 | 0 | 11 | 2-14 | 3 | SSYTSSSWV | 749 | 9 | | | |
| neGFP+M14-H16 | 4-61 | / | / | 4 | 1 | ATKLLSFDY | 737 | 1 | 9 | | | | -- | | | | |
| neGFP+M14-L18 | 3-21 | 2-2 | 3 | 4 | 3 | DQSPSHDIVVVPAAIYFDY | 738 | 1 | 19 | | | | -- | | | | |
| neGFP+M14-H48 | 1-46 | 3-16 | 1 | 4 | 4 | DHHYEGLRLGELSLFDY | 739 | 3 | 17 | | | | | | | | |

Figure 27

Repertoire and reactivity of antibodies from new emigrant B cells of Mouse #15 GFP+ PTPN22 WT expression

| Ig | HEAVY CHAIN | | | | | | | | | LIGHT CHAIN | | | | | REACTIVITY | | |
|---|---|---|---|---|---|---|---|---|---|---|---|---|---|---|---|---|---|
| | VH | D | RF | JH | (-) | CDR3 (aa) | SEQ ID NO | (+) | Length | Vκ | Jκ | CDR3(aa) | SEQ ID NO | Length | Poly | HEp-2 | Staining |
| neGFP+M15-K49 | 3-33 | 6-13 | 2 | 3 | 1 | STRTYSSSWYAFDI | 750 | 1 | 14 | 1-33 | 5 | QQYDNLPLSFKVT | 770 | 13 | - | + | - |
| neGFP+M15-K51 | 3-30-3 | 6-6 | 2 | 3 | 2 | RRIHSYSSLDAFDI | 751 | 3 | 14 | 3-20 | 1 | QQYGSSRT | 614 | 8 | + | + | - |
| neGFP+M15-K52 | 3-33 | 3-16 | 2 | 4 | 2 | EAVWGFDY | 752 | 0 | 8 | 1-6 | 1 | LQDYNYPWT | 771 | 9 | - | - | - |
| neGFP+M15-K59 | 4-34 | 4-17 | 2 | 4 | 2 | GLYGDYFDY | 753 | 0 | 9 | 1-8 | 1 | QQYYSYPRT | 772 | 9 | - | - | - |
| neGFP+M15-K60 | 3-72 | 7-27 | 3 | 3 | 1 | AGLTGVGAFDI | 754 | 0 | 11 | 3-20 | 1 | QQYGSSRT | 614 | 8 | - | - | - |
| neGFP+M15-K67 | 3-74 | 3-3 | 1 | 4 | 3 | DEGYLRFDY | 755 | 1 | 9 | 1-17 | 4 | LQHNSYPLT | 335 | 9 | - | - | - |
| neGFP+M15-K77 | 4-34 | 3-9 | 2 | 4 | 2 | AGYYDILTGYYYFDY | 756 | 0 | 15 | 3-20 | 4 | QQYGSSPAKLT | 773 | 11 | - | + | - |
| neGFP+M15-K79# | 3-30 | 3-3 | 2 | 6 | 3 | DHDFWSGYYYYGMDV | 757 | 1 | 16 | 1-12 | 4 | QQANSFPLT | 774 | 9 | - | - | - |
| neGFP+M15-K80 | 3-33 | 6-6 | 2 | 4 | 2 | DPYSSSYYFDY | 758 | 0 | 11 | 1-39 | 4 | QQSYSTPLT | 56 | 9 | - | - | - |
| neGFP+M15-K83 | 3-43 | 4-17 | 2 | 4 | 3 | AIDYGDYYFDY | 759 | 0 | 11 | 1-5 | 2 | QQYNSYSYT | 334 | 9 | - | - | - |
| neGFP+M15-K86 | 4-61 | 3-22 | 2 | 4 | 1 | GGRQRGSGYFDY | 760 | 2 | 12 | 3-20 | 4 | QQYGSSPFT | 181 | 9 | - | + | - |
| neGFP+M15-K94 | 4-39 | 3-22 | 2 | 4 | 3 | HQIDSRSTYYYDSSGYYFDY | 761 | 2 | 20 | 3-20 | 3 | QQYGSSPT | 43 | 8 | - | - | - |
| neGFP+M15-L54# | 1-46 | 1-1 | 1 | 4 | 2 | DLQLGRYYFDY | 762 | 1 | 11 | 2-23 | 1 | CSYAGSSTSYV | 775 | 11 | - | - | - |
| neGFP+M15-L55 | 1-2 | 6-6 | 2 | 4 | 2 | SPDSSSMSKLPYFDY | 763 | 1 | 15 | 2-23 | 1 | CSYAGSSTV | 776 | 9 | - | - | - |
| neGFP+M15-L57 | 1-2 | 7-27 | 2 | 3 | 4 | DLREANWDAFDI | 764 | 1 | 12 | 2-23 | 1 | CSYAGSSTV | 776 | 9 | - | - | - |
| neGFP+M15-L66 | 4-61 | 6-6 | 2 | 3 | 1 | YSSSFFAFDI | 765 | 0 | 11 | 1-51 | 1 | GTWDSSLSAHV | 777 | 11 | - | - | - |
| neGFP+M15-L89 | 1-8 | 2-2 | 2 | 6 | 1 | GYCSSTSCYYYYMDV | 766 | 0 | 16 | 1-44 | 3 | AAWDDSLNGPV | 69 | 11 | - | - | - |
| neGFP+M15-H62 | 4-31 | 7-27 | 3 | 3 | 3 | DRRGDLGAFDI | 767 | 2 | 11 | | | | -- | | | | |
| neGFP+M15-H69 | 3-15 | 4-23 | 2 | 3 | 1 | NYGGNKNAFDI | 768 | 1 | 11 | | | | -- | | | | |
| neGFP+M15-H93 | 4-61 | 6-6 | 3 | 4 | 1 | SIAARPVDY | 769 | 1 | 9 | | | | | | | | |

Figure 28

Repertoire and reactivity of antibodies from new emigrant B cells of Mouse #16 GFP+ PTPN22 263Q expression

| Ig | Heavy Chain | | | | | | | Light Chain | | | | | Reactivity | |
|---|---|---|---|---|---|---|---|---|---|---|---|---|---|---|
| | VH | D | RFJH | JH | CDR3 (aa) | SEQ ID NO | Length | Vκ | Jκ | CDR3 (aa) | SEQ ID NO | Length | Poly | HEp-2 Staining |
| neGFP+M16-K2 | 3-30 | 1-26 | 2 | 4 | TDHSGSYFDY | 778 | 10 | 1-5 | 2 | QQYNSYSMYT | 807 | 10 | - | - |
| neGFP+M16-K9 | 3-11 | 7-27 | 2 | 4 | SETNWGDDAFDI | 779 | 12 | 3-11 | 3 | QQRSNWPFT | 423 | 9 | - | - |
| neGFP+M16-K10 | 4-34 | 7-27 | 3 | 4 | EARTGAFFDY | 780 | 10 | 1-5 | 2 | QQYNNYSYS | 808 | 9 | - | + |
| neGFP+M16-K19 | 3-33 | 3-3 | 2 | 3 | DYNFWSGYYTGDAFDI | 781 | 16 | 2-28 | 4 | MQALQTPLT | 49 | 9 | - | + |
| neGFP+M16-K21 | 3-30 | 7-27 | 2 | 4 | HEDPNWGQPLDY | 782 | 12 | 1-39 | 4 | QQSYSTPLT | 56 | 9 | - | - |
| neGFP+M16-K24 | 4-34 | 4-17 | 2 | 4 | GVFDDPLDYGDYFDY | 783 | 15 | 1-17 | 1 | LQHNSYPRT | 809 | 9 | - | - |
| neGFP+M16-K32 | 3-30 | 4-17 | 2 | 4 | GLGYGDYVSLYFDY | 784 | 14 | 4-1 | 2 | QQYSTAYT | 810 | 9 | - | - |
| neGFP+M16-K33# | 4-59 | 5-5 | 3 | 4 | AQEAMVIFDY | 785 | 10 | 1D-8 | 4 | QQYSFPLT | 235 | 9 | - | - |
| neGFP+M16-K37# | 4-34 | 3-10 | 3 | 4 | APITMVRGVPIYFDY | 786 | 15 | 3-11 | 5 | QQRSNWIT | 811 | 8 | - | - |
| neGFP+M16-K41 | 4-34 | 2-2 | 2 | 3 | LPCSSTSCYAFDI | 787 | 13 | 3-11 | 4 | QQRSTWPPT | 812 | 9 | - | - |
| neGFP+M16-K42# | 3-33 | / | 2 | 3 | DGAPGTGAFDI | 788 | 11 | 1-39 | 1 | QQSYSTPWT | 44 | 9 | | |
| neGFP+M16-K44 | 4-61 | 6-13 | 2 | 2 | DQRYSSWYWYFDL | 789 | 14 | 1-39 | 3 | QQSYSTPFT | 58 | 9 | - | - |
| neGFP+M16-K45# | 3-33 | 1-1 | 3 | 4 | EPTGTTGTFDY | 790 | 11 | 3-20 | 2 | QQYGSSPPYT | 60 | 10 | + | - |
| neGFP+M16-L1# | 3-15 | / | / | 4 | GCGADGY | 791 | 7 | 2-14 | 3 | SSYTSSGWV | 813 | 9 | | |
| neGFP+M16-L8 | 4-34 | 4-17 | 2 | 4 | TFYGDYFDY | 792 | 9 | 2-14 | 3 | SSYTSSSTWV | 388 | 10 | - | - |
| neGFP+M16-L15 | 3-30 | 6-19 | 2 | 4 | ADSSGWYYFDY | 793 | 11 | 1-47 | 3 | AAWDDSLSGQV | 814 | 11 | - | - |
| neGFP+M16-L16 | 6-1 | 5-5 | 1 | 4 | GQLWFDY | 794 | 7 | 2-14 | 1 | SSYTSSSTKV | 815 | 10 | - | - |
| neGFP+M16-L20 | 3-15 | 2-21 | 3 | 1 | AGVVTAIRAEYFQH | 795 | 15 | 3-1 | 2 | QAWDSSTAVV | 816 | 10 | - | - |
| neGFP+M16-L26 | 3-23 | / | / | 4 | DRRYYFDY | 796 | 8 | 1-40 | 3 | QSYDSSLSGWV | 345 | 11 | - | + |
| neGFP+M16-L27 | 3-7 | 6-19 | 2 | 4 | TSSGWYFDY | 797 | 9 | 2-11 | 1 | CSYAGSYTFV | 817 | 10 | - | - |
| neGFP+M16-L29 | 4-39 | / | / | 4 | SARDFDY | 798 | 7 | 1-47 | 3 | AAWDDSLSGWV | 73 | 11 | + | + |
| neGFP+M16-L31 | 3-74 | 6-6 | 2 | 4 | DRIGDSSSYYFDY | 799 | 13 | 3-1 | 2 | QAWDSSTVV | 143 | 9 | - | - |
| neGFP+M16-L36 | 4-59 | / | / | 3 | PGPGHDAFDI | 800 | 10 | 2-23 | 3 | CSYAGVWV | 818 | 8 | - | - |
| neGFP+M16-L37# | 4-34 | 3-10 | 3 | 4 | APITMVRGVPIYFDY | 786 | 15 | 1-47 | 2 | AAWDDSLSGVV | 290 | 11 | - | - |
| neGFP+M16-L40 | 4-34 | 6-6 | 3 | 3 | GKAARAFDI | 801 | 9 | 3-1 | 2 | QAWDSSTVV | 143 | 9 | - | - |
| neGFP+M16-L43# | 4-59 | 6-19 | 3 | 3 | DGGIAVADAFDI | 802 | 12 | 3-10 | 3 | YSTDSSGNHRV | 344 | 11 | - | - |
| neGFP+M16-K23 | 3-15 | 6-13 | 2 | 4 | DLREYSSSWRFDY | 803 | 13 | | | | -- | | | |
| neGFP+M16-K35 | 4-34 | 1-26 | 2 | 4 | GLGSYYFDY | 804 | 9 | | | | -- | | | |
| neGFP+M16-L38 | 4-59 | 3-9 | 2 | 3 | AHYDILTGYYAFDI | 805 | 14 | | | | -- | | | |
| neGFP+M16-L39 | 1-46 | 6-13 | 2 | 4 | DRSLPYSSSWYYFDY | 806 | 15 | | | | -- | | | |

Figure 29

Repertoire and reactivity of antibodies from new emigrant B cells of Mouse #17 GFP+ PTPN22 263Q expression

| Ig | HEAVY CHAIN | | | | | | | | | LIGHT CHAIN | | | | | | REACTIVITY | | |
|---|---|---|---|---|---|---|---|---|---|---|---|---|---|---|---|---|---|---|
| | VH | D | RF | JH | (-) | CDR3 (aa) | SEQ ID NO | (+) | Length | Vκ | Jk | CDR3(aa) | SEQ ID NO | Length | Poly | HEp-2 | Staining |
| neGFP+M17-K1 | 3-30-3 | 1-7 | 2 | 4 | 1 | VPASNWNYFDY | 819 | 0 | 11 | 1D-8 | 2 | QQYYSFPYT | 333 | 9 | - | - | - |
| neGFP+M17-K4 | 3-23D | 7-27 | 2 | 4 | 2 | SDWGYFDY | 820 | 0 | 8 | 3-11 | 1 | QQRSTWPRT | 844 | 9 | - | - | - |
| neGFP+M17-K10 | 3-30-3 | 6-13 | 3 | 3 | 2 | WRAAADAFDI | 821 | 1 | 10 | 1-17 | 4 | LQHNSYPLT | 335 | 9 | - | - | - |
| neGFP+M17-K14 | 4-34 | 7-27 | 2 | 2 | 1 | LKKANWGSGTHWYFDL | 822 | 3 | 16 | 3-11 | 3 | QQRSNWPLT | 46 | 9 | + | + | - |
| neGFP+M17-K15 | 3-30 | 6-13 | 2 | 4 | 2 | DVSSSWYFDY | 823 | 0 | 10 | 1D-8 | 2 | QQYYSFPYT | 333 | 9 | - | - | - |
| neGFP+M17-K32 | 4-34 | 6-6 | 3 | 6 | 1 | RPPSIAARYYYYMDV | 824 | 2 | 16 | 3-11 | 4 | QQRSNWLT | 197 | 8 | + | + | - |
| neGFP+M17-K48# | 3-30-3 | 6-6 | 2 | 4 | 2 | GTEYSSSYFDY | 825 | 0 | 12 | 1D-8 | 1 | QQYSFPWT | 428 | 9 | - | - | - |
| neGFP+M17-K55 | 3-33 | 7-27 | 3 | 4 | 3 | DRPTGDLDY | 826 | 1 | 9 | 3-11 | 4 | QQRSNWPPLT | 685 | 10 | - | + | - |
| neGFP+M17-K72 | 3-30 | 6-19 | 2 | 4 | 2 | DGAYSSGWYFDY | 827 | 0 | 13 | 1D-8 | 2 | QQYYSFPYT | 333 | 9 | - | - | - |
| neGFP+M17-K78 | 4-39 | 6-19 | 3 | 4 | 1 | ILTAGVDY | 828 | 0 | 8 | 1-39 | 1 | QQSYSTPPT | 845 | 9 | - | - | - |
| neGFP+M17-K80 | 3-30 | 6-13 | 2 | 4 | 2 | DVSSSWYFDY | 823 | 0 | 10 | 1D-8 | 2 | QQYYSFPYT | 333 | 9 | - | - | - |
| neGFP+M17-K83 | 3-30-3 | 1-7 | 2 | 4 | 1 | VPASNWNYFDY | 819 | 0 | 11 | 1D-8 | 2 | QQYYSFPYT | 333 | 9 | - | - | - |
| neGFP+M17-K89 | 3-30-3 | 6-6 | 2 | 4 | 2 | GTEYSSSYFDY | 825 | 0 | 12 | 1D-8 | 1 | QQYSFPWT | 428 | 9 | - | - | - |
| neGFP+M17-K90 | 3-15 | 6-13 | 2 | 4 | 2 | DHVYSSSWYFDY | 829 | 1 | 12 | 3-15 | 3 | QQYNNWLPFT | 846 | 10 | - | - | - |
| neGFP+M17-L3 | 4-34 | 3-10 | 3 | 2 | 1 | GIRAYWYFDL | 830 | 1 | 10 | 2-14 | 1 | SSYTSSSTKV | 815 | 10 | - | - | - |
| neGFP+M17-L6 | 1-2 | 3-3 | 3 | 4 | 0 | IFGVIYY | 831 | 0 | 8 | 2-14 | 3 | SSYTSSSTWV | 388 | 10 | - | + | - |
| neGFP+M17-L7 | 3-23 | 6-6 | 2 | 1 | 2 | DDRFKYSSSSYFQH | 832 | 3 | 14 | 2-14 | 1 | SSYTSSSTLYV | 291 | 11 | - | - | - |
| neGFP+M17-L16 | 1-2 | 3-3 | 3 | 4 | 0 | IFGVIYY | 831 | 0 | 8 | 2-14 | 3 | SSYTSSSTWV | 388 | 10 | - | + | - |
| neGFP+M17-L19 | 1-2 | 3-10 | 1 | 4 | 3 | EPWFGEFYFDY | 833 | 0 | 11 | 2-14 | 3 | SSYTSSSTRV | 243 | 10 | - | - | - |
| neGFP+M17-L25 | 3-30-3 | 1-26 | 3 | 4 | 1 | DQGVGRFDY | 834 | 1 | 9 | 1-40 | 2 | QSYDSSLSGSV | 135 | 11 | - | - | - |
| neGFP+M17-L38 | 3-23D | 6-13 | 3 | 4 | 1 | KVPAAGIFDY | 835 | 1 | 10 | 5-37 | 1 | MIWPSNAYV | 847 | 9 | - | - | - |
| neGFP+M17-L39 | 3-48 | 5-24 | 2 | 4 | 2 | DRRGTGFDY | 836 | 2 | 9 | 2-11 | 1 | CSYAGSYTV | 136 | 9 | - | - | - |
| neGFP+M17-L40 | 3-7 | / | / | 4 | 1 | ISRAFDY | 837 | 1 | 7 | 2-11 | 3 | CSYAGSYTWV | 339 | 10 | - | + | + |
| neGFP+M17-L53 | 1-2 | 3-3 | 3 | 4 | 0 | IFGVIYY | 831 | 0 | 8 | 2-14 | 3 | SSYTSSSTWV | 388 | 10 | - | + | + |
| neGFP+M17-L63# | 1-69 | 5-5 | 2 | 4 | 2 | VGPYSYGYDYSNYYFDY | 838 | 0 | 17 | 2-14 | 3 | SSYTSSSTLGWV | 848 | 12 | | | |
| neGFP+M17-L66 | 3-7 | 4-11 | 2 | 4 | 2 | DHPQYYFDY | 839 | 1 | 9 | 1-44 | 3 | AAWDDSLNGWV | 286 | 11 | - | - | - |
| neGFP+M17-L71 | 3-33 | 7-27 | 2 | 4 | 1 | ANWGFYYFDY | 840 | 0 | 10 | 1-44 | 3 | AAWDDSLNGWV | 286 | 11 | - | - | - |
| neGFP+M17-L81 | 1-2 | 3-10 | 2 | 4 | 2 | GDYGSGSYYNDY | 841 | 0 | 12 | 7-46 | 3 | LLSYSGAWV | 849 | 9 | - | - | - |
| neGFP+M17-L94# | 1-69 | 4-17 | 2 | 5 | 2 | HGDYWFDP | 842 | 1 | 8 | 1-47 | 3 | AAWDDSLSGRV | 476 | 11 | - | + | + |
| neGFP+M17-L95# | 4-61 | 6-6 | 2 | 3 | 2 | AYSSSGDAFDI | 843 | 0 | 12 | 2-11 | 2 | CSYAGSYHVV | 850 | 10 | | | |

Figure 30

Repertoire and reactivity of antibodies from new emigrant B cells of Mouse #18 treated with 0.75 mg of LTV-1 PTPN22 inhibitor

| Ig | Heavy Chain | | | | | | | Light Chain | | | | | Reactivity | |
|---|---|---|---|---|---|---|---|---|---|---|---|---|---|---|
| | VH | D | RFJH | CDR3 (aa) | SEQ ID NO | Length | | Vκ | Jκ | CDR3 (aa) | SEQ ID NO | Length | Poly | HEp-2 Staining |
| neM18-K13 | 3-23 | 2-21 | 3 | 6 | DRRIVVTAINYYYYMDV | 851 | 19 | 1-39 | 1 | QQSYSTRT | 884 | 8 | + | + |
| neM18-K15 | 3-23 | 3-10 | 2 | 4 | EGLGDYFDY | 852 | 9 | 1-5 | 1 | QQYNSYSRT | 190 | 9 | - | - |
| neM18-K19 | 1-3 | 7-27 | 1 | 4 | GELGPFDY | 853 | 8 | 1-16 | 4 | QQYNSYPLT | 125 | 9 | - | - |
| neM18-K20 | 3-74 | / | / | 3 | GPRSFAFDI | 854 | 9 | 3-15 | 2 | QQYNNWPPYS | 885 | 10 | - | + |
| neM18-K21 | 3-23 | 5-12 | 2 | 4 | YSGYDFTYYFDY | 155 | 12 | 1-5 | 1 | QQYNSYSRT | 190 | 9 | - | - |
| neM18-K25# | 3-23 | 3-22 | 2 | 4 | GVGSGYYYFDY | 855 | 11 | 1-9 | 5 | QQLNSYLSIT | 886 | 10 | | + |
| neM18-K27# | 1-24 | 4-17 | 2 | 5 | DLLPSRYGDYNWFDP | 856 | 15 | 2-10 | 1 | MQGTHWWT | 887 | 8 | | |
| neM18-K29 | 3-30 | 7-27 | 3 | 4 | ERTGAFDY | 857 | 8 | 3-20 | 4 | QQYATSLT | 888 | 8 | - | - |
| neM18-K30# | 4-59 | 2-2 | 2 | 2 | STTNAVYWYFDL | 858 | 12 | 1-8 | 5 | QQYYSYPIT | 889 | 9 | - | - |
| neM18-K33 | 4-34 | 6-13 | 2 | 4 | GHLKSSYSSSWYSY | 859 | 14 | 2-24 | 1 | MQATQFPWT | 116 | 9 | - | - |
| neM18-K34 | 3-9 | 1-7 | 3 | 4 | DTRGTGTTYYFDY | 860 | 13 | 3-20 | 4 | QQYGSSLLT | 890 | 9 | - | - |
| neM18-K35 | 3-23 | 6-13 | 3 | 4 | APASHIAAAGRIYFDY | 861 | 16 | 3-20 | 1 | QQYGSSPWT | 468 | 9 | - | - |
| neM18-K37 | 3-7 | / | / | 4 | TGPYYFDY | 862 | 8 | 1-39 | 2 | QQSYSTPYT | 130 | 9 | - | + |
| neM18-K39 | 3-13 | 6-19 | 2 | 2 | QVRGWYFDL | 863 | 9 | 3-15 | 3 | QQYNNWPFT | 185 | 9 | - | + |
| neM18-K44 | 3-48 | 1-26 | 2 | 4 | DLGSYDY | 864 | 8 | 1-17 | 1 | LQHQTYPRT | 891 | 9 | - | + |
| neM18-K45 | 4-34 | / | / | 2 | PLTADYWYFDL | 865 | 11 | 3-20 | 1 | QQYGSSPV | 892 | 8 | - | - |
| neM18-K47# | 3-13 | / | / | 3 | AGTGAFDI | 866 | 8 | 3-11 | 4 | QQRSTWPLT | 893 | 9 | | |

Figure 31

| Ig | Heavy Chain | | | | | | | Light Chain | | | | | Reactivity | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neM18-L02 | 3-30-3 | 1-26 | 2 | 3 | DYQLGGSYYDAFDI | 867 | 14 | 2-23 | 2 | CSYAGSSTLV | 206 | 10 | - | - |
| neM18-L03 | 4-38-2 | 2-21 | 2 | 4 | SPAYDCGGDCRFDY | 868 | 14 | 3-25 | 3 | QSADSSGTWV | 894 | 10 | - | - |
| neM18-L04 | 4-30-4 | 6-13 | 3 | 5 | AGTAAAGTGWFDP | 869 | 13 | 3-25 | 3 | QSADSSGTWV | 894 | 10 | - | - |
| neM18-L16 | 3-23 | 3-10 | 2 | 4 | DQGYYYGSGSYLDY | 870 | 14 | 2-23 | 3 | CSYAGSRV | 713 | 8 | - | - |
| neM18-L17 | 4-39 | 7-27 | 2 | 3 | QANWGSEEAFDI | 871 | 12 | 1-47 | 2 | AAWDDSLSGVV | 290 | 11 | - | - |
| neM18-L18# | 1-18 | 4-17 | 2 | 5 | GYGDYWFDP | 872 | 9 | 2-23 | 2 | CSYAGSSTHVV | 895 | 11 | - | - |
| neM18-L23 | 3-30 | / | 2 | 4 | EWVY | 873 | 4 | 1-44 | 2 | AAWDDSLNGVV | 240 | 11 | - | - |
| neM18-L28# | 3-30 | 7-27 | 3 | 4 | SVTGGLPMHY | 874 | 10 | 5-37 | 3 | MIWASNAWV | 896 | 9 | | |
| neM18-L31 | 3-15 | 3-16 | 2 | 5 | GVYYDYV | 875 | 7 | 3-1 | 2 | QAWDSSTVV | 143 | 9 | - | - |
| neM18-L32 | 3-33 | 1-26 | 1 | 4 | NGRWELPTSRFNYFDY | 876 | 16 | 3-21 | 3 | QVVWDSSSDHWV | 654 | 11 | - | + |
| neM18-L36 | 1-2 | / | / | 4 | SKRTGEGDY | 877 | 9 | 3-21 | 2 | QVVWDSSSDHPV | 575 | 11 | - | - |
| neM18-L38 | 3-30 | 7-27 | 3 | 4 | DGAPTGDPILDY | 878 | 12 | 2-14 | 2 | SSYTSSSTLV | 74 | 10 | - | - |
| neM18-L43# | 3-23 | 1-26 | 3 | 1 | VIAEGATKYFQH | 879 | 12 | 3-1 | 1 | QAWDSSTGV | 897 | 9 | | |
| neM18-L46 | 1-2 | 7-27 | 2 | 3 | ISPNWGSGAFDI | 880 | 12 | 2-23 | 2 | CSYAGSSTFVV | 616 | 11 | - | - |
| neM18-L48# | 3-21 | 3-22 | 2 | 5 | DFSPLYDSSGYYFDP | 881 | 15 | 2-23 | 2 | CSYAGSSTYVV | 70 | 11 | | |
| neM18-K05# | 3-30 | 7-27 | 3 | 2 | RTGDHWYFDL | 882 | 10 | | | | -- | | | |
| neM18-K40 | 1-69 | 1-26 | 2 | 5 | AIRRYSGSYYWFDP | 883 | 14 | | | | -- | | | |

Figure 31 (Cont'd)

Repertoire and reactivity of antibodies from new emigrant B cells of Mouse #19 treated with 0.75 mg of LTV-1 PTPN22 inhibitor

| Ig | VH | D | RF JH | | Heavy Chain | | | Light Chain | | | | | Reactivity | |
|---|---|---|---|---|---|---|---|---|---|---|---|---|---|---|
| | | | | | CDR3 (aa) | SEQ ID NO | Length | Vκ | Jκ | CDR3 (aa) | SEQ ID NO | Length | Poly | HEp-2 Staining |
| neM19-K50 | 1-69 | 6-6 | 3 | 4 | DFFRSIAARPSWGPFDY | 898 | 17 | 3-20 | 2 | QQYGSSPYT | 376 | 9 | + | + |
| neM19-K53 | 4-34 | 4-4 | 3 | 5 | GSCGQTTENWFDP | 899 | 13 | 3-20 | 2 | QQYGSSPMYT | 933 | 10 | - | - |
| neM19-K55 | 3-11 | 2-2 | 2 | 6 | GGYCSSTSCFNYGMDV | 900 | 16 | 3-20 | 2 | QQYGSSPPYT | 60 | 10 | - | - |
| neM19-K62 | 4-31 | 3-22 | 2 | 4 | VFWTPRYDSSGYYYFDY | 901 | 17 | 3-20 | 4 | QQYGSSLT | 279 | 8 | - | - |
| neM19-K63 | 3-64 | 2-21 | 2 | 5 | DRAYCGGDCYSGTGGFDP | 902 | 18 | 4-1 | 2 | QQYYSTPYT | 934 | 9 | - | - |
| neM19-K64 | 4-59 | 3-10 | 2 | 5 | DSVYYYGSGSYYNEGSTLPKYNWFDP | 903 | 26 | 3-15 | 1 | QQYNNWPQT | 55 | 9 | + | + |
| neM19-K66# | 4-39 | 3-22 | 3 | 4 | LLFRLTMIVVVTGGIDY | 904 | 17 | 3-20 | 3 | QQYGSSPFY | 935 | 9 | | - |
| neM19-K68 | 3-23 | 1-7 | 3 | 5 | EPPGTTSPSLTNWFDP | 905 | 16 | 3-20 | 4 | QQYGSSPLT | 122 | 9 | - | - |
| neM19-K73 | 3-21 | 4-17 | 2 | 5 | DPFIYDRNDYGDYGWFDP | 906 | 18 | 3-11 | 2 | QQRSTWPYT | 936 | 9 | - | + |
| neM19-K74 | 3-66 | 5-24 | 3 | 6 | VGVEMATTGRCYYGMDV | 907 | 17 | 3-15 | 4 | QQYNNWPPLT | 330 | 10 | - | + |
| neM19-K76# | 3-23 | 3-10 | 1 | 6 | CRASSGFGELGDYYGMDV | 908 | 18 | 1-17 | 1 | LQHNSYPWT | 467 | 9 | | - |
| neM19-K78 | 3-30-3 | 4-17 | 3 | 4 | GPVTNGYYFDY | 909 | 11 | 3-20 | 1 | QQYGSSPQT | 128 | 9 | - | - |
| neM19-K85# | 3-21 | 3-22 | 2 | 4 | DQGYYDSSGYYGFDY | 910 | 15 | 3-20 | 1 | QQYGSSPRT | 54 | 9 | | |
| neM19-K87 | 4-59 | 1-26 | 3 | 4 | ARLGATFDY | 911 | 9 | 1-17 | 1 | LQHNSYPWT | 467 | 9 | - | - |
| neM19-K88 | 4-30-2 | 2-2 | 3 | 5 | AGGALIPAAIDWFDP | 912 | 15 | 1-39 | 3 | QQSYSTPFT | 58 | 9 | - | - |
| neM19-K90 | 3-7 | 2-15 | 2 | 3 | DHISGGSCYSAFDI | 913 | 14 | 3-11 | 5 | QQRSNWPIT | 937 | 9 | - | + |
| neM19-K92 | 3-74 | 3-3 | 3 | 4 | GTIFGVVYSDY | 914 | 11 | 3-15 | 2 | QQYNNWPYA | 938 | 9 | + | + |
| neM19-K93# | 1-69 | / | / | 4 | PLNRSGFDY | 915 | 9 | 3-15 | 1 | QQYNNWPRT | 610 | 9 | | |
| neM19-K79 | | | | | | -- | | 1-5 | 1 | QQYNSYST | 611 | 8 | | |

Figure 32

| Ig | | Heavy Chain | | | | | | Light Chain | | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM19-L56 | 4-61 | 3-22 | 2 | 4 | MEGSYYYDSSGYPFFDY | 916 | 17 | 1-51 | 3 | GTWDSSLSAEV | 939 | 11 | - | - | - |
| neM19-L58 | 3-23 | 5-5 | 1 | 4 | VPATTWIQLWGLDY | 917 | 14 | 2-14 | 1 | SSYTSSSTLV | 74 | 10 | - | - | - |
| neM19-L60 | 3-11 | 4-23 | 2 | 3 | YGGNGGGLVGAFDI | 918 | 14 | 2-14 | 3 | SSYTSSSTLV | 74 | 10 | - | - | - |
| neM19-L67 | 1-3 | 3-10 | 2 | 5 | GLRVGYVSGSYYNDWFDP | 919 | 18 | 1-44 | 3 | AAWDDSLNGWV | 286 | 11 | - | - | - |
| neM19-L69 | 1-18 | 3-10 | 3 | 4 | DGREELNSRITMVRGPFDY | 920 | 19 | 2-14 | 3 | SSYTSSSTWV | 388 | 10 | - | - | - |
| neM19-L77 | 3-21 | 2-15 | 2 | 5 | VPPLGYCSGGSCLNWFDP | 921 | 18 | 5-37 | 3 | MIWPSNAWV | 940 | 9 | - | + | - |
| neM19-L80 | 3-66 | 1-26 | 2 | 4 | EIGDSGSYYFDY | 922 | 12 | 1-47 | 3 | AWDDSLSGPS | 941 | 10 | - | - | - |
| neM19-L81# | 3-53 | 3-3 | 3 | 5 | FGVVKAGNWFDP | 923 | 12 | 1-44 | 3 | AAWDDSLNGRV | 287 | 11 | | | |
| neM19-L83# | 3-33 | 1-20 | 2 | 6 | GGQMNLNDGPVLYYYGMDV | 924 | 20 | 2-23 | 1 | CSYAGSSTNYV | 942 | 11 | - | - | - |
| neM19-L84# | 4-31 | 3-22 | 2 | 4 | VDTYYYDSSGYSRYYFDY | 925 | 18 | 2-23 | 3 | AGSSTLVV | 943 | 8 | | | |
| neM19-L89 | 3-15 | 2-15 | 2 | 4 | VSPKINCSGGSCFITHFDY | 926 | 19 | 1-40 | 1 | QSYDSSLSGPYV | 944 | 12 | - | - | - |
| neM19-L94 | 3-15 | 3-10 | 2 | 5 | DLGDPRVEDWFDP | 927 | 13 | 2-23 | 1 | CSYAGSSTYV | 70 | 10 | - | - | - |
| neM19-L95 | 3-74 | 2-22 | 2 | 4 | ALPYCSSTSCYQYYFDY | 928 | 17 | 2-23 | 1 | AGSSTYV | 945 | 7 | - | + | - |
| neM19-L96 | 3-23 | 4-17 | 2 | 4 | DQVSYGDYRGYYFDY | 929 | 15 | 2-11 | 3 | CSYAGSYTV | 946 | 9 | - | - | - |
| neM19-L71 | | | | | | -- | | 1-47 | 2 | AAWDDSLSGHVV | 947 | 12 | | | |
| neM19-L82 | | | | | | -- | | 1-44 | 3 | AAWDDSLNGWV | 286 | 12 | | | |
| neM19-K52 | 3-7 | 5-5 | 3 | 4 | DQVDTAMVLDY | 930 | 11 | | | | | | | | |
| neM19-H59 | 4-39 | 3-22 | 2 | 4 | LTYYYDSSGYYYFDY | 931 | 15 | | | | -- | | | | |
| neM19-H72 | 1-69 | 6-19 | 2 | 4 | DQDSYSSGWVGLDY | 932 | 14 | | | | -- | | | | |

Figure 32 (Cont'd)

Repertoire and reactivity of antibodies from new emigrant B cells of Mouse #20 treated with 0.15 mg of LTV-1 PTPN22 inhibitor

| Ig | Heavy Chain | | | | | | | Light Chain | | | | | Reactivity | |
|---|---|---|---|---|---|---|---|---|---|---|---|---|---|---|
|  | VH | D | RF | JH | CDR3 (aa) | SEQ ID NO | Length | Vκ | Jκ | CDR3 (aa) | SEQ ID NO | Length | Poly | HEp-2 Staining |
| neM20-K02 | 4-61 | 3-9 | 2 | 4 | AHYDILTGYWFDY | 948 | 13 | 2-30 | 1 | MQGTHWPPT | 985 | 9 | + | + |
| neM20-K05 | 3-30 | 3-22 | 2 | 4 | SGDSSGYYFDY | 949 | 11 | 3-15 | 4 | QQYNNWPLT | 193 | 9 | - | - |
| neM20-K06 | 3-30-3 | 6-13 | 2 | 4 | TAGYSSSWFDY | 950 | 11 | 1-16 | 3 | QQYNSYPFT | 420 | 9 | - | - |
| neM20-K07 | 3-74 | 2-2 | 3 | 4 | DIVVPAATPGVSGFDY | 951 | 17 | 1-27 | 3 | QKYNSAPFT | 986 | 9 | - | - |
| neM20-K10 | 1-8 | 1-26 | 1 | 3 | GPSVVMWELSSDAFDI | 952 | 16 | 3-15 | 2 | QQYNNWPLYT | 422 | 10 | - | - |
| neM20-K11 | 4-59 | 6-19 | 2 | 5 | EWAGYSSGWSDYNWFDP | 953 | 17 | 1-17 | 1 | LQHNSYPRT | 809 | 9 | - | - |
| neM20-K13 | 4-31 | 7-27 | 3 | 2 | SAGDWGWYFDL | 954 | 11 | 3-20 | 2 | QQYGSSPLYT | 426 | 10 | - | + |
| neM20-K14 | 4-34 | 4-11 | 2 | 4 | VGDYSNYPADY | 955 | 11 | 3-11 | 4 | QQRSNWPPLI | 685 | 10 | - | - |
| neM20-K22 | 3-23 | 6-13 | 2 | 4 | TYSSSWLYIDY | 956 | 11 | 3-15 | 1 | QQYNNWPPVWT | 987 | 11 | + | + |
| neM20-K23 | 3-21 | 6-13 | 2 | 5 | DLVGYSSSWNWFDP | 957 | 14 | 1-NL1 | 2 | QQYYSTPYT | 934 | 9 | + | - |
| neM20-K27 | 3-23 | 3-22 | 2 | 4 | DLYYDSSGYPLGGGFDY | 958 | 18 | 3-20 | 2 | QQYGSSPYT | 376 | 9 | - | - |
| neM20-K32 | 4-59 | 7-27 | 3 | 4 | GTKQELGKYYFDY | 959 | 13 | 3-15 | 1 | QQYNNWT | 988 | 7 | - | - |
| neM20-K34 | 3-23 | 6-6 | 1 | 4 | AGQLEPHYFDY | 960 | 11 | 1-5 | 1 | QQYNSYSRT | 190 | 9 | - | - |
| neM20-K36 | 1-8 | 3-22 | 2 | 4 | GLSYYDSRGDYFDY | 961 | 14 | 3-20 | 1 | QQYGSSPGT | 127 | 9 | - | - |
| neM20-K37 | 3-48 | 1-26 | 3 | 4 | NNGATTWRADY | 962 | 11 | 3-20 | 5 | QQYGSSPIT | 989 | 9 | - | - |
| neM20-K39 | 3-23 | 2-15 | 2 | 3 | DWGDNCSGGSCYSNKVPDAFDI | 963 | 22 | 1-5 | 1 | QQYNSYRT | 990 | 8 | - | - |
| neM20-K41 | 3-66 | 4-17 | 2 | 4 | NEGYGDYLYYFDY | 964 | 13 | 3-11 | 3 | QQRSNCT | 991 | 7 | + | + |
| neM20-K45 | 3-72 | 1-26 | 3 | 5 | ERVAIGIVGATTARGGQQYNWFDP | 965 | 24 | 3-11 | 3 | QQRSNWPT | 184 | 8 | - | + |

Figure 33

| Ig | Heavy Chain | | | | | | | Light Chain | | | | | | Reactivity | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neM20-K47# | 3-53 | 3-22 | 2 | 4 | QLLNYYDSSGYYYY | 966 | 14 | 3-20 | 2 | QQYGSSPLVT | 992 | 10 | | | |
| neM20-K48 | 4-34 | / | / | 4 | HGSGTYQHFDY | 967 | 11 | 3-11 | 2 | QQRSNWYT | 993 | 8 | - | - | - |
| neM20-L01 | 4-39 | 3-22 | 2 | 5 | HFPAIGDSSGYVGAYNWFDP | 968 | 20 | 8-61 | 3 | VLYMGSGVWV | 994 | 10 | - | - | - |
| neM20-L08 | 1-2 | 6-13 | 3 | 3 | EPNLAAAGTKKNAFDI | 969 | 16 | 2-14 | 1 | SSYTSSSTLV | 74 | 10 | - | - | - |
| neM20-L12 | 4-39 | 1-26 | 3 | 3 | HFEVGAHRFDP | 970 | 11 | 3-1 | 2 | QAWDSSTYVV | 204 | 10 | - | - | - |
| neM20-L15 | 3-23 | 6-13 | 3 | 6 | DGRGIAAAGTPYYYGMDV | 971 | 18 | 3-1 | 1 | QAWDSSTYV | 204 | 9 | - | - | - |
| neM20-L16 | 3-48 | 7-27 | 3 | 3 | DLTGDRGNAFDI | 972 | 12 | 3-21 | 3 | QVWDSSSDHWV | 654 | 11 | - | - | - |
| neM20-L17 | 3-9 | 2-21 | 3 | 3 | DFGAIVVTDAFDI | 973 | 14 | 2-11 | 2 | CSYAGSYTVV | 995 | 10 | - | - | - |
| neM20-L18 | 3-33 | 5-5 | 3 | 6 | GASDTAMVTYYYGMDV | 974 | 17 | 2-14 | 1 | SSYTSSSTLV | 74 | 10 | - | + | - |
| neM20-L19 | 3-73 | 6-19 | 3 | 3 | HAPPPIAVAGTVAFDI | 975 | 16 | 1-44 | 3 | AAWDDSLNGWV | 286 | 11 | - | - | - |
| neM20-L24 | 3-15 | 3-3 | 3 | 4 | EVWSGYTIFGVVIY | 976 | 14 | 2-14 | 3 | SSYTSSSTWV | 388 | 10 | - | + | - |
| neM20-L26 | 3-21 | 6-19 | 2 | 5 | TGYSSGWNWFDP | 977 | 12 | 2-11 | 1 | CSYAGSYTYV | 136 | 10 | - | - | - |
| neM20-L28 | 4-61 | 3-10 | 2 | 5 | FGSSPHHSGSAVDWFDP | 978 | 17 | 1-36 | 2 | AAWDDSLNGVV | 240 | 11 | - | - | - |
| neM20-L29 | 3-23 | 3-22 | 2 | 3 | DRVDYYDSSGYPTDAFDI | 979 | 19 | 1-44 | 2 | AAWDDSLNVV | 996 | 10 | - | + | - |
| neM20-L31 | 3-15 | / | / | 4 | DPPGKGTQSFDY | 980 | 12 | 2-14 | 3 | SSYTSSSTWV | 388 | 10 | - | - | - |
| neM20-L42 | 3-30 | 6-13 | 3 | 2 | AGGPLVRYAAAGYWYFDL | 981 | 18 | 2-23 | 1 | CSYAGSSTYV | 70 | 10 | + | + | - |
| neM20-L43 | 4-34 | 3-10 | 3 | 5 | RGTMVRGVNVGWFDP | 982 | 15 | 2-11 | 3 | CSYAGSYTWV | 339 | 10 | - | - | - |
| neM20-H25 | 3-66 | 5-5 | 2 | 4 | DLGYSYGYTDY | 983 | 11 | | | | - | | | | |
| neM20-H30 | 3-49 | 3-9 | 2 | 4 | DQYDILTGFDY | 984 | 11 | | | | - | | | | |

Figure 33 (Cont'd)

Repertoire and reactivity of antibodies from new emigrant B cells of Mouse #21 GFP-

| Ig | Heavy Chain | | | | | | | Light Chain | | | | | Reactivity | | |
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP-M21-K2 | 3-30 | 4-23 | 2 | 3 | GASPYGGNSGAFDI | 997 | 14 | 1-5 | 2 | QQYNSYST | 611 | 8 | + | - | - |
| neGFP-M21-K11 | 3-15 | 1-7 | 2 | 2 | GPNYPNQSRYFDL | 998 | 13 | 3-15 | 2 | QQYNNWPPYT | 331 | 10 | + | + | - |
| neGFP-M21-K12 | 1-69 | 2-15 | 2 | 4 | KTDGGGGSSSHFDY | 999 | 14 | 3-15 | 3 | QQYNNWPPSST | 1033 | 11 | - | - | - |
| neGFP-M21-K13 | 3-30 | 3-22 | 3 | 3 | DPTSVVVMSDAFDI | 1000 | 14 | 3-15 | 1 | QQYNNWLWT | 1034 | 9 | + | + | - |
| neGFP-M21-K14 | 3-23 | 6-19 | 1 | 1 | DTVGGWLGKYFQH | 1001 | 13 | 1-39 | 4 | QQSYSTPLT | 56 | 9 | + | + | - |
| neGFP-M21-K17 | 4-39 | 1-26 | 2 | 4 | RSGSNRGLGYFDY | 1002 | 13 | 3-15 | 1 | QQYNNWPPWT | 238 | 10 | + | + | - |
| neGFP-M21-K18 | 3-7 | 4-23 | 3 | 2 | TNTVGYWYFDL | 1003 | 12 | 1-12 | 1 | QQANSFPWT | 1035 | 9 | - | - | - |
| neGFP-M21-K19 | 3-23 | 2-21 | 2 | 4 | DRGGDYFDY | 1004 | 9 | 1-5 | 2 | QQYNSYSHT | 1036 | 9 | - | + | - |
| neGFP-M21-K20 | 1-2 | 6-6 | 3 | 4 | PGSIAARVLDY | 1005 | 11 | 4-1 | 2 | QQYYSTPYT | 934 | 9 | - | + | C |
| neGFP-M21-K23 | 4-39 | 6-13 | 3 | 4 | HRGIAAAGDY | 1006 | 10 | 1-39 | 1 | QQSYSTPWT | 44 | 9 | - | + | - |
| neGFP-M21-K24 | 4-39 | 2-15 | 3 | 5 | HPIQDIVVVAANWFDP | 1007 | 17 | 3-11 | 3 | QQRNLVT | 1037 | 7 | - | - | - |
| neGFP-M21-K25# | 4-61 | 3-22 | 2 | 6 | DRYYDSSGYSDYYYGMDV | 1008 | 18 | 3-20 | 2 | QQYGSSPYT | 376 | 9 | - | - | - |
| neGFP-M21-K29 | 3-23 | 6-19 | 3 | 4 | DPGGSIAVAGDY | 1009 | 12 | 3-11 | 4 | QQRSNWLT | 197 | 8 | - | - | - |
| neGFP-M21-K30 | 4-4 | 4-17 | 2 | 6 | VGWEDDYGDQGGRYYYYGMDV | 1010 | 21 | 2-28 | 4 | MQALQTLT | 1038 | 8 | - | - | - |
| neGFP-M21-K33 | 4-31 | 4-17 | 3 | 2 | GAMTTVTTGGPAAGYFDL | 1011 | 18 | 1-39 | 1 | QQSYSTPGP | 1039 | 9 | - | + | - |
| neGFP-M21-K34 | 1-18 | 5-24 | 2 | 4 | AGRRDGYNYYFDY | 1012 | 13 | 3-15 | 2 | QQYNNWPYT | 189 | 9 | - | + | - |
| neGFP-M21-K39 | 3-64 | 3-9 | 2 | 5 | DPHYDILTGYSHNWFDP | 1013 | 17 | 2-28 | 2 | MQALQTPYT | 1040 | 9 | - | - | - |
| neGFP-M21-K40# | 3-74 | 5-24 | 3 | 6 | DRVEMATIYYYYGMDV | 1014 | 17 | 2-28 | 1 | MQALQTPRT | 1041 | 9 | | | |
| neGFP-M21-K42 | 3-33 | 3-22 | 2 | 4 | DAHYYDSSGYPPAYYFDY | 1015 | 18 | 1-5 | 1 | QQYNSYPWT | 1042 | 9 | + | + | - |

Figure 34

| Ig | Heavy Chain ||||||| Light Chain ||||| Reactivity |||
|---|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 | Staining |
| neGFP-M21-K45 | 4-61 | 4-23 | 3 | 4 | EGVVTKFPDY | 1016 | 10 | 1-17 | 1 | LQHNSYPWT | 467 | 9 | - | - | - |
| neGFP-M21-K46 | 4-61 | 2-2 | 2 | 4 | WGVSNSCSSTSCYSSRLYYFDY | 1017 | 22 | 1-17 | 3 | LQHNSYLFT | 1043 | 9 | - | + | - |
| neGFP-M21-K47 | 3-11 | / | / | 4 | DTGHTGDY | 1018 | 8 | 1-39 | 2 | QQSYSTPRT | 615 | 9 | - | + | - |
| neGFP-M21-K48 | 3-30 | 2-2 | 2 | 3 | GYCSSTSCYRGAFDI | 1019 | 15 | 3-20 | 3 | QQYGSSPFT | 181 | 9 | - | + | - |
| neGFP-M21-L1 | 3-33 | 2-8 | 2 | 4 | GNVGYCTNGVCSSISFDY | 1020 | 18 | 1-51 | 1 | GTWDSSLSAHYV | 1044 | 12 | - | + | - |
| neGFP-M21-L3 | 4-61 | 5-5 | 2 | 5 | EFKRGYSYGYVWFDP | 1021 | 15 | 1-51 | 3 | GTWDSSLSAGV | 78 | 11 | + | + | N |
| neGFP-M21-L4 | 3-23 | 3-3 | 3 | 4 | STIFGVVITPFDY | 1022 | 13 | 2-11 | 3 | CSYAGSVV | 1045 | 8 | - | - | - |
| neGFP-M21-L5 | 3-11 | 4-4 | 3 | 5 | VGGLRPTVTTGYNWFDP | 1023 | 17 | 2-14 | 3 | SSYTSSSTWV | 388 | 10 | - | - | - |
| neGFP-M21-L6 | 3-30 | 4-17 | 2 | 4 | PKADYGDYTPAQYYFDY | 1024 | 17 | 2-11 | 2 | CSYAGSYHVV | 850 | 10 | - | - | - |
| neGFP-M21-L8 | 3-9 | / | / | 6 | VTHPLNYYGMDV | 1025 | 13 | 1-47 | 3 | AAWDDSLSGPV | 526 | 11 | - | - | - |
| neGFP-M21-L9 | 3-30 | 3-10 | 1 | 4 | DRGRFGEGYFDY | 1026 | 12 | 1-51 | 3 | GTWDSSLSAWV | 1046 | 11 | - | - | - |
| neGFP-M21-L10 | 3-30 | 3-3 | 2 | 4 | DSFPRFWSGYCSFDY | 1027 | 15 | 1-44 | 1 | AAWDDSHYV | 1047 | 9 | - | + | - |
| neGFP-M21-L16 | 3-74 | 2-2 | 1 | 6 | DRVVPHRGTRQLNGMDV | 1028 | 17 | 2-11 | 2 | CSYAGSYTLV | 1048 | 10 | - | - | - |
| neGFP-M21-L22 | 3-11 | 3-9 | 2 | 5 | DRTPTYDILTGQLNWFDP | 1029 | 18 | 2-8 | 2 | SSYAGSNNVV | 1049 | 10 | - | - | - |
| neGFP-M21-L27 | 3-23 | 2-2 | 2 | 4 | SLNCSSTSWY1PRVGFDY | 1030 | 18 | 2-14 | 3 | SSYTSSSIWV | 1050 | 10 | - | - | - |
| neGFP-M21-L38 | 3-21 | 6-6 | 3 | 4 | VVAARWDIYYFDY | 1031 | 13 | 2-14 | 2 | SSYTSSSIPVV | 1051 | 11 | - | - | - |
| neGFP-M21-L43 | 3-33 | 4-4 | 2 | 5 | GSEKNDYSNYMNWFDP | 1032 | 16 | 1-51 | 3 | GTWDSSLSAGV | 78 | 11 | - | - | - |

Figure 34 (Cont'd)

Repertoire and reactivity of antibodies from new emigrant B cells of Mouse #21 GFP+ shRNA PTPN22

| Ig | Heavy Chain | | | | | | | Light Chain | | | | | Reactivity | |
|---|---|---|---|---|---|---|---|---|---|---|---|---|---|---|
| | VH | D | RF | JH | CDR3 (aa) | SEQ ID NO | Length | Vκ | Jκ | CDR3 (aa) | SEQ ID NO | Length | Poly | HEp-2 Staining |
| neGFP+M21-K49 | 3-15 | 6-19 | 3 | 4 | DRYAVAGTVDY | 1052 | 12 | 3-11 | 3 | QQRSNLFT | 1079 | 8 | - | - |
| neGFP+M21-K58 | 4-4 | 6-6 | 2 | 4 | AGPYSSSYFDY | 1053 | 12 | 1-17 | 1 | LQHNSYPWT | 467 | 9 | - | + |
| neGFP+M21-K65# | 1-46 | 2-15 | 1 | 4 | TLRGWCPDY | 1054 | 9 | 1-16 | 2 | QQYNSYPHT | 1080 | 9 | | |
| neGFP+M21-K67# | 3-48 | 4-4 | 2 | 4 | ADDYSNYFDY | 1055 | 10 | 1-33 | 4 | QQYDNLPLT | 1081 | 9 | | |
| neGFP+M21-K68# | 3-30 | 2-8 | 2 | 6 | DGANGARLGGHYYYYGMDV | 1056 | 20 | 3-11 | 5 | QQRSNWPPIT | 1082 | 10 | | |
| neGFP+M21-K71 | 3-11 | 2-2 | 2 | 6 | DHTARGACSSTSCYIYYYGMDV | 1057 | 22 | 1-17 | 2 | LQHNSYPYT | 282 | 9 | - | + |
| neGFP+M21-K74# | 3-33 | 6-19 | 1 | 3 | DYFFGQWLAAGDAFDI | 1058 | 16 | 2-30 | 3 | MQGTHWPRVT | 1083 | 10 | | |
| neGFP+M21-K77 | 3-7 | 6-13 | 3 | 4 | GVAAGIFGY | 1059 | 9 | 3-20 | 4 | QQYGSSPLT | 122 | 9 | + | + |
| neGFP+M21-K86 | 4-61 | 2-21 | 3 | 1 | TYFVVVMEAEYFQH | 1060 | 14 | 3-11 | 4 | QQRRTWSLT | 1084 | 9 | - | + |
| neGFP+M21-K87 | 3-30 | 2-15 | 3 | 4 | DGGRGVVAATLLYFDY | 1061 | 16 | 1-8 | 4 | QQYYSFPLT | 235 | 9 | - | + |
| neGFP+M21-K90 | 3-21 | 6-6 | 2 | 6 | DLSEYSSSSFFRYYGMDV | 1062 | 19 | 1-39 | 3 | QQSYSTPQT | 1085 | 9 | - | + |
| neGFP+M21-L51 | 3-30 | 6-19 | 2 | 4 | DGRYSSGWSYFDY | 1063 | 13 | 1-40 | 2 | QSYDSSLSGSV | 135 | 11 | - | + |
| neGFP+M21-L52# | 3-23 | 3-9 | 2 | 6 | EPPPSYDILTGSNYYYYGMDV | 1064 | 21 | 1-44 | 3 | AAWDDSLNGWV | 286 | 11 | | |
| neGFP+M21-L60 | 4-61 | 2-2 | 2 | 5 | VSGCSSTSCFGGWFDP | 1065 | 16 | 2-23 | 3 | RSYAGSSTWV | 1086 | 10 | - | - |
| neGFP+M21-L62 | 3-23 | 3-22 | 2 | 3 | VDTETDDSSGYAFDI | 1066 | 15 | 1-47 | 1 | AAWDDSLSGVV | 290 | 11 | - | - |
| neGFP+M21-L64 | 3-23 | 2-15 | 2 | 3 | DRCSGGSCPDAFDI | 1067 | 14 | 2-23 | 1 | CSYAGSSTLYV | 1087 | 11 | - | - |
| neGFP+M21-L69 | 4-59 | 4-17 | 2 | 2 | DRNGDYPWYFDL | 1068 | 12 | 1-40 | 2 | QSYDSSLSVV | 1088 | 10 | - | - |
| neGFP+M21-L75 | 1-18 | 4-23 | 3 | 4 | GAVVTPGYFDY | 1069 | 11 | 2-14 | 1 | SSYTSSKV | 1089 | 8 | - | - |
| neGFP+M21-L79 | 3-30 | 2-21 | 3 | 4 | SYCGGDCYFDY | 1070 | 11 | 2-14 | 1 | QSYDSSLSGYV | 64 | 11 | - | - |
| neGFP+M21-L81# | 1-69 | 5-24 | 1 | 4 | PSGDGYNYLEY | 1071 | 11 | 2-14 | 3 | SSYTSSSTWV | 388 | 10 | - | - |
| neGFP+M21-L82 | 3-20 | 3-22 | 2 | 4 | VQSNPLYYDSSGYYYDY | 1072 | 18 | 2-14 | 1 | SSYTSSNYV | 1090 | 9 | - | - |
| neGFP+M21-L83 | 1-81 | 2-2 | 2 | 3 | VEPPTRVAHCSSTSCYYLGAFDI | 1073 | 23 | 2-14 | 1 | SSYTSSSYV | 1091 | 9 | - | - |
| neGFP+M21-L84 | 4-34 | 4-17 | 2 | 3 | GLYGDYVDAFDI | 1074 | 12 | 1-44 | 3 | AAWDDSLNGWV | 286 | 11 | - | - |
| neGFP+M21-L85 | 4-39 | 3-10 | 2 | 6 | HGVHLPPYGSGSYYYYYGMDV | 1075 | 21 | 1-40 | 3 | QSYDSSLSGWV | 345 | 11 | - | - |
| neGFP+M21-L89 | 1-3 | 6-13 | 3 | 4 | GKIAAAGFDY | 1076 | 10 | 3-21 | 2 | QVWDSSSDHPV | 575 | 11 | - | - |
| neGFP+M21-L91 | 1-46 | 4-4 | 3 | 4 | TTTVIYYFDY | 1077 | 10 | 2-11 | 1 | CSYAGSYTYV | 136 | 10 | - | - |
| neGFP+M21-L96 | 3-48 | 4-17 | 2 | 4 | GKYQEPYYGDYFPTRGFDY | 1078 | 19 | 1-51 | 1 | GTWDSSLSAYV | 75 | 11 | - | - |

Figure 35

Repertoire and reactivity of antibodies from new emigrant B cells of Mouse #22 GFP-

| Ig | Heavy Chain | | | | | | | Light Chain | | | | | Reactivity | |
|---|---|---|---|---|---|---|---|---|---|---|---|---|---|---|
| | VH | D | RF | JH | CDR3 (aa) | SEQ ID NO | Length | Vk | Jk | CDR3 (aa) | SEQ ID NO | Length | Poly | HEp-2 Staining |
| neGFP-M22-K01 | 3-23 | 1-26 | 3 | 5 | RKGATGDWFDP | 1092 | 11 | 1-8 | 2 | QQYYSYPYT | 380 | 9 | + | - |
| neGFP-M22-K02# | 4-34 | 3-22 | 2 | 4 | SDDSSGYYRSKAFDY | 1093 | 15 | 3-11 | 1 | QQRSTWPPWT | 520 | 10 | | + |
| neGFP-M22-K09 | 3-15 | 2-15 | 2 | 6 | APSGYCSGGSCYYYYGMDV | 1094 | 19 | 2-28 | 2 | MQALQTPYT | 1040 | 9 | - | + |
| neGFP-M22-K16# | 1-2 | 3-10 | 2 | 6 | LYYYGSGSYSQYYYYGMDV | 1095 | 19 | 3-11 | 4 | QQRSTWPPLT | 1129 | 10 | | |
| neGFP-M22-H25 | 4-59 | 2-8 | 1 | 2 | STGYYWYFDL | 399 | 10 | 4-1 | 1 | QQYYDTPRA | 1130 | 9 | - | - |
| neGFP-M22-K29# | 1-2 | 2-2 | 3 | 4 | ESDIVVPAASRASRYYDY | 1096 | 19 | 3-15 | 2 | QQYNNWPSYT | 1131 | 10 | | |
| neGFP-M22-K35 | 3-33 | 3-22 | 2 | 4 | VSRDYYDSSGYYGPFADY | 1097 | 18 | 1-12 | 4 | QQANSFPLT | 774 | 9 | - | + |
| neGFP-M22-K40# | 3-53 | 5-12 | 3 | 5 | DSGGVATWGQGTLVTVSSARTSQDP | 1098 | 25 | 1-8 | 1 | QQYYSYPRT | 772 | 9 | | |
| neGFP-M22-K41 | 3-30 | 3-10 | 3 | 5 | DRRITMVRGVTNWFDP | 1099 | 17 | 2-28 | 1 | MQALQTPWT | 1132 | 9 | + | + |
| neGFP-M22-K43# | 3-9 | 3-10 | 2 | 2 | DMRMHYGSGGYWYFDL | 1100 | 16 | 3-15 | 2 | QQYNNWPPYT | 331 | 10 | | |
| neGFP-M22-K44# | 1-2 | 6-6 | 1 | 4 | ALIWQLATSPLDY | 1101 | 13 | 1-5 | 1 | QQYNSYSQWT | 1133 | 10 | | |
| neGFP-M22-K47# | 4-34 | 3-9 | 2 | 5 | EREPYYDISNWFDP | 1102 | 14 | 3-11 | 4 | QQRSTWPLT | 893 | 9 | | |
| neGFP-M22-K22 | | | | | | | | 1-39 | 2 | QQSYSTPYT | 130 | 9 | | |
| neGFP-M22-L03 | 3-9 | 3-10 | 2 | 3 | GRVYDILTIGSGSLYAFDI | 1103 | 19 | 2-14 | 2 | SSYTSSSTLV | 74 | 10 | - | - |
| neGFP-M22-L04 | 3-30 | 2-15 | 2 | 5 | PYCSGGSCYSVGSRALYNWFDP | 1104 | 22 | 2-14 | 1 | SSYTSSSTLYV | 291 | 11 | - | - |
| neGFP-M22-L05 | 1-2 | 2-2 | 3 | 6 | EAVVPARSGMDV | 1105 | 12 | 2-11 | 2 | CSYAGSYTVV | 995 | 10 | - | - |
| neGFP-M22-L06# | 1-18 | 5-12 | 2 | 4 | DPGSGYDGNDY | 1106 | 11 | 3-25 | 3 | QSADSSGTWV | 894 | 10 | | |
| neGFP-M22-L11 | 3-9 | / | / | 4 | DRQMPQGIGAQGFDY | 1107 | 15 | 3-1 | 2 | QAWDSSTVV | 143 | 9 | - | + |
| neGFP-M22-L12# | 3-23 | 6-13 | 2 | 6 | HSGYSSSWPNVMDV | 1108 | 14 | 3-21 | 2 | QVWDSSSDHVV | 77 | 11 | | |
| neGFP-M22-L13 | 3-33 | 6-13 | 2 | 3 | GTRQDSSSWWGHAFDI | 1109 | 16 | 1-51 | 1 | GTWDSSLSAYV | 75 | 11 | - | - |
| neGFP-M22-L14# | 1-69 | 6-13 | 2 | 5 | EGGVSSSSWPYNWFDP | 1110 | 16 | 1-40 | 3 | QSYDSSLSGWV | 345 | 11 | | |
| neGFP-M22-L18# | 3-9 | 6-13 | 3 | 4 | DGAAAGLRY | 1111 | 9 | 1-44 | 3 | AAWDDSLNGWV | 286 | 11 | | |
| neGFP-M22-L19# | 3-33 | 6-6 | 1 | 6 | DRTQQLVPYYYYGMDV | 1112 | 16 | 2-8 | 2 | SSYAGSNNLV | 66 | 10 | | |

Figure 36

| Ig | | Heavy Chain | | | | | | | Light Chain | | | | | | Reactivity | |
|---|---|---|---|---|---|---|---|---|---|---|---|---|---|---|---|---|
| | VH | D | RF | JH | CDR3 (aa) | SEQ ID NO | Length | | CDR3 (aa) | SEQ ID NO | Length | Vκ | Jκ | Poly | HEp-2 | Staining |
| neGFP-M22-L20 | 1-2 | 3-10 | 1 | 4 | DLLRFGELWDY | 1113 | 11 | 1-47 | 1 | AAWDDSLSGPV | 526 | 11 | - | + | C |
| neGFP-M22-L21 | 3-9 | 2-15 | 2 | 4 | DVTNGRDCSGGSCYSFDY | 1114 | 18 | 1-44 | 2 | AAWDDSLNGVV | 240 | 11 | - | - | - |
| neGFP-M22-L23 | 3-48 | 2-2 | 2 | 2 | DTHCSSTSCYSDWYFDL | 1115 | 17 | 2-23 | 3 | CSYAGSST | 343 | 8 | - | - | - |
| neGFP-M22-L24 | 1-2 | 2-2 | 3 | 5 | EGDIVVVPAAHGWFDP | 1116 | 16 | 2-23 | 1 | AGSSTYNYV | 1134 | 9 | - | - | - |
| neGFP-M22-L25 | 4-59 | 2-8 | 1 | 2 | STGYYWYFDL | 399 | 10 | 3-1 | 2 | QAWDSSTVV | 143 | 9 | - | - | - |
| neGFP-M22-L26 | 4-34 | 6-13 | 2 | 1 | PGYSSSWYYFQH | 1117 | 12 | 2-14 | 3 | SSYTSSSTL | 1135 | 9 | + | + | - |
| neGFP-M22-L27 | 3-11 | 3-16 | 3 | 5 | GTLETYDLYPRLGRGLYNWFDP | 1118 | 22 | 1-47 | 3 | AAWDDSLSGWV | 73 | 11 | + | + | - |
| neGFP-M22-L28 | 3-33 | 3-10 | 2 | 4 | YYYGSGSYLGLRALHFDY | 1119 | 18 | 2-11 | 2 | CSYAGSYTLVV | 1135 | 11 | - | + | - |
| neGFP-M22-L30 | 3-21 | 2-21 | 3 | 6 | DRVVVIAEGLGYYYYGMDV | 1120 | 20 | 2-14 | 3 | SSYTSSSRV | 1136 | 9 | - | - | - |
| neGFP-M22-L31 | 3-30 | 3-10 | 1 | 3 | GLKFGAVRSAFDI | 1121 | 13 | 1-51 | 3 | GTWDSSLSTNWV | 1137 | 12 | + | + | - |
| neGFP-M22-L39# | 4-34 | 6-13 | 2 | 3 | GCRNSSSWVEKSDAFDI | 1122 | 18 | 1-44 | 2 | AAWDDSLNGHVV | 72 | 12 | - | - | - |
| neGFP-M22-L46 | 3-23 | 3-22 | 2 | 6 | PPYYYDSSGYYLYYGMDV | 1123 | 18 | 1-40 | 2 | QSYDSSLSGVV | 71 | 11 | - | - | - |
| neGFP-M22-L48# | 3-33 | 5-5 | 2 | 3 | GRAWHSYGDDAFDI | 1124 | 14 | 1-51 | 1 | GTWDSSLSAYV | 75 | 11 | - | - | - |
| neGFP-M22-L10 | | | | | | -- | | 1-40 | 3 | QSYDSSLSGWV | 345 | 11 | | | |
| neGFP-M22-L38 | | | | | | -- | | 3-1 | 2 | QAWDSSTVV | 143 | 9 | | | |
| neGFP-M22-L08 | 7-4 | 2-2 | 1 | 5 | GSEYQLLRGWFDP | 1125 | 13 | | | | -- | | | | |
| neGFP-M22-H17 | 3-30 | 1-26 | 3 | 6 | VLPVGAGHYYYGMDV | 1126 | 15 | | | | -- | | | | |
| neGFP-M22-H29 | 1-2 | 2-2 | 3 | 4 | ESDIVVPAASRASRYYDY | 1096 | 19 | | | | -- | | | | |
| neGFP-M22-H34 | 5-51 | 1-7 | 2 | 4 | LWGLYNWNYFDY | 1127 | 12 | | | | -- | | | | |
| neGFP-M22-H35 | 3-33 | 3-22 | 2 | 4 | VSRDYYDSSGYYGPFADY | 1097 | 18 | | | | -- | | | | |
| neGFP-M22-H41 | 3-30 | 3-10 | 3 | 5 | DRRRITMVRGVTNWFDP | 1099 | 17 | | | | -- | | | | |
| neGFP-M22-H43 | 3-9 | 3-10 | 2 | 2 | DMRMHYGSGGYWYFDL | 1100 | 16 | | | | -- | | | | |
| neGFP-M22-H44 | 1-2 | 6-6 | 1 | 4 | ALIWQLATSPLDY | 1101 | 13 | | | | -- | | | | |
| neGFP-M22-H47 | 4-34 | 3-9 | 2 | 5 | EREPYYDISNWFDP | 1102 | 14 | | | | -- | | | | |

Figure 36 (Cont'd)

Repertoire and reactivity of antibodies from new emigrant B cells of Mouse #22 GFP+ PTPN22 shRNA

| Ig | HEAVY CHAIN | | | | | | | | | LIGHT CHAIN | | | | | REACTIVITY | |
|---|---|---|---|---|---|---|---|---|---|---|---|---|---|---|---|---|
| | VH | D | RF | JH | (-) | CDR3 (aa) | SEQ ID NO | (+) | Length | Vκ | Jκ | CDR3(aa) | SEQ ID NO | Length | Poly | HEp-2 Staining |
| neGFP+M22-K49 | 3-30-3 | 3-10 | 2 | 3 | 2 | GAYYGSGYYKDAFDI | 1138 | 1 | 16 | 1-17 | 4 | LQHNSYPLT | 335 | 9 | - | - |
| neGFP+M22-K52 | 3-11 | 6-6 | 2 | 4 | 2 | AGSDSSSSAVFDY | 1139 | 0 | 13 | 1-33 | 2 | QQYDNLP | 545 | 7 | - | + |
| neGFP+M22-K54# | 1-18 | 1-26 | 2 | 6 | 2 | DPRVPGGSYYYYGMDV | 1140 | 1 | 16 | 1-16 | 4 | QQYNSYPLT | 125 | 9 | - | - |
| neGFP+M22-K55 | 3-21 | / | / | 4 | 1 | EPAPLGVAGGY | 1141 | 0 | 11 | 1-17 | 3 | LQHNSYPFT | 432 | 9 | - | + |
| neGFP+M22-K56 | 3-11 | 3-3 | 2 | 3 | 3 | LPFLDLFWSGYYADAFDI | 1142 | 0 | 18 | 3-15 | 4 | QQYNNWPLT | 193 | 9 | - | + |
| neGFP+M22-K63 | 3-7 | / | / | 4 | 3 | VQDNRAPDFDY | 1143 | 1 | 11 | 1-17 | 1 | LQHNSYPWT | 467 | 9 | - | + |
| neGFP+M22-H65 | 1-2 | 6-13 | 2 | 4 | 1 | AGGGSSSWYYFDY | 1144 | 0 | 13 | 3-20 | 5 | QQYGSSPIT | 989 | 9 | - | - |
| neGFP+M22-K68 | 3-7 | 6-13 | 2 | 4 | 1 | SKYSSSWYGDY | 1145 | 1 | 11 | 3-11 | 1 | QQRSNWW | 1176 | 7 | - | + |
| neGFP+M22-K72 | 4-34 | 6-13 | 3 | 6 | 1 | GNRLIAAAGSYYYYGMDV | 1146 | 1 | 18 | 1-39 | 4 | QQSYSTLT | 1177 | 8 | - | - |
| neGFP+M22-K79 | 3-23 | 3-10 | 2 | 4 | 1 | VTNYGSGSYYNGFDY | 1147 | 0 | 15 | 1-39 | 1 | QQSYSTWT | 1178 | 8 | - | - |
| neGFP+M22-H80 | 3-30-3 | 6-13 | 3 | 1 | 2 | DLSDSIAAAGVGYFQH | 1148 | 1 | 16 | 3-20 | 3 | QQYGSSPT | 43 | 8 | - | - |
| neGFP+M22-K83 | 3-74 | 4-4 | 3 | 4 | 1 | LLTVTSYFDY | 1149 | 0 | 10 | 1-13 | 5 | QQLNSYPPIT | 1179 | 10 | - | - |
| neGFP+M22-K84 | 4-59 | 6-13 | 2 | 4 | 1 | GPYSSSWFSIDY | 1150 | 1 | 12 | 1-39 | 2 | QQSYSTPYT | 130 | 9 | - | - |
| neGFP+M22-K85 | 3-15 | 1-26 | 2 | 6 | 2 | DRVGGSYYYYGMDV | 1151 | 1 | 15 | 1-39 | 5 | QQSYSTPPIT | 1180 | 10 | - | - |
| neGFP+M22-K89 | 1-2 | 1-26 | 1 | 4 | 2 | GQWELDY | 1152 | 0 | 7 | 3-20 | 4 | QQYGSSLT | 279 | 8 | - | - |
| neGFP+M22-K92 | 3-33 | 7-27 | 2 | 4 | 2 | DRNWGFDY | 1153 | 1 | 8 | 3-20 | 2 | QQYGSSPYT | 376 | 9 | - | - |
| neGFP+M22-K94## | 1-2 | / | / | 4 | 1 | GLLGLFDY | 1154 | 0 | 8 | 2-30 | 2 | MQGTHWPYT | 1181 | 9 | | |
| neGFP+M22-K95# | 4-39 | 3-10 | 1 | 4 | 2 | LGFGELSHDY | 1155 | 1 | 10 | 1-39 | 5 | QQSYSTPPIT | 1180 | 10 | - | - |
| neGFP+M22-K51 | | | | | | | --- | | | 3-11 | 4 | QQRSNWPPVT | 1182 | 10 | - | - |
| neGFP+M22-K75 | | | | | | | --- | | | 2-30 | 1 | MQGTHWPPT | 985 | 9 | | |
| neGFP+M22-L50 | 3-33 | 5-5 | 2 | 2 | 2 | DSMGQSTGYSYGYPYWYFDL | 1156 | 0 | 20 | 1-40 | 2 | QSYDSSLSGHVV | 1183 | 12 | - | - |

Figure 37

| Ig | HEAVY CHAIN | | | | | | | | LIGHT CHAIN | | | | | | REACTIVITY | |
|---|---|---|---|---|---|---|---|---|---|---|---|---|---|---|---|---|
| | VH | D | RF | JH | (-) | CDR3 (aa) | SEQ ID NO | (+) | Length | Vκ | Jκ | CDR3(aa) | SEQ ID NO | Length | Poly | HEp-2 Staining |
| neGFP+M22-L53 | 3-30 | 6-19 | 2 | 3 | 3 | CYSSGWDDAFDI | 1157 | 0 | 12 | 1-47 | 3 | AWDDSLSGWV | 1184 | 10 | - | - |
| neGFP+M22-L60# | 7-4-1 | 3-10 | 3 | 5 | 1 | PSITMVRGVIIFNWFDP | 1158 | 1 | 17 | 1-40 | 2 | QSYDSSLSGDVV | 1185 | 12 | - | - |
| neGFP+M22-L61 | 1-2 | 6-19 | 3 | 4 | 0 | SNFQYSYGYY | 1159 | 0 | 10 | 2-8 | 1 | SSYAGSNNYV | 289 | 10 | + | + |
| neGFP+M22-L62 | 1-2 | 6-13 | 2 | 4 | 3 | DRVKDGGSSWPDY | 1160 | 2 | 13 | 2-14 | 2 | SSYTSSSTLV | 74 | 10 | - | - |
| neGFP+M22-L64 | 3-7 | 1-7 | 3 | 5 | 2 | ETGITGTTGWFDP | 1161 | 0 | 13 | 3-1 | 1 | QAWDSSTAYV | 576 | 10 | - | - |
| neGFP+M22-L66 | 4-59 | 6-13 | 1 | 6 | 1 | VLSGGQQHPSYYYYGMDV | 1162 | 1 | 19 | 1-51 | 1 | GTWDSSLSARYV | 1186 | 12 | - | - |
| neGFP+M22-L70 | 3-48 | / | 2 | 4 | 1 | GMLFLGWYFDY | 1163 | 0 | 12 | 2-11 | 2 | CSYAGSYTLV | 1048 | 10 | - | - |
| neGFP+M22-L73 | 3-53 | 3-22 | 2 | 3 | 2 | SSGYRHDAFDI | 1164 | 2 | 11 | 2-23 | 2 | CSYAGSSTHVV | 895 | 11 | - | - |
| neGFP+M22-L77 | 3-11 | 2-15 | 2 | 2 | 2 | VGSWVDYWYFDL | 1165 | 0 | 12 | 1-44 | 3 | AAWDDSLNGWV | 286 | 11 | - | - |
| neGFP+M22-L81# | 3-15 | 7-27 | 2 | 4 | 3 | GPPNWGEQRQDDY | 1166 | 1 | 13 | 2-14 | 2 | SSYTSSSTVV | 340 | 10 | - | - |
| neGFP+M22-L82 | 3-9 | / | / | 3 | 2 | DSPASGLAFDI | 1167 | 0 | 11 | 2-14 | 1 | SSYTSSSTYV | 285 | 10 | ↑ | - |
| neGFP+M22-L96 | 3-48 | 3-3 | 2 | 4 | 1 | GASGSGQIGGFDY | 1168 | 0 | 13 | 6-57 | 3 | QSYDSSNHWV | 1187 | 10 | - | - |
| neGFP+M22-H58 | 4-34 | 3-22 | 2 | 3 | 2 | HYYYDSSGYYARLNAFDI | 1169 | 2 | 18 | | | | | | | |
| neGFP+M22-H59 | 4-34 | 6-19 | 3 | 4 | 1 | VSLHIAVAGTGPFDY | 1170 | 1 | 15 | | | | | | | |
| neGFP+M22-K69 | 1-2 | 7-27 | 3 | 3 | 4 | EGTGDPDAFDI | 1171 | 0 | 11 | | | | | | | |
| neGFP+M22-H71 | 4-34 | 2-8 | 2 | 3 | 1 | GLVVRCTNGVCYNHAFDI | 1172 | 2 | 18 | | | | | | | |
| neGFP+M22-H74 | 3-30-3 | 3-9 | 2 | 4 | 3 | DQYYDILTGSAVPFDY | 1173 | 0 | 16 | | | | | | | |
| neGFP+M22-H76 | 4-30-2 | / | / | 2 | 2 | VGGDRYWYFDL | 1174 | 1 | 11 | | | | | | | |
| neGFP+M22-H80 | 3-30-3 | 6-13 | 3 | 1 | 2 | DLSDSIAAAGVGYFQH | 1148 | 1 | 16 | | | | | | | |
| neGFP+M22-H88 | 3-15 | 1-26 | 2 | 6 | 2 | DRVGGSYYYYGMDV | 1151 | 1 | 15 | | | | | | | |
| neGFP+M22-H91 | 3-33 | 2-21 | 2 | 6 | 3 | DGQYCGGDCYSPYYYYGMDV | 1175 | 0 | 21 | | | | | | | |

Figure 37 (Cont'd)

Repertoire and reactivity of antibodies from new emigrant B cells of Mouse #23 GFP-

| Ig | VH | D | RF | JH | Heavy Chain CDR3 (aa) | SEQ ID NO | Length | Vκ | Jκ | Light Chain CDR3 (aa) | SEQ ID NO | Length | Reactivity Poly | HEp-2 Staining |
|---|---|---|---|---|---|---|---|---|---|---|---|---|---|---|
| neGFP-M23-K51 | 4-31 | 5-5 | 2 | 4 | EMGMAAGYSYGFDY | 1188 | 14 | 1-17 | 3 | LQHNSYPFT | 432 | 9 | + | - |
| neGFP-M23-K56 | 3-53 | / | / | 4 | DRGEFDY | 1189 | 7 | 3-15 | 2 | QQYNNWPLYS | 1218 | 10 | + | + |
| neGFP-M23-K57 | 3-48 | 1-7 | 3 | 4 | GRGITGTNYFDY | 1190 | 12 | 3-20 | 3 | QQYGSSPPFT | 1219 | 10 | - | - |
| neGFP-M23-K58 | 3-33 | 6-6 | 3 | 4 | DSSVVAARFDY | 1191 | 11 | 1-39 | 3 | QQSYSTPFT | 58 | 9 | - | - |
| neGFP-M23-K59 | 3-33 | 7-27 | 3 | 4 | EGTGFDY | 1192 | 7 | 1-5 | 4 | QQYNSYSPLT | 1220 | 10 | + | + |
| neGFP-M23-K61 | 1-2 | 3-10 | 2 | 5 | DLREYKGDWFDP | 1193 | 12 | 3-20 | 4 | QQYGSSPPLT | 47 | 10 | - | + |
| neGFP-M23-K63 | 3-7 | 3-10 | 2 | 4 | DGAYYYGSGSSTFDY | 1194 | 15 | 3-20 | 3 | QQYGSSLFT | 1221 | 9 | - | - |
| neGFP-M23-K64 | 3-7 | 3-22 | 2 | 4 | GRRNFSRGDYYDSSGYYTPFDY | 1195 | 23 | 1-5 | 2 | QQYNSYSPNS | 1222 | 10 | - | - |
| neGFP-M23-K65 | 3-30 | 2-8 | 2 | 3 | DKTGASRLGYCTNGVCPDAFDI | 1196 | 22 | 3-15 | 2 | QQYNNWPPYS | 885 | 10 | - | + |
| neGFP-M23-K67 | 3-21 | 6-19 | 2 | 3 | DSGYSSGWSHDAFDI | 1197 | 15 | 3-20 | 1 | QQYGSSPRT | 54 | 9 | - | + |
| neGFP-M23-K68 | 1-46 | 6-13 | 3 | 4 | DWPGAAAGLDY | 1198 | 11 | 3-20 | 4 | QQYGSSPPLT | 47 | 10 | - | - |
| neGFP-M23-K71 | 4-34 | 3-22 | 3 | 3 | GLFITMIVVGDAFDI | 1199 | 15 | 2-24 | 2 | MQATQFPRT | 1223 | 9 | - | - |
| neGFP-M23-K72 | 1-2 | 2-2 | 3 | 3 | DKIVVVPAAMGGNYFDY | 1200 | 17 | 1-8 | 3 | QQYYSYPLFT | 1224 | 10 | + | + |
| neGFP-M23-K75 | 3-48 | 1-26 | 1 | 4 | ERWELRTDAFDI | 1201 | 12 | 3-15 | 2 | QQYNNWPPYS | 885 | 10 | - | + |
| neGFP-M23-K76 | 3-7 | 2-15 | 3 | 3 | DGAGVVVAATLLDDAFDI | 1202 | 19 | 3-20 | 4 | MQGTHWPLT | 53 | 9 | - | - |
| neGFP-M23-K84 | 3-30 | 6-6 | 2 | 4 | ISSIAALPDY | 1203 | 10 | 1-17 | 4 | LQHNSYPLT | 335 | 9 | - | - |
| neGFP-M23-L54 | 3-7 | 3-16 | 2 | 3 | KNWGGCYAFDI | 1204 | 11 | 2-14 | 3 | SSYTSSSTGV | 743 | 10 | - | + |
| neGFP-M23-L60 | 4-30-4 | 3-16 | 1 | 4 | LNGLGAFDI | 1205 | 9 | 1-47 | 3 | AAWDDSLSGWV | 73 | 11 | - | - |
| neGFP-M23-L79 | 3-9 | 3-3 | 1 | 4 | DIRFLEWFDY | 1206 | 10 | 3-21 | 1 | QVWDSSSDHYV | 76 | 11 | - | - |
| neGFP-M23-L80 | 1-2 | 1-26 | 2 | 4 | DTAGGELLPYYFDY | 1207 | 14 | 2-23 | 2 | CSYAGSSTLV | 206 | 10 | + | + |
| neGFP-M23-L83 | 5-10 | 4-11 | 1 | 4 | LLVGRGLQKHYYFDY | 1208 | 15 | 2-14 | 2 | SSYTSSSTVV | 340 | 10 | - | - |
| neGFP-M23-L89 | 1-8 | 6-13 | 3 | 4 | GRAAGGIDY | 1209 | 9 | 8-61 | 3 | VLYMGSGIWV | 1225 | 10 | - | - |
| neGFP-M23-L90 | 3-7 | 3-10 | 3 | 5 | IITMVRGVIITYNWFDP | 1210 | 17 | 2-23 | 2 | CSYAGSSTFVV | 616 | 11 | - | - |
| neGFP-M23-L94 | 1-8 | 7-27 | 2 | 4 | GNWDGGLFHY | 1211 | 10 | 1-51 | 2 | GTWDSSLSAVV | 201 | 11 | - | - |
| neGFP-M23-H50 | 3-21 | 6-19 | 2 | 2 | PGYSSGWDYWYFDL | 1212 | 14 | | | | | | - | - |
| neGFP-M23-H52 | 4-61 | 1-26 | 3 | 3 | EDIVGAIRRAFDI | 1213 | 13 | | | | | | - | - |
| neGFP-M23-H55 | 1-2 | 1-26 | 2 | 3 | DGGSYSAFDI | 1214 | 10 | | | | | | - | - |
| neGFP-M23-H70 | 3-30-3 | 6-6 | 3 | 4 | DLSPNLIAARDAIDY | 1215 | 15 | | | | | | - | - |
| neGFP-M23-H73 | 3-33 | / | / | 3 | GLGRATSYGDAFDI | 1216 | 14 | | | | | | - | - |
| neGFP-M23-H78 | 3-23 | / | / | 4 | DRPVDY | 1217 | 6 | | | | | | - | - |
| neGFP-M23-H80 | 1-2 | 1-26 | 1 | 4 | DTAGGELLPYYFDY | 1207 | 14 | | | | | | - | - |

Figure 38

Repertoire and reactivity of antibodies from new emigrant B cells of Mouse #23 GFP+ PTPN22 shRNA

| Ig | HEAVY CHAIN | | | | | | | | | LIGHT CHAIN | | | | | REACTIVITY | |
|---|---|---|---|---|---|---|---|---|---|---|---|---|---|---|---|---|
| | VH | D | RF | JH | (-) | (+) | CDR3 (aa) | SEQ ID NO | Length | Vκ | Jκ | CDR3(aa) | SEQ ID NO | Length | Poly | HEp-2 Staining |
| neGFP+M23-K1 | 3-30-3 | 6-19 | 2 | 3 | 2 | 2 | GRQVGGGWKDAFDI | 1226 | 14 | 3-20 | 4 | QQYGSSPPLT | 47 | 10 | - | - |
| neGFP+M23-K4 | 4-34 | 6-19 | 2 | 4 | 2 | 0 | GLWSEGVYYFDY | 1227 | 12 | 2D-29 | 4 | MQSIQLPLT | 1247 | 9 | - | + |
| neGFP+M23-K5 | 1-69 | 1-26 | 3 | 3 | 1 | 1 | HGGSQPGIVGATLAFDI | 1228 | 17 | 3-15 | 4 | QQYNNWPLT | 193 | 9 | + | - |
| neGFP+M23-K6 | 4-34 | 4-17 | 3 | 5 | 1 | 0 | GTGTVTTNWFDP | 1229 | 12 | 3-20 | 2 | KRYGNSPYT | 1248 | 9 | - | + |
| neGFP+M23-K8 | 3-15 | / | / | 6 | 2 | 2 | DRLHYYYYMDV | 1230 | 13 | 3-20 | 3 | QQYGSSPFT | 181 | 9 | - | - |
| neGFP+M23-K11 | 4-34 | / | / | 4 | 1 | 0 | GEGVLGY | 1231 | 7 | 1-8 | 1 | QQYYSYPRT | 772 | 9 | - | + |
| neGFP+M23-K15 | 3-30 | 5-24 | 3 | 4 | 3 | 2 | SQFLREMATIRNLTTDDY | 1232 | 19 | 1-16 | 2 | QQYNSYPRT | 1249 | 9 | - | + |
| neGFP+M23-K22 | 3-33 | 6-13 | 3 | 4 | 2 | 0 | EGAAAGTSYYFDY | 1233 | 13 | 3-11 | 3 | QQRSTWPPFT | 1250 | 10 | - | - |
| neGFP+M23-K28 | 3-15 | 7-27 | 1 | 4 | 2 | 1 | DGLGIRGVADY | 1234 | 11 | 1-39 | 3 | QQSYSTPFT | 58 | 9 | - | - |
| neGFP+M23-K29 | 5-10-1 | 4-11 | 3 | 4 | 1 | 2 | HGSRPVTTYDY | 1235 | 11 | 1-9 | 2 | QQLNSYPYT | 1251 | 9 | - | - |
| neGFP+M23-K31 | 3-15 | / | / | 3 | 1 | 0 | SGTGAFDI | 1236 | 8 | 1D-33 | 3 | QQYDNLPPLFT | 1252 | 11 | - | - |
| neGFP+M23-K34# | 3-30-3 | 1-26 | 1 | 1 | 2 | 2 | VFLGSVRELLAEYFQH | 1237 | 16 | 3-11 | 4 | QQRSNWPRLT | 1253 | 10 | - | - |
| neGFP+M23-K38## | 3-21 | 7-27 | 1 | 3 | 2 | 0 | AWGSDAFDI | 1238 | 10 | 3-20 | 3 | QQYGSSPPFT | 1219 | 10 | - | - |
| neGFP+M23-L22 | | | | | | | See Kappa | 1239 | | 2-14 | 2 | SSYTSSSTVV | 340 | 10 | - | - |
| neGFP+M23-L23 | 3-33 | 3-3 | 3 | 3 | 2 | 0 | TISDAFDI | 1240 | 8 | 2-14 | 2 | SSYTSSSTIV | 74 | 10 | - | - |
| neGFP+M23-L25 | 4-4 | 1-26 | 2 | 4 | 3 | 1 | DEGHSGSYFDY | 1241 | 11 | 3-9 | 2 | QVWDSSTVV | 1254 | 9 | - | - |
| neGFP+M23-L26 | 3-21 | / | / | 3 | 3 | 0 | DPGDAFDI | 1242 | 8 | 1-44 | 3 | AAWDDSLNVWV | 1255 | 11 | - | - |
| neGFP+M23-L27 | 3-7 | / | / | 4 | 1 | 2 | KRGVFDY | 1243 | 7 | 2-14 | 2 | SSYTSSSTVV | 340 | 10 | - | - |
| neGFP+M23-L35 | 1-2 | 6-6 | 2 | 6 | 3 | 0 | DSPIEYSSSSGPYYYYYGMDV | 1244 | 22 | 2-8 | 1 | SSYAGSNNYV | 289 | 10 | - | - |
| neGFP+M23-L40 | 3-33 | 1-26 | 2 | 4 | 3 | 0 | EGGDSGSYYFDY | 1245 | 12 | 3-25 | 3 | QSADSSGTYWV | 577 | 11 | - | - |
| neGFP+M23-L44 | 3-30 | 3-22 | 3 | 4 | 1 | 1 | ASARIVVITNVDY | 1246 | 14 | | | | | | - | - |

Figure 39

COMPOSITIONS AND METHODS FOR INHIBITING PTPN22

This application is a U.S. national phase application filed under 35 U.S.C. § 371 claiming benefit to PCT International Patent Application No. PCT/US2017/034720, filed on May 26, 2017, which claims priority to U.S. Provisional Application No. 62/342,250, filed May 27, 2016, each of which disclosures is incorporated herein by reference in its entirety.

BACKGROUND OF THE INVENTION

A role for B cells in autoimmune disease is now established both in mouse models as well as in humans by successful treatment of rheumatoid arthritis and by showing efficacy at delaying other autoimmune diseases with anti-CD20 monoclonal antibodies that eliminate B cells. However, B cell depletion is a severe insult to the immune system that may be harmful for patients. In addition, patients often relapse after anti-B cell therapy several months later coinciding with the reappearance of B cells in the blood of these subjects. These newly generated B cells likely include many autoreactive clones because patients with rheumatoid arthritis (RA), systemic lupus erythematosus (SLE) and type 1 diabetes (T1D) display abnormal early B-cell tolerance checkpoints resulting in a failure to remove developing autoreactive B cells. Hence, the efficacy of anti-B cell therapy may be limited because it may not fix the intrinsic tolerance mechanisms defective in autoimmune diseases, such as RA, SLE and T1D.

Rituximab, an anti-CD20 monoclonal antibody that eliminates B cells, has shown efficacy in T1D, RA and multiple sclerosis (MS), and exposes a role for B cells in promoting autoimmunity (Pescovitz et al., 2009, NEJM 361:2143-52; Edwards et al., 2004, NEJM 350:2572-81; Hauser et al., 2008, NEJM 358:676-88). However, anti-B cell therapy does not reset early B cell tolerance checkpoints defective in T1D likely because these impaired autoreactive B cell counterselection steps may be primary to the development of this autoimmune disease (Chamberlain et al., 2015, J Clin Invest 126:282-7). Indeed, asymptomatic individuals carrying the PTPN22 T allele display elevated frequencies of autoreactive B cells in their blood similar to those in T1D, RA and SLE patients (Menard et al., 2011, J Clin Invest 121:3635-44).

There is thus a need in the art for restoring human central B-cell tolerance and for prevention or treatment of autoimmunity. The present invention addresses this unmet need in the art.

SUMMARY OF THE INVENTION

In one aspect, the invention provides compositions and methods for treating or preventing an abnormal early B-cell tolerance checkpoint. In one embodiment, the composition of the invention comprises an inhibitor of PTPN22.

In one embodiment, the inhibitor of PTPN22 is at least one selected from the group consisting of a protein, a peptide, a peptidomemetic, an antibody, a ribozyme, a small molecule chemical compound, a nucleic acid, a vector, an antisense nucleic acid molecule.

In one embodiment, the inhibitor of PTPN22 is a small molecule chemical compound. For example, in one embodiment, the inhibitor of PTPN22 is

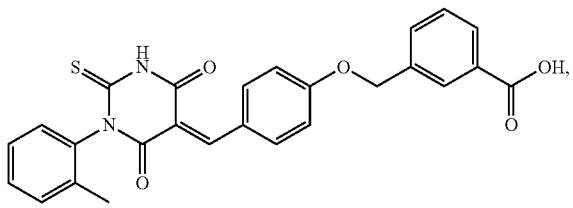 [SMILES: Cc1ccccc1N1C(=O)/C(=C/c2ccc(OCc3cccc(C(=O)O)c3)cc2)C(=O)NC1=S]

a derivative thereof, or a salt thereof.

In one embodiment, the inhibitor of PTPN22 is a nucleic acid. For example, in one embodiment, the inhibitor of PTPN22 is a nucleic acid comprising a nucleoctide sequence selected from SEQ ID NO:1 and SEQ ID NO:2.

In one embodiment, the abnormal early B-cell tolerance checkpoint is associated with an autoimmune disease or disorder. For example, in one embodiment, the autoimmune disease or disorder is selected from the group consisting of type 1 diabetes, rheumatoid arthritis, multiple sclerosis, systemic lupus erythematosus, systemic sclerosis, Sjögren's syndrome, autoimmune thyroiditis, myasthenia gravis, and pemphigus.

In one aspect, the invention provides a method for treating or preventing an autoimmune disease or disorder. The invention also provides a method for restoring human central B-cell tolerance in a subject. In one embodiment, the method comprises administering a composition comprising an inhibitor of PTPN22 to a subject in need thereof.

In one embodiment, the inhibitor of PTPN22 is at least one of the group consisting of a chemical compound, a protein, a peptide, a peptidomemetic, an antibody, a ribozyme, a small molecule chemical compound, a nucleic acid, a vector, an antisense nucleic acid molecule.

In one embodiment, the autoimmune disease or disorder is selected from the group consisting of type 1 diabetes, rheumatoid arthritis, multiple sclerosis, and systemic lupus erythematosus.

In one embodiment, the subject fails to properly remove developing autoreactive B cells. In one embodiment, the subject has a 1858T PTPN22 polymorphism on at least one allele. In one embodiment, the subject is human.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings.

FIG. 1, comprising FIG. 1A depicts a schematic diagram depicting the generation of humanized mice. CD34+ hematopoietic stem cells (HSCs) carrying or not PTPN22 T allele(s) were injected in the liver of 3-day-old recipient NOD.Cg-Prkdcscid Il2rgtm1Wjl/SzJ (NSG) mice. FIG. 1B depicts representative flow cytometry analysis of the frequency of human CD45+, CD3+ and CD19+ cells in the blood of the indicated recipient mice. The summary of blood engraftment from NSG mice transplanted with PTPN22 C/C, C/T or T/T HSCs is represented. Each dot represents an individual mouse and bars indicate mean values. FIG. 1C depicts the frequencies of polyreactive new emigrant B cells from different types of humanized mice transplanted with indicated HSCs were determined and compared to those of healthy donors carrying or not PTPN22 T allele(s). Dotted line shows positive control. For each B-cell fraction, the frequency of reactive (filled area) and non-reactive (open area) clones is summarized in pie charts, with the total number of clones tested indicated in the center. In summarized reactivity panels on the right, each diamond represents an individual and each dot a mouse. Averages are shown with a bar. FIG. 1D depicts the frequencies of HEp-2 reactive new emigrant B cells from different types of humanized mice transplanted with indicated HSCs were determined and compared to those of healthy donors carrying or not PTPN22 T allele(s). Dotted line shows positive control. For each B-cell fraction, the frequency of reactive (filled area) and non-reactive (open area) clones is summarized in pie charts, with the total number of clones tested indicated in the center. In summarized reactivity panels on the right, each diamond represents an individual and each dot a mouse. Averages are shown with a bar.

FIG. 2, comprising FIG. 2A through FIG. 2D depicts results of experiments demonstrating new migrant B cells isolated from NSG mice engrafted with PTPN22 C/T or T/T HSCs display normal IgH repertoire.

FIG. 3, comprising FIG. 3A depicts the frequencies of polyreactive new emigrant B cells from different types of humanized mice transplanted with indicated HSCs were determined and compared to those of healthy donors carrying or not PTPN22 T allele(s). Dotted line shows positive control. For each B-cell fraction, the frequency of reactive (filled area) and non-reactive (open area) clones is summarized in pie charts with the total number of clones tested indicated in the center. FIG. 3B depicts the frequencies of HEp-2 reactive new emigrant B cells from different types of humanized mice transplanted with indicated HSCs were determined and compared to those of healthy donors carrying or not PTPN22 T allele(s). Dotted line shows positive control. For each B-cell fraction, the frequency of reactive (filled area) and non-reactive (open area) clones is summarized in pie charts with the total number of clones tested indicated in the center. FIG. 3C depicts the frequencies of antinuclear new emigrant B cells are compared between mouse engrafted with HSCs carrying or not the PTPN22 T allele.

FIG. 4, comprising FIG. 4A depicts a schematic of the experimental design. Humanized mice were generated with CD34+ HSCs transduced with lentiviruses allowing the expression of different variants of PTPN22 before being injected in the liver of 3-day-old recipient NSG mice. FIG. 4B depicts the frequencies of polyreactive new emigrant B cells from sorted GFP+ fractions expressing 620W PTPN22, 620R PTPN22 or 263Q PTPN22 were determined and compared to those of GFP− new emigrant B cells. Dotted line shows positive control. For each B-cell fraction, the frequency of reactive (filled area) and non-reactive (open area) clones is summarized in pie charts, with the total number of clones tested indicated in the center. In summarized reactivity panels on the right, each symbols represents a mouse overexpressing 620W PTPN22 (green dots), 620R PTPN22 (green squares) or 263Q PTPN22 (green triangles) and averages are shown with a bar. FIG. 4C depicts the frequencies of HEp-2 reactive new emigrant B cells from sorted GFP+ fractions expressing 620W PTPN22, 620R PTPN22 or 263Q PTPN22 were determined and compared to those of GFP− new emigrant B cells. Dotted line shows positive control. For each B-cell fraction, the frequency of reactive (filled area) and non-reactive (open area) clones is summarized in pie charts, with the total number of clones tested indicated in the center. In summarized reactivity panels on the right, each symbol represents a mouse overexpressing 620W PTPN22 (green dots), 620R PTPN22 (green squares) or 263Q PTPN22 (green triangles) and averages are shown with a bar.

FIG. 5, comprising FIG. 5A depicts western blot analysis of PTPN22 protein expression in Ramos B cell transduced with lentiviruses allowing the overexpression of PTPN22 620W variant. β-actin is used for normalization of protein expression. FIG. 5B depicts representative flow cytometry analysis of CD19+ cells isolated from the spleen of NSG mice engrafted with HSCs transduced with a GFP-tagged lentivirus expressing 620W PTPN22, 620R PTPN22 and 263Q PTPN22. CD19+ were stained with anti-hCD19, anti-IgM and anti-hCD10 antibodies. The frequencies of GFP− and GFP+ shRNA+ new emigrant B cells are shown.

FIG. 6, comprising FIG. 6A depicts the frequencies of polyreactive new emigrant B cells from sorted GFP+ fractions expressing 620W PTPN22, 620R PTPN22 or 263Q PTPN22 were determined and compared to those of GFP− new emigrant B cells. Dotted line shows positive control. For each B-cell fraction, the frequency of reactive (filled area) and non-reactive (open area) clones is summarized in pie charts with the total number of clones tested indicated in the center. FIG. 6B depicts the frequencies of HEp-2 reactive new emigrant B cells from sorted GFP+ fractions expressing 620W PTPN22, 620R PTPN22 or 263Q PTPN22 were determined and compared to those of GFP− new emigrant B cells. Dotted line shows positive control. For each B-cell fraction, the frequency of reactive (filled area) and non-reactive (open area) clones is summarized in pie charts with the total number of clones tested indicated in the center. FIG. 6C depicts the frequencies of antinuclear new emigrant B cells are compared between GFP− and GFP+ few emigrant B cells expressing 620W PTPN22, 620R PTPN22 or 263Q PTPN22. FIG. 6D depicts autoreactive antibodies from GFP+620W PTPN22 expressing new emigrant B cells show various patterns of anti-nuclear HEp-2 staining. Original magnification, ×40.

FIG. 7, comprising FIG. 7A through FIG. 7C depicts results of experiments showing inhibition of PTPN22 enzymatic activity resets central B cell tolerance.

FIG. 9, comprising FIG. 9A depicts a schematic of the experimental design. CD34+ HSCs carrying PTPN22 T allele(s) were transduced with lentiviruses allowing the expression of PTPN22 shRNA before injection in the liver of 3 day-old NSG mice. FIG. 9B depicts representative flow cytometry analysis of CD19+ cells isolated from the spleen of NSG mouse engrafted with PTPN22 C/T HSCs transduced with a GFP-tagged lentivirus expressing PTPN22 specific shRNA. CD19+ B cells were stained with anti-hCD19, anti-IgM and anti-hCD10 antibodies. The frequencies of GFP− and GFP+ shRNA+ new emigrant B cells are shown. FIG. 9C depicts PTPN22 protein expression in GFP− and GFP+ shRNA+ hCD19+ cells isolated from the spleen of NSG mice; β-actin is used for normalization of protein expression. Percentage of knock-down is indicated. FIG. 9D depicts results of experiments demonstrating that B-cell intrinsic PTPN22 expression is required for central B-cell tolerance. The frequencies of polyreactive new emigrant B cells from sorted GFP+ fractions expressing PTPN22 shRNA were determined and compared to those of GFP− new emigrant B cells. Dotted line shows positive control. For each B cell fraction, the frequency of reactive (filled area) and non-reactive (open area) clones is summarized in pie charts with the total number of clones tested indicated in the center. In summarized reactivity panels on the right, each symbol represents a mouse and the average is shown with a bar. FIG. 9E depicts results of experiments demonstrating that B-cell intrinsic PTPN22 expression is required for central B-cell tolerance. The frequencies of HEp-2 reactive new emigrant B cells from sorted GFP+ fractions expressing PTPN22 shRNA were determined and compared to those of GFP− new emigrant B cells. Dotted line shows positive control. For each B cell fraction, the frequency of reactive (filled area) and non-reactive (open area) clones is summarized in pie charts with the total number of clones tested indicated in the center. In summarized reactivity panels on the right, each symbol represents a mouse and the average is shown with a bar.

FIG. 10, comprising FIG. 10A through FIG. 10D, depicts results from experiments demonstrating inhibition of PTPN22 expression during B cell development resets central B cell tolerance. FIG. 10A depicts flow cytometry analysis of Ramos B cells transduction efficiency. Ramos B cells were transduced with three different GFP-tagged shRNA PTPN22 expressing lentiviruses and probed for GFP expression. Right panel shows PTPN22 protein expression in GFP− and GFP+ shRNA+ Ramos B cells. β-actin is used for normalization of protein expression. Percentage of knock-down is indicated. FIG. 10B depicts the frequencies of polyreactive new emigrant B cells from sorted GFP− fractions were determined. Dotted line shows positive control. For each B-cell fraction, the frequency of reactive (filled area) and non-reactive (open area) clones is summarized in pie charts with the total number of clones tested indicated in the center. FIG. 10C depicts the frequencies of HEp-2 reactive new emigrant B cells from sorted GFP− fractions were determined. Dotted line shows positive control. For each B-cell fraction, the frequency of reactive (filled area) and non-reactive (open area) clones is summarized in pie charts with the total number of clones tested indicated in the center. FIG. 10D depicts the frequencies of antinuclear new emigrant B cells are compared between GFP− and GFP+ shRNA+ new emigrant B cells.

FIG. 11 depicts results from experiments demonstrating the repertoire and reactivity of antibodies from new emigrant B cells of Mouse #1.

FIG. 12 depicts results from experiments demonstrating the repertoire and reactivity of antibodies from new emigrant B cells of Mouse #2.

FIG. 13 depicts results from experiments demonstrating the repertoire and reactivity of antibodies from new emigrant B cells of Mouse #3.

FIG. 14 depicts results from experiments demonstrating the repertoire and reactivity of antibodies from new emigrant B cells of Mouse #4.

FIG. 15 depicts results from experiments demonstrating the repertoire and reactivity of antibodies from new emigrant B cells of Mouse #5.

FIG. 16 depicts results from experiments demonstrating the repertoire and reactivity of antibodies from new emigrant B cells of Mouse #6.

FIG. 17 depicts results from experiments demonstrating the repertoire and reactivity of antibodies from new emigrant B cells of Mouse #7.

FIG. 18 depicts results from experiments demonstrating the repertoire and reactivity of antibodies from new emigrant B cells of Mouse #8.

FIG. 19 depicts results from experiments demonstrating the repertoire and reactivity of antibodies from new emigrant B cells of Mouse #9.

FIG. 20 depicts results from experiments demonstrating the repertoire and reactivity of antibodies from new emigrant B cells of Mouse #10.

FIG. 21 depicts results from experiments demonstrating the repertoire and reactivity of antibodies from new emigrant B cells of Mouse #11 GFP.

FIG. 22 depicts results from experiments demonstrating the repertoire and reactivity of antibodies from new emigrant B cells of Mouse #11 GFP+ PTPN22 620W expression.

FIG. 23 depicts results from experiments demonstrating the repertoire and reactivity of antibodies from new emigrant B cells of Mouse #12 GFP.

FIG. 24 depicts results from experiments demonstrating the repertoire and reactivity of antibodies from new emigrant B cells of Mouse #12 GFP+ PTPN22 620W expression.

FIG. 25 depicts results from experiments demonstrating the repertoire and reactivity of antibodies from new emigrant B cells of Mouse #13 GFP.

FIG. 26 depicts results from experiments demonstrating the repertoire and reactivity of antibodies from new emigrant B cells of Mouse #13 GFP+ PTPN22 620W expression.

FIG. 27 depicts results from experiments demonstrating the repertoire and reactivity of antibodies from new emigrant B cells of Mouse #14 GFP+ PTPN22 WT expression.

FIG. 28 depicts results from experiments demonstrating the repertoire and reactivity of antibodies from new emigrant B cells of Mouse #15 GFP+ PTPN22 WT expression.

FIG. 29 depicts results from experiments demonstrating the repertoire and reactivity of antibodies from new emigrant B cells of Mouse #16 GFP+ PTPN22 263Q expression.

FIG. 30 depicts results from experiments demonstrating the repertoire and reactivity of antibodies from new emigrant B cells of Mouse #17 GFP+ PTPN22 263Q expression.

FIG. 31 depicts results from experiments demonstrating the repertoire and reactivity of antibodies from new emigrant B cells of Mouse #18 treated with 0.75 mg of LTV-1 PTPN22 inhibitor.

FIG. 32 depicts results from experiments demonstrating the repertoire and reactivity of antibodies from new emigrant B cells of Mouse #19 treated with 0.75 mg of LTV-1 PTPN22 inhibitor.

FIG. 33 depicts results from experiments demonstrating the repertoire and reactivity of antibodies from new emigrant B cells of Mouse #20 treated with 0.15 mg of LTV-1 PTPN22 inhibitor.

FIG. 34 depicts results from experiments demonstrating the repertoire and reactivity of antibodies from new emigrant B cells of Mouse #21 GFP.

FIG. 35 depicts results from experiments demonstrating the repertoire and reactivity of antibodies from new emigrant B cells of Mouse #21 GFP+ shRNA PTPN22.

FIG. 36 depicts results from experiments demonstrating the repertoire and reactivity of antibodies from new emigrant B cells of Mouse #22 GFP.

FIG. 37 depicts results from experiments demonstrating the repertoire and reactivity of antibodies from new emigrant B cells of Mouse #22 GFP+ PTPN22 shRNA.

FIG. 38 depicts results from experiments demonstrating the repertoire and reactivity of antibodies from new emigrant B cells of Mouse #23 GFP.

FIG. 39 depicts results from experiments demonstrating the repertoire and reactivity of antibodies from new emigrant B cells of Mouse #23 GFP+ PTPN22 shRNA.

FIG. 40, comprising FIG. 40A depicts the phosphorylation of SHIP1, Lyn and ERK1/2 in total cell lysates of Ramos B cells treated or not with the PTPN22 inhibitor LTV-1 (5 µg/mL) for the indicated times. The cells were subjected to immunoblot analysis of P-LYN P-SHIP1, P-ERK1/2, and β-ACTIN. FIG. 40B depicts flow cytometry analysis of calcium flux of Ramos B cells treated or not with the PTPN22 inhibitor LTV-1 (5 µg/mL) for the indicated times followed by stimulation with anti-IgM F(ab')2 at the indicated concentrations. FIG. 40C depicts flow cytometry analysis of calcium flux of splenocyte cells treated or not with LTV-1 (0.75 mg) twice daily for 7 days and stimulated with anti-IgM F(ab')2 (25 µg/mL). FIG. 40D depicts flow cytometry analysis of calcium flux of splenocyte expressing PTPN22 shRNA and stimulated with anti-IgM F(ab')2 (25 µg/mL).

FIG. 41, comprising FIG. 41A depicts a schematic diagram depicting the LTV-1 PTPN22 inhibitor treatment strategy. A NSG+thymus mouse generated with CD34$^+$ HSCs and thymic graft carrying the 1858T PTPN22 allele was injected twice daily with 0.75 mg of PTPN22 inhibitor for four weeks. FIG. 41B depicts the frequencies of HEp-2 reactive mature naive B cells from NSG+thymus mice treated or not with the PTPN22 inhibitor were determined. Dotted line shows positive control. For each B cell fraction, the frequency of reactive (filled area) and non-reactive (open area) clones is summarized in pie charts with the total number of clones tested indicated in the center. In summarized reactivity panels on the right, each symbol represents either a subject or a humanized mouse. Averages are shown with a bar. Statistically significant differences are indicated **$P \leq 0.0001$, *$P \leq 0.001$. FIG. 41C depicts the frequencies of polyreactive mature naive B cells from NSG+thymus mice treated or not with the PTPN22 inhibitor were determined. Dotted line shows positive control. For each B cell fraction, the frequency of reactive (filled area) and non-reactive (open area) clones is summarized in pie charts with the total number of clones tested indicated in the center. In summarized reactivity panels on the right, each symbol represents either a subject or a humanized mouse. Averages are shown with a bar. Statistically significant differences are indicated **$P \leq 0.0001$, *$P \leq 0.001$.

DETAILED DESCRIPTION

Figures 1A, 1B:
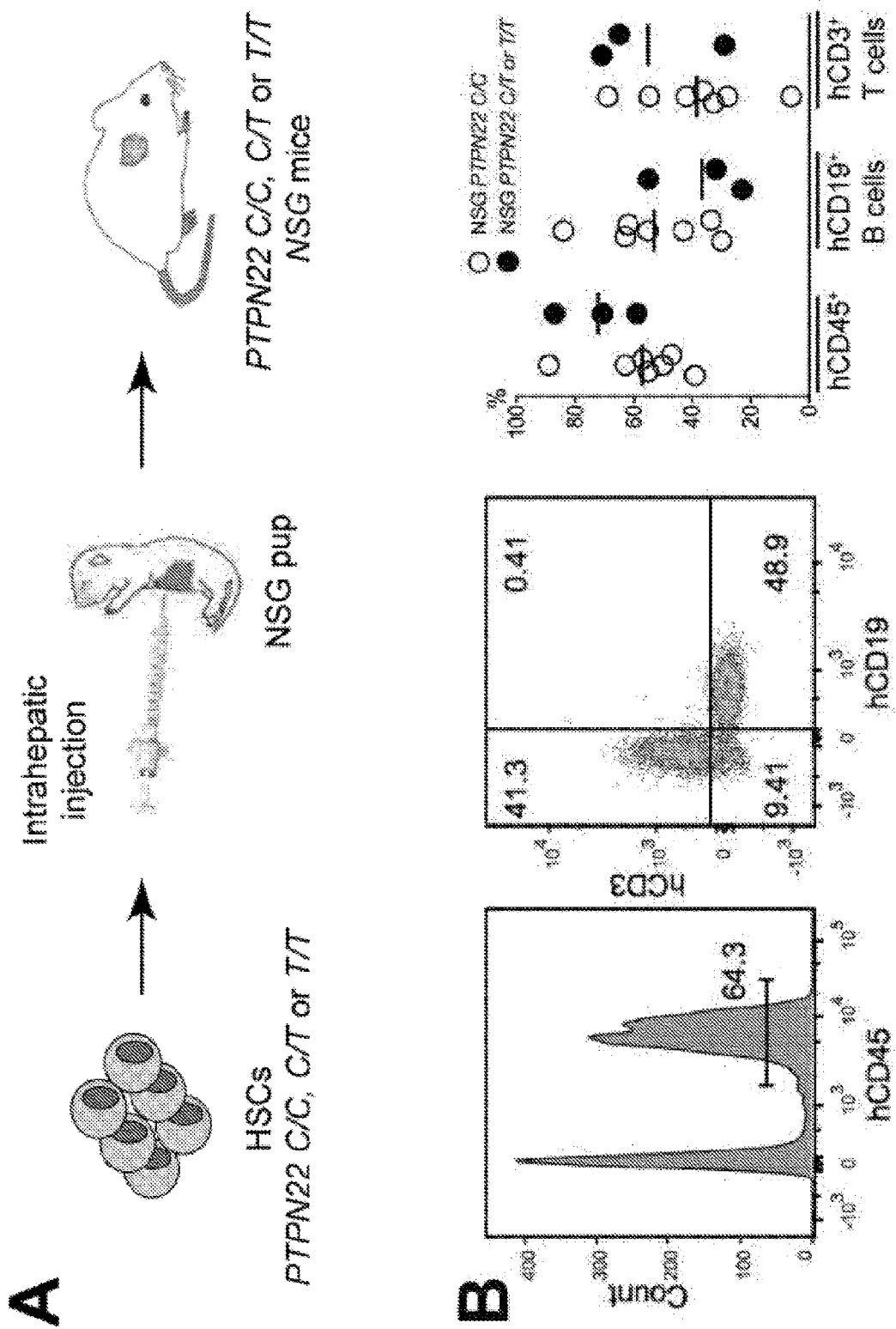
FIG. 1A through FIG. 1D, depicts results of experiments demonstrating defective central B-cell tolerance in humanized mouse engrafted with HSCs carrying PTPN22 T allele(s).
Figure 1C:
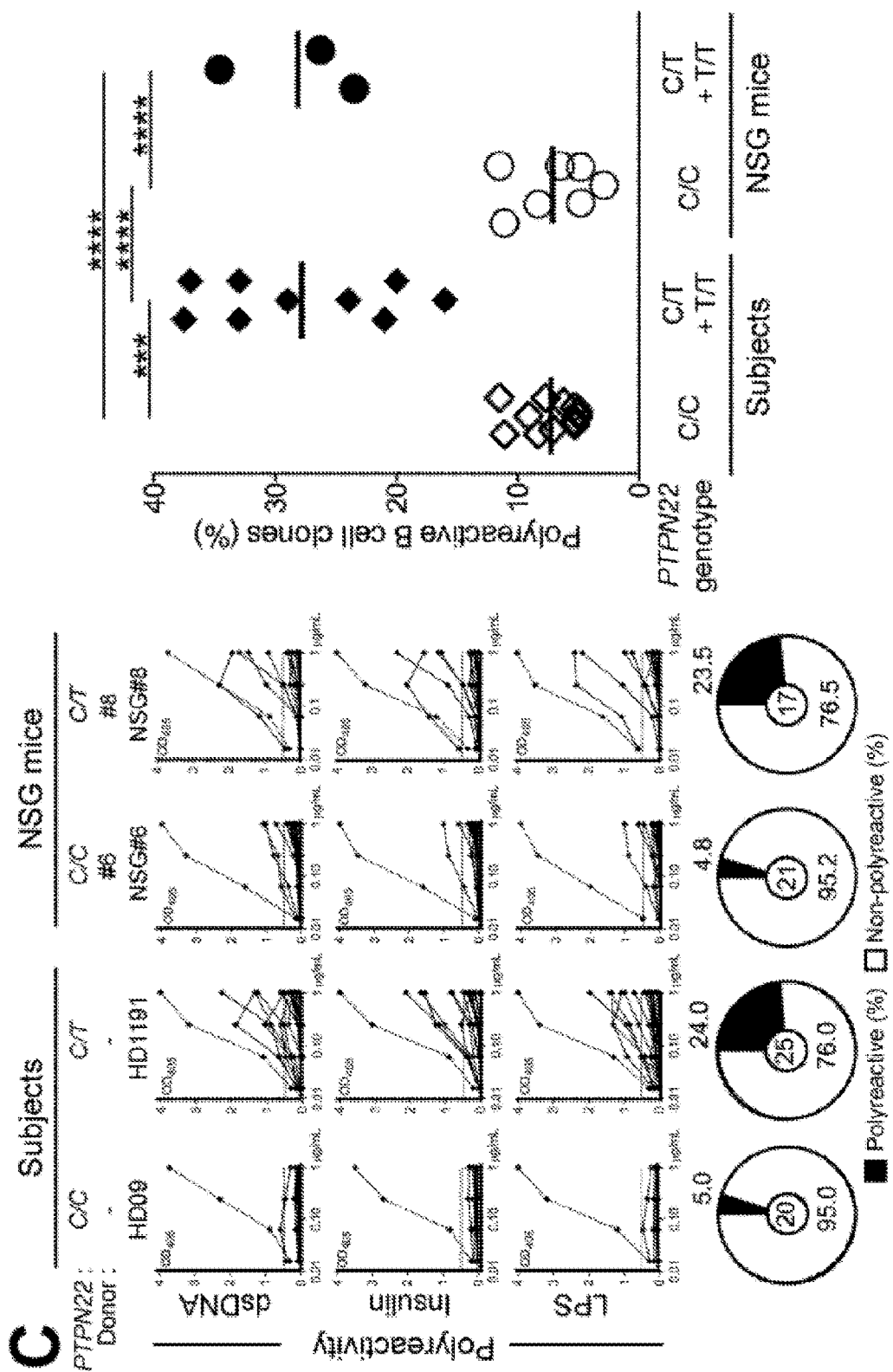

The present invention relates to compositions and methods for restoring human central B-cell tolerance in a subject. In certain instances, the subject is one who fails to properly remove developing autoreactive B cells. For example, in one embodiment, the subject has an autoimmune disease. In certain instances, the compositions and methods described herein relate to inhibiting protein tyrosine phosphatase non-receptor type 22 (PTPN22).

In one embodiment, the composition of the present invention comprises an inhibitor of PTPN22. For example, in one embodiment, the inhibitor of PTPN22 inhibits the expression, activity, or both of PTPN22. In one embodiment, PTPN22 of the subject comprises a nucleotide change (cytidine to thymidine) at residue 1858 that results in an amino acid substitution from arginine to tryptophan at position 620 of the PTPN22.

In one embodiment, the method of the present invention comprises restoring human central B-cell tolerance in a subject. In another embodiment, the method of the present invention comprises treating or preventing an autoimmune disease. For example, in some embodiments, the method of the present invention comprises treating or preventing type 1 diabetes (T1D), rheumatoid arthritis (RA), multiple sclerosis (MS), or systemic lupus erythematosus (SLE). In one embodiment, the method comprises administering to a subject an effective amount of a composition comprising an inhibitor of PTPN22.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of a compound which is sufficient to provide a beneficial effect to the subject to which the compound is administered.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "DNA" as used herein is defined as deoxyribonucleic acid.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

The term "RNA" as used herein is defined as ribonucleic acid.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods.

As used herein, "conjugated" refers to covalent attachment of one molecule to a second molecule.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for treating or preventing an autoimmune disease or for restoring human central B-cell tolerance in a subject. The present invention is based upon the finding that that the PTPN22 T allele interferes with the establishment of central B cell tolerance using NOD-scid-common gamma chain (γc) knockout (NSG) mice engrafted with human hematopoietic stem cells (HSCs) expressing this allele. In contrast, the inhibition of either PTPN22 enzymatic activity or its expression by RNA interference restored defective central B cell tolerance in this model. Thus, the present invention relates to compositions and method to inhibit PTPN22 in order to restore human central B-cell tolerance.

In one embodiment, the composition of the present invention comprises an inhibitor of PTPN22. In one embodiment, the composition comprises an inhibitor PTPN22 expression. For example, in one embodiment, the composition comprises an isolated nucleic acid (e.g., siRNA, miRNA, ribozyme, antisense RNA, etc.) that reduces the expression level of PTPN22 in a cell.

In one embodiment, the composition comprises an inhibitor of PTPN22 activity. For example, in one embodiment, the composition comprises a nucleic acid, peptide, antibody, small molecule, antagonist, aptamer, or peptidomimetic that reduces the activity of PTPN22.

In one embodiment, the present invention provides a method for restoring human central B-cell tolerance in a subject. In one embodiment, the method comprises administering to a subject an effective amount of a composition comprising an inhibitor of PTPN22.

In another embodiment, the present invention provides a method for treating or preventing autoimmune disease in a subject. In one embodiment, the method comprises administering to a subject an effective amount of a composition comprising an inhibitor of PTPN22. In one embodiment, the autoimmune disease is T1D, RA, MS, or SLE. In another embodiment, the subject has at an 1858T PTPN22 polymorphism on at least one allele.

Inhibitors

In one embodiment, the present invention provides a composition for treating or preventing a disease or disorder associated with abnormal early B-cell tolerance checkpoints in a subject. In certain embodiments, the composition inhibits the expression, activity, or both of PTPN22 in the subject.

In one embodiment, the composition of the invention comprises an inhibitor of PTPN22. An inhibitor of PTPN22 is any compound, molecule, or agent that reduces, inhibits, or prevents the function of PTPN22. For example, an inhibitor of PTPN22 is any compound, molecule, or agent that reduces PTPN22 expression, activity, or both. In one embodiment, an inhibitor of PTPN22 comprises a nucleic acid, a peptide, a small molecule, a siRNA, a ribozyme, an antisense nucleic acid, an antagonist, an aptamer, a peptidomimetic, or any combination thereof.

Small Molecule Inhibitors

In various embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to treat an autoimmune disease or disorder.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In one embodiment, the small molecule inhibitor is

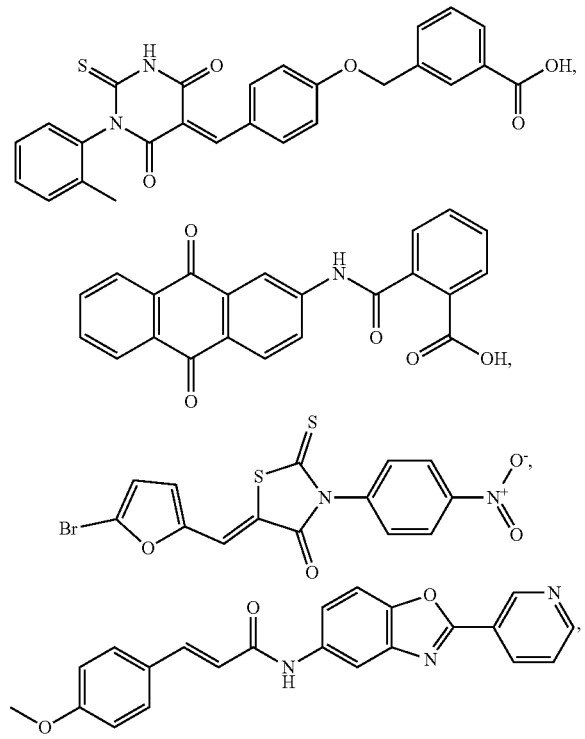

19
-continued
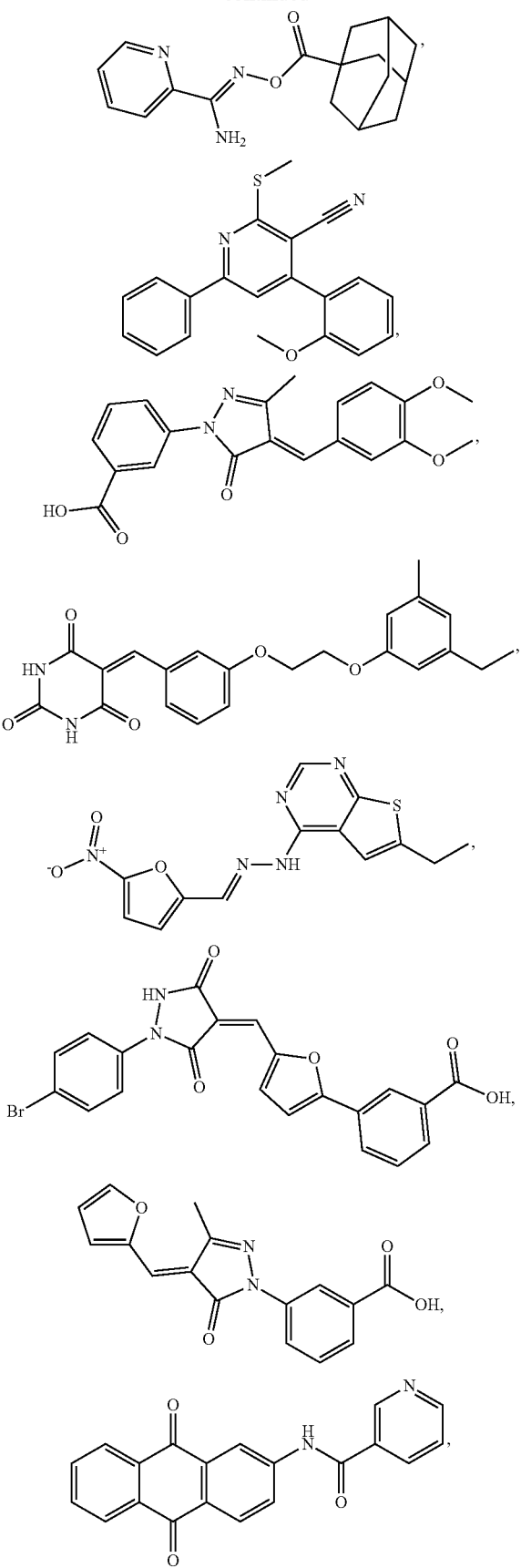
20
-continued
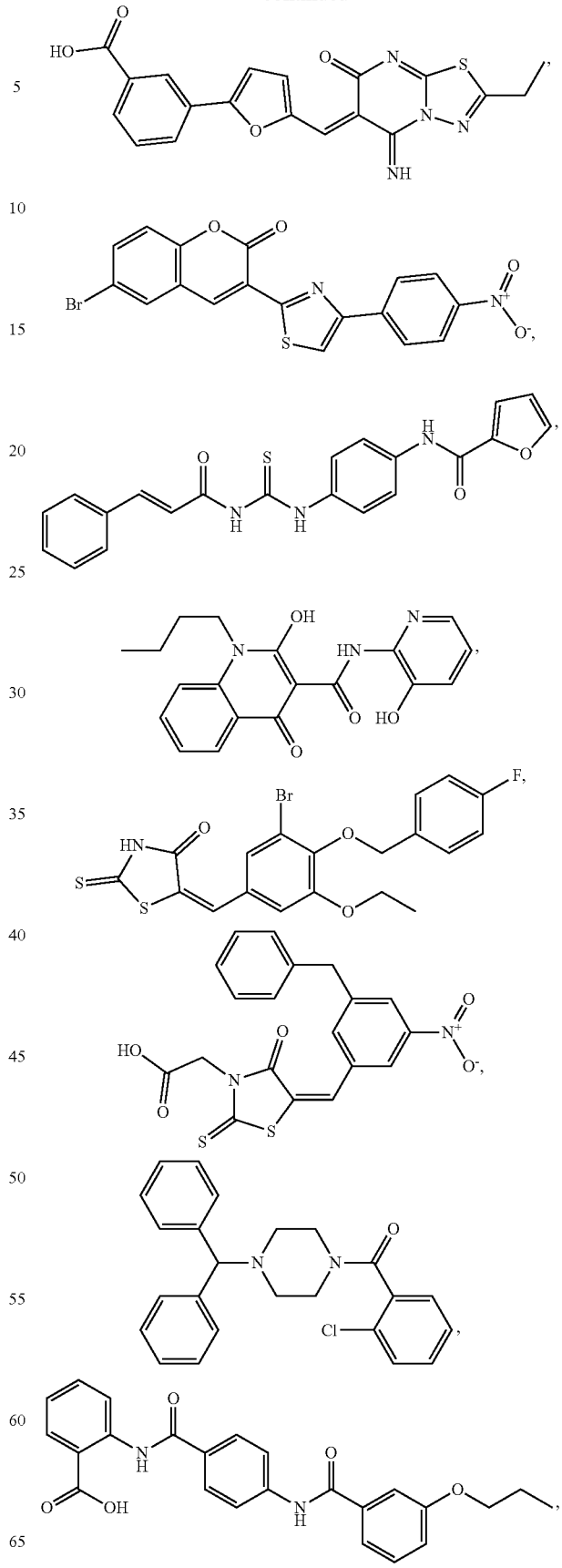

21
-continued
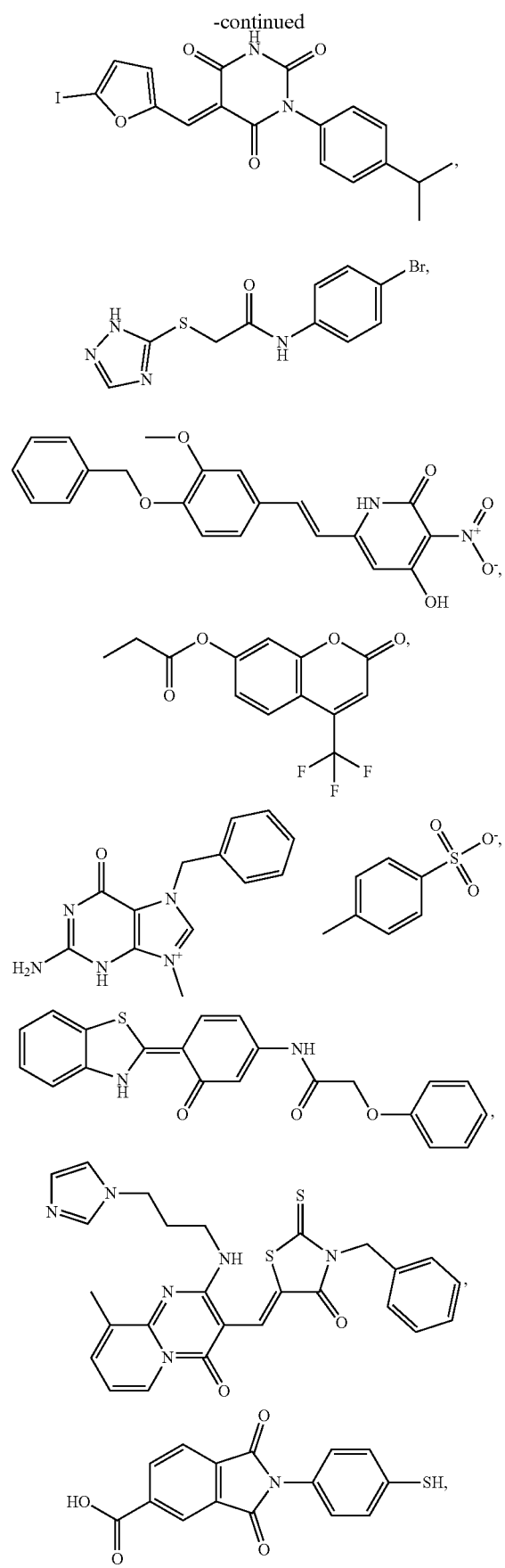
22
-continued
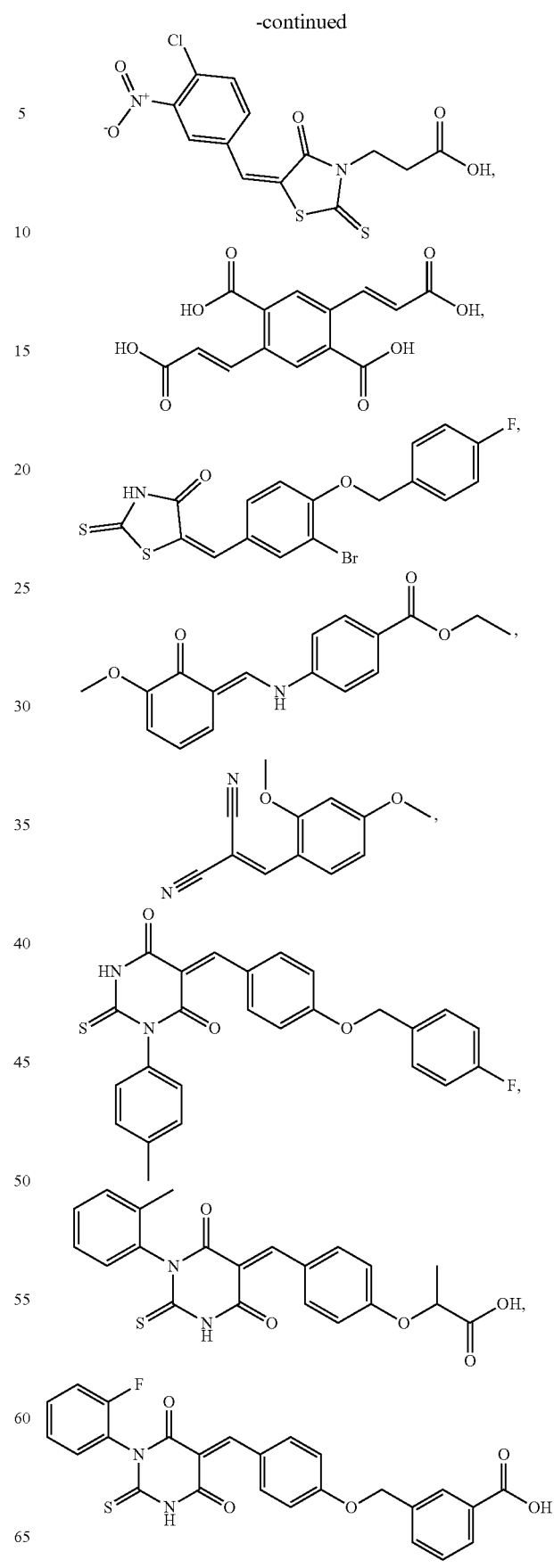

-continued
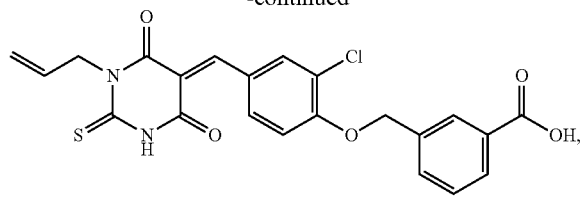
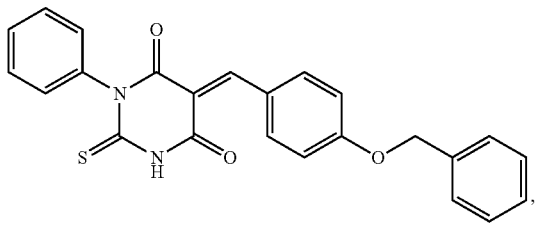
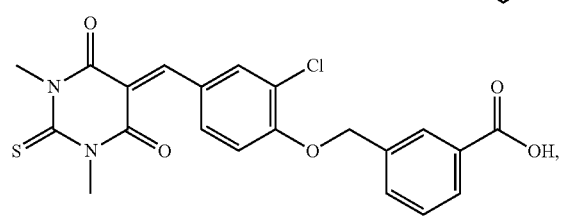
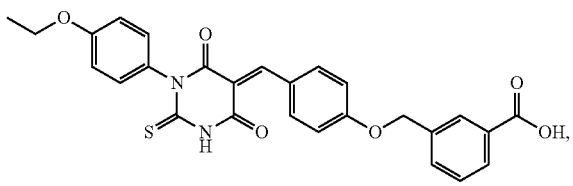
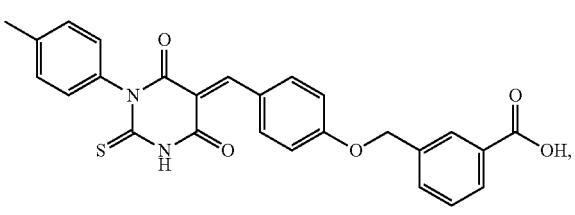
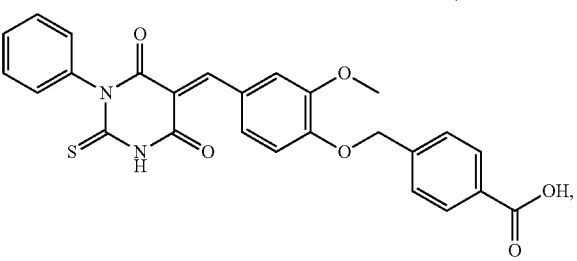
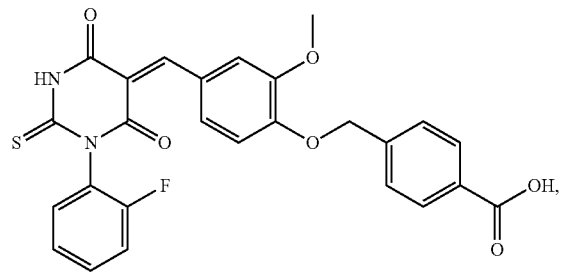
-continued
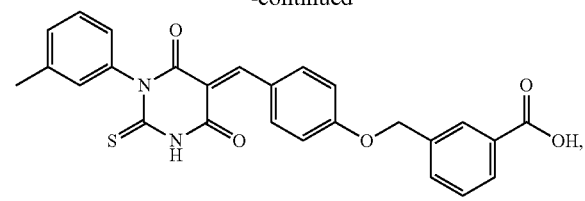
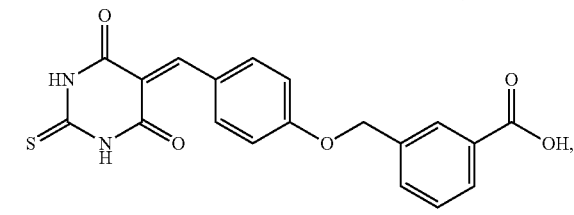
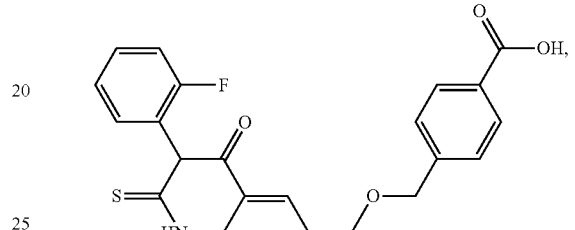
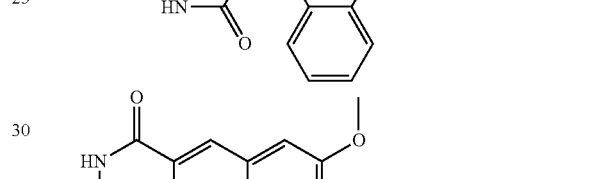
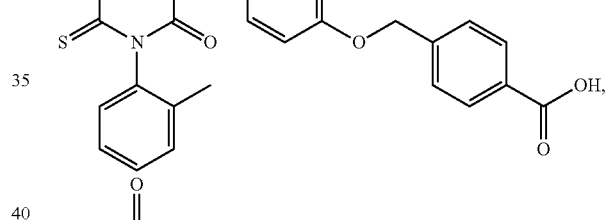
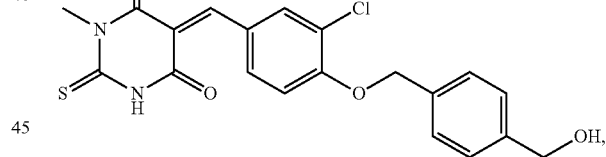
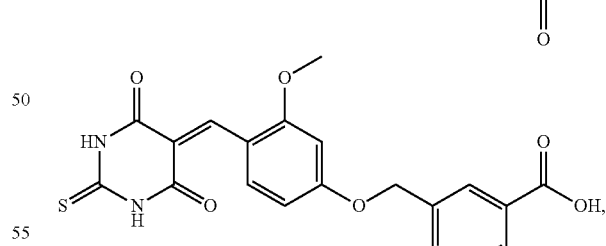
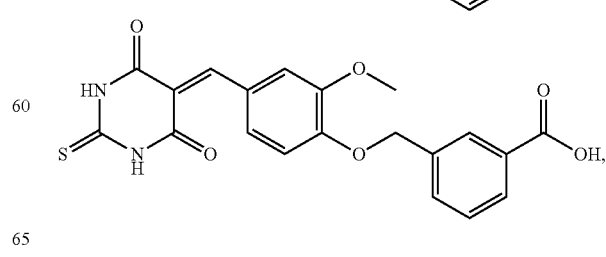
derivatives thereof and salts thereof.

Nucleic Acid Inhibitors

In other related aspects, the invention includes an isolated nucleic acid. In some instances, the inhibitor is an siRNA, miRNA, or antisense molecule, which inhibits PTPN22. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, PTPN22, can be inhibited by way of inactivating and/or sequestering PTPN22. As such, inhibiting the activity of PTPN22 can be accomplished by using a transdominant negative mutant.

In one embodiment, siRNA is used to decrease the level of PTPN22 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of PTPN22 using RNAi technology.

In another aspect, the invention includes a vector comprising an siRNA or antisense polynucleotide. Preferably, the siRNA or antisense polynucleotide is capable of inhibiting the expression of a target polypeptide, wherein the target polypeptide is PTPN22. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

In some embodiments, the shRNA inhibitors comprise a sequence of CTAGTGCTCTTGGTGTATATT (SEQ ID NO:1) or AAGAATCCACCTGACTTCC (SEQ ID NO:2).

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid, which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules, which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene, which facilitates the selection of transformed or transfected host cells. Suitable selectable marker genes are genes encoding proteins such as G418 and hygromycin, which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence, which is expressed by a plasmid vector is used to inhibit PTPN22 protein expression. The antisense expressing vector is used to transfect a mammalian cell or the mammal itself, thereby causing reduced endogenous expression of PTPN22.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit PTPN22 protein expression. Ribozymes useful for inhibiting the expression of a target molecule may be designed by incorporating target sequences into the basic ribozyme structure, which are complementary, for example, to the mRNA sequence encoding PTPN22. Ribozymes targeting PTPN22, may be synthesized using commercially available reagents (Applied Biosystems, Inc., Foster City, Calif.) or they may be genetically expressed from DNA encoding them.

In one embodiment, the inhibitor of PTPN22 may comprise one or more components of a CRISPR-Cas system. CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligo to hybridize to target and recruit the Cas/gRNA complex. In one embodiment, a guide RNA (gRNA) targeted to a gene encoding PTPN22, and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

Polypeptide Inhibitors

In other related aspects, the invention includes an isolated peptide inhibitor that inhibits PTPN22. For example, in one embodiment, the peptide inhibitor of the invention inhibits PTPN22 directly by binding to PTPN22 thereby preventing the normal functional activity of PTPN22. In another embodiment, the peptide inhibitor of the invention inhibits PTPN22 by competing with endogenous PTPN22. In yet another embodiment, the peptide inhibitor of the invention inhibits the activity of PTPN22 by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

The invention also contemplates an inhibitor of PTPN22 comprising an antibody, or antibody fragment, specific for PTPN22. That is, the antibody can inhibit PTPN22 to provide a beneficial effect. In some embodiments, the antibody specifically binds PTPN22.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, humanized antibodies, fragments and chimeras, may be prepared using methods known to those skilled in the art.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker. Bispecific antibodies can comprise a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Combinations

In one embodiment, the composition of the present invention comprises a combination of PTPN22 inhibitors described herein. In certain embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

In some embodiments, the composition of the present invention comprises a combination of a PTPN22 inhibitor and second therapeutic agent. For example, in one embodiment the second therapeutic agents include, but are not limited to, a diabetes therapeutic, a rheumatoid arthritis therapeutic, a multiple sclerosis therapeutic, a systemic lupus erythematosus therapeutic and anti-inflammation therapeutics. In some embodiments, therapeutic agents include Rituximab, Anti-BAFF therapies, and anti-TNF therapies.

In some embodiments, the second therapeutic is a diabetes therapeutic. Exemplary diabetes therapeutics include, but are not limited to, non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, inhibitors of cholesterol uptake and/or bile acid re-absorption, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, melanin-concentrating hormone receptor agonists, SNRIs, a fibroblast growth factor 21 (FGF21) mimetic, a fibroblast growth factor receptor 1c (FGFR1c) agonist, an inhibitor of advanced glycation end product formation, such as, but not limited to, aminoguanidine, and protein tyrosine phosphatase inhibitors.

In some embodiments, the second therapeutic is a rheumatoid arthritis therapeutic. Exemplary rheumatoid arthritis therapeutics include, but are not limited to, Nonsteroidal anti-inflammatory drugs (NSAIDs), corticosteroids, methotrexate, leflunomide, hydroxychloroquine, sulfasalazine, abatacept, adalimumab, anakinra, certolizumab, etanercept, golimumab, infliximab, rituximab, tocilizumab and tofacitinib.

In some embodiments, the second therapeutic is a multiple sclerosis therapeutic or treatment. Exemplary multiple sclerosis therapeutics include, but are not limited to, corticosteroids, plasmapheresis, ocrelizumab, β-interferons, Glatiramer acetate, Dimethyl fumarate, Fingolimod, Teriflunomide, Natalizumab, Alemtuzumab, Mitoxantrone, baclofen, and tizanidine.

In some embodiments, the second therapeutic is a systemic lupus erythematosus therapeutic. Exemplary systemic lupus erythematosus therapeutics include, but are not limited to, glucocorticoid, prednisone, hydroxychloroquine, methotrexate and azathioprine.

A composition comprising a combination of inhibitors comprises individual inhibitors in any suitable ratio. For example, in one embodiment, the composition comprises a 1:1 ratio of two individual inhibitors. However, the combination is not limited to any particular ratio. Rather any ratio that is shown to be effective is encompassed.

Therapeutic Methods

The present invention also provides methods of restoring central B-cell tolerance in a subject. For example, in one embodiment, the method of the invention increases calcium flux, and BCR signaling. In one embodiment, the method of the invention decreases the phosphorylation of LYN and SHIP1.

In certain embodiments, the method is used to treat or prevent a disease or disorder in a subject associated with abnormal early B-cell tolerance checkpoints. In one embodiment, the invention also provides methods of treating or preventing autoimmune disease in a subject. Exemplary autoimmune diseases include, but are not limited to, type 1 diabetes, rheumatoid arthritis, multiple sclerosis, systemic lupus erythematosus, systemic sclerosis, Sjögren's syndrome, autoimmune thyroiditis, myasthenia gravis, and pemphigus.

In one embodiment, the subject fails to properly remove developing autoreactive B cells. In another embodiment, the subject has a 1858T PTPN22 polymorphism on at least one allele. In yet another embodiment, the subject is human.

It will be appreciated by one of skill in the art, when armed with the present disclosure including the methods detailed herein, that the invention is not limited to treatment of autoimmune disease that is already established. Particularly, the disease or disorder need not have manifested to the point of detriment to the subject; indeed, the disease or disorder need not be detected in a subject before treatment is administered. That is, significant signs or symptoms of autoimmune disease do not have to occur before the present invention may provide benefit. Therefore, the present invention includes a method for preventing autoimmune disease, in that a composition, as discussed previously elsewhere herein, can be administered to a subject prior to the onset of autoimmune disease, thereby preventing autoimmune disease.

One of skill in the art, when armed with the disclosure herein, would appreciate that the prevention of an autoimmune disease or disorder, encompasses administering to a subject a composition as a preventative measure against the development of, or progression of autoimmune disease. As more fully discussed elsewhere herein, methods of modulating the level or activity of a gene, or gene product, encompass a wide plethora of techniques for modulating not only the level and activity of polypeptide gene products, but also for modulating expression of a nucleic acid, including either transcription, translation, or both.

The invention encompasses administration of an inhibitor of PTPN22, or a combination thereof. To practice the methods of the invention; the skilled artisan would understand, based on the disclosure provided herein, how to formulate and administer the appropriate modulator composition to a subject. The present invention is not limited to any particular method of administration or treatment regimen.

In one embodiment, the method comprises administering to the subject in need an effective amount of a composition that reduces or inhibits the expression or activity of PTPN22.

One of skill in the art will appreciate that the inhibitors of the invention can be administered singly or in any combination. Further, the inhibitors of the invention can be administered singly or in any combination in a temporal sense, in that they may be administered concurrently, or before, and/or after each other. One of ordinary skill in the art will appreciate, based on the disclosure provided herein, that the inhibitor compositions of the invention can be used to prevent or to treat an autoimmune disease or disorder, and that an inhibitor composition can be used alone or in any combination with another modulator to affect a therapeutic result. In various embodiments, any of the inhibitor compositions of the invention described herein can be administered alone or in combination with other modulators of other molecules associated with autoimmune diseases.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. However, the method is not limited to any particular ratio. Rather any ratio that is shown to be effective is encompassed.

Pharmaceutical Compositions and Formulations

The invention also encompasses the use of pharmaceutical compositions of the invention or salts thereof to practice the methods of the invention. Such a pharmaceutical composition may consist of at least one modulator composition of the invention or a salt thereof in a form suitable for administration to a subject, or the pharmaceutical composition may comprise at least one modulator composition of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, parenteral, sublingual, transdermal, transmucosal (e.g., sublingual, lingual, (trans)buccal, and (intra)nasal), intravesical, intraduodenal, intragastrical, rectal, intra-peritoneal, subcutaneous, intramuscular, intradermal, intra-arterial, intravenous, or administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: PTPN22 Inhibition Resets Defective Human Central B Cell Tolerance

The data presented herein examines if inhibiting PTPN22 favors the elimination of autoreactive B cells. It is demonstrated herein that the PTPN22 T allele interferes with the establishment of central B cell tolerance using NOD-scid-common gamma chain (γc) knockout (NSG) mice engrafted with human hematopoietic stem cells (HSCs) expressing this allele. In contrast, the inhibition of either PTPN22 enzymatic activity or its expression by RNA interference restored defective central B cell tolerance in this model. Thus, PTPN22 blockade may represent a novel therapeutic strategy for the prevention or treatment of autoimmunity.

The materials and methods employed in these experiments are now described.

Human Progenitor Cell Isolation and Injection in NSG Mice

Human $CD34^+$ cells were purified from fetal liver samples by density gradient centrifugation followed by positive immunomagnetic selection with anti-human CD34 microbeads (Miltenyi). Newborn NSG mice (within first 3 days of life) were sublethally irradiated (X-ray irradiation with X-RAD 320 irradiator at 180 cGy) and 100,000-150,000 $CD34^+$ cells in 20 µL of PBS were injected into the liver with a 22-gauge needle (Hamilton Company). Mice were used for experiments 10-12 weeks after transplantation. NSG mice treated with the PTPN22 inhibitor were injected twice daily i.p. with 0.75 mg or 0.15 mg of PTPN22 inhibitor for a week.

PTPN22 Overexpression and Silencing and $CD34^+$ HSCs Transduction

The pTRIP-Ubi-GFP lentiviral vector has been used for overexpression of PTPN22 variants and short hairpin RNA (shRNA) delivery. Vector constructions have been described previously (Cantaert et al., 2015, Immunity 43:884-95; Ruer-Laventie et al., 2015, Immun Inflamm Dis 3:265-79). The following sequence are used for human PTPN22 targeting: shRNA1 5'-CTAGTGCTCTTGGTGTATATT-3' (SEQ ID NO: 1), shRNA2 5'-CTGTTGCCAA-CATCCTCTA-3'(SEQ ID NO: 3), or shRNA3 5'-AAGAATCCACCTGACTTCC-3'(SEQ ID NO: 2). Lentiviral particles were produced by transient transfection of 293T cells, as previously described (Schickel et al., 2012, EMBO Mol Med 4:1261-75). Viruses were then used to transduce $CD34^+$ HSCs in the presence of protamine sulfate (Sigma).

Single-Cell Sorting

B cells were enriched from splenocytes using magnetic separation with CD19 microbeads (Miltenyi Biotech) and stained with CD19-Pacific Blue, CD10-PE-Cy7, CD21-APC and IgM-biotin (all from Biolegend) prior to purification. Single $CD19^+CD10^+CD21^{low}GFP^-$ or $GFP^+$ new emigrant B cells were sorted on a FACSAria (BD Biosciences) into 96-well PCR plates and immediately frozen on dry ice.

cDNA Synthesis, Ig Genes Amplification, Antibody Production, and Purification

RNA from single cells was reverse-transcribed in the original 96 well plate in 12.5 µl reactions containing 100U of Superscript II RT (Gibco BRL) for 45 min at 42° C. RT-PCR reactions, primer sequences, cloning strategy, expression vectors, antibody expression and purification were as described (Tiller et al., 2008, J Immunol Methods 329:112-24).

ELISAs and Immunofluorescence Assays

Antibody reactivity analysis was performed as described previously with the highly polyreactive ED38 antibody as positive control for HEp-2 reactivity and polyreactivity (Wardemann, 2003, Science 301:1374-7). Antibodies were considered polyreactive when they recognized all 3 distinct antigens: dsDNA, insulin and LPS. For indirect immunofluorescence assays, HEp-2 cell-coated slides (Bion Enterprises Ltd.) were incubated in a moist chamber at room temperature with purified recombinant antibodies at 50-100 µg/mL according to the manufacturer's instructions. FITC-conjugated goat anti-human IgG was used as detection reagent.

Flow Cytometry

The following monoclonal antibodies against human antigens were used: anti-CD10 (HI10a), anti-CD19 (HIB19), anti-CD27 (O323), anti-CD45 (HI30) (all from Biolegend) and anti-CD21 (B-ly4) and anti-IgM (G20-127; from BD Biosciences). Cells were acquired with a LSR II (BD Biosciences) and analyzed with FlowJo software.

Immunoblot

Total cell lysates were separated by SDS page, transferred to PVDF membranes, probed with mouse anti-PTPN22 (Invitrogen) and detected by chemiluminescence (Amersham ECL Prime Western Blotting detection Reagent) using a GBox documentation system (Syngene). For quantification, blots were stripped with stripping buffer (Pierce) and reprobed with a mouse anti-β-Actin antibody (Sigma-Aldrich).

Statistical Analysis

Statistical analysis was performed using GraphPad Prism (version 5.0; GraphPad, San Diego, Calif.). Data are reported as mean±standard deviation. Differences between groups of research subjects were analyzed for statistical significance with unpaired two-tailed Student's t-tests. A P-value of ≤0.05 was considered significant.

The results of the experiments are now described.

Figure 1D:
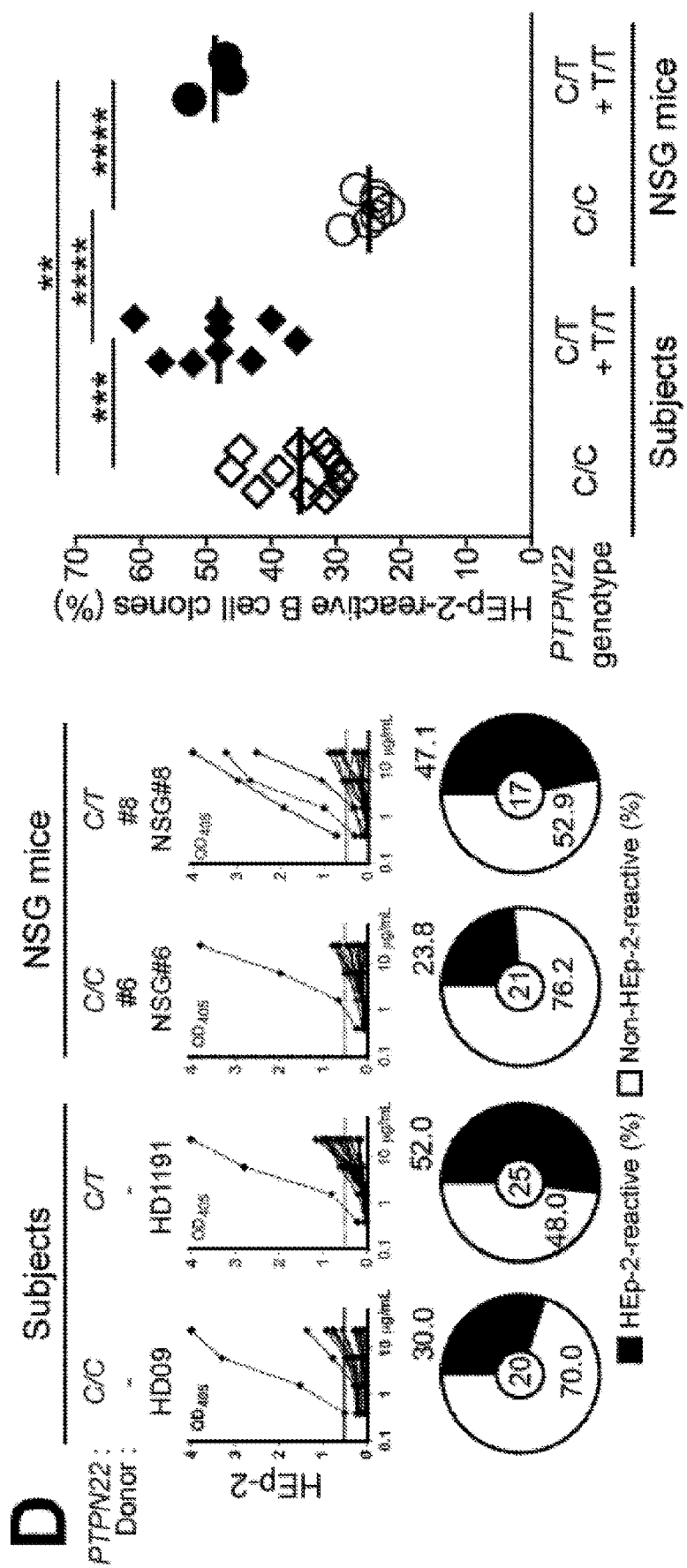
Figures 2A, 2B:
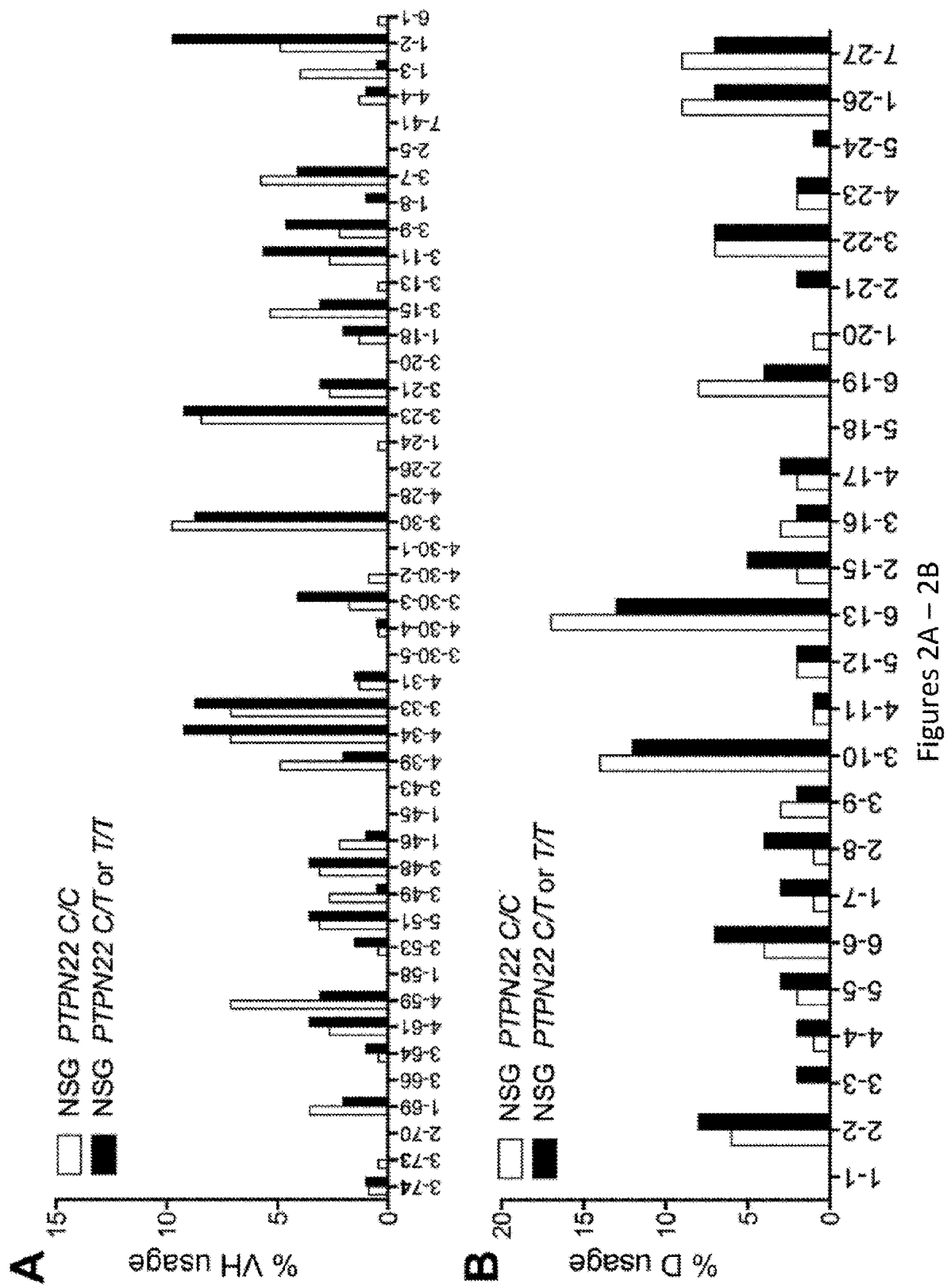
FIG. 2A depicts VH gene-usage frequencies in new emigrant B cells are represented for 7 NSG mice engrafted with PTPN22 C/C HSCs and 6 NSG mice engrafted with PTPN22 C/T or T/T HSCs. Sequences from 226 NSG PTPN22 C/C and 203 NSG PTPN22 C/T or T/T single transitional B cells were pooled.
FIG. 2B depicts D gene-usage frequencies in new emigrant B cells are represented for 7 NSG mice engrafted with PTPN22 C/C HSCs and 6 NSG mice engrafted with PTPN22 C/T or T/T HSCs. Sequences from 226 NSG PTPN22 C/C and 203 NSG PTPN22 C/T or T/T single transitional B cells were pooled.
Figures 2C, 2D:
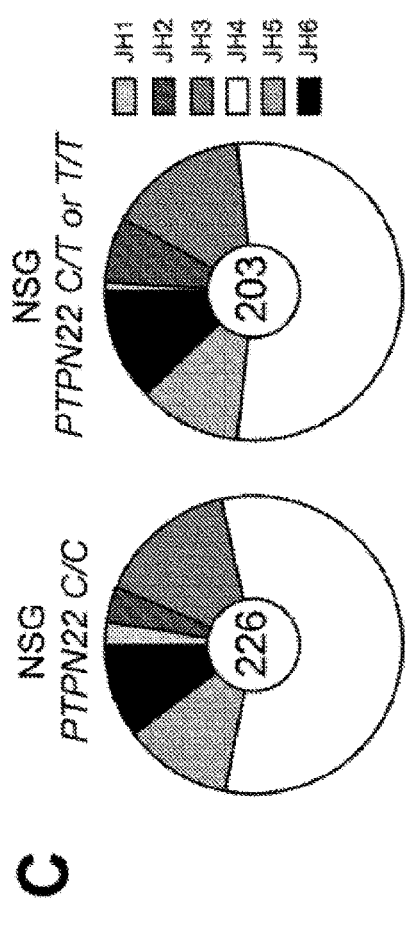
FIG. 2C depicts JH gene-usage frequencies in new emigrant B cells are represented for 7 NSG mice engrafted with PTPN22 C/C HSCs and 6 NSG mice engrafted with PTPN22 C/T or T/T HSCs. Sequences from 226 NSG PTPN22 C/C and 203 NSG PTPN22 C/T or T/T single transitional B cells were pooled.
FIG. 2D depicts reading frame (RF) usages for the D6-6 and D3-22 genes are compared between new emigrant/transitional B cells from 7 NSG mice engrafted with PTPN22 C/C HSCs and 6 NSG mice engrafted with PTPN22 C/T or T/T HSCs.
Figure 3A:
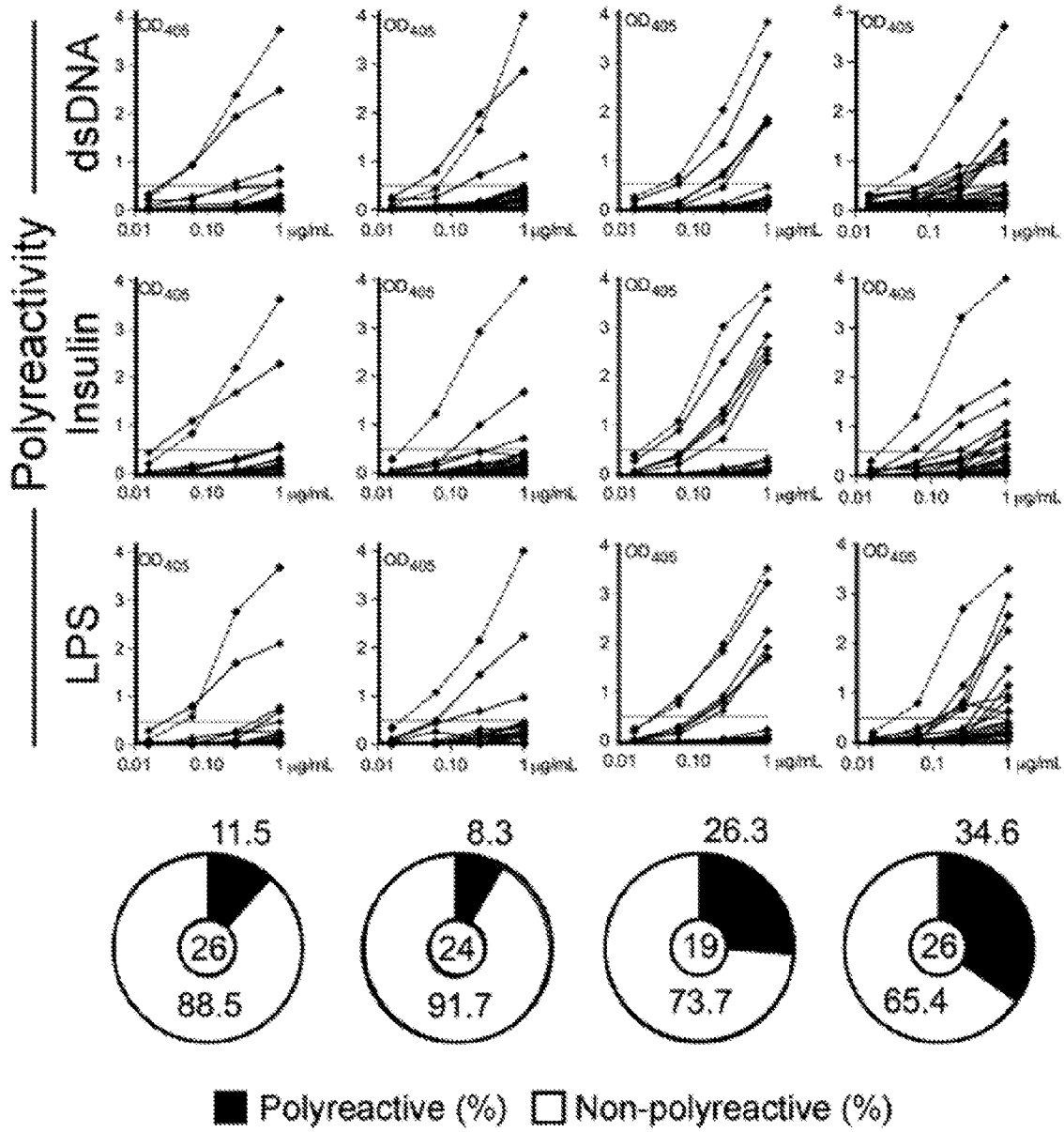
FIG. 3A through FIG. 3C, depicts results from experiments demonstrating defective central B-cell tolerance in humanized mouse engrafted with HSCs carrying PTPN22 T allele(s).
Figure 3B:
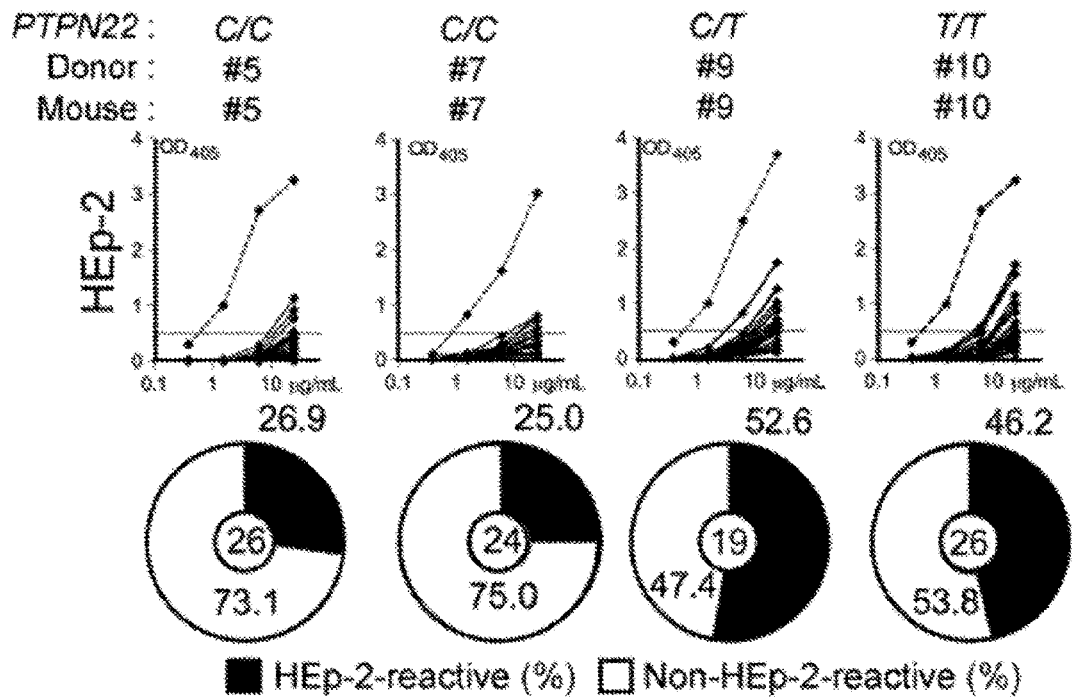
Figure 3C:
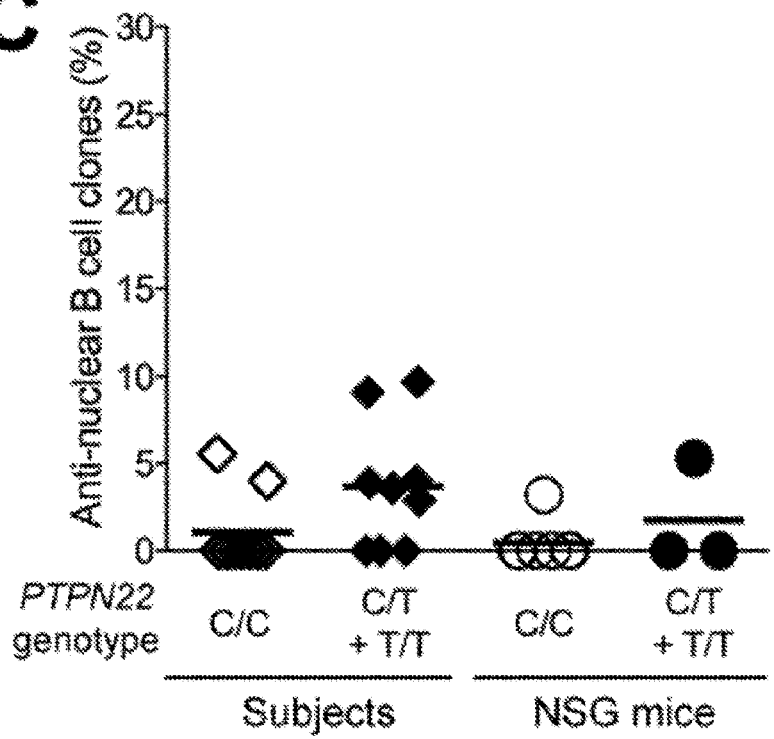

To further study the impact of PTPN22 variants on central B cell tolerance NOD-scid-common gamma chain (γc) knockout (NSG) immunodeficient mice were engrafted with CD34$^+$ hematopoietic stem cells (HSCs) isolated from human fetuses carrying or not PTPN22 T allele(s) (Shultz et al., 2005, J Immunol 174:6477-89; Rongvaux et al., 2014, Nat Biotech 32:364-72; Kalscheuer et al., 2012, Sci Transl Med 4:125ra30) (FIG. 1A and Table 1). Humanized NSG mice displayed high frequencies of CD45$^+$ human cells detected by flow cytometry around three months post-engraftment with HSCs regardless of the presence of PTPN22 T allele(s) (FIG. 1B). Ratios between human CD19$^+$ B and CD3$^+$ T lymphocytes were also similar in NSG mice transplanted with PTPN22 C/C, PTPN22 C/T or PTPN22 T/T HSCs, demonstrating that the PTPN22 T allele does not affect either B- or T-cell development (FIG. 1B). Pooled immunoglobulin heavy-chain (IgH) sequence analyses from new emigrant B cells of PTPN22 C/T or T/T NSG mice revealed no consistent differences in IgH variable (VH), diversity (D), or joining (J) gene usage compared to PTPN22 C/C NSG mice (FIGS. 2A, 2B and 2C). However, in contrast to new emigrant B cells of PTPN22 C/C NSG mice, the presence of a PTPN22 T allele favored the usage of different D reading frames encoding hydrophobic residues known to favor self-reactivity and which correlated with an abnormal central B cell tolerance checkpoint (Corbett et al., 1997, J Mol Biol 270:587-97; Ng et al., 2004, J Exp Med 200:927-34; Meyers et al., 2011, PNAS 108:11554-9) (FIG. 2D). The analyses of antibody reactivity revealed that frequencies of polyreactive clones in splenic CD19$^+$CD27$^-$CD10$^+$IgM$^{hi}$CD21$^{lo}$ new emigrant/transitional B cells from NSG mice transplanted with PTPN22 C/C HSCs isolated from seven distinct fetuses were low and similar to those of new emigrant/transitional B cells isolated from the blood of PTPN22 C/C healthy donors (FIGS. 1C, 3A, 11-17). The low frequencies of HEp-2 reactive new emigrant/transitional B cells and the virtual absence of anti-nuclear clones in this B cell compartment reveals that central B cell tolerance is established normally in humanized mice in the absence of the PTPN22 T allele (FIGS. 1D, 3B and 3C). In contrast, new emigrant/transitional B cells isolated from the spleen of NSG mice engrafted with PTPN22 C/T or T/T HSCs contained many autoreactive clones expressing polyreactive and HEp-2 reactive antibodies with similar frequencies to those observed in healthy donors carrying PTPN22 T allele(s) (Menard et al., 2011, J Clin Invest 121:3635-44) (FIGS. 1C, 1D, 3A, 3B and 18-20). Indirect immunofluorescence assays with HEp-2 cell-coated slides revealed that the proportions of anti-nuclear clones in NSG mice engrafted with PTPN22 C/T or T/T HSCs new emigrant B cells were increased but failed to reach significance (FIG. 3C). These data demonstrate that the presence of the PTPN22 T allele in HSCs results in defective central B cell tolerance and the release of large numbers of autoreactive B cells from the bone marrow.

TABLE 1

| Fetal donor characteristics | | | |
|---|---|---|---|
| Donor # | PTPN22 genotype | Age (days) | Gender |
| 1 | C/C | 105 | Female |
| 2 | C/C | 115 | Female |
| 3 | C/C | 108 | Male |
| 4 | C/C | 110 | Female |
| 5 | C/C | 120 | Male |
| 6 | C/C | 137 | Female |
| 7 | C/C | 112 | Female |
| 8 | C/T | 122 | Female |
| 9 | C/T | 125 | Female |
| 10 | T/T | 105 | Female |
| 11 | C/C | 111 | Female |
| 12 | C/C | 108 | Female |

C/C: homozygote for the PTPN22 C allele in position 1858
C/T: heterozygote for the PTPN22 T allele in position 1858
T/T: homozygote for the PTPN22 T allele in position 1858

Figure 4A:
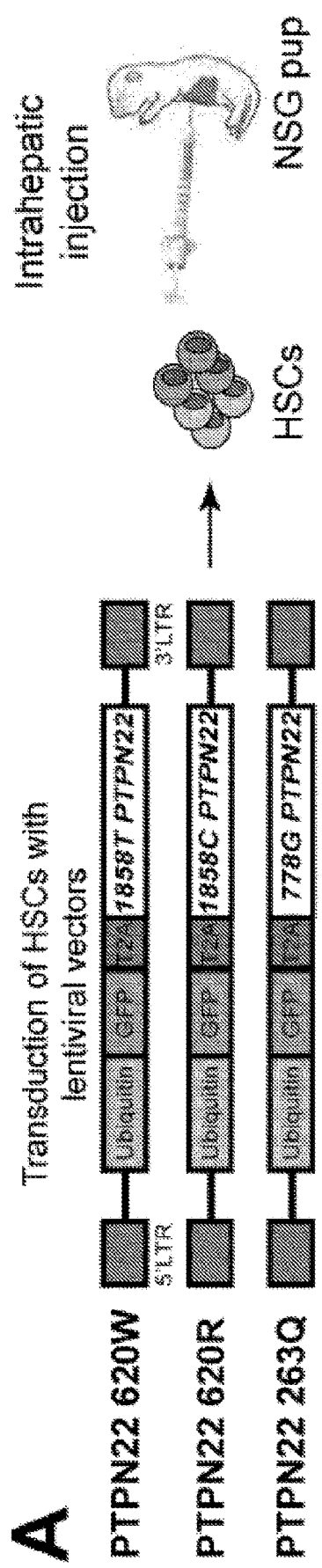
FIG. 4A through FIG. 4C, depicts results from experiments demonstrating PTPN22 620W overexpression interferes with central B cell tolerance.
Figure 4B:
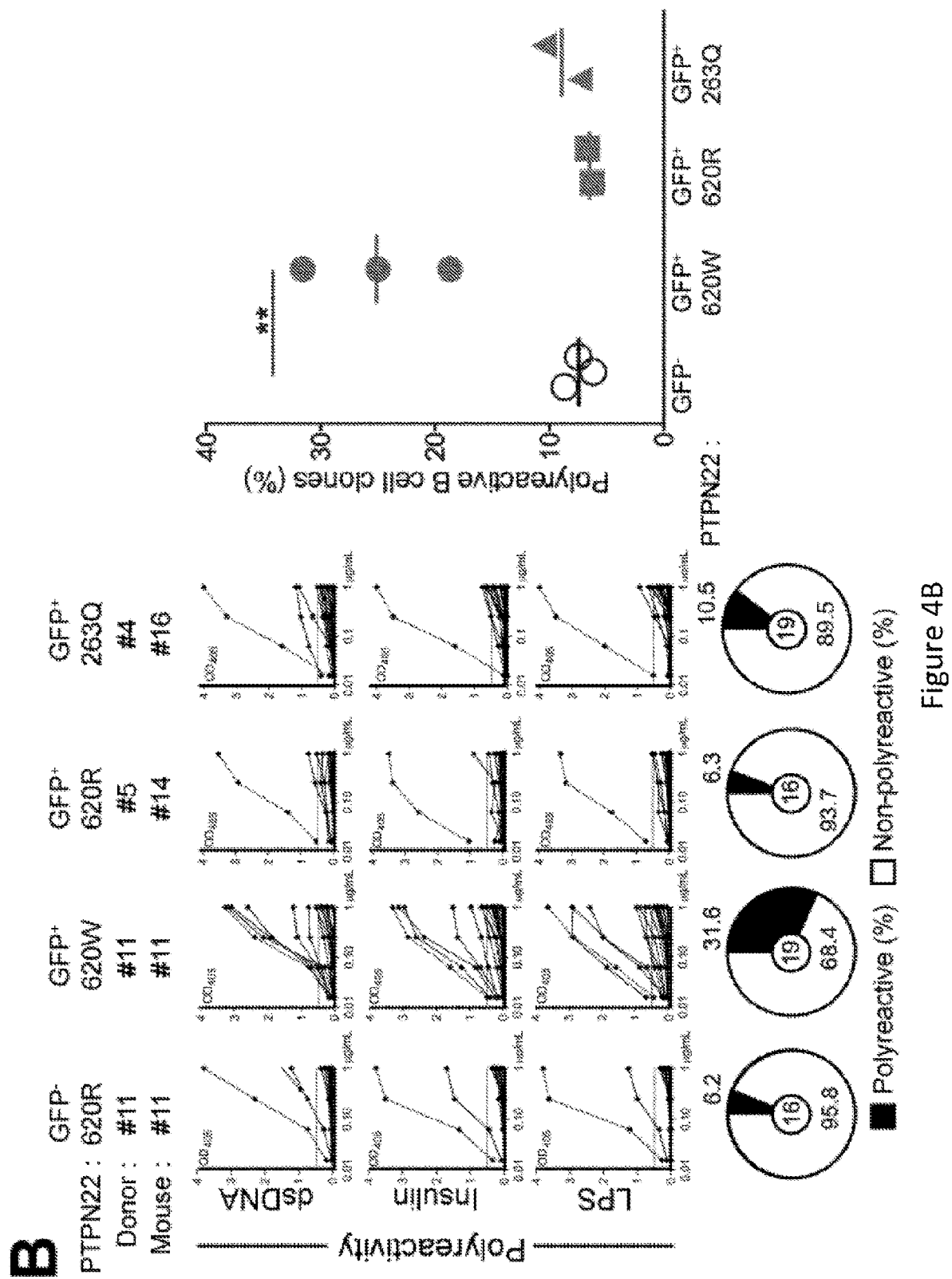
Figure 4C:
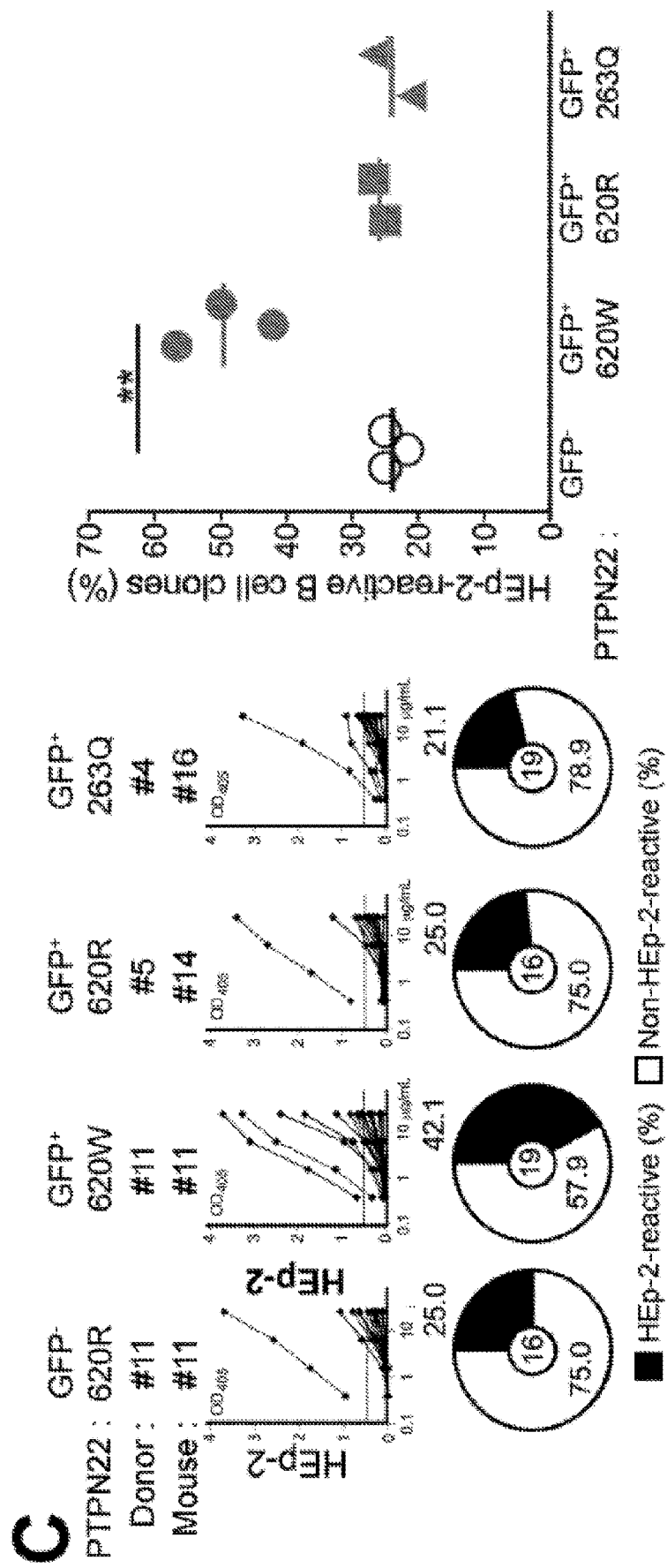
Figures 5A, 5B:
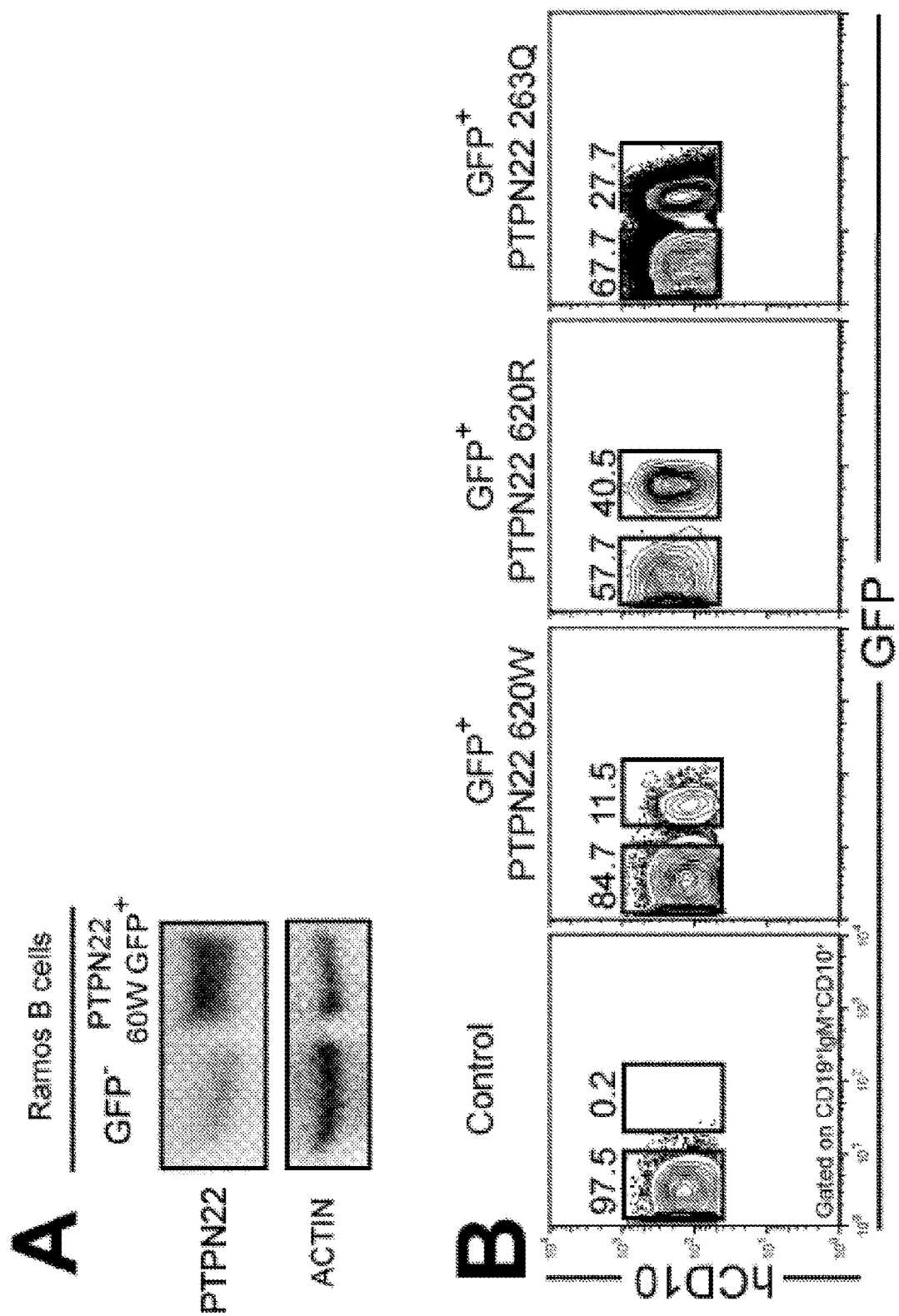
FIG. 5A and FIG. 5B, depicts results from experiments demonstrating overexpression of PTPN22 variants in NSG mice.
Figure 6A:
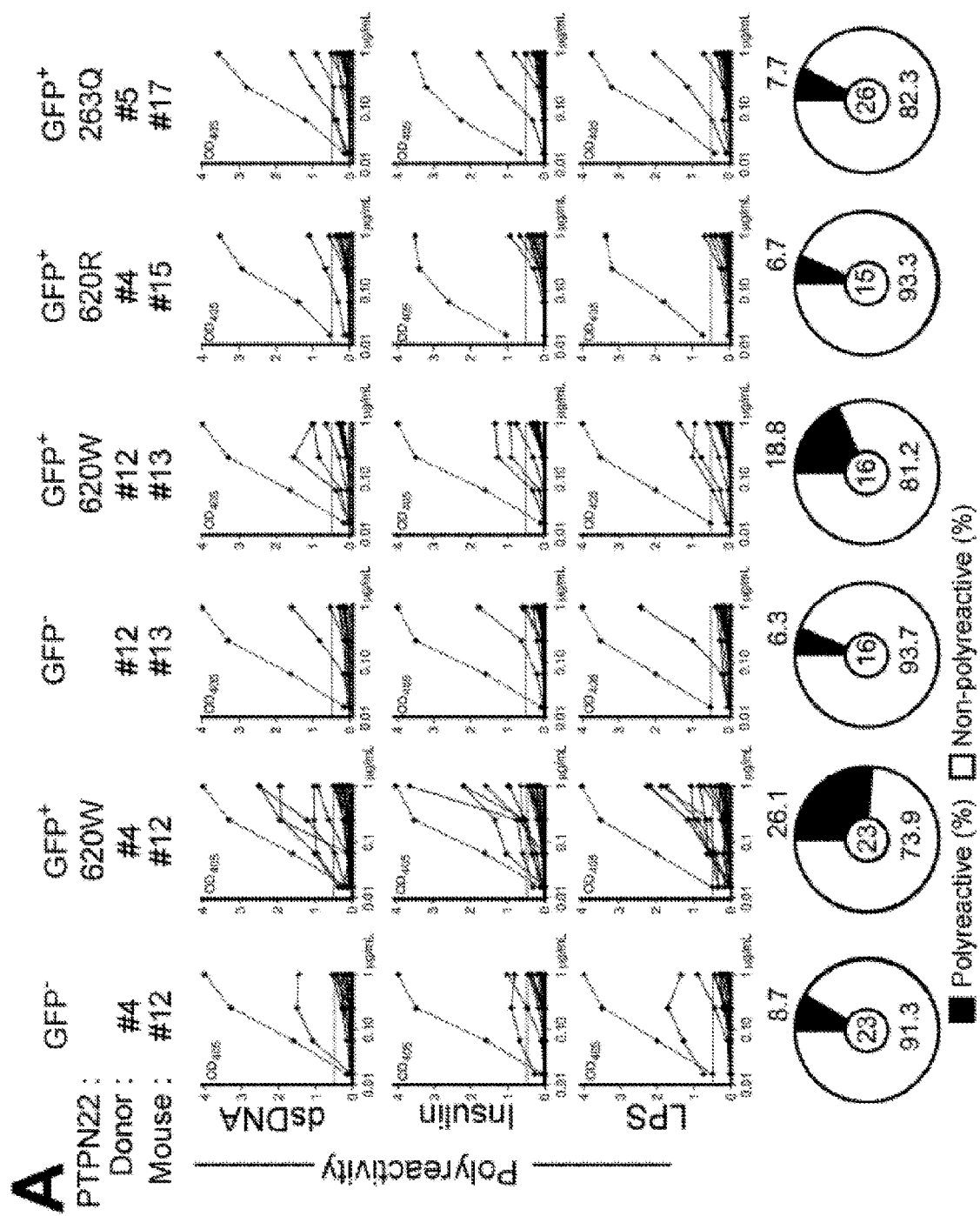
FIG. 6A through FIG. 6D, depicts results from experiments demonstrating 620W PTPN22 overexpression interferes with the central B cell tolerance checkpoint.
Figure 6B:
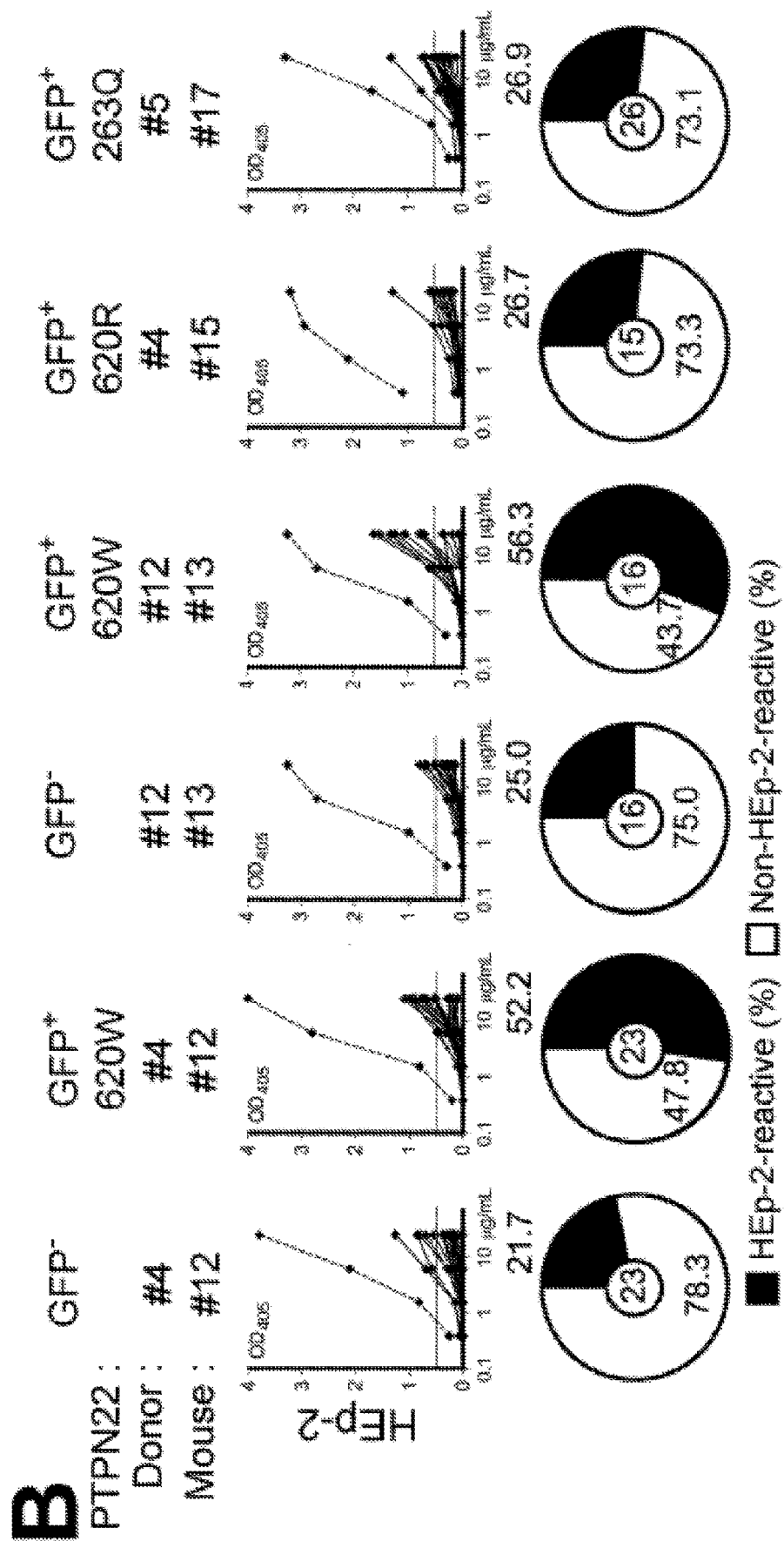
Figure 6C:
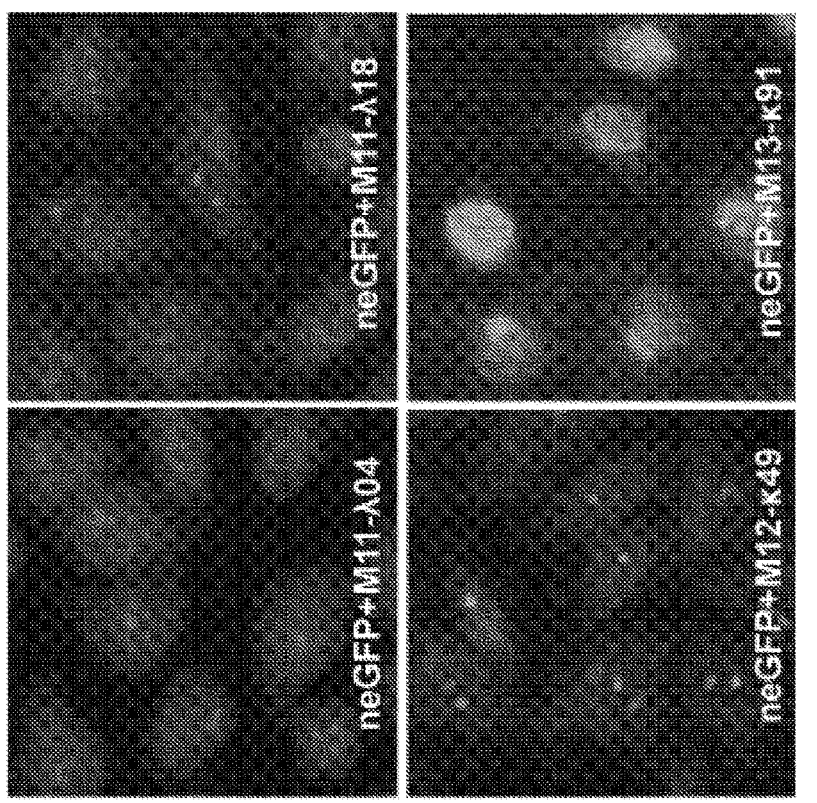
Figure 6D:
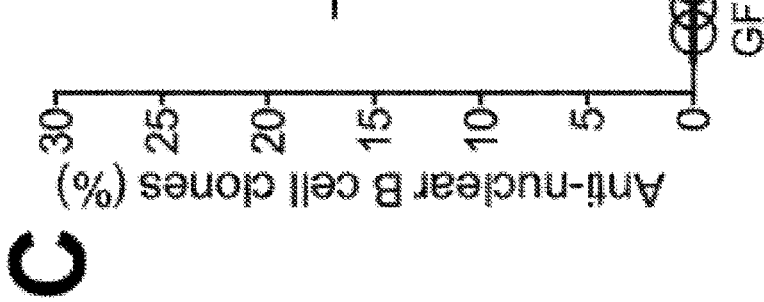

To determine whether B-cell intrinsic expression of 620W PTPN22 phosphatases is sufficient to interfere with the removal of developing autoreactive immature B cells in the bone marrow, PTPN22 C/C HSCs were transduced with lentiviruses expressing green fluorescent proteins (GFP) and the 620W PTPN22 autoimmunity-favoring variant, the common 620R or the 263Q loss-of-function PTPN22 enzyme (FIG. 4A). Human CD19$^+$ B cells developed in NSG mice engrafted with HSCs transduced or not with the different lentiviruses, revealing that lentiviral transduction did not alter HSC engraftment or B cell development (FIGS. 5A and 5B). The presence of 620W PTPN22 alters the counterselection of developing autoreactive B cells as GFP$^+$ new emigrant/transitional B cells expressing this variant contained many autoreactive clones producing polyreactive antibodies (FIGS. 4B, 5A, and 21-26). High proportions of HEp-2 reactive and anti-nuclear GFP$^+$ new emigrant/transitional B cells corroborated this defective central B cell tolerance checkpoint (FIGS. 4C, 6B, 6C, and 6D). In contrast, GFP$^-$ B cell counterparts that developed in the same NSG mice rarely expressed polyreactive antibodies and displayed low frequencies of HEp-2 reactive and anti-nuclear clones revealing that these B cells were properly selected in the absence of 620W PTPN22 expression (FIGS. 4B, 4C, 6A, 6B, 6C, and 6D). In addition, GFP$^+$ new emigrant/transitional B cells expressing either 620R PTPN22 or the loss-of-function 263Q PTPN22 variant displayed normal proportions of polyreactive, HEp-2 reactive and anti-nuclear clones demonstrating normal central B cell tolerance (FIGS. 4B, 4C, 6A, 6B, 6C, 6D, and 27-30). Regardless of how the 620W amino acid replacement alters PTPN22 function, our data demonstrate that B-cell intrinsic 620W PTPN22 expression is sufficient to interfere with the removal of developing autoreactive B cells and the establishment of human central B cell tolerance.

Figure 7A:
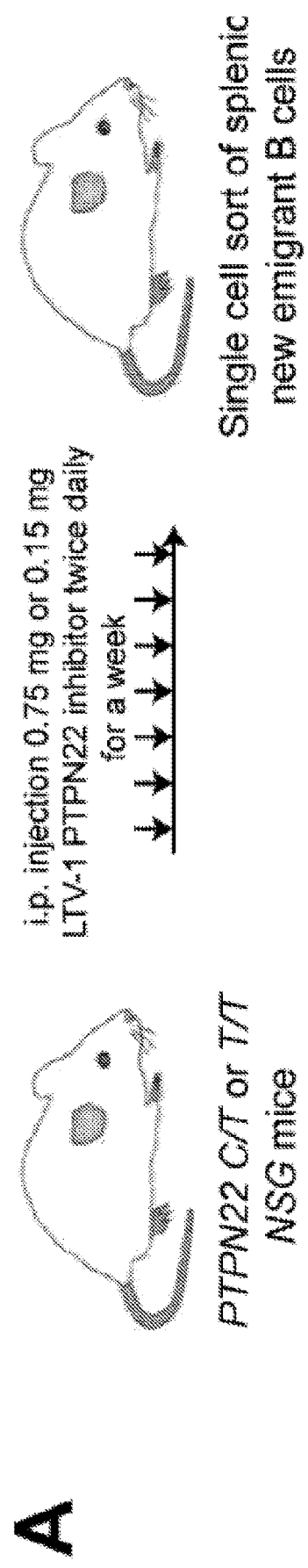
FIG. 7A depicts a schematic diagram depicting the PTPN22 inhibitor treatment strategy. NSG mice generated with CD34+ HSCs carrying PTPN22 T allele(s) were injected twice daily with 0.75 mg or 0.15 mg of PTPN22 inhibitor for one week.
Figure 7B:
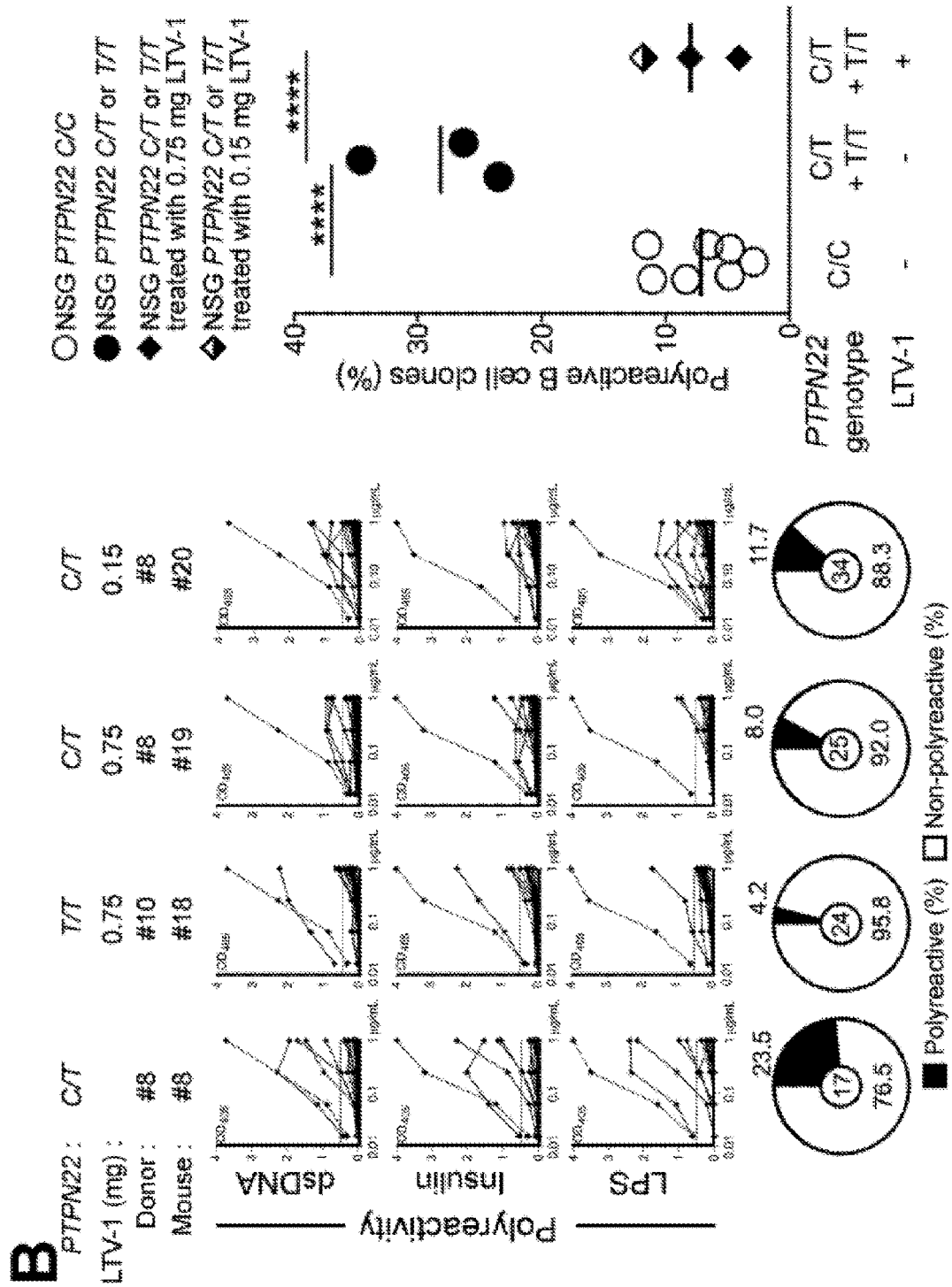
FIG. 7B depicts the frequencies of polyreactive new emigrant B cells from NSG mice carrying PTPN22 T allele(s) and treated with the PTPN22 inhibitor were determined and compared to those of non-treated NSG mice. Dotted line shows positive control. For each B-cell fraction, the frequency of reactive (filled area) and non-reactive (open area) clones is summarized in pie charts with the total number of clones tested indicated in the center. In summarized reactivity panels on the right, each dot represents an untreated mouse and full and half-filled diamonds mice treated with either 0.75 or 0.15 mg of LTV-1 PTPN22 inhibitor, respectively. Averages are shown with a bar.
Figure 7C:
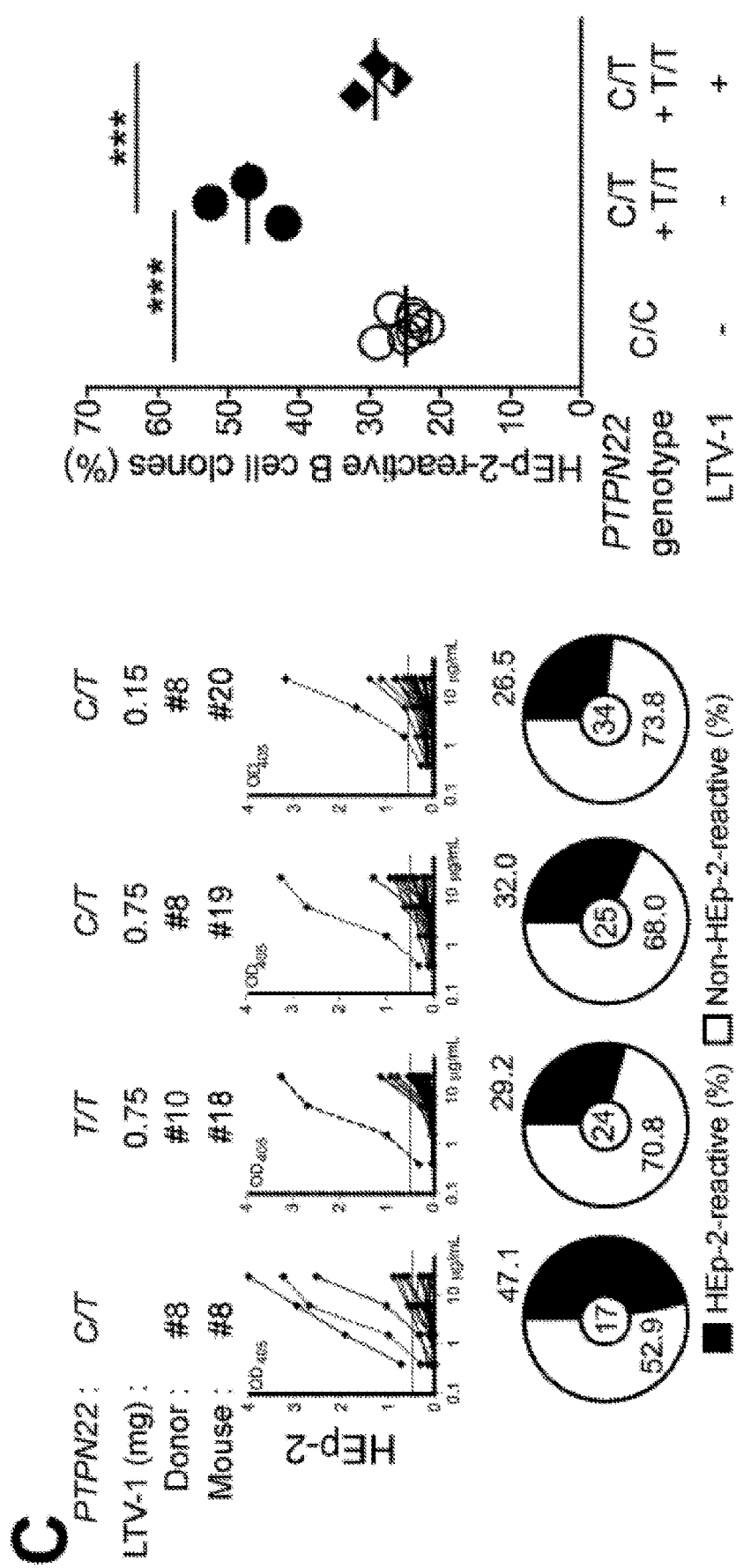
FIG. 7C depicts the frequencies of HEp-2 reactive new emigrant B cells from NSG mice carrying PTPN22 T allele(s) and treated with the PTPN22 inhibitor were determined and compared to those of non-treated NSG mice. Dotted line shows positive control. For each B-cell fraction, the frequency of reactive (filled area) and non-reactive (open area) clones is summarized in pie charts with the total number of clones tested indicated in the center. In summarized reactivity panels on the right, each dot represents an untreated mouse and full and half-filled diamonds mice treated with either 0.75 or 0.15 mg of LTV-1 PTPN22 inhibitor, respectively. Averages are shown with a bar.
Figure 8:
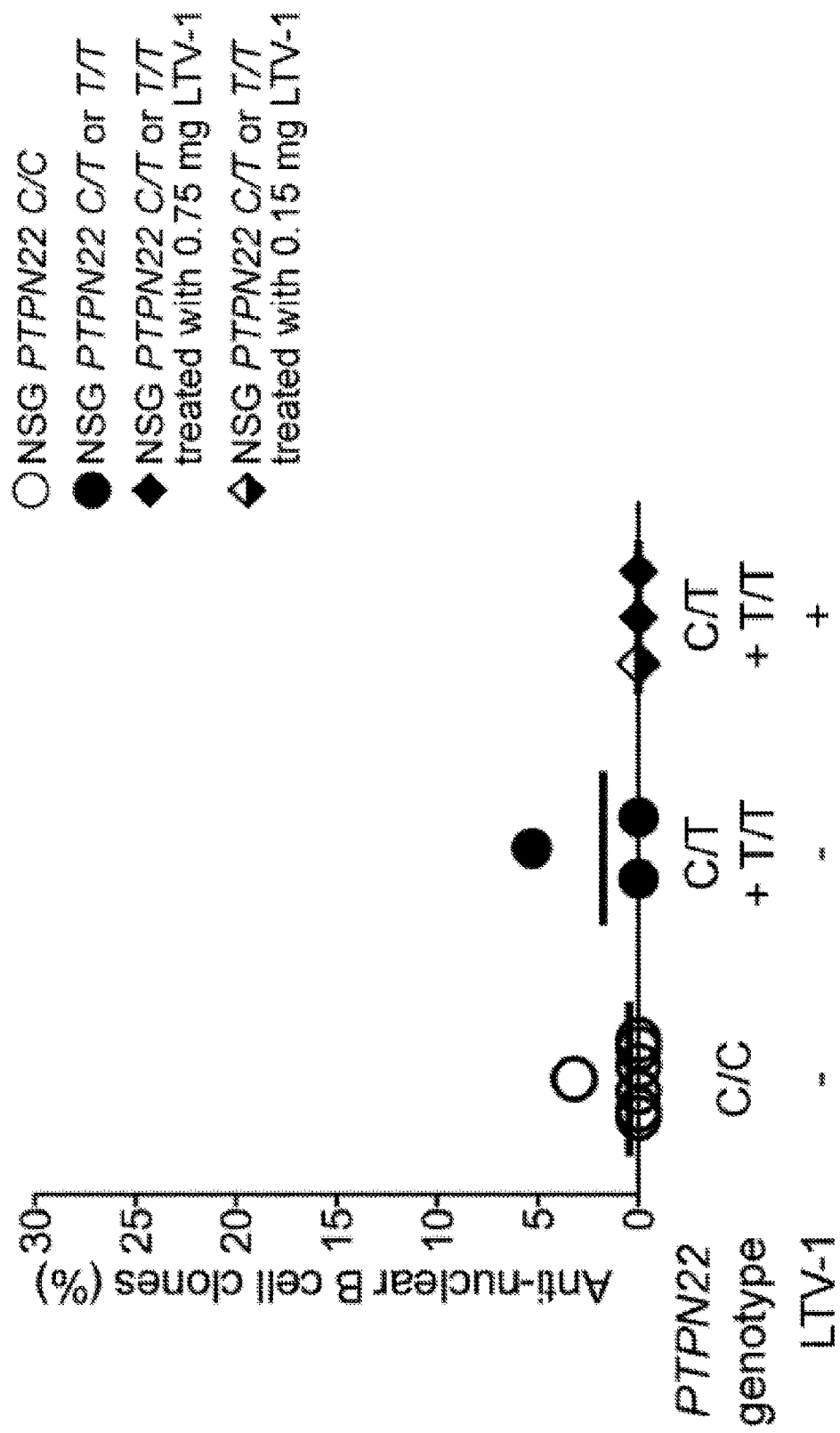
FIG. 8 depicts frequencies of anti-nuclear new emigrant B cells in PTPN22 C/T or T/T NSG mice treated with the LTV-1 PTPN22 inhibitor. Anti-nuclear frequencies are compared between the PTPN22 C/T or T/T NSG mice treated or not with 0.75 mg or 0.15 mg of LTV-1 PTPN22 inhibitor. Each symbol represents a mouse and horizontal bars denote means.

PTPN22 enzymatic activity can be inhibited in T cells in vitro by the LTV-1 specific inhibitor (Vang et al., 2012, Nat Chem Biol 8:437-46). To assess the impact of the inhibition of 620W PTPN22 enzymatic activity on central B cell tolerance, PTPN22 C/T or T/T engrafted NSG mice were injected about 3 months post transplant with 0.75 mg of LTV-1 compound twice daily for a week and determined the frequency of autoreactive new emigrant/transitional B cells (FIG. 7A). LTV-1 treatment significantly reduced the frequencies of polyreactive new emigrant/transitional B cells in PTPN22 C/T or T/T transplanted mice, similar to those in NSG mice engrafted with HSCs that did not carry the PTPN22 T allele (FIGS. 7B and 31-33). In addition, PTPN22 inhibition by LTV-1 also normalized the frequencies of HEp-2 reactive new emigrant/transitional B cells in PTPN22 C/T or T/T engrafted mice (FIG. 7C) and anti-nuclear clone frequencies remained very low (FIG. 8). Similar results were obtained with 0.15 mg of LTV-1 injections, revealing a large range for effective PTPN22 inhibition by this compound (FIG. 3B, C). Hence, inhibition of 620W PTPN22 enzymatic activity resets central B cell tolerance that is normally impaired by the presence of the PTPN22 T allele.

Figures 9A, 9B, 9C:
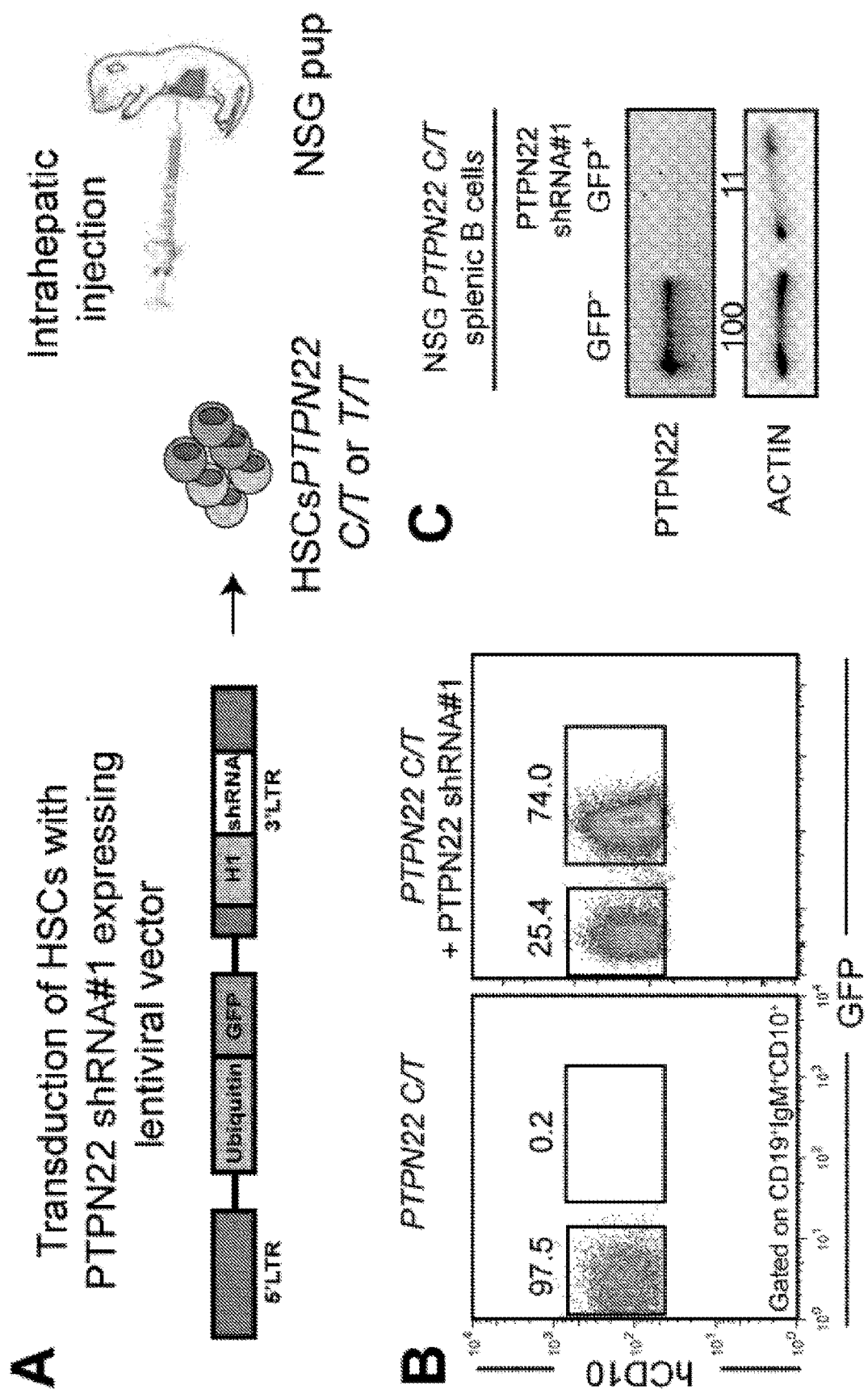
FIG. 9A through FIG. 9E, depicts results from experiments demonstrating inhibition of PTPN22 expression during B cell development resets central B cell tolerance.
Figure 9D:
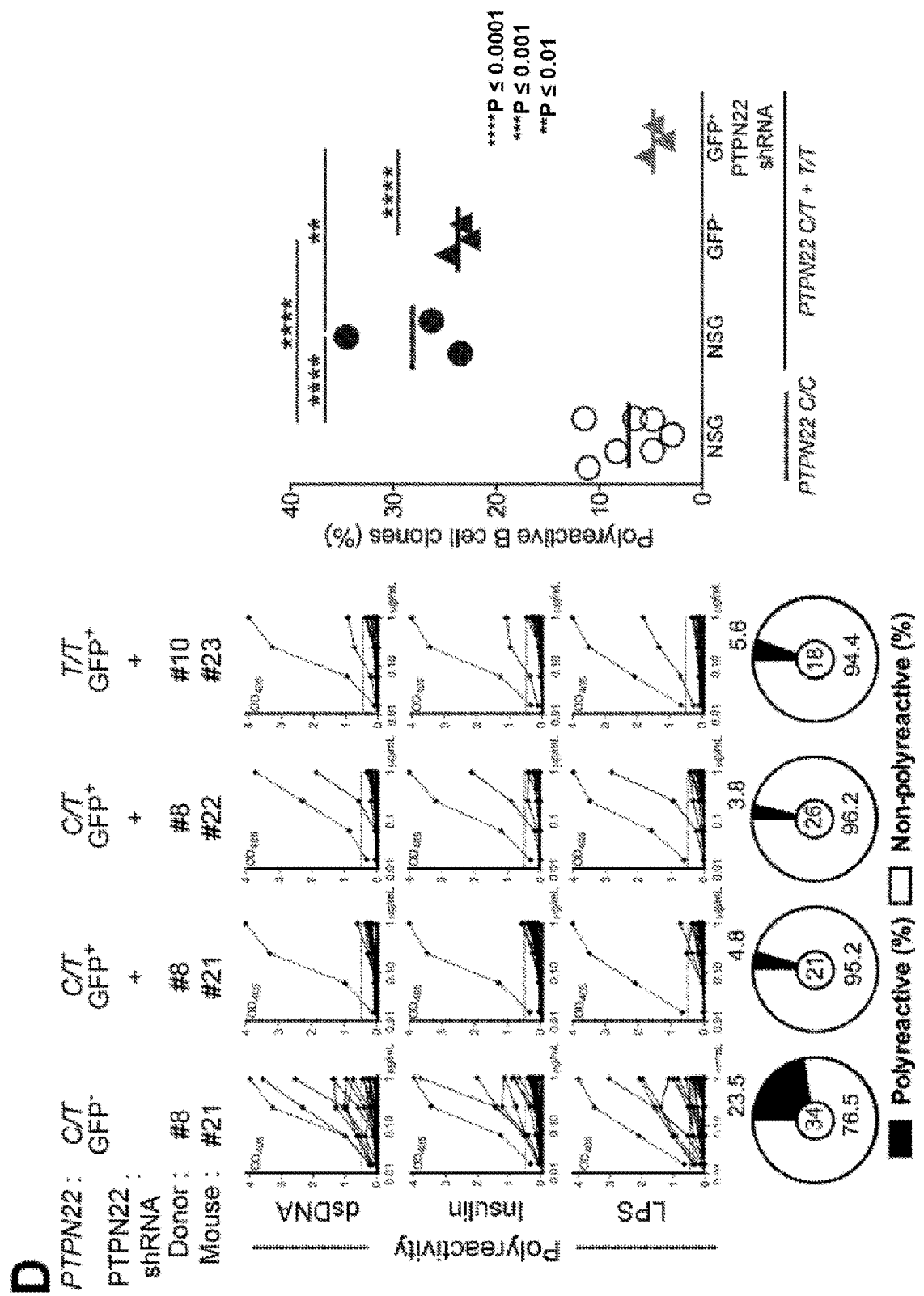
Figure 9E:
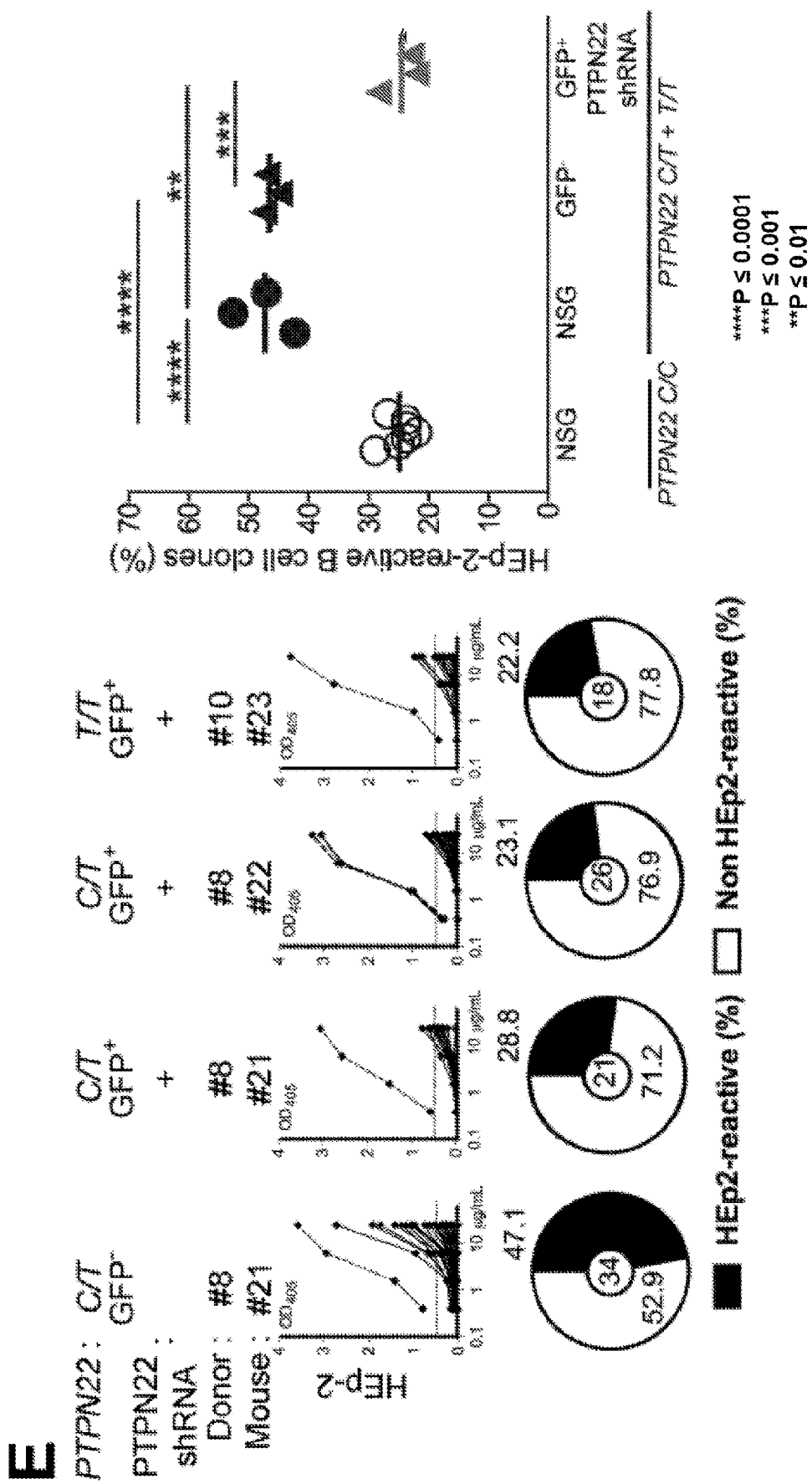
Figure 10A:
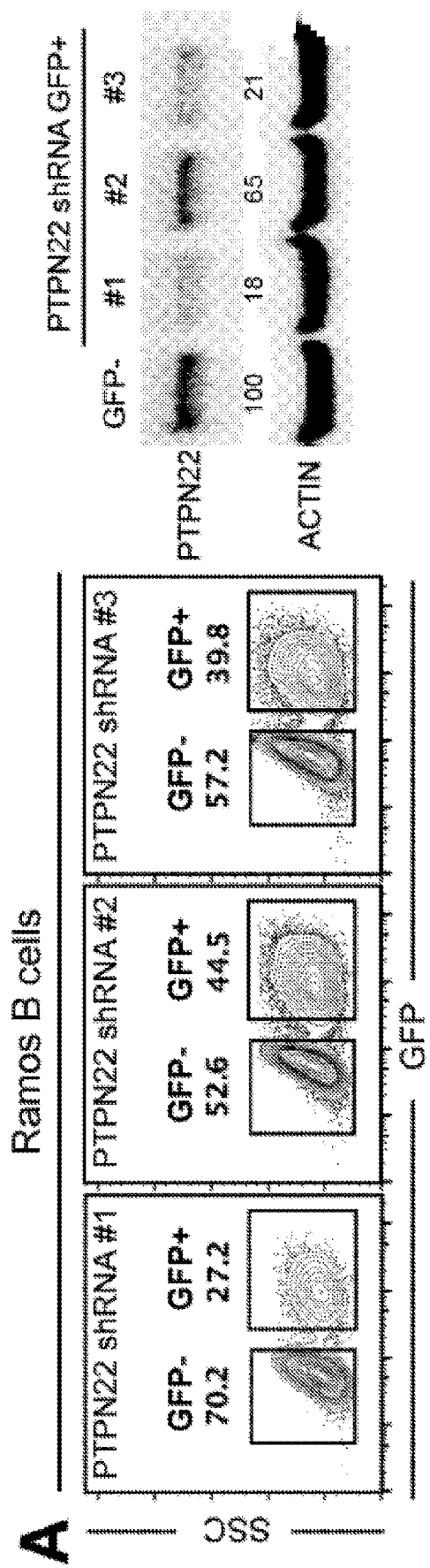
Figure 10B:
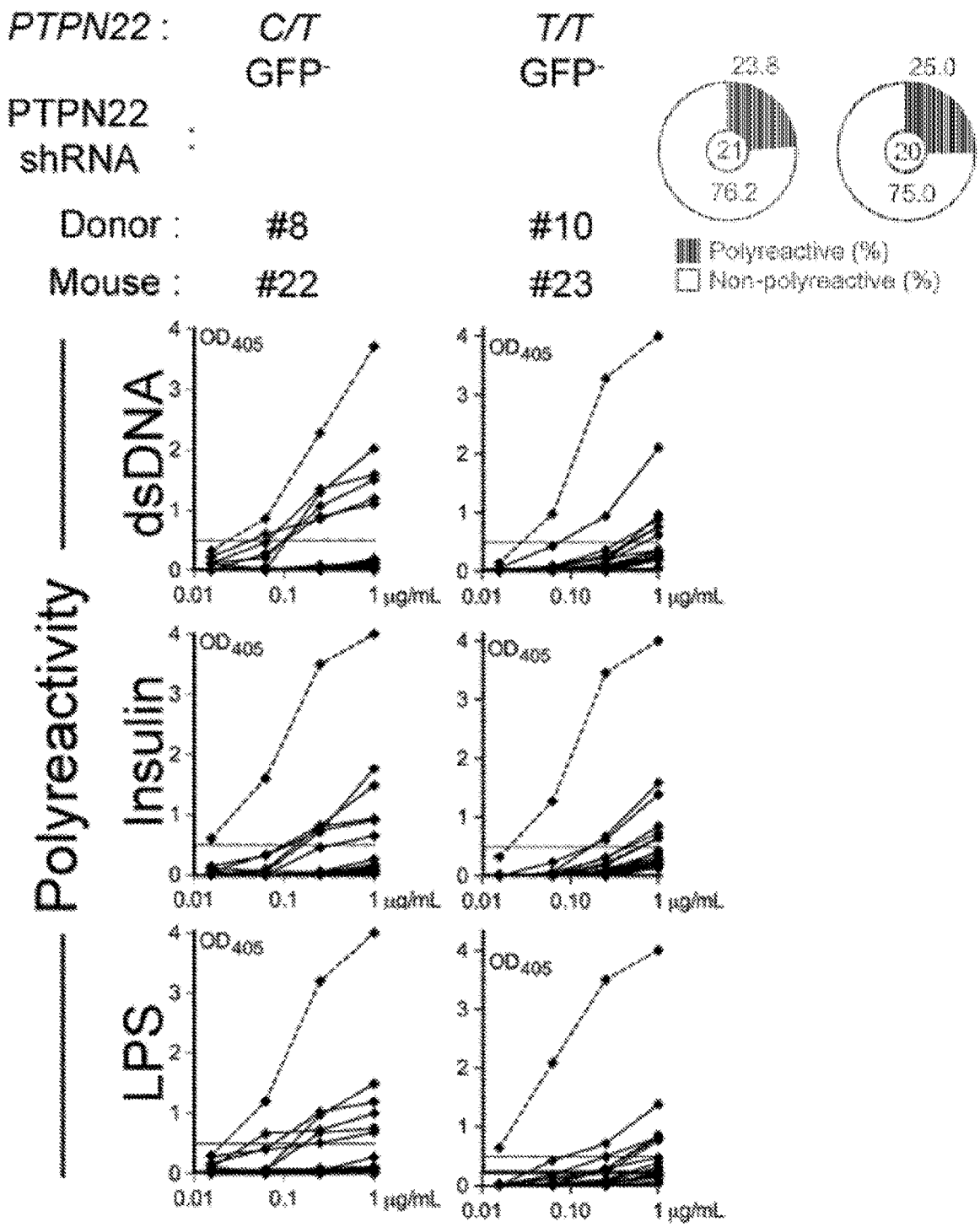

Although central B cell tolerance appears to be mainly regulated by B-cell intrinsic pathways involving B-cell receptor (BCR) and potentially Toll-like receptor (TLR) signaling (Meffre, 2011, Ann N Y Acad Sci 1246:1-10), this checkpoint might be restored via B-cell extrinsic pathways normalized by 620W PTPN22 inhibition. In addition, the LTV-1 PTPN22 inhibitor may also non-specifically alter the function of other phosphatases. To determine if specific B-cell intrinsic PTPN22 blockade is responsible for the correction of central tolerance, a strategy to inhibit the expression of PTPN22 in developing B cells using RNA interference was developed (Cantaert et al., 2015, Immunity 43:884-95). NSG mice were engrafted with PTPN22 C/T or T/T HSCs transduced with a GFP-tagged lentivirus expressing PTPN22 specific shRNA (FIG. 9A). Two PTPN22 specific shRNA, shRNA #1 and #3, were identified that could inhibit about 80% of PTPN22 expression detected by western blot using human RAMOS B cell line and chose shRNA #1 for all further experiments (FIG. 10A). A high proportion of GFP$^+$ human B cells expressing PTPN22 shRNA #1 developed in NSG mice, revealing that transduced HSCs retained engraftment and B cell development capacities (FIG. 9B). In addition, GFP expression correlated with more than 90% decrease of PTPN22 expression in developing B cells (FIG. 9C). Blocking PTPN22 expression in GFP$^+$ PTPN22 C/T or T/T new emigrant/transitional B cells significantly reduced the production of polyreactive and HEp-2 reactive clones compared to GFP$^-$ counterparts that often expressed autoreactive antibodies (FIGS. 9D, 9E, 10B, 10C, and 34-39). In addition, it was previously shown using control shRNA lentiviruses that HSC transduction per se does not interfere with the counterselection of autoreactive B cells (Cantaert et al., 2015, Immunity 43:884-95). Altogether, these data demonstrate that the inhibition of PTPN22 expression in developing B cells can induce efficient removal of autoreactive clones and therefore restore central B cell tolerance that is otherwise impaired when the 620W PTPN22 variant is expressed.

In conclusion, the PTPN22 T allele is responsible for the production of autoreactive B cells that escape central tolerance (Menard et al., 2011, J Clin Invest 121:3635-44). These observations may explain why the PTPN22 T allele confers high risk to develop many autoimmune diseases as it induces central B cell tolerance defects observed in patients with T1D, RA and SLE (Chamberlain et al., 2015, J Clin Invest 126:282-7; Samuels, 2005, J Exp Med 201:1659-67; Yurasov, 2006, J Exp Med 201:703-11). Increased frequencies of autoreactive B cells may increase the probability to present self-antigens and initiate autoimmunity. In addition, the data presented herein shows that central B cell tolerance could likely be reset in PTPN22 C/T or T/T subjects by inhibiting PTPN22 enzymatic activity or expression. These data are in agreement with previous studies that have demonstrated that the 620W PTPN22 variant requires its enzymatic activity to mediate alternative outcomes but it remains to be determined how the 620W mutation modifies its function (Dai et al., 2013, J Clin Invest 123:2024-36). In addition, PTPN22 inhibition might also reset the T cell receptor (TCR) signaling threshold altered by 620W PTPN22 variants (Rieck et al., 2007, J Immunol 179:4704-10; Salmond et a., 2014, Nat Immunol 15:875-83) and therefore modify the TCR repertoire of both T effector and regulatory T cells selected in the thymus of PTPN22 T carriers. In conclusion, PTPN22 is a major regulator of human central B cell tolerance; its inhibition can normalize the elimination of developing autoreactive B cells and may thereby thwart the development of autoimmunity.

Figure 40A:
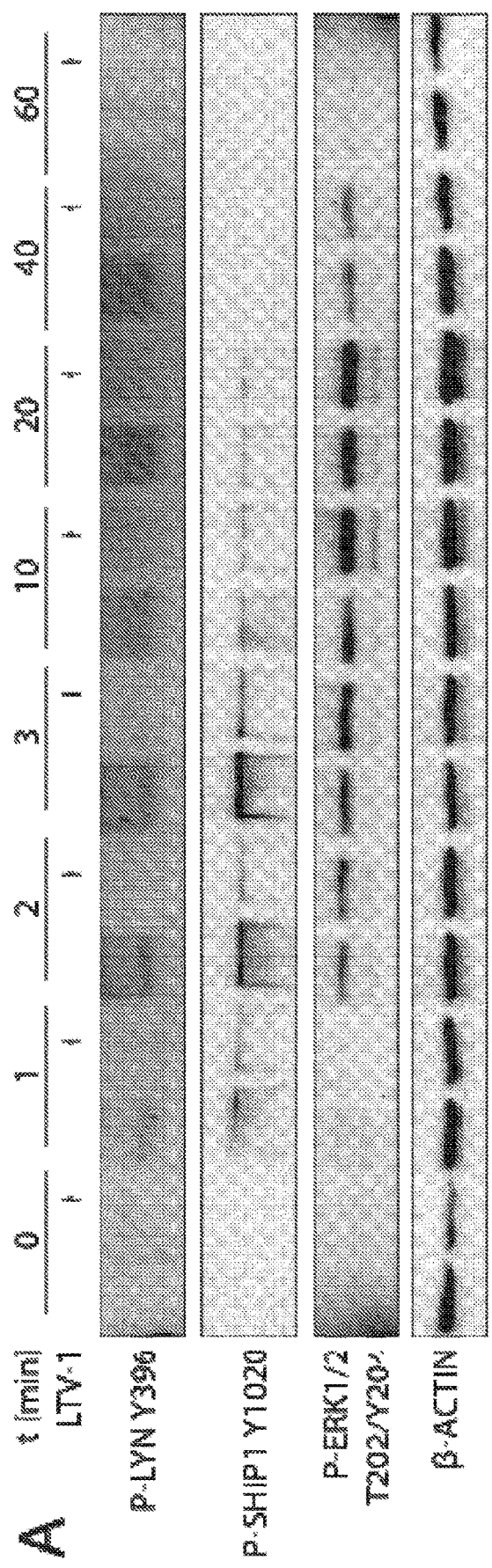
FIG. 40A through FIG. 40D, depicts experimental results demonstrating that inhibition of PTPN22 diminishes the activation of Lyn and SHIP1 and augments calcium flux in B cells.
Figures 40B, 40C, 40D:
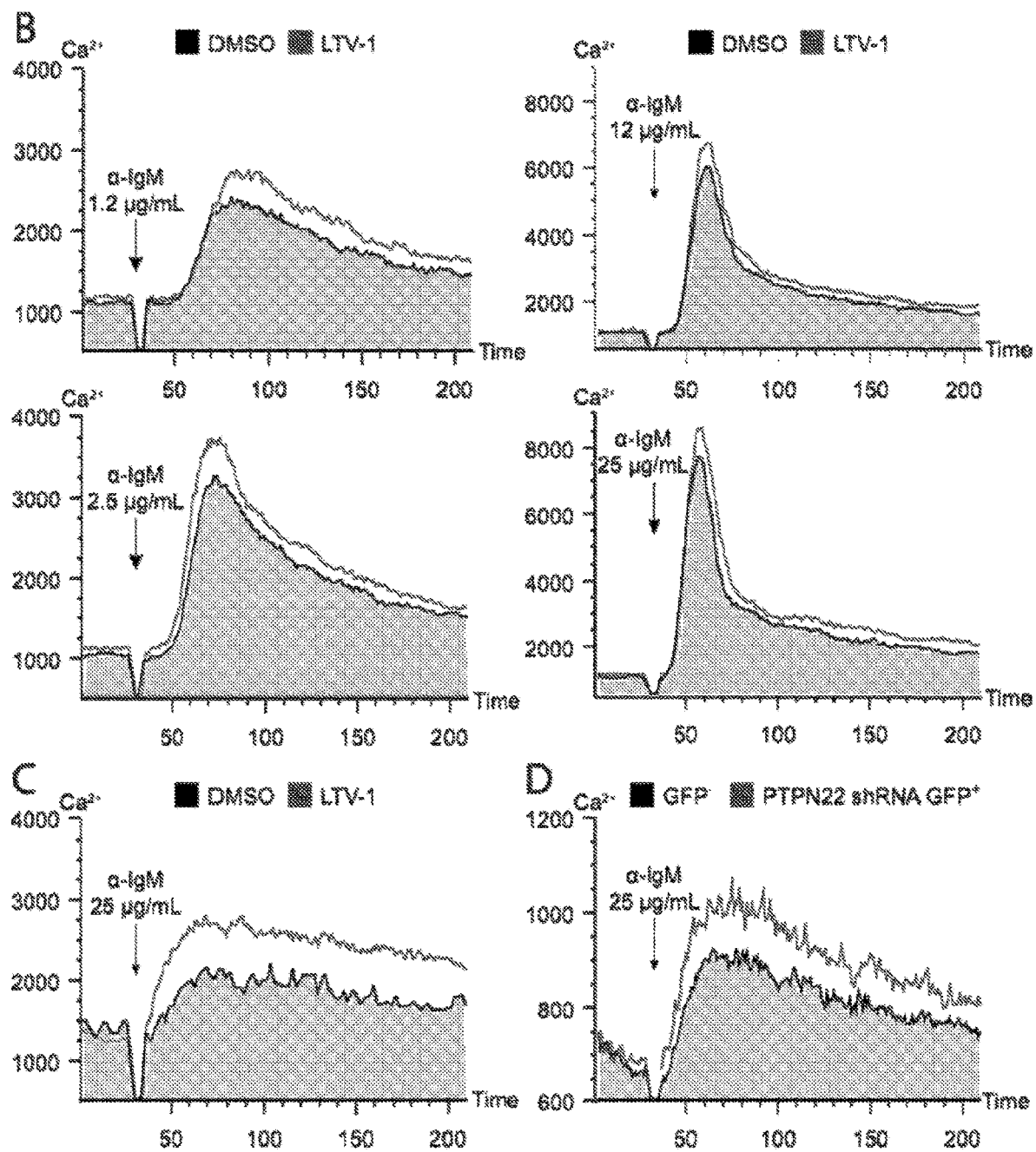

Example 2: PTPN22 Inhibition Restores Proper BCR Signaling Regulating Central B Cell Tolerance The data presented herein demonstrates how PTPN22 inhibition may affect B cell responses, and specifically BCR function, and restores central B cell tolerance. Phosphorylation kinetics of LYN and SHIP1, an important regulator of calcium flux, and ERK in RAMOS cells after BCR triggering with or without PTPN22 enzymatic inhibition by LTV-1 suggest that PTPN22 inhibition decreases the phosphorylation of LYN at position Y396 and SHIP1 at position Y2010, which activates these molecules (FIG. 40A). However, downstream ERK phosphorylation was not affected by PTPN22 inhibition (FIG. 40A). Since PTPN22 inhibition enhanced TCR signaling in Jurkat cell line, it was investigated if PTPN22 blockade may also increase BCR signaling and calcium flux induced by BCR triggering was measured in RAMOS cells in the presence or not of LTV-1. Calcium flux was increased by PTPN22 inhibition, especially at lower concentration of BCR triggering agent (FIG. 40B). Similarly, calcium flux was enhanced in B cells isolated from humanized mice treated with LTV-1 compared to non-treated counterparts (FIG. 40C). Decreased SHIP1 phosphorylation after PTPN22 inhibition shown in FIG. 40A likely contributes to this phenotype since SHIP1 normally mediates calcium flux downregulation. In addition, GFP$^+$ B cells isolated from a humanized NSG mouse in which PTPN22 production is inhibited by GFP-tagged lentivirus expressing PTPN22 specific shRNA also displayed increased calcium flux after BCR triggering compared to GFP$^-$ counterparts that express PTPN22 (FIG. 40D). Thus, while not wishing to be bound to any particular theory, PTPN22 blockade may restore central B cell tolerance by increasing BCR signaling and the deletion of immature B cells binding self-antigens in the bone marrow.

Figure 41A:
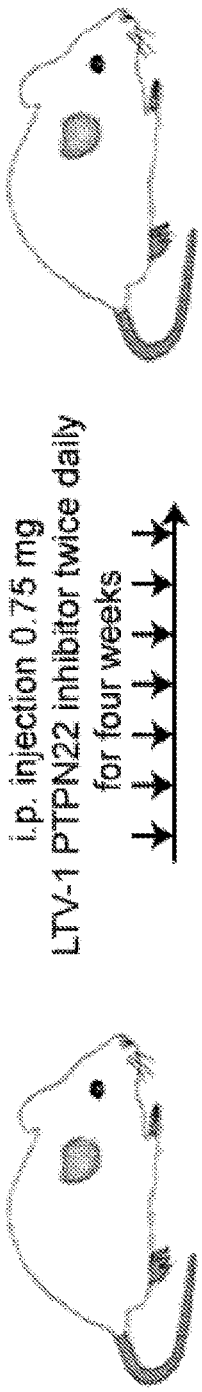
FIG. 41A through FIG. 41C, depicts experimental results demonstrating that PTPN22 enzymatic inhibition restores peripheral B cell tolerance.
Figure 41B:
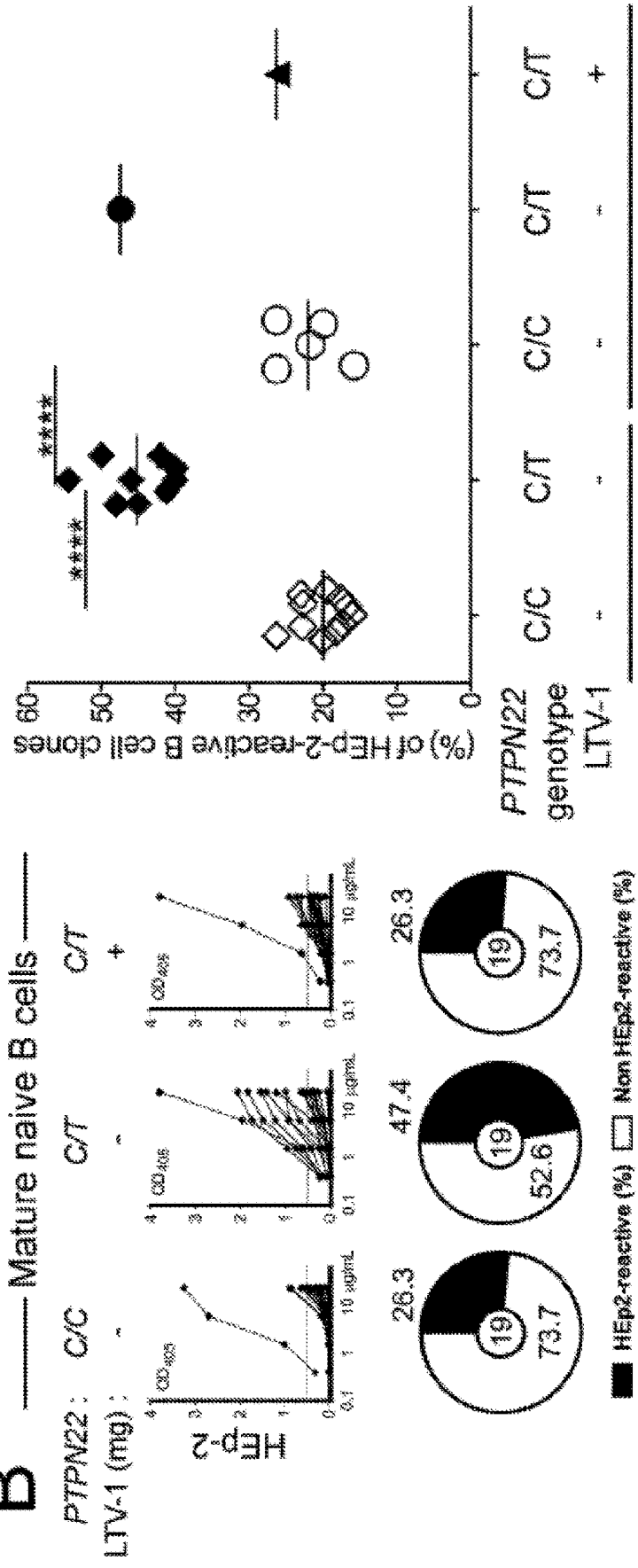
Figure 41C:
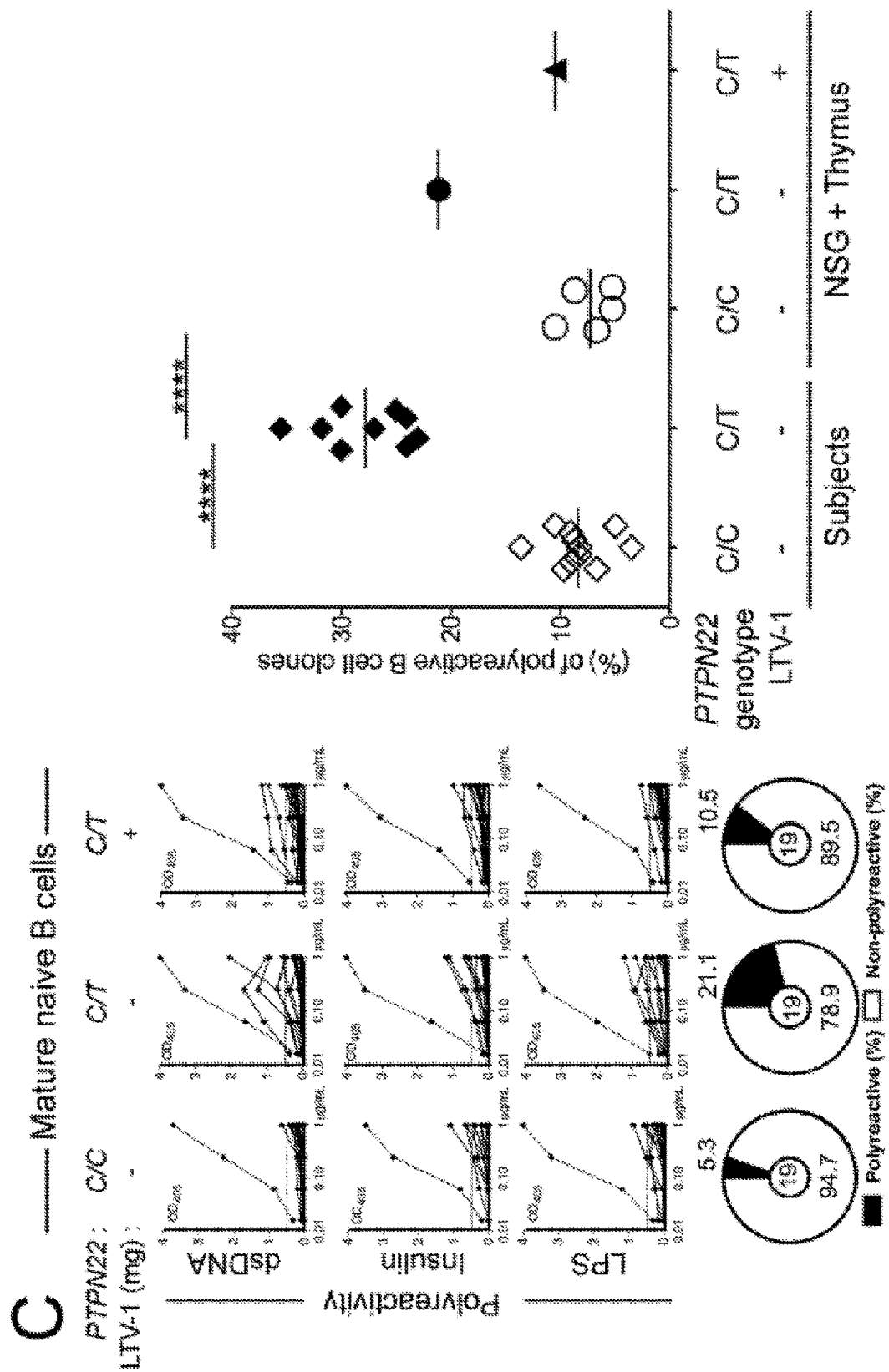

Example 3: PTPN22 Blockage Prevents the Accumulation of Autoreactive B Cells in the Periphery The data presented herein demonstrates the peripheral B cell tolerance checkpoint in NSG mouse engrafted with fetal HSCs and autologous thymic tissue both carrying the 1858T PTPN22 allele. Autoreactive clones accumulated in the mature naïve B cell compartment in the spleen of this mouse, a situation that resembles that of asymptomatic 1858T PTPN22 carrier subjects who display elevated proportions of autoreactive mature naïve B cells in their blood (FIG. 41). PTPN22 inhibition by LTV-1 treatment for a month effectively restored this impaired peripheral B cell tolerance checkpoint (FIG. 41). Hence, these data show that NSG mice+Thymus when engrafted with fetal tissues carrying the PTPN22 T allele, represent a good model for the accumulation of autoreactive B cells in the periphery induced by the presence of the 1858T PTPN22 allele and its correction by PTPN22 blockade.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating or preventing an autoimmune disease or disorder the method comprising administering a composition comprising an inhibitor of PTPN22 to a subject in need thereof, wherein the inhibitor of PTPN22 is

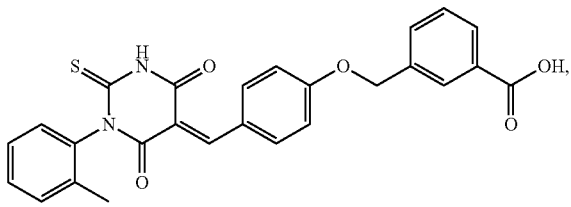 [SMILES: Cc1ccccc1N1C(=O)/C(=C/c2ccc(OCc3cccc(C(=O)O)c3)cc2)C(=O)NC1=S]

or a salt thereof.

2. The method of claim 1, wherein the autoimmune disease or disorder is selected from the group consisting of type I diabetes, rheumatoid arthritis, multiple sclerosis, and systemic lupus erythematosus.

3. The method of claim 1 wherein the subject has a 1858T PTPN22 polymorphism on at least one allele.

4. The method of claim 1, wherein the subject is human.

5. A method of treating an abnormal early B-cell tolerance checkpoint in a subject the method comprising administering a composition comprising an inhibitor of PTPN22 to a subject in need thereof, wherein the inhibitor of PTPN22

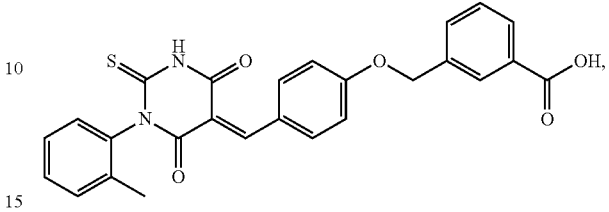

or a salt thereof.

6. The method of claim 5, wherein the subject fails to remove autoreactive B cells.

7. The method of claim 5 wherein the subject has a 1858T PTPN22 polymorphism on at least one allele.

8. The method of claim 5, wherein the subject is human.

* * * * *

```
                        SEQUENCE LISTING

<160> NUMBER OF SEQ ID NOS: 1253

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
ctagtgctct tggtgtatat t                                              21

<210> SEQ ID NO 2
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 2
aagaatccac ctgacttcc                                                 19

<210> SEQ ID NO 3
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 3
ctgttgccaa catcctcta                                                 19

<210> SEQ ID NO 4
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 4

Asp Leu Glu Leu Tyr Tyr Phe Asp Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 5

Ile Ser Gly Ser Tyr Tyr Asn Tyr
1               5
```

```
<210> SEQ ID NO 6
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 6

Ser Pro Pro Phe Asp Trp Ile Tyr Tyr Phe Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 7

Arg Tyr Gly Gly Asn Tyr Tyr Phe Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 8

Gln Thr Glu Trp Glu Leu Asp Ala Phe Asp Ile
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 9

Asp Pro Gly Lys Gly Tyr Tyr Gly Ser Gly Ser Tyr Tyr Tyr Tyr
1               5                   10                  15

Gly Met Asp Val
            20

<210> SEQ ID NO 10
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 10

Thr Asn Glu Pro Asn Ala Phe Asp Ile
1               5

<210> SEQ ID NO 11
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 11
```

```
Asp Arg Ala Asp Tyr Tyr Asp Ser Ser Gly Tyr Tyr Ala Phe Asp
1               5                   10                  15

Ile

<210> SEQ ID NO 12
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 12

Asn Arg Pro Pro Gly Ala Ile Asn Tyr Tyr Gly Met Asp Val
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 13

Gly Gly Gly Ala Thr Glu Tyr
1               5

<210> SEQ ID NO 14
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 14

Thr His Pro Gln Ser Asp Ala Phe Asp Ile
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 15

Ile Leu Gly Gly Ile Thr Met Val Arg Gly Ala Glu Asp Ala Phe Asp
1               5                   10                  15

Ile

<210> SEQ ID NO 16
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 16

Glu Lys Gly Trp Phe Gly Glu Leu Glu Gly Leu Ala Ile Asp Tyr
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Chemically Synthesized
```

```
<400> SEQUENCE: 17

Gly Leu Thr Gly Asp Ser Gly Thr Asp Trp Tyr Phe Asp Leu
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 18

His Pro Tyr Ser Ser Ser Phe Asp Tyr
1               5

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 19

Asp Pro Arg Leu Gly Ser Gly Ser Tyr Tyr Tyr Tyr Gly Met Asp Val
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 20

Asn Lys Leu Asn Trp Gly Leu Asp Tyr
1               5

<210> SEQ ID NO 21
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 21

Gly Trp Gly Phe Gly Asn Trp Phe Asp Pro
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 22

Ser Phe Ser Arg Leu Ala Ser Phe Asp Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Chemically Synthesized
```

```
<400> SEQUENCE: 23

Val Gly Gly Arg Gly Gly Asp Phe Asp Tyr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 24

Ser Gly Ser Ser Trp Tyr Tyr Phe Asp Tyr
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 25

Val Met Ala Val Tyr Tyr Phe Asp Tyr
1               5

<210> SEQ ID NO 26
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 26

Gly Pro Ser Arg Gly Gly Glu Val Phe Asp Tyr
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 27

Leu Arg Ile Pro Asp Tyr Asp Ser Ser Gly Tyr Tyr Phe Asp Tyr
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 28

Gly Ser Ile Pro Ser Asp Tyr Tyr Phe Asp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 29
```

```
Thr Ile Tyr Ser Ser Ser Trp Tyr Trp Phe Asp Pro
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 30

Asp Tyr Tyr Asp Ser Ser Gly Tyr Tyr Tyr Trp Tyr Phe Asp Leu
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 31

Gly Gly Arg Asp Ser Ser Trp Tyr Ile Ala Phe Asp Ile
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 32

Gly Gln Thr Thr Asn Leu Gly Met Gly Pro Asn Trp Phe Asp Pro
1               5                   10                  15

<210> SEQ ID NO 33
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 33

Asp Pro Leu Ser Arg Tyr Cys Ser Gly Gly Ser Cys Tyr Ser Gly Ala
1               5                   10                  15

Phe Asp Ile

<210> SEQ ID NO 34
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 34

Gly Ile Ala Val Ala Gly Tyr Phe Asp Tyr
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Chemically Synthesized
```

<400> SEQUENCE: 35

Asp Arg Leu Gly Ser Phe Asp Tyr
1               5

<210> SEQ ID NO 36
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 36

Asp Ala Ala Leu Arg Tyr Phe Asp Trp Leu Leu Asp Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 37

Asp Leu Val Gly Ile Arg Ala Thr Asp Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 38

Asp Val Asn Ala Ala Ala Gly Asn Arg Ala Tyr Phe Gln His
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 39

Asp Gly Asp Ser Gly Ser Tyr Phe Asp Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 40

Val Cys Ser Pro Glu Leu Gly Gln Trp Ile Asp Ile
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 41

```
Asp Trp Gly Thr Arg Ala Phe Asp Ile
1               5

<210> SEQ ID NO 42
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 42

Gly Ile Val Ala Val Ala Gly Asn Leu Asp Tyr
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 43

Gln Gln Tyr Gly Ser Ser Pro Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 44

Gln Gln Ser Tyr Ser Thr Pro Trp Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 45

Gln Gln Tyr Gly Ser Ser Pro Trp Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 46

Gln Gln Arg Ser Asn Trp Pro Leu Thr
1               5

<210> SEQ ID NO 47
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 47
```

Gln Gln Tyr Gly Ser Ser Pro Pro Leu Thr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 48

Leu Gln Asp Tyr Asn Tyr Pro Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 49

Met Gln Ala Leu Gln Thr Pro Leu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 50

Leu Gln His Asn Ser Tyr Pro Pro Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 51

Gln Gln Arg Ser Asn Trp Pro Trp Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 52

Leu Gln His Asn Ser Tyr Leu Trp Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 53

Met Gln Gly Thr His Trp Pro Leu Thr

```
1               5
```

<210> SEQ ID NO 54
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 54

```
Gln Gln Tyr Gly Ser Ser Pro Arg Thr
1               5
```

<210> SEQ ID NO 55
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 55

```
Gln Gln Tyr Asn Asn Trp Pro Gln Thr
1               5
```

<210> SEQ ID NO 56
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 56

```
Gln Gln Ser Tyr Ser Thr Pro Leu Thr
1               5
```

<210> SEQ ID NO 57
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 57

```
Gln Gln Tyr Gly Ser Ser Tyr Thr
1               5
```

<210> SEQ ID NO 58
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 58

```
Gln Gln Ser Tyr Ser Thr Pro Phe Thr
1               5
```

<210> SEQ ID NO 59
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 59

```
Gln Gln Tyr Asn Ser Tyr Ser Pro Trp Thr
1               5                   10
```

```
<210> SEQ ID NO 60
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 60

Gln Gln Tyr Gly Ser Ser Pro Pro Tyr Thr
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 61

Gln Gln Tyr Gly Ser Ser Leu Gly Thr
1               5

<210> SEQ ID NO 62
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 62

Gln Gln Tyr Asp Asn Leu Pro Arg Val Thr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 63

Ser Ser Tyr Thr Ser Ser Ser Thr Val
1               5

<210> SEQ ID NO 64
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 64

Gln Ser Tyr Asp Ser Ser Leu Ser Gly Tyr Val
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 65

Gln Val Trp Asp Ser Ser Ser Asp Gln Asn Trp Val
1               5                   10
```

<210> SEQ ID NO 66
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 66

Ser Ser Tyr Ala Gly Ser Asn Asn Leu Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 67

Gln Ser Ala Asp Ser Ser Gly Thr Tyr Pro Val
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 68

Met Ile Trp Pro Ser Asn Ala Tyr Val Val
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 69

Ala Ala Trp Asp Asp Ser Leu Asn Gly Pro Val
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 70

Cys Ser Tyr Ala Gly Ser Ser Thr Tyr Val
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 71

Gln Ser Tyr Asp Ser Ser Leu Ser Gly Val Val
1               5                   10

```
<210> SEQ ID NO 72
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 72

Ala Ala Trp Asp Asp Ser Leu Asn Gly His Val Val
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 73

Ala Ala Trp Asp Asp Ser Leu Ser Gly Trp Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 74

Ser Ser Tyr Thr Ser Ser Ser Thr Leu Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 75

Gly Thr Trp Asp Ser Ser Leu Ser Ala Tyr Val
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 76

Gln Val Trp Asp Ser Ser Ser Asp His Tyr Val
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 77

Gln Val Trp Asp Ser Ser Ser Asp His Val Val
1               5                   10

<210> SEQ ID NO 78
```

```
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 78

Gly Thr Trp Asp Ser Ser Leu Ser Ala Gly Val
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 79

Pro Arg Pro Arg Gly Glu Pro Leu Leu Asn Trp Ser Trp Ala Phe Asp
1               5                   10                  15

Ile

<210> SEQ ID NO 80
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 80

Ala Glu Glu Gly Val Gly Gly Ser Tyr Phe Asp Tyr
1               5                   10

<210> SEQ ID NO 81
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 81

Asn Pro Ala Arg Glu Tyr Tyr Tyr Asp Ser Ser Gly Tyr Tyr Gly Tyr
1               5                   10                  15

Ala Phe Asp Ile
            20

<210> SEQ ID NO 82
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 82

Ala Arg Glu Arg Gly Val Val Val Pro Ala Ala Ile Val Gly Asp Tyr
1               5                   10                  15

<210> SEQ ID NO 83
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 83

Gly Gln Gln Asp Asn Ala Pro His Thr Pro Leu Tyr Tyr
```

<210> SEQ ID NO 84
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 84

Gly Thr His Thr Ser Ser Ser Gly Ala Phe Asp Ile
1               5                   10

<210> SEQ ID NO 85
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 85

Val Ser His Ile Val Val Val Pro Ala Ala Ile Arg Gly Gly Asp Ala
1               5                   10                  15

Phe Asp Ile

<210> SEQ ID NO 86
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 86

Asp Pro Val Gly Ala Cys Val Phe Asp Tyr
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 87

Thr Val Asp Tyr Tyr Asp Ser Ser Gly Tyr Tyr Tyr Ser Ala Phe Asp
1               5                   10                  15

Ile

<210> SEQ ID NO 88
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 88

Gly Gly Asp Asp Ser Arg Ser Pro Asn Gly Gly Tyr Cys Leu Asp Tyr
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Chemically Synthesized

```
<400> SEQUENCE: 89

Glu Gly Pro Gly Ile Val Gly Val His His Pro Tyr Phe Asp Tyr
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 90

Gly Ser Ile Gly Val Gly Gly Ser Leu Tyr Gly Asn Trp Phe Asp Pro
1               5                   10                  15

<210> SEQ ID NO 91
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 91

Arg Gly Leu Gly Ile Val His Tyr Phe Asp Tyr
1               5                   10

<210> SEQ ID NO 92
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 92

Leu Trp Gly Gly Ile Lys Pro Gly Ile Ala Ala Ala Gly Thr Ala Phe
1               5                   10                  15

Asp Ile

<210> SEQ ID NO 93
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 93

Ala Arg Leu Ala Glu His Tyr Gln Arg Tyr Gly Gly Asn Ser Gly Pro
1               5                   10                  15

Phe Asp Tyr

<210> SEQ ID NO 94
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 94

Arg Gly Lys Leu Thr Met Asp Arg Gly Asn Trp Phe Asp Pro
1               5                   10

<210> SEQ ID NO 95
<211> LENGTH: 12
<212> TYPE: PRT
<213> ORGANISM: Artificial Sequence
```

```
<220> FEATURE:
<223> OTHER INFORMATION: Chemically Synthesized

<400> SEQUENCE: 95

Asp His Leu Ile Gly Ser Gly Ser Tyr Phe Asp Tyr
1               5                   10

<210> SEQ ID NO 96
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 96

Asp Pro Leu Glu Gly Lys Ser Ile Ala Ala Gly Pro Trp Asp Phe
1               5                   10                  15

Asp Tyr

<210> SEQ ID NO 97
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 97

Gly Ile Ala Val Ala Gly Glu Ser Val Asp Tyr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 98

Leu Arg Asp Ser Gly Ser Ser Tyr Phe Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 99

Ala Gly Tyr Ser Ser Ser Trp Ser Ala Phe Asp Tyr
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 100

Asp Lys Ala Ala Ala Gly Thr Asp Tyr Tyr Tyr Gly Met Asp Val
1               5                   10                  15

<210> SEQ ID NO 101
<211> LENGTH: 13
<212> TYPE: PRT
```

<213> ORGANISM: Artificial Sequence
<220> FEATURE:
<223> OTHER INFORMATION: Chemically Synthesized

<400> SEQUENCE: 101

Asp Arg Ala Gly Tyr Ser Ser Ser Asp Trp Phe Asp Pro
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 102

Asp Thr Ala Ala Ala Gly Leu Gln Ser Arg Tyr Tyr Phe Asp Tyr
1               5                   10                  15

<210> SEQ ID NO 103
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 103

Asp Pro Cys Ser Asp Tyr Gly Asp Ser Tyr Phe Asp Tyr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 104

Asp Met Ala Ala Ala Gly Pro Tyr Tyr Phe Asp Tyr
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 105

Val His Ala Arg Ile Ala Val Ala Ala Arg Asn Asp Tyr
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 106

Asp Gly Gly Asp Gly Tyr Lys Tyr Gly Tyr Phe Gln His
1               5                   10

<210> SEQ ID NO 107
<211> LENGTH: 14
<212> TYPE: PRT
<213> ORGANISM: Artificial Sequence

```
<220> FEATURE:
<223> OTHER INFORMATION: Chemically Synthesized

<400> SEQUENCE: 107

Val Trp Gly Ala Thr Thr Met Gly Gly His Tyr Phe Asp Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 108

Asp Val Arg Ile Ala Val Ala Gly Phe Asp Tyr
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 109

Arg Gln Leu Gly Leu Ser Ile Glu Tyr Trp Tyr Phe Asp Leu
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 110

Ala Leu Gly Arg Tyr Ser Ser Gly Trp Thr Gly Trp Phe Asp Pro
1               5                   10                  15

<210> SEQ ID NO 111
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 111

Gly Gly Gly Ser Pro Trp Gly Trp Tyr Phe Asp Leu
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 112

Ala Ser His His Arg Asn Thr Tyr Cys Ser Ser Thr Ser Cys Phe Asp
1               5                   10                  15

Tyr

<210> SEQ ID NO 113
<211> LENGTH: 14
<212> TYPE: PRT
```

```
<213> ORGANISM: Artificial Sequence
<220> FEATURE:
<223> OTHER INFORMATION: Chemically Synthesized

<400> SEQUENCE: 113

Gly Gly Met Val Asp Ser Ser Gly Trp Tyr Tyr Phe Asp Tyr
1               5                   10

<210> SEQ ID NO 114
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 114

Asp Ile Ser Leu Tyr Tyr Tyr Asp Ser Ser Gly Tyr Ser Ala Gly Val
1               5                   10                  15

Phe Asp Tyr

<210> SEQ ID NO 115
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 115

Gln His Tyr Asn Pro Tyr Ser Arg Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 116

Met Gln Ala Thr Gln Phe Pro Trp Thr
1               5

<210> SEQ ID NO 117
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 117

Gln Gln Tyr Tyr Ser Thr Pro Phe Met Tyr Thr
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 118

Gln Gln Tyr Tyr Ser Ala Pro Gln Thr
1               5

<210> SEQ ID NO 119
<211> LENGTH: 8
```

```
<212> TYPE: PRT
<213> ORGANISM: Artificial Sequence
<220> FEATURE:
<223> OTHER INFORMATION: Chemically Synthesized

<400> SEQUENCE: 119

Met Gln Ala Leu Gln Thr Pro Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 120

Gln Gln Tyr Tyr Ser Thr Pro Leu Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 121

Gln Gln Tyr Tyr Ser Thr Pro Cys Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 122

Gln Gln Tyr Gly Ser Ser Pro Leu Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 123

Gln Gln Tyr Gly Ser Ser Pro Pro Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 124

Met Gln Gly Ile His Leu Arg Tyr Thr
1               5

<210> SEQ ID NO 125
<211> LENGTH: 9
<212> TYPE: PRT
```

<213> ORGANISM: Artificial Sequence
<220> FEATURE:
<223> OTHER INFORMATION: Chemically Synthesized

<400> SEQUENCE: 125

Gln Gln Tyr Asn Ser Tyr Pro Leu Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 126

Gln Gln Arg Ile Asn Trp Leu Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 127

Gln Gln Tyr Gly Ser Ser Pro Gly Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 128

Gln Gln Tyr Gly Ser Ser Pro Gln Thr
1               5

<210> SEQ ID NO 129
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 129

Met Gln Gly Thr His Trp Pro Pro Tyr Thr
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 130

Gln Gln Ser Tyr Ser Thr Pro Tyr Thr
1               5

<210> SEQ ID NO 131
<211> LENGTH: 10
<212> TYPE: PRT
<213> ORGANISM: Artificial Sequence

```
<220> FEATURE:
<223> OTHER INFORMATION: Chemically Synthesized

<400> SEQUENCE: 131

Ala Trp Asp Asp Ser Leu Asn Gly Pro Val
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 132

Ser Ser Tyr Thr Ser Ser Ser Asn Val Val
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 133

Thr Trp Asp Ser Ser Leu Ser Ala Val Val
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 134

Gln Ser Tyr Asp Ser Ser Asn His Val Val
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 135

Gln Ser Tyr Asp Ser Ser Leu Ser Gly Ser Val
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 136

Cys Ser Tyr Ala Gly Ser Tyr Thr Tyr Val
1               5                   10

<210> SEQ ID NO 137
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 137

Tyr Asp Ser Ser Leu Ser Gly Ser Val Val
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 138

Ser Ser Tyr Thr Ser Ser Ser Thr Phe Gly Val
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 139

Ser Ser Phe Thr Ser Ile Thr Tyr Val Val
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 140

Ala Trp Asp Asp Ser Leu Asn Gly Val Val
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 141

Ser Ser Tyr Thr Ser Ser Ser Thr Phe Val Val
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 142

Ala Gly Ser Ser Thr Phe His Tyr Val
1               5

<210> SEQ ID NO 143
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 143

Gln Ala Trp Asp Ser Ser Thr Val Val
1               5

<210> SEQ ID NO 144
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 144

Gly Ala Asp His Gly Ser Gly Ser Asn Phe Val Trp Val
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 145

Gly Thr Trp Asp Ser Ser Leu Ser Ala Pro Trp Val
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 146

Ser Ser Tyr Ala Gly Ser Asn Asn Phe Tyr Val
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 147

Pro Arg Gly Arg Tyr Trp Tyr Phe Asp Leu
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 148

Gly Leu Gly Val Ser Gly Trp Phe Asp Tyr
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Chemically Synthesized

```
<400> SEQUENCE: 149

His Gln Ala Arg Pro Tyr Tyr Tyr Gly Met Asp Val
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 150

Val Ser Gly Asp Ala Phe Asp Ile
1               5

<210> SEQ ID NO 151
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 151

Ala Asn Trp Gly Ser Tyr Asn Trp Phe Asp Pro
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 152

Asp Leu Ser Trp Gly Pro Tyr Trp Tyr Phe Asp Leu
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 153

Gln Pro Gly Gln Tyr Ser Ser Ser Trp Tyr Ala Phe Asp Ile
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 154

Asp Arg Trp Ala Gly Ile Thr Gly Thr Thr Pro Phe Asp Tyr
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 155
```

```
Tyr Ser Gly Tyr Asp Phe Thr Tyr Tyr Phe Asp Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 156

Arg Asp Ser Ala Tyr Ser Ser Gly Phe Asp Tyr
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 157

Ala Val Phe Ile Asp Tyr
1               5

<210> SEQ ID NO 158
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 158

Asp Pro Pro Glu Leu Gly Met Gly Glu Ser Gly Phe Asp Tyr
1               5                   10

<210> SEQ ID NO 159
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 159

Asp Leu Gly Ser Asn Tyr Asp Tyr
1               5

<210> SEQ ID NO 160
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 160

Asp Pro Arg Ser Ser Trp Tyr Phe Asp Tyr
1               5                   10

<210> SEQ ID NO 161
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 161
```

Asp Arg Ile Ala Ala Ala Gly Thr Trp Tyr Phe Asp Leu
1               5                   10

<210> SEQ ID NO 162
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 162

Gly Ala Gly Tyr Tyr Phe Asp Tyr
1               5

<210> SEQ ID NO 163
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 163

Asp Ser Ser Ala His Glu Pro Ser Trp Gly Tyr Phe Asp Tyr
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 164

Asp Leu Gly Ala Asp Ser Ser Ser Trp Thr Phe Asp Tyr
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 165

Gly His Pro Lys Gly Asn Trp Phe Asp Pro
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 166

Ala Pro Arg Phe Gly Glu Leu Tyr Phe Asp Tyr
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 167

Ala Val Gly Ala Thr Val Asp Phe Asp Tyr

```
1               5               10

<210> SEQ ID NO 168
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 168

Gln Pro Gly Tyr Ser Tyr Gly Phe Asp Tyr
1               5               10

<210> SEQ ID NO 169
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 169

Asp Gly Trp Glu Leu Tyr His Trp Phe Asp Pro
1               5               10

<210> SEQ ID NO 170
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 170

Gly Arg Asp Thr Thr Lys Ala Ser Tyr Tyr Asp Ser Ser Gly Tyr Tyr
1               5               10              15

Tyr

<210> SEQ ID NO 171
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 171

Val Leu Tyr Pro Gly Asn Ala Phe Asp Ile
1               5               10

<210> SEQ ID NO 172
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 172

Asn Ser Gly Ser Tyr Tyr Phe Asp Tyr
1               5

<210> SEQ ID NO 173
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 173
```

Asp Ser Ser Ala Tyr Ser Gly Ser Tyr Tyr Phe Asp Tyr
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 174

Arg Gly Ser Ser Ser Trp Gly Tyr Phe Asp Tyr
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 175

Asp Leu Ala Gly Thr Asn Tyr Tyr Tyr Gly Met Asp Val
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 176

His Tyr Ser Ser Arg Ala Glu Tyr Phe Gln His
1               5                   10

<210> SEQ ID NO 177
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 177

Arg Arg Asp Tyr Ser Asn Tyr Asp Tyr
1               5

<210> SEQ ID NO 178
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 178

Ala Asn Gly Ser Gly Ser Tyr Tyr Asn Tyr Tyr Tyr Gly Met Asp Val
1               5                   10                  15

<210> SEQ ID NO 179
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 179

Gly Thr Ala His Ser Asn Tyr Ser Gly Phe Asp Tyr

```
1               5                    10
```

<210> SEQ ID NO 180
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 180

Gln Gln His Asp Asn Leu Pro Tyr Thr
1               5

<210> SEQ ID NO 181
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 181

Gln Gln Tyr Gly Ser Ser Pro Phe Thr
1               5

<210> SEQ ID NO 182
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 182

Gln Gln Tyr Gly Ser Ser Pro Lys Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 183

Gln Gln Leu Asn Ser Tyr Pro Leu Thr
1               5

<210> SEQ ID NO 184
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 184

Gln Gln Arg Ser Asn Trp Pro Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 185

Gln Gln Tyr Asn Asn Trp Pro Phe Thr
1               5

<210> SEQ ID NO 186
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 186

Gln Gln Tyr Asp Asn Leu Pro Ile Phe Thr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 187

Gln Gln Tyr Asn Asn Trp Pro Pro Phe Thr
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 188

Gln Gln Tyr Tyr Ser Phe Pro Phe Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 189

Gln Gln Tyr Asn Asn Trp Pro Tyr Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 190

Gln Gln Tyr Asn Ser Tyr Ser Arg Thr
1               5

<210> SEQ ID NO 191
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 191

Gln Gln Tyr Asp Asn Leu Pro Pro Leu Thr
1               5                   10

```
<210> SEQ ID NO 192
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 192

Gln Gln Arg Ser Asn Trp Arg Gly Thr
1               5

<210> SEQ ID NO 193
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 193

Gln Gln Tyr Asn Asn Trp Pro Leu Thr
1               5

<210> SEQ ID NO 194
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 194

Gln Gln Tyr Asn Asn Trp Pro Met Tyr Thr
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 195

Gln Gln Tyr Gly Ser Ser Arg Tyr Thr
1               5

<210> SEQ ID NO 196
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 196

Gln Gln Tyr Asn Asn Trp Trp Thr
1               5

<210> SEQ ID NO 197
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 197

Gln Gln Arg Ser Asn Trp Leu Thr
1               5
```

<210> SEQ ID NO 198
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 198

Cys Ser Tyr Ala Gly Ser Tyr Val Val
1               5

<210> SEQ ID NO 199
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 199

Cys Ser Tyr Ala Gly Arg Val
1               5

<210> SEQ ID NO 200
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 200

Ala Ala Trp Asp Asp Ser Leu Ser Gly Tyr Val
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 201

Gly Thr Trp Asp Ser Ser Leu Ser Ala Val Val
1               5                   10

<210> SEQ ID NO 202
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 202

Gly Thr Trp Asp Ser Ser Leu Ser Val
1               5

<210> SEQ ID NO 203
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 203

Gly Ala Asp His Gly Ser Gly Ser Asn Phe Val Tyr Val
1               5                   10

<210> SEQ ID NO 204

```
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 204

Gln Ala Trp Asp Ser Ser Thr Tyr Val
1               5

<210> SEQ ID NO 205
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 205

Gln Ser Ala Asp Ser Ser Gly Thr Tyr Gly Val
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 206

Cys Ser Tyr Ala Gly Ser Ser Thr Leu Val
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 207

Gln Gly Val Thr Ser Ala Tyr Asn Trp Phe Asp Pro
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 208

Asp Gly Pro Ala Gly Val Gly Val Gly Phe Asp Tyr
1               5                   10

<210> SEQ ID NO 209
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 209

Gly Phe Ser Ala Ser Thr Gly Thr Thr Thr Asp Ala Phe Asp Ile
1               5                   10                  15

<210> SEQ ID NO 210
<211> LENGTH: 17
```

```
<212> TYPE: PRT
<213> ORGANISM: Artificial Sequence
<220> FEATURE:
<223> OTHER INFORMATION: Chemically Synthesized

<400> SEQUENCE: 210

Asp Phe Gln Pro Trp Gly Tyr Phe Asp Trp Pro Leu Asn Trp Phe Asp
1               5                   10                  15

Pro

<210> SEQ ID NO 211
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 211

Val Arg Arg Gly Gly Ala Ala Ala Gly Ile Val Asp Trp Tyr Tyr Tyr
1               5                   10                  15

Tyr Gly Met Asp Val
            20

<210> SEQ ID NO 212
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 212

Arg Arg Tyr Ser Ser Ser Phe Asp Tyr
1               5

<210> SEQ ID NO 213
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 213

Ala Asn Ile Val Val Val Pro Ala Ala Met Tyr Asn Trp Phe Asp Pro
1               5                   10                  15

<210> SEQ ID NO 214
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 214

Val Arg Gly Gly Ile Ala Ala Ala Gly Phe Leu Ala Gly Glu Asn Gly
1               5                   10                  15

Ser Phe Asp Tyr
            20

<210> SEQ ID NO 215
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 215
```

```
Asp Trp Ala Asp Tyr Asp Ile Leu Thr Gly Ser Gln Ser Gly Pro Tyr
1               5                   10                  15

Trp Phe Asp Pro
            20

<210> SEQ ID NO 216
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 216

Asn Pro Thr Thr Ile Thr Thr Ile Ile Trp Phe Asn Pro
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 217

Val Pro Gly Ser Ile Ala Ala Arg Pro Asn Leu Phe Asp Tyr
1               5                   10

<210> SEQ ID NO 218
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 218

Gly Pro Gly Tyr Tyr Tyr Asp Ser Ser Gly Pro Tyr Tyr Gly Met Asp
1               5                   10                  15

Val

<210> SEQ ID NO 219
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 219

Val Gly Cys Ser Ser Thr Ser Cys Tyr Glu Asp Phe Asp Leu
1               5                   10

<210> SEQ ID NO 220
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 220

Asp Arg Asn Ser Val Asp Tyr
1               5

<210> SEQ ID NO 221
<211> LENGTH: 14
<212> TYPE: PRT
<213> ORGANISM: Artificial Sequence
```

```
-continued

<220> FEATURE:
<223> OTHER INFORMATION: Chemically Synthesized

<400> SEQUENCE: 221

Asp Pro Asp Leu Arg Tyr Ser Ser Ser Ser Phe Asp Tyr
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 222

Leu His Ala Pro Asn Leu Tyr Tyr Met Asp Val
1               5                   10

<210> SEQ ID NO 223
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 223

Asp Cys Leu Gly Thr Trp Arg Tyr Cys Ser Ser Thr Ser Cys Ser Val
1               5                   10                  15

Gly Ala Asp Tyr
            20

<210> SEQ ID NO 224
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 224

Asp Lys Gly Ser Ala Ala Ala Asp Asn Trp Phe Asp Pro
1               5                   10

<210> SEQ ID NO 225
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 225

Met Lys Arg Leu Gly Ile Asp Tyr
1               5

<210> SEQ ID NO 226
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 226

Ser Tyr Glu Gly Ile Ala Ala Asp Lys Asn Tyr Tyr Tyr Tyr Gly Met
1               5                   10                  15

Asp Val
```

```
<210> SEQ ID NO 227
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 227

Ala Pro Arg Gly Val Pro Ala Ala Asn Trp Phe Asp Pro
1               5                   10

<210> SEQ ID NO 228
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 228

Ala Cys Glu Arg Asp Ile Val Val Pro Ala Val Asn Gly Ala Phe
1               5                   10                  15

Asp Ile

<210> SEQ ID NO 229
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 229

Asp Leu Asn Lys Thr Ser Leu Ala Ala Ala Gly Asp Arg Asp Ala Phe
1               5                   10                  15

Asp Ile

<210> SEQ ID NO 230
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 230

Gln Gln Ser Tyr Ser Thr Pro Arg Tyr Thr
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 231

Arg Gln Ser Tyr Ser Thr Pro Arg Leu Thr
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 232

Gln Gln Arg Ser Asn Trp Pro Pro Trp Thr
```

```
<210> SEQ ID NO 233
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 233

Met Gln Ala Leu Leu Thr Gln Phe Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 234

Gln Gln Tyr Tyr Ser Tyr Pro Gln Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 235

Gln Gln Tyr Tyr Ser Phe Pro Leu Thr
1               5

<210> SEQ ID NO 236
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 236

Leu Gln His Asn Ser Tyr Pro Val Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 237

Gln Gln Leu Asn Ser Tyr Pro Pro Thr
1               5

<210> SEQ ID NO 238
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 238

Gln Gln Tyr Asn Asn Trp Pro Pro Trp Thr
1               5                   10
```

<210> SEQ ID NO 239
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 239

Cys Ser Tyr Ala Gly Ser Ser Thr Pro Asn Tyr Val
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 240

Ala Ala Trp Asp Asp Ser Leu Asn Gly Val Val
1               5                   10

<210> SEQ ID NO 241
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 241

Gln Ser Tyr Asp Ser Ser Asn Gln Val
1               5

<210> SEQ ID NO 242
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 242

Ser Ser Tyr Thr Arg Ser Ser Thr Leu Val
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 243

Ser Ser Tyr Thr Ser Ser Ser Thr Arg Val
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 244

Gly Thr Trp Asp Ser Ser Leu Ser Ala Gly Val Val
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 245

Glu Gly Ser Leu Asn His Asp Ala Phe Asp Ile
1               5                   10

<210> SEQ ID NO 246
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 246

Gly Ser Thr Glu Asn Arg Ile Ala Val Ala Gly Arg Pro Gly Val Gly
1               5                   10                  15

Ala Asp Tyr

<210> SEQ ID NO 247
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 247

Gly Pro Ser Ser Gly Val Pro Phe Ala Phe Asp Tyr
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 248

Arg Trp Thr Gly Gly Ser Tyr Gly Tyr
1               5

<210> SEQ ID NO 249
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 249

Leu Val Arg Glu Glu Arg Tyr Ser Tyr Gly Leu Thr Asn Arg Asp Asp
1               5                   10                  15

Tyr

<210> SEQ ID NO 250
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 250

Val Asp Asn Ser Ser Pro Tyr Asn Trp Phe Asp Pro
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 251

Arg Thr Val Val Gly Lys Lys Gly Asp Trp Tyr Phe Asp Leu
1               5                   10

<210> SEQ ID NO 252
<211> LENGTH: 23
<212> TYPE: PRT
<213> ORGANISM: Artificial Sequence
<220> FEATURE:
<223> OTHER INFORMATION: Chemically Synthesized

<400> SEQUENCE: 252

Glu Ala Tyr Cys Thr Gly Gly Val Cys Tyr Thr Gly Val Leu Gly Tyr
1               5                   10                  15

Tyr Tyr Tyr Tyr Met Asp Val
            20

<210> SEQ ID NO 253
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 253

Asp Thr Gly Ile Thr Gly Thr Phe Asp Tyr
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 254

Gly Arg Ala Gln Asp Ser Ser Gly Pro Asn Pro Leu Asp Tyr
1               5                   10

<210> SEQ ID NO 255
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 255

Asp Leu His Asp Tyr Asp Ile Leu Thr Gly Tyr Tyr Ile Phe Asp Tyr
1               5                   10                  15

<210> SEQ ID NO 256
<211> LENGTH: 21
<212> TYPE: PRT
<213> ORGANISM: Artificial Sequence
<220> FEATURE:
<223> OTHER INFORMATION: Chemically Synthesized -continued

<400> SEQUENCE: 256

Gly Phe Lys Trp Ser Gly Arg Asn Ser Ser Ser Leu Asn Tyr Tyr
1               5                   10                  15

Tyr Tyr Met Asp Val
            20

<210> SEQ ID NO 257
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 257

Gly Pro Arg Leu Gly Thr Ala Arg Lys Pro Phe Asp Tyr
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 258

Leu Gly Ser Asp Tyr Lys Pro Phe Asp Tyr
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 259

Val Glu Gly Leu Ser Val Val Gly Leu Pro Tyr
1               5                   10

<210> SEQ ID NO 260
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 260

Asp Arg Gly Ser Gly Ser Tyr Leu Thr Tyr Tyr Tyr Tyr Tyr Gly Met
1               5                   10                  15

Asp Val

<210> SEQ ID NO 261
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 261

Asp Glu Leu Pro Pro Ile Asp Asp Glu Ser Glu Arg Phe Asp Tyr
1               5                   10                  15

<210> SEQ ID NO 262
<211> LENGTH: 20
<212> TYPE: PRT

<213> ORGANISM: Artificial Sequence
<220> FEATURE:
<223> OTHER INFORMATION: Chemically Synthesized

<400> SEQUENCE: 262

Ser Lys Thr Asp Val Ala Asp His Leu Pro Arg Tyr Ser Gly Tyr Asp
1               5                   10                  15

Pro Gly Asn Tyr
            20

<210> SEQ ID NO 263
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 263

Ala Pro Gly Asp Ser Thr Arg Met Val Asp Tyr
1               5                   10

<210> SEQ ID NO 264
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 264

Trp Tyr Ala Asn Leu Gly Tyr Cys Ser Ser Thr Ser Cys Tyr Thr Ala
1               5                   10                  15

Gly Met Asp Val
            20

<210> SEQ ID NO 265
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 265

Asp Leu Asp Glu Tyr Ser Ser Ser Val Pro Phe Asp Tyr
1               5                   10

<210> SEQ ID NO 266
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 266

Gln Ile Val Val Val Val Asp Ala Ile Arg Asp Ala Phe Asp Ile
1               5                   10                  15

<210> SEQ ID NO 267
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 267

Ser Asp Ser Ser Ser Trp Gly Ala Phe Asp Ile
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 268

Asp Val Trp Gly Ser Tyr Arg Tyr Leu Asp Tyr
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 269

Gly Trp Ile Thr Gly Thr Ser Pro Asp Phe Asp Tyr
1               5                   10

<210> SEQ ID NO 270
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 270

Gly Asp Leu His Gly Asp Leu Asp Tyr
1               5

<210> SEQ ID NO 271
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 271

Gly Gly Ser Gly Trp Ser Pro Pro Asn Tyr Tyr Tyr Tyr Met Asp Val
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 272

Asp Pro Val Val Val Pro Ala Ala Met Trp Gly Thr Phe Asp Tyr
1               5                   10                  15

<210> SEQ ID NO 273
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 273

Gly Ala Pro Arg Gly Ala Phe Asp Ile
1               5

<210> SEQ ID NO 274
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 274

Glu Arg Asp Tyr Val Trp Gly Ser Tyr Arg Tyr Thr Gly Pro Trp Phe
1               5                   10                  15

Asp Pro

<210> SEQ ID NO 275
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 275

Gly Arg Tyr Gly Ala Ile Ala Ala Ala Gly Thr Val Leu Asp Tyr
1               5                   10                  15

<210> SEQ ID NO 276
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 276

Gln Asp Ile Asp Ile Val Val Val Ala Ala Thr Pro Arg Gly Ile
1               5                   10                  15

Asp Tyr

<210> SEQ ID NO 277
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 277

Gln Gln Tyr Gly Ser Ser Pro Met Gln Ser
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 278

Gln Gln Tyr Gly Ser Ser Pro Pro Asn Thr
1               5                   10

<210> SEQ ID NO 279
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 279

Gln Gln Tyr Gly Ser Ser Leu Thr
1               5

<210> SEQ ID NO 280
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 280

Gln Gln Ser Tyr Ser Thr Pro Thr Arg Gly Met Thr
1               5                   10

<210> SEQ ID NO 281
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 281

Leu Gln His Asn Ser Tyr Pro Tyr Thr
1               5

<210> SEQ ID NO 282
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 282

Gln Ser Ala Asp Ser Ser Gly Thr Tyr Val Val
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 283

Ala Trp Asp Asp Ser Leu Ser Gly Val Val
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 284

Ser Ser Tyr Thr Ser Ser Ser Thr Tyr Val
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 285

Ala Ala Trp Asp Asp Ser Leu Asn Gly Trp Val

```
1               5                   10
```

<210> SEQ ID NO 286
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 286

```
Ala Ala Trp Asp Asp Ser Leu Asn Gly Arg Val
1               5                   10
```

<210> SEQ ID NO 287
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 287

```
Cys Ser Tyr Ala Gly Ser Ser Tyr Val
1               5
```

<210> SEQ ID NO 288
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 288

```
Ser Ser Tyr Ala Gly Ser Asn Asn Tyr Val
1               5                   10
```

<210> SEQ ID NO 289
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 289

```
Ala Ala Trp Asp Asp Ser Leu Ser Gly Val Val
1               5                   10
```

<210> SEQ ID NO 290
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 290

```
Ser Ser Tyr Thr Ser Ser Ser Thr Leu Tyr Val
1               5                   10
```

<210> SEQ ID NO 291
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 291

```
Gln Ser Tyr Asp Ser Asn Val Val
1               5
```

<210> SEQ ID NO 292
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 292

Gln Ala Trp Asp Ser Ser Thr Asn Tyr Val
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 293

Gln Val Trp Asp Ser Ser Ser Asp His Arg Val
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 294

Cys Ser Tyr Ala Gly Ser Ser Ser Val Val
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 295

Gly Ile Ala Ala Ala Gly Thr Trp Phe Asp Pro
1               5                   10

<210> SEQ ID NO 296
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 296

Asp Pro Phe Arg Arg Phe Gly Gly Tyr Tyr Asp Ser Ser Gly Tyr Tyr
1               5                   10                  15

Asp Tyr

<210> SEQ ID NO 297
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 297

Gly Ile Ala Ala Ala Gly Thr Pro Tyr Trp Phe Asp Pro

<210> SEQ ID NO 298
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 298

Gly Ala Ala Val Val Thr Pro Tyr
1               5

<210> SEQ ID NO 299
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 299

Glu Lys Asp Tyr Tyr Asp Ser Ser Gly Arg Thr Ser Asn Tyr Tyr Tyr
1               5                   10                  15

Tyr Gly Met Asp Val
            20

<210> SEQ ID NO 300
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 300

Arg Met Thr Ala Asn Trp Asp Tyr Tyr Tyr Gly Met Asp Val
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 301

Asp Ala Lys Tyr Asn Trp Asn Asp Gly Arg Ser Trp Phe Asp Pro
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 302

Asp Ser Ser Ile Ala Ala Ala Gly Thr Ser Asp Ala Phe Asp Ile
1               5                   10                  15

<210> SEQ ID NO 303
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 303

```
Asp Arg Thr Thr Val Thr Thr Ile Asn Trp Phe Asp Pro
1               5                   10

<210> SEQ ID NO 304
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 304

Ser Lys Ile Asn Ser Pro Val Thr Met Ile Val Val Gly Ala Lys Gly
1               5                   10                  15

Phe Asp Tyr

<210> SEQ ID NO 305
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 305

Val Arg Met Leu Gly Asp Tyr Asp Tyr Val His Tyr Tyr Tyr Gly Met
1               5                   10                  15

Asp Val

<210> SEQ ID NO 306
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 306

Asp Thr Pro Ala Gly Arg Ser Tyr
1               5

<210> SEQ ID NO 307
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 307

Pro His Ser Ser Ser Ser Asp Tyr Phe Asp Tyr
1               5                   10

<210> SEQ ID NO 308
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 308

Val Leu Thr Val Val Pro Ala Ala Asp Ala Phe Asp Ile
1               5                   10

<210> SEQ ID NO 309
<211> LENGTH: 9
<212> TYPE: PRT
<213> ORGANISM: Artificial Sequence
<220> FEATURE:
```

<223> OTHER INFORMATION: Chemically Synthesized

<400> SEQUENCE: 309

Ile Ile Val Asp Thr Ile Phe Asp Tyr
1               5

<210> SEQ ID NO 310
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 310

Asp Pro Lys Gly Ile Gly Tyr
1               5

<210> SEQ ID NO 311
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 311

Asp Arg Thr Gln Leu Gly Asn Thr Gly Thr Tyr Trp Tyr Phe Asp Leu
1               5                   10                  15

<210> SEQ ID NO 312
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 312

Glu Arg Val Arg Arg Leu Ala Val Ala Gly Pro Tyr Tyr Tyr Tyr Tyr
1               5                   10                  15

Gly Met Asp Val
            20

<210> SEQ ID NO 313
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 313

Lys Gly Ser Ser Ser Gln Tyr Tyr Tyr Tyr Tyr Gly Met Asp Val
1               5                   10                  15

<210> SEQ ID NO 314
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 314

Tyr Gly Tyr Ser Ser Ser Trp Tyr Tyr Tyr Tyr Gly Met Asp Val
1               5                   10                  15

<210> SEQ ID NO 315
<211> LENGTH: 13
<212> TYPE: PRT

```
<213> ORGANISM: Artificial Sequence
<220> FEATURE:
<223> OTHER INFORMATION: Chemically Synthesized

<400> SEQUENCE: 315

Ala Leu Tyr Tyr Tyr Gly Ser Gly Ser Tyr Phe Asp Tyr
1               5                   10

<210> SEQ ID NO 316
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 316

Leu Arg Ala Arg Gly Val Ile Asp Tyr
1               5

<210> SEQ ID NO 317
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 317

Gly Gly Ser Ser Ser Trp Phe Asp Ala Phe Asp Ile
1               5                   10

<210> SEQ ID NO 318
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 318

Asn Ser Ser Ser Ser Ala Phe Asp Ile
1               5

<210> SEQ ID NO 319
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 319

Ser Phe Ser Gly Gly Asp Tyr Asp Tyr
1               5

<210> SEQ ID NO 320
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 320

His Pro Gly Thr Tyr Asp Ile Leu Thr Gly Tyr Tyr Phe Asp Tyr
1               5                   10                  15

<210> SEQ ID NO 321
<211> LENGTH: 12
<212> TYPE: PRT
<213> ORGANISM: Artificial Sequence
```

```
<220> FEATURE:
<223> OTHER INFORMATION: Chemically Synthesized

<400> SEQUENCE: 321

Arg Arg Val Val Arg Gly Val Met Ile Phe Asp Tyr
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 322

Asp Asp Tyr Tyr Gly Ser Gly Ser Pro Tyr Tyr
1               5                   10

<210> SEQ ID NO 323
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 323

Asp Asn Arg Asp His Asp Tyr Gly Gly Asn Ser Pro Trp Phe Asp Pro
1               5                   10                  15

<210> SEQ ID NO 324
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 324

Asp Lys Glu Met Tyr Tyr Tyr Gly Ser Gly Ser Tyr Tyr Trp Phe Asp
1               5                   10                  15

Pro

<210> SEQ ID NO 325
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 325

Glu Asp Asp Pro Leu Trp Phe Gly Asp Tyr
1               5                   10

<210> SEQ ID NO 326
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 326

Gln Phe Ala Gly Trp Glu Leu Arg Lys Gln Tyr Lys Asn Phe Asp Tyr
1               5                   10                  15

<210> SEQ ID NO 327
<211> LENGTH: 10
<212> TYPE: PRT
```

```
<213> ORGANISM: Artificial Sequence
<220> FEATURE:
<223> OTHER INFORMATION: Chemically Synthesized

<400> SEQUENCE: 327

Leu Ile Ser Gly Ser Tyr Tyr Phe Asp Tyr
1               5                   10

<210> SEQ ID NO 328
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 328

Gly Ala Gly Tyr Ser Ser Ser Trp Tyr Tyr Phe Asp Tyr
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 329

Gln Gln Tyr Asn Asn Trp Pro Pro Leu Thr
1               5                   10

<210> SEQ ID NO 330
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 330

Gln Gln Tyr Asn Asn Trp Pro Pro Tyr Thr
1               5                   10

<210> SEQ ID NO 331
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 331

Gln Gln Ser Tyr Ser Thr Arg Thr Phe
1               5

<210> SEQ ID NO 332
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 332

Gln Gln Tyr Tyr Ser Phe Pro Tyr Thr
1               5

<210> SEQ ID NO 333
<211> LENGTH: 9
<212> TYPE: PRT
<213> ORGANISM: Artificial Sequence
```

```
<220> FEATURE:
<223> OTHER INFORMATION: Chemically Synthesized

<400> SEQUENCE: 333

Gln Gln Tyr Asn Ser Tyr Ser Tyr Thr
1               5

<210> SEQ ID NO 334
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 334

Leu Gln His Asn Ser Tyr Pro Leu Thr
1               5

<210> SEQ ID NO 335
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 335

Gln Gln Arg Ser Asn Trp Pro Arg Tyr Thr
1               5                   10

<210> SEQ ID NO 336
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 336

Gln Gln Tyr Tyr Ser Phe Pro Pro Phe Thr
1               5                   10

<210> SEQ ID NO 337
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 337

Gln Gln Tyr Asn Ser Tyr Ser Thr Phe Gly
1               5                   10

<210> SEQ ID NO 338
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 338

Cys Ser Tyr Ala Gly Ser Tyr Thr Trp Val
1               5                   10

<210> SEQ ID NO 339
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 339

Ser Ser Tyr Thr Ser Ser Ser Thr Val Val
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 340

Ser Ser Tyr Thr Ser Ser Ser Thr His Val Val
1               5                   10

<210> SEQ ID NO 341
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 341

Gln Ala Trp Asp Ser Ser Thr Ala Val
1               5

<210> SEQ ID NO 342
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 342

Cys Ser Tyr Ala Gly Ser Ser Thr
1               5

<210> SEQ ID NO 343
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 343

Tyr Ser Thr Asp Ser Ser Gly Asn His Arg Val
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 344

Gln Ser Tyr Asp Ser Ser Leu Ser Gly Trp Val
1               5                   10

<210> SEQ ID NO 345
<211> LENGTH: 15
<212> TYPE: PRT
<213> ORGANISM: Artificial Sequence
<220> FEATURE:
<223> OTHER INFORMATION: Chemically Synthesized

```
<400> SEQUENCE: 345

Gly Trp Ala Gly Asn Trp Gly Leu Gly Ser Asp Ala Phe Asp Ile
1               5                   10                  15

<210> SEQ ID NO 346
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 346

Cys Asp Ile Leu Thr Gly Tyr Tyr Leu Phe Asp Tyr
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 347

Ser Ile Ala Ala Ala Val His Tyr Phe Asp Tyr
1               5                   10

<210> SEQ ID NO 348
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 348

Gly Arg Gly Gly Asn Trp Gly Ser Thr Gln Pro Gly Tyr Tyr Phe Asp
1               5                   10                  15

Tyr

<210> SEQ ID NO 349
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 349

Gly Pro Ile Val Ala Trp Ala Asp Ala Phe Asp Ile
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 350

Val Asn Pro Ser Phe Gly Asp Gln Asp Phe Asp Tyr
1               5                   10

<210> SEQ ID NO 351
<211> LENGTH: 16
<212> TYPE: PRT
<213> ORGANISM: Artificial Sequence
<220> FEATURE:
```

<223> OTHER INFORMATION: Chemically Synthesized

<400> SEQUENCE: 351

Gly Arg Gly Trp Ile Gln Leu Trp Thr Asp Leu Tyr Tyr Phe Asp Tyr
1               5                   10                  15

<210> SEQ ID NO 352
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 352

Asp Tyr Arg Gly Gly Phe Gly Glu Leu Leu Tyr Phe Gln His
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 353

Val Lys Gly Ile Ala Ala Ala Gly Ser Phe Asp Tyr
1               5                   10

<210> SEQ ID NO 354
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 354

Pro Gln Lys Arg Tyr Tyr Tyr Gly Ser Gly Ser Tyr Asp Glu Tyr Phe
1               5                   10                  15

Gln His

<210> SEQ ID NO 355
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 355

Gly Gly Arg Ser Gly Ser Tyr Phe Asp Tyr
1               5                   10

<210> SEQ ID NO 356
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 356

His Ala Ala Val Ala Gly Thr Pro Tyr Tyr Phe Asp Tyr
1               5                   10

<210> SEQ ID NO 357
<211> LENGTH: 12
<212> TYPE: PRT
<213> ORGANISM: Artificial Sequence

```
<220> FEATURE:
<223> OTHER INFORMATION: Chemically Synthesized

<400> SEQUENCE: 357

Gly Gly Ser Gly Ser Tyr Tyr Asn Leu Phe Asp Tyr
1               5                   10

<210> SEQ ID NO 358
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 358

Val Ala Met Val Arg Gly Val Ile Ser Ala Phe Asp Ile
1               5                   10

<210> SEQ ID NO 359
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 359

Asp Arg Tyr Tyr Tyr Asp Ser Ser Gly Tyr Tyr Tyr Tyr Tyr Tyr
1               5                   10                  15

Met Asp Val

<210> SEQ ID NO 360
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 360

Arg Gly Lys Tyr Tyr Phe Asp Tyr
1               5

<210> SEQ ID NO 361
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 361

Asn Tyr Gly Asp Tyr Val Gly Phe Asp Tyr
1               5                   10

<210> SEQ ID NO 362
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 362

His Ile Gly Gly Ala Gly Tyr Ser Gly Pro Phe Asp Tyr
1               5                   10

<210> SEQ ID NO 363
<211> LENGTH: 13
<212> TYPE: PRT
```

```
<213> ORGANISM: Artificial Sequence
<220> FEATURE:
<223> OTHER INFORMATION: Chemically Synthesized

<400> SEQUENCE: 363

Asp Ser Asp Tyr Tyr Gly Ser Gly Ser Tyr Phe Asp Tyr
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 364

Arg Tyr Cys Ser Ser Thr Ser Cys Trp Phe Asp Pro
1               5                   10

<210> SEQ ID NO 365
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 365

Gly Gly Arg Lys Tyr Tyr Gly Ser Gly Ser Tyr Tyr Asp Leu Asp Ala
1               5                   10                  15

Phe Asp Ile

<210> SEQ ID NO 366
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 366

Leu Gly Leu Lys Gly Leu Gly Pro Tyr Phe Asp Tyr
1               5                   10

<210> SEQ ID NO 367
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 367

Arg Tyr Cys Ser Ser Thr Ser Cys Tyr Val Asn Trp Phe Asp Pro
1               5                   10                  15

<210> SEQ ID NO 368
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 368

Ser Tyr Ser Ser Gly Trp Phe Asp Tyr
1               5

<210> SEQ ID NO 369
<211> LENGTH: 14
```

```
<212> TYPE: PRT
<213> ORGANISM: Artificial Sequence
<220> FEATURE:
<223> OTHER INFORMATION: Chemically Synthesized

<400> SEQUENCE: 369

Arg Ser Glu Trp Glu Pro Glu Gly Val Asp Ala Phe Asp Ile
1               5                   10

<210> SEQ ID NO 370
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 370

Asn Pro Tyr Tyr Tyr Gly Ser Gly Arg Pro Pro Phe Asp Tyr
1               5                   10

<210> SEQ ID NO 371
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 371

Val Gly Tyr Gly Ser Gly Ser Tyr Phe Asp Tyr
1               5                   10

<210> SEQ ID NO 372
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 372

His Arg Asp His Ser Ser Ser Trp Asp Thr Leu Gly Tyr Phe Asp Tyr
1               5                   10                  15

<210> SEQ ID NO 373
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 373

Gln Gln Tyr Asn Ser Tyr Trp Thr
1               5

<210> SEQ ID NO 374
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 374

Gln Gln Tyr Asn Asn Arg Pro Pro Tyr Pro
1               5                   10

<210> SEQ ID NO 375
<211> LENGTH: 9
<212> TYPE: PRT
```

```
<213> ORGANISM: Artificial Sequence
<220> FEATURE:
<223> OTHER INFORMATION: Chemically Synthesized

<400> SEQUENCE: 375

Gln Gln Tyr Gly Ser Ser Pro Tyr Thr
1               5

<210> SEQ ID NO 376
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 376

Gln Gln Tyr Tyr Ser Tyr Pro Phe Thr
1               5

<210> SEQ ID NO 377
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 377

Gln Gln Tyr Asn Ser Tyr Ser Pro Tyr Thr
1               5                   10

<210> SEQ ID NO 378
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 378

Gln Gln Arg Ser Asn Trp Pro Pro Tyr Thr
1               5                   10

<210> SEQ ID NO 379
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 379

Gln Gln Tyr Tyr Ser Tyr Pro Tyr Thr
1               5

<210> SEQ ID NO 380
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 380

Gln Gln Arg Ser Asn Ser Leu Thr
1               5

<210> SEQ ID NO 381
<211> LENGTH: 10
<212> TYPE: PRT
<213> ORGANISM: Artificial Sequence
```

```
<220> FEATURE:
<223> OTHER INFORMATION: Chemically Synthesized

<400> SEQUENCE: 381

Gln Gln Tyr Gly Ser Ser Pro Pro Gly Thr
1               5                   10

<210> SEQ ID NO 382
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 382

Gln Gln Tyr Asn Asn Trp Pro Pro Thr Cys Thr
1               5                   10

<210> SEQ ID NO 383
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 383

Gln Gln Tyr Gly Ser Ser Pro Pro Tyr
1               5

<210> SEQ ID NO 384
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 384

Gln Gln Tyr Tyr Ser Phe Pro Arg Thr
1               5

<210> SEQ ID NO 385
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 385

Gln Gln Ala Asn Ser Phe Pro Pro Leu Thr
1               5                   10

<210> SEQ ID NO 386
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 386

Gln Gln Tyr Gly Ser Phe Leu Thr
1               5

<210> SEQ ID NO 387
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 387

Ser Ser Tyr Thr Ser Ser Ser Thr Trp Val
1               5                   10

<210> SEQ ID NO 388
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 388

Cys Ser Tyr Ala Gly Ser Ser Thr Lys Val
1               5                   10

<210> SEQ ID NO 389
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 389

Ser Ser Tyr Thr Ser Ser Ser Thr Tyr Trp Val
1               5                   10

<210> SEQ ID NO 390
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 390

Gln Val Trp Asp Ser Ser Asp His Val Val
1               5                   10

<210> SEQ ID NO 391
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 391

Ser Leu Ser Gly Pro Asp Gly Thr Gly Thr Lys Val Thr Val Leu
1               5                   10                  15

<210> SEQ ID NO 392
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 392

Tyr Ser Thr Asp Ser Ser Gly Asn Gln Gly Val
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Chemically Synthesized

```
<400> SEQUENCE: 393

Cys Ser Tyr Ala Gly Ser Ser Thr Trp Val
1               5                   10

<210> SEQ ID NO 394
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 394

Gly Gln Leu His Val Leu Leu Trp Phe Gly Glu Leu Leu Ser Ser His
1               5                   10                  15

Ile Phe Asp Tyr
            20

<210> SEQ ID NO 395
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 395

Arg Ser Asp Tyr Asp Ser Ser Gly Tyr Pro Ile Ser Val Asp Tyr
1               5                   10                  15

<210> SEQ ID NO 396
<211> LENGTH: 23
<212> TYPE: PRT
<213> ORGANISM: Artificial Sequence
<220> FEATURE:
<223> OTHER INFORMATION: Chemically Synthesized

<400> SEQUENCE: 396

Val Gly Asp Pro Lys Asp Tyr Tyr Gly Ser Gly Gly Gly Asn Tyr
1               5                   10                  15

Tyr Tyr Tyr Gly Met Asp Val
            20

<210> SEQ ID NO 397
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 397

His Val Val Ala Thr Thr Asn Leu Ala Ser Tyr Tyr Tyr Gly Met
1               5                   10                  15

Asp Val

<210> SEQ ID NO 398
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 398

Ser Thr Gly Tyr Tyr Trp Tyr Phe Asp Leu
1               5                   10
```

<210> SEQ ID NO 399
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 399

Val Phe Ser Arg Ser Val Val Thr Tyr Tyr Tyr Tyr Tyr Gly Met Asp
1               5                   10                  15

Val

<210> SEQ ID NO 400
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 400

Tyr Tyr Gly Ser Gly Ser Leu Ser Asp
1               5

<210> SEQ ID NO 401
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 401

Glu Thr Thr Arg Gly Asp Thr Ala Met Val Thr Pro Cys Asn Tyr
1               5                   10                  15

<210> SEQ ID NO 402
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 402

Asp Leu Cys Arg Gly Gly Gly Tyr Asp Ile Leu Thr His Asp Ala Phe
1               5                   10                  15

Asp Ile

<210> SEQ ID NO 403
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 403

Asp Arg Tyr Cys Ser Ser Thr Ser Cys Tyr Ser Tyr Tyr Tyr Tyr Gly
1               5                   10                  15

Met Asp Val

<210> SEQ ID NO 404
<211> LENGTH: 17
<212> TYPE: PRT
<213> ORGANISM: Artificial Sequence
<220> FEATURE:
<223> OTHER INFORMATION: Chemically Synthesized

```
<400> SEQUENCE: 404

Val Ala Lys Glu Asp Asp Tyr Ser Lys Leu Lys Val Tyr Tyr Phe Asp
1               5                   10                  15
Tyr

<210> SEQ ID NO 405
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 405

Val Ser Thr Ala Gly Met Asp Val
1               5

<210> SEQ ID NO 406
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 406

Ala Asp Phe Ile Asp Tyr
1               5

<210> SEQ ID NO 407
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 407

His Arg Ile Ala Ala Ala Gly Thr Trp Tyr Phe Asp Leu
1               5                   10

<210> SEQ ID NO 408
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 408

Arg Met Thr Gly Met Asp Val
1               5

<210> SEQ ID NO 409
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 409

Asp Pro Pro Tyr Gly Asp Tyr Asp Gly Trp Phe Asp Pro
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Chemically Synthesized
```

<400> SEQUENCE: 410

Gly Leu Ser Ser Ser Pro Tyr Tyr Phe Asp Tyr
1               5                   10

<210> SEQ ID NO 411
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 411

Asp Phe Leu Tyr Tyr Phe Asp Tyr
1               5

<210> SEQ ID NO 412
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 412

Ile Gly Tyr Cys Ser Gly Gly Ser Cys Tyr Ser Gln Gly Asp Tyr Phe
1               5                   10                  15

Asp Tyr

<210> SEQ ID NO 413
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 413

Glu Glu Gly Tyr
1

<210> SEQ ID NO 414
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 414

Pro Arg Arg Gly Thr Ala Met Ala Phe Gly Tyr Ser Tyr Gly Pro Tyr
1               5                   10                  15

Tyr Phe Asp Tyr
            20

<210> SEQ ID NO 415
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 415

Ser Pro Tyr Gly Asp Ser Leu Pro Ile Asp Tyr
1               5                   10

<210> SEQ ID NO 416
<211> LENGTH: 20

```
<212> TYPE: PRT
<213> ORGANISM: Artificial Sequence
<220> FEATURE:
<223> OTHER INFORMATION: Chemically Synthesized

<400> SEQUENCE: 416

Asp Gly Tyr Cys Ser Gly Gly Ser Cys Tyr Ala Pro Tyr Tyr Tyr Tyr
1               5                   10                  15

Gly Met Asp Val
            20

<210> SEQ ID NO 417
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 417

Asp Gln Ser Val Thr Met Ile Val Val Ile Trp Pro Glu Tyr Tyr
1               5                   10                  15

Phe Asp Tyr

<210> SEQ ID NO 418
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 418

Ala Ser Gly Trp Asn Tyr Tyr Tyr Gly Met Asp Val
1               5                   10

<210> SEQ ID NO 419
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 419

Gln Gln Tyr Asn Ser Tyr Pro Phe Thr
1               5

<210> SEQ ID NO 420
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 420

Gln Gln Tyr Gly Ser Ser Pro Pro Val Phe Thr
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 421

Gln Gln Tyr Asn Asn Trp Pro Leu Tyr Thr
1               5                   10
```

```
<210> SEQ ID NO 422
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 422

Gln Gln Arg Ser Asn Trp Pro Phe Thr
1               5

<210> SEQ ID NO 423
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 423

Met Gln Ala Leu Gln Thr Pro Pro Thr
1               5

<210> SEQ ID NO 424
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 424

Gln Gln Ala Asn Ser Phe Pro Phe Thr
1               5

<210> SEQ ID NO 425
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 425

Gln Gln Tyr Gly Ser Ser Pro Leu Tyr Thr
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 426

Gln Gln Tyr Gly Ser Ser Pro Pro Ile Thr
1               5                   10

<210> SEQ ID NO 427
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 427

Gln Gln Tyr Tyr Ser Phe Pro Trp Thr
1               5
```

<210> SEQ ID NO 428
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 428

Gln Gln Tyr Gly Ser Ser Pro His Thr
1               5

<210> SEQ ID NO 429
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 429

Gln Gln Arg Ser Thr Trp Val Thr
1               5

<210> SEQ ID NO 430
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 430

Gln Gln Tyr Asn Ser Tyr Ser Gln Thr
1               5

<210> SEQ ID NO 431
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 431

Leu Gln His Asn Ser Tyr Pro Phe Thr
1               5

<210> SEQ ID NO 432
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 432

Gln Gln Tyr Tyr Ser Tyr Pro Pro Leu
1               5

<210> SEQ ID NO 433
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 433

Met Gln Gly Thr His Trp Pro Ile Thr
1               5

-continued

```
<210> SEQ ID NO 434
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 434

Gln Ser Ala Asp Ser Ser Gly Thr Tyr Val
1               5                   10

<210> SEQ ID NO 435
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 435

Ser Ser Tyr Thr Ser Ser Ser Thr Gln Val
1               5                   10

<210> SEQ ID NO 436
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 436

Leu Leu Tyr Tyr Gly Gly Ala Val Val
1               5

<210> SEQ ID NO 437
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 437

Ala Trp Asp Asp Ser Leu Ser Gly Pro Val
1               5                   10

<210> SEQ ID NO 438
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 438

Val Gly Cys Gly Gly Asp Cys Pro Leu Asp Tyr
1               5                   10

<210> SEQ ID NO 439
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 439

Leu Lys Ala Val Arg Gly Val Tyr Tyr Tyr Tyr Met Asp Val
1               5                   10

<210> SEQ ID NO 440
```

```
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 440

Asp Gln Gly Gly Tyr Cys Ser Ser Thr Ser Cys Pro Asp Ala Phe Asp
1               5                   10                  15

Ile

<210> SEQ ID NO 441
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 441

Asp Gly Ala Asp Thr Gly Ser Ile Ala Ser Ser Ser Gly Tyr Phe Asp
1               5                   10                  15

Tyr

<210> SEQ ID NO 442
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 442

Ala Thr Gly Asp Arg Gly Asn Trp Tyr Phe Asp Leu
1               5                   10

<210> SEQ ID NO 443
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 443

Gly Val Ser Glu Tyr Gly Ser Gly Ser Tyr Tyr Phe Asp Tyr
1               5                   10

<210> SEQ ID NO 444
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 444

Asp Pro Thr Leu Leu Tyr Cys Thr Asn Gly Val Cys His Ser Phe Asp
1               5                   10                  15

Tyr

<210> SEQ ID NO 445
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 445
```

Glu Ser Thr Thr Gln Trp Leu Asp Leu Asp Tyr
1               5                   10

<210> SEQ ID NO 446
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 446

Gly Gly Thr Gly Ala Gln Gly Phe Ala Phe Asp Ile
1               5                   10

<210> SEQ ID NO 447
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 447

Gly Asp Arg His Tyr Phe Asp Tyr
1               5

<210> SEQ ID NO 448
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 448

Gln Pro Leu Gly Lys Gly Leu Asp Phe Asp
1               5                   10

<210> SEQ ID NO 449
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 449

Gly Gly Ile Ala Ala Ala Gly Ser Leu Gly His Gly Tyr
1               5                   10

<210> SEQ ID NO 450
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 450

Glu Ala Ser Leu Pro Tyr Asp Ser Ser Gly Arg Val Gly Glu Ala Thr
1               5                   10                  15

Asp Tyr

<210> SEQ ID NO 451
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 451

```
Asp Cys Val Ser Gly Ala Phe Asp Ile
1               5

<210> SEQ ID NO 452
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 452

Gly Asn Pro Thr Pro Thr Tyr Ser Ser Ser Tyr Tyr Phe Asp Tyr
1               5                   10                  15

<210> SEQ ID NO 453
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 453

Asn Ser Gly Ser Tyr His Leu Phe Asp Tyr
1               5                   10

<210> SEQ ID NO 454
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 454

Asp Arg Asp Trp Gly Phe Ile Asp Tyr
1               5

<210> SEQ ID NO 455
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 455

Pro Leu Gly Phe Asp Tyr
1               5

<210> SEQ ID NO 456
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 456

Pro Leu Ala Ala Ala Gly Leu Tyr
1               5

<210> SEQ ID NO 457
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 457
```

Asp His Gly Tyr Ser Gly Ser Tyr Tyr Ala Phe Asp Ile
1               5                   10

<210> SEQ ID NO 458
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 458

Asp Pro Pro Leu Ser Arg Thr Gly Gly Ser Asp Tyr
1               5                   10

<210> SEQ ID NO 459
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 459

Val Ala Leu Ser Pro Ala Ala Glu Leu Gly Met Arg Pro Phe Asp Tyr
1               5                   10                  15

<210> SEQ ID NO 460
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 460

Ser Cys Leu Ser Gln Met Val Tyr Ala Phe Asp Tyr
1               5                   10

<210> SEQ ID NO 461
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 461

Asp Gln Asp Pro Arg Pro Ser Tyr Phe Asp Leu
1               5                   10

<210> SEQ ID NO 462
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 462

Gln Gln Ser Tyr Ser Thr Pro Pro Trp Thr
1               5                   10

<210> SEQ ID NO 463
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 463

Gln Gln Tyr Asn Ser Tyr Pro Tyr Thr

```
1               5

<210> SEQ ID NO 464
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 464

Gln Gln Tyr Gly Ser Ser Ser Pro Leu Thr
1               5                   10

<210> SEQ ID NO 465
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 465

Gln Gln Asn Ser Tyr Pro Leu Thr
1               5

<210> SEQ ID NO 466
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 466

Leu Gln His Asn Ser Tyr Pro Trp Thr
1               5

<210> SEQ ID NO 467
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 467

Gln Gln Tyr Gly Ser Ser Pro Trp Thr
1               5

<210> SEQ ID NO 468
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 468

Gln Gln Tyr Gly Ser Ser Pro Thr Trp Thr
1               5                   10

<210> SEQ ID NO 469
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 469

Met Gln Ala Leu Gln Thr Pro Gln Thr
1               5
```

```
<210> SEQ ID NO 470
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 470

Met Gln Gly Thr His Trp Pro Pro Leu Thr
1               5                   10

<210> SEQ ID NO 471
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 471

Gly Thr Trp Asp Ser Ser Leu Ser Ala Val
1               5                   10

<210> SEQ ID NO 472
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 472

Gly Thr Trp Asp Ser Ser Leu Ser Val Val
1               5                   10

<210> SEQ ID NO 473
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 473

Ser Ser Tyr Thr Ser Ser Ser Thr Leu Asn Val Val
1               5                   10

<210> SEQ ID NO 474
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 474

Gln Ala Trp Asp Ser Ser Thr Ala His Val Val
1               5                   10

<210> SEQ ID NO 475
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 475

Ala Ala Trp Asp Asp Ser Leu Ser Gly Arg Val
1               5                   10
```

<210> SEQ ID NO 476
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 476

Ala Ser Leu Gly Asn Asp Arg Asn Trp Tyr Phe Asp Leu
1               5                   10

<210> SEQ ID NO 477
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 477

Leu Pro Gly Ile Ala Ala Ala Gly Ala Ser Tyr Tyr Tyr Tyr Tyr
1               5                   10                  15

Met Asp Val

<210> SEQ ID NO 478
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 478

Asp Arg Trp Gly Ala Phe Asp Ile
1               5

<210> SEQ ID NO 479
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 479

Gly Tyr Ser Ser Ser Trp Tyr Phe Asp Tyr
1               5                   10

<210> SEQ ID NO 480
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 480

His Trp Gly Ser Gly Ala Phe Asp Ile
1               5

<210> SEQ ID NO 481
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 481

Asp Phe Pro Tyr Ser Thr Tyr Tyr Phe Asp Tyr
1               5                   10

<210> SEQ ID NO 482
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 482

Asp Thr Gly Thr Gly Ala Gly Asp Arg Phe Asp Tyr
1               5                   10

<210> SEQ ID NO 483
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 483

Gly Gly Val Gln Leu Gly Met Val Lys Gly Trp Tyr Phe Asp Leu
1               5                   10                  15

<210> SEQ ID NO 484
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 484

Ala Ser Tyr Asn Trp Asn Tyr Tyr Phe Asp Tyr
1               5                   10

<210> SEQ ID NO 485
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 485

Arg Ser Ser Ser Tyr Trp Phe Asp Pro
1               5

<210> SEQ ID NO 486
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 486

Gly Lys Asp Cys Ser Ser Thr Ser Cys Tyr Leu Ser Glu Tyr Phe Gln
1               5                   10                  15

His

<210> SEQ ID NO 487
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 487

Asp Ser Asn Gly Gly Ser Tyr Tyr Phe Asp Tyr

```
1               5                   10
```

<210> SEQ ID NO 488
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 488

```
Gly Ser Ser Met Ser Asp Pro Gln Leu Val Ser Thr Asp Ala Phe Asp
1               5                   10                  15

Ile
```

<210> SEQ ID NO 489
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 489

```
Glu Trp Arg Asn Thr Ala Met Val Asp Tyr
1               5                   10
```

<210> SEQ ID NO 490
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 490

```
Ala Ser Arg Ala Ser Ser Gly Ser Tyr Tyr Phe Asp Tyr
1               5                   10
```

<210> SEQ ID NO 491
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 491

```
Asp Gln Ser Phe Lys Ala Ala Ala Gly Pro Ile Asp Tyr
1               5                   10
```

<210> SEQ ID NO 492
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 492

```
Asp Arg Leu Gly Gly Tyr Ser Ser Ser Trp Tyr Phe Asp Tyr
1               5                   10
```

<210> SEQ ID NO 493
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 493

Ile Thr Gly Asp His His Tyr Phe Asp Tyr
1               5                   10

<210> SEQ ID NO 494
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 494

Ser Arg Tyr Tyr Gly Ser Gly Ser Tyr Tyr Tyr Phe Asp Tyr
1               5                   10                  15

<210> SEQ ID NO 495
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 495

Arg Pro Gly Ala Gly Asp Tyr
1               5

<210> SEQ ID NO 496
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 496

Asp Arg Gly Gln Leu Gly Ile Phe Asp Tyr
1               5                   10

<210> SEQ ID NO 497
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 497

Leu Val Asp Phe Ser Gly Val Gly Ser Gly Tyr Cys Gly Gly Asp Cys
1               5                   10                  15

Tyr Phe Asp Tyr
            20

<210> SEQ ID NO 498
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 498

Asp Leu Val Gly Arg Gln Thr Glu Tyr Tyr Tyr Tyr Gly Met Asp
1               5                   10                  15

Val

<210> SEQ ID NO 499
<211> LENGTH: 14
<212> TYPE: PRT
<213> ORGANISM: Artificial Sequence
<220> FEATURE:

<223> OTHER INFORMATION: Chemically Synthesized

<400> SEQUENCE: 499

Arg Tyr Cys Ser Gly Gly Ser Cys Tyr Ser Ala Phe Asp Ile
1               5                   10

<210> SEQ ID NO 500
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 500

Thr Ala Tyr Gly Ser Gly Ser Tyr Tyr Ile Asp Tyr
1               5                   10

<210> SEQ ID NO 501
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 501

Glu Ala Thr Asn Gly Val Cys Phe Asp Tyr
1               5                   10

<210> SEQ ID NO 502
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 502

Asp Arg Ser Trp Gly Ser Asn Tyr Phe Asp Tyr
1               5                   10

<210> SEQ ID NO 503
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 503

Val Met Val Arg Gly Val Asn Ala Phe Asp Ile
1               5                   10

<210> SEQ ID NO 504
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 504

Glu Arg Thr Ser Tyr Gly Asp Tyr Phe Asp Tyr
1               5                   10

<210> SEQ ID NO 505
<211> LENGTH: 10
<212> TYPE: PRT
<213> ORGANISM: Artificial Sequence
<220> FEATURE:
<223> OTHER INFORMATION: Chemically Synthesized

```
<400> SEQUENCE: 505

Asp Ser Gly Ser Tyr Tyr Tyr Phe Asp Tyr
1               5                   10

<210> SEQ ID NO 506
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 506

Trp Asp Tyr Tyr Asp Ser Ser Gly Tyr Tyr Ala Phe Asp Ile
1               5                   10

<210> SEQ ID NO 507
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 507

Ile Ile Thr Gly Glu Asn Ala Phe Asp Ile
1               5                   10

<210> SEQ ID NO 508
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 508

Glu Gly Gln Leu Val Gly Asp Tyr Phe Asp Tyr
1               5                   10

<210> SEQ ID NO 509
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 509

Thr Tyr Tyr Tyr Gly Ser Gly Ser Arg Tyr Tyr Phe Asp Tyr
1               5                   10

<210> SEQ ID NO 510
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 510

Gly Gly Glu Gln Gln Leu Val Ser Trp Tyr Phe Asp Leu
1               5                   10

<210> SEQ ID NO 511
<211> LENGTH: 11
<212> TYPE: PRT
<213> ORGANISM: Artificial Sequence
<220> FEATURE:
<223> OTHER INFORMATION: Chemically Synthesized
```

```
<400> SEQUENCE: 511

Gly Gly Ser Ser Ser Trp Tyr Tyr Phe Asp Tyr
1               5                   10

<210> SEQ ID NO 512
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 512

Glu Arg Trp Gly Asp Tyr
1               5

<210> SEQ ID NO 513
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 513

Gln Arg Thr Tyr Asn Ala Pro
1               5

<210> SEQ ID NO 514
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 514

Gln Gln Tyr Tyr Ser Tyr Pro Leu Thr
1               5

<210> SEQ ID NO 515
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 515

Gln Gln Tyr Tyr Ser Tyr His Gly Thr
1               5

<210> SEQ ID NO 516
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 516

Gln Gln Arg Ser Asn Trp Pro Pro Phe Thr
1               5                   10

<210> SEQ ID NO 517
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 517
```

```
Gln Gln Tyr Tyr Ser Tyr Pro Tyr Ser
1               5
```

<210> SEQ ID NO 518
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 518

```
Gln Gln Tyr Gly Ser Ser Arg Leu Thr
1               5
```

<210> SEQ ID NO 519
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 519

```
Gln Gln Arg Ser Thr Trp Pro Pro Trp Thr
1               5                   10
```

<210> SEQ ID NO 520
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 520

```
Gln Gln Ala Asn Ser Phe Pro Gln Thr
1               5
```

<210> SEQ ID NO 521
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 521

```
Gln Lys Tyr Asn Ser Ala Pro Arg Asp
1               5
```

<210> SEQ ID NO 522
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 522

```
Gln Gln Ser Tyr Ser Thr Pro Pro Tyr Thr
1               5                   10
```

<210> SEQ ID NO 523
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 523

Gln Gln Ala Asn Ser Phe Pro Pro Tyr Thr
1               5                   10

<210> SEQ ID NO 524
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 524

Gln Gln Tyr Asn Asn Trp Pro Tyr Ser
1               5

<210> SEQ ID NO 525
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 525

Ala Ala Trp Asp Asp Ser Leu Ser Gly Pro Val
1               5                   10

<210> SEQ ID NO 526
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 526

Val Leu Ser Ser Gly His Phe Asp Tyr
1               5

<210> SEQ ID NO 527
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 527

Glu Glu Glu Gly Gly Ser Tyr Ala Phe Asp Ile
1               5                   10

<210> SEQ ID NO 528
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 528

Arg Tyr Cys Ser Ser Thr Ser Cys Tyr Tyr Phe Asp Tyr
1               5                   10

<210> SEQ ID NO 529
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 529

Arg Asp Leu Asn Tyr Tyr Asp Ser Ser Gly Tyr Tyr Ser Trp Phe Asp

```
1               5                   10                  15
Pro

<210> SEQ ID NO 530
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 530

Asp Pro Gln Arg Ile Ala Ala Ala Gly Pro Phe Gln His
1               5                   10

<210> SEQ ID NO 531
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 531

Asp Ser Gln Leu Gly Arg Gly Tyr Phe Asp Leu
1               5                   10

<210> SEQ ID NO 532
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 532

Gly Ser Ser Asn Arg Asn Thr Asn Asp Tyr
1               5                   10

<210> SEQ ID NO 533
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 533

Gly Val Ala Ala Asn Arg Leu Arg Ser Pro Gly Leu Asp Tyr
1               5                   10

<210> SEQ ID NO 534
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 534

Pro Tyr Ser Ser Gly Trp Tyr Phe Asp Tyr
1               5                   10

<210> SEQ ID NO 535
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 535
```

His Leu Pro Val Arg Tyr Ser Gly Ser Tyr Pro Ser Ser Asp Tyr
1               5                   10                  15

<210> SEQ ID NO 536
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 536

Ile Arg Pro Thr Thr Asn Trp Gly Phe Thr Lys Tyr Tyr Phe Asp Tyr
1               5                   10                  15

<210> SEQ ID NO 537
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 537

Gly Val Ala Gly Leu Gly Tyr
1               5

<210> SEQ ID NO 538
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 538

Ala Ala Phe Asp Ile
1               5

<210> SEQ ID NO 539
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 539

Val Pro His Tyr Gly Asp Tyr His Asp Ala Phe Asp Ile
1               5                   10

<210> SEQ ID NO 540
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 540

Val Lys Ala Asn Arg Gly Ala Glu Asp Ala Phe Asp Ile
1               5                   10

<210> SEQ ID NO 541
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 541

Ser His Ala Ser Ser Gly Tyr Tyr Ala Phe Asp Ile

```
<210> SEQ ID NO 542
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 542

Leu Ile Arg Val Phe Asp Tyr Tyr Gly Ser Gly Ser Ala Phe Asp Tyr
1               5                   10                  15

<210> SEQ ID NO 543
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 543

Asp Pro Pro Leu Phe Asp Tyr
1               5

<210> SEQ ID NO 544
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 544

Gln Gln Tyr Asp Asn Leu Pro
1               5

<210> SEQ ID NO 545
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 545

Gln Gln Tyr Gly Ser Ser Tyr Ser
1               5

<210> SEQ ID NO 546
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 546

Gln Gln Arg Ser Asn Trp Leu Tyr Thr
1               5

<210> SEQ ID NO 547
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 547

Leu Gln His Asn Ser Tyr Pro Gln Tyr Ser
1               5                   10
```

```
<210> SEQ ID NO 548
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 548

Gln Gln Tyr Gly Ser Ser Pro Pro Tyr Ser
1               5                   10

<210> SEQ ID NO 549
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 549

Ala Ala Trp Asp Asp Ser Leu Ser Gly Ser Tyr Val
1               5                   10

<210> SEQ ID NO 550
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 550

Asp Arg Gly Ile Ala Ala Ala Gly Thr Phe Asp Tyr
1               5                   10

<210> SEQ ID NO 551
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 551

Gly Arg Phe Thr Ala Asp Tyr Tyr Tyr Tyr Met Asp Val
1               5                   10

<210> SEQ ID NO 552
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 552

Ala Glu Gly Asp Leu Leu Glu Trp Leu Ser Ile Gly Cys Phe Asp Tyr
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 553

Ala Glu Tyr Phe Leu Gly Asp Trp His His Asp Ala Phe Asp Ile
1               5                   10                  15
```

```
<210> SEQ ID NO 554
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 554

Ala Thr Val Val Val Thr Ala Gln Tyr Tyr Phe Asp Tyr
1               5                   10

<210> SEQ ID NO 555
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 555

Arg Gly Trp Gly His Ala Phe Asp Ile
1               5

<210> SEQ ID NO 556
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 556

His Ser Trp Tyr Tyr Phe Asp Tyr
1               5

<210> SEQ ID NO 557
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 557

Lys Ser Pro Pro Tyr Cys Gly Gly Asp Cys Tyr Ser Arg Asp Asp Ala
1               5                   10                  15

Phe Asp Ile

<210> SEQ ID NO 558
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 558

Asp Glu Arg Gly Ile Gly Trp Tyr Phe Asp Tyr
1               5                   10

<210> SEQ ID NO 559
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 559

Val Arg Gly Ile Ala Ala Arg Arg Pro Asp Ala Phe Asp Ile
1               5                   10
```

<210> SEQ ID NO 560
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 560

Arg Asp Tyr Gly Asp Tyr Gly Arg Gly Gly Pro Arg Trp Tyr Phe Asp
1               5                   10                  15
Tyr

<210> SEQ ID NO 561
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 561

Asn Asp Tyr Ser Asn Tyr Gly Ala Phe Asp Tyr
1               5                   10

<210> SEQ ID NO 562
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 562

Gly Arg Val Thr Met Ile Val Val Asp Ala Phe Asp Ile
1               5                   10

<210> SEQ ID NO 563
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 563

Glu Gly Ala Ser Ile Ala Ala Arg Pro Tyr Asn Trp Phe Asp Pro
1               5                   10                  15

<210> SEQ ID NO 564
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 564

Ser Pro Gly Tyr Tyr Asp Ser Ser Gly Tyr Tyr Gly Tyr
1               5                   10

<210> SEQ ID NO 565
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 565

Gly Glu Gln Leu Ser Asp Phe Asp Tyr Tyr Tyr Tyr Gly Met Asp Val

```
                1               5                  10                  15

<210> SEQ ID NO 566
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 566

Glu Arg Ile Thr Ile Phe Gly Val Ala Gly Ser Phe Asp Tyr
1               5                   10

<210> SEQ ID NO 567
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 567

Glu Gly Thr Ile Thr Gly Pro Gly Tyr Phe Asp Tyr
1               5                   10

<210> SEQ ID NO 568
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 568

Gln Gln Ser Tyr Ser Thr Arg Tyr Ser
1               5

<210> SEQ ID NO 569
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 569

Gln Gln Tyr Asn Asn Trp Pro Thr
1               5

<210> SEQ ID NO 570
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 570

Gln Lys Tyr Asn Ser Ala Leu Leu Thr
1               5

<210> SEQ ID NO 571
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 571

Gln Gln Tyr Asp Asn Leu Pro Pro Arg Gly Thr Ala
1               5                   10
```

<210> SEQ ID NO 572
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 572

Gln Gln Arg Ser Asn Trp Trp Thr
1               5

<210> SEQ ID NO 573
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 573

Gln Gln Tyr Gly Ser Ser Val Thr
1               5

<210> SEQ ID NO 574
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 574

Gln Val Trp Asp Ser Ser Ser Asp His Pro Val
1               5                   10

<210> SEQ ID NO 575
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 575

Gln Ala Trp Asp Ser Ser Thr Ala Tyr Val
1               5                   10

<210> SEQ ID NO 576
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 576

Gln Ser Ala Asp Ser Ser Gly Thr Tyr Trp Val
1               5                   10

<210> SEQ ID NO 577
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 577

Gly Trp Ser Thr Val Thr Asn Trp Phe Asp Pro
1               5                   10

<210> SEQ ID NO 578
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 578

Pro Ala Leu His Glu Gln Gln Leu Asp Tyr Tyr Phe Asp Tyr
1               5                   10

<210> SEQ ID NO 579
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 579

Asp Cys Gly Ile Ala Ala Ala Gly Asn Trp Phe Asp Pro
1               5                   10

<210> SEQ ID NO 580
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 580

Val Val Glu Thr Gly Val Glu Asn Tyr
1               5

<210> SEQ ID NO 581
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 581

Gly Arg Ile Pro Phe Asp Ile
1               5

<210> SEQ ID NO 582
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 582

Ala Gly Met Ala Phe Asp Tyr
1               5

<210> SEQ ID NO 583
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 583

Pro Gly Thr Gly Thr Asn Ile Asp Tyr
1               5

```
<210> SEQ ID NO 584
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 584

Ser Arg His Ala Arg Lys Glu Leu Gly Leu Leu Asp Tyr
1               5                   10

<210> SEQ ID NO 585
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 585

Ala Arg Thr Arg Thr Gly His Arg Asp Asp Ala Phe Asp Ile
1               5                   10

<210> SEQ ID NO 586
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 586

Leu Gly Gly Phe Leu Thr Gly Tyr Tyr Asn Asp Ala Phe Asp Ile
1               5                   10                  15

<210> SEQ ID NO 587
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 587

Asp Gly Tyr Cys Gly Gly Asp Cys Tyr Ser Val Asp Tyr
1               5                   10

<210> SEQ ID NO 588
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 588

Val Gly Glu Asp Pro Arg Asp Tyr
1               5

<210> SEQ ID NO 589
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 589

Asp Leu Gly Met Val Gly Met Asp Val
1               5

<210> SEQ ID NO 590
```

<211> LENGTH: 11
<212> TYPE: PRT
<213> ORGANISM: Artificial Sequence
<220> FEATURE:
<223> OTHER INFORMATION: Chemically Synthesized

<400> SEQUENCE: 590

Gly Arg Gly Pro Pro Ala Gly Asp Phe Asp Tyr
1               5                   10

<210> SEQ ID NO 591
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 591

Val Gln Ser Gly Tyr Ser Tyr Gly Tyr Ala Phe Asp Ile
1               5                   10

<210> SEQ ID NO 592
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 592

Asp His Gly Ile Ala Ala Ala Gly Thr Phe Asp Tyr
1               5                   10

<210> SEQ ID NO 593
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 593

Asp Tyr Gly Gly Asn Ser Val Gly Tyr Phe Asp Tyr
1               5                   10

<210> SEQ ID NO 594
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 594

Gly Arg Asp Tyr Tyr Asp Ser Ser Gly Tyr Tyr Phe Asp Tyr
1               5                   10

<210> SEQ ID NO 595
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 595

Asp Trp Gly Asp Ile Thr Gly Thr Asn Trp Phe Asp Pro
1               5                   10

<210> SEQ ID NO 596
<211> LENGTH: 18

```
<212> TYPE: PRT
<213> ORGANISM: Artificial Sequence
<220> FEATURE:
<223> OTHER INFORMATION: Chemically Synthesized

<400> SEQUENCE: 596

Asp Lys Pro Phe Asp Tyr Tyr Gly Ser Gly Ser Tyr Tyr Asn Tyr Phe
1               5                   10                  15

Asp Tyr

<210> SEQ ID NO 597
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 597

Ser Lys Leu Thr Pro Asp Ala Phe Asp Ile
1               5                   10

<210> SEQ ID NO 598
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 598

Asp Pro Gly Ile Thr Ile Phe Gly Val Val Ile Asp Tyr
1               5                   10

<210> SEQ ID NO 599
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 599

Asp Leu Lys Arg Glu Ala Gly Trp Tyr Phe Asp Leu
1               5                   10

<210> SEQ ID NO 600
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 600

Thr Gly Gly Tyr Ser Ser Ser Trp Tyr Phe Asp Tyr
1               5                   10

<210> SEQ ID NO 601
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 601

Asp Arg Arg Ile Ala Ala Ala Asp Asp Ala Phe Asp Ile
1               5                   10

<210> SEQ ID NO 602
```

```
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 602

Asp His Ser Ser Gly Trp Tyr Tyr Phe Asp Tyr
1               5                   10

<210> SEQ ID NO 603
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 603

Ile Pro Gly Asp Trp Tyr Phe Asp Leu
1               5

<210> SEQ ID NO 604
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 604

Glu Glu Leu Gly Ile Asp Tyr
1               5

<210> SEQ ID NO 605
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 605

Gln Gln Tyr Asn Asn Trp Pro Arg Trp Thr
1               5                   10

<210> SEQ ID NO 606
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 606

Gln Gln Arg Arg Asn Trp Pro Pro Trp Thr
1               5                   10

<210> SEQ ID NO 607
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 607

Gln Gln Tyr Gly Ser Pro Pro Gly Thr
1               5

<210> SEQ ID NO 608
<211> LENGTH: 9
```

```
<212> TYPE: PRT
<213> ORGANISM: Artificial Sequence
<220> FEATURE:
<223> OTHER INFORMATION: Chemically Synthesized

<400> SEQUENCE: 608

Gln Gln Tyr Asn Ser Tyr Ser Trp Thr
1               5

<210> SEQ ID NO 609
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 609

Gln Gln Tyr Asn Asn Trp Pro Arg Thr
1               5

<210> SEQ ID NO 610
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 610

Gln Gln Tyr Asn Ser Tyr Ser Thr
1               5

<210> SEQ ID NO 611
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 611

Gln Gln Tyr Tyr Ser Thr Pro Trp Thr
1               5

<210> SEQ ID NO 612
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 612

Met Gln Gly Thr His Trp Pro Trp Thr
1               5

<210> SEQ ID NO 613
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 613

Gln Gln Tyr Gly Ser Ser Arg Thr
1               5

<210> SEQ ID NO 614
<211> LENGTH: 9
<212> TYPE: PRT
```

<213> ORGANISM: Artificial Sequence
<220> FEATURE:
<223> OTHER INFORMATION: Chemically Synthesized

<400> SEQUENCE: 614

Gln Gln Ser Tyr Ser Thr Pro Arg Thr
1               5

<210> SEQ ID NO 615
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 615

Cys Ser Tyr Ala Gly Ser Ser Thr Phe Val Val
1               5                   10

<210> SEQ ID NO 616
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 616

Ser Ser Tyr Thr Ser Ser Ser Thr Pro Tyr Val Val
1               5                   10

<210> SEQ ID NO 617
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 617

Ala Ala Trp Asp Asp Ser Leu Asn Gly Pro Tyr Val
1               5                   10

<210> SEQ ID NO 618
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 618

Asp Gly Arg Thr Phe Phe Asp Tyr
1               5

<210> SEQ ID NO 619
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 619

Thr Gly Tyr Ser Ser Ser Trp Tyr Arg Ala Phe Asp Ile
1               5                   10

<210> SEQ ID NO 620
<211> LENGTH: 9
<212> TYPE: PRT
<213> ORGANISM: Artificial Sequence

```
<220> FEATURE:
<223> OTHER INFORMATION: Chemically Synthesized

<400> SEQUENCE: 620

Asp Tyr Tyr Tyr Tyr Gly Met Asp Val
1               5

<210> SEQ ID NO 621
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 621

Ala Glu Leu Gly Gly Gly Tyr Trp Tyr Phe Asp Leu
1               5                   10

<210> SEQ ID NO 622
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 622

Val Gly Pro Arg Arg Asp Trp Phe Asp Pro
1               5                   10

<210> SEQ ID NO 623
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 623

Arg Gly Ile Gly Gly Leu Asp Tyr
1               5

<210> SEQ ID NO 624
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 624

Val Gly Lys Ala Pro Asp Glu Lys Leu Thr His Tyr Tyr Phe Asp Tyr
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 625

Ser Val Leu Leu Pro Gly Asp Gln Arg His Asp Ala Phe Asp Ile
1               5                   10                  15

<210> SEQ ID NO 626
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 626

Val Ser Gly Ser Tyr Tyr Tyr Phe Asp Tyr
1               5                   10

<210> SEQ ID NO 627
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 627

Asp Gly Asp Trp Tyr Phe Asp Leu
1               5

<210> SEQ ID NO 628
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 628

Asp Leu Gly Arg Phe Asp Tyr
1               5

<210> SEQ ID NO 629
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 629

Gly Ala Thr Gly Asp Ser Phe Asp Tyr
1               5

<210> SEQ ID NO 630
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 630

Asp Ser Trp Pro Ser Tyr Tyr Phe Asp Tyr
1               5                   10

<210> SEQ ID NO 631
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 631

His Ser Thr Glu Lys Lys Asn Asp Ala Phe Asp Ile
1               5                   10

<210> SEQ ID NO 632
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 632

Tyr Leu Leu Gly Tyr Ser Tyr Gly Tyr Trp Phe Asp Pro
1               5                   10

<210> SEQ ID NO 633
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 633

Asp Arg Gln Leu Thr Gly Asp Leu His Asp Ala Phe Asp Ile
1               5                   10

<210> SEQ ID NO 634
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 634

Leu Gly Ala Asp Arg Gly Trp Tyr Phe Asp Tyr
1               5                   10

<210> SEQ ID NO 635
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 635

Glu Arg Leu Gln Ser Tyr Tyr Gly Ser Gly Ser Tyr Tyr Phe Asp Tyr
1               5                   10                  15

<210> SEQ ID NO 636
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 636

Ala Gly Leu Gly Tyr Cys Ser Ser Thr Ser Cys Tyr Ala Glu Tyr Phe
1               5                   10                  15

Gln His

<210> SEQ ID NO 637
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 637

Asn Asp Ser Ser Asn Trp Phe Asp Pro
1               5

<210> SEQ ID NO 638
<211> LENGTH: 13
<212> TYPE: PRT
<213> ORGANISM: Artificial Sequence
<220> FEATURE:

<223> OTHER INFORMATION: Chemically Synthesized

<400> SEQUENCE: 638

Gly Gly Arg Met Thr Thr Val Thr Asp Tyr Phe Asp Tyr
1               5                   10

<210> SEQ ID NO 639
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 639

Asp Gln Phe Gly Asp Arg Thr Leu His Phe Asp Leu
1               5                   10

<210> SEQ ID NO 640
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 640

Arg Gln Thr Ala Ala Ala Phe Asp Tyr
1               5

<210> SEQ ID NO 641
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 641

Arg Val Leu Gly Ile Gly Arg Tyr Phe Asp Leu
1               5                   10

<210> SEQ ID NO 642
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 642

Asp Leu Glu Thr Gly Asp Leu Gly Phe Asp Tyr
1               5                   10

<210> SEQ ID NO 643
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 643

Glu Gly Phe His Glu Arg Trp Asp Ser Ser Ser Asn Trp Phe Asp
1               5                   10                  15

Pro

<210> SEQ ID NO 644
<211> LENGTH: 11
<212> TYPE: PRT
<213> ORGANISM: Artificial Sequence

```
<220> FEATURE:
<223> OTHER INFORMATION: Chemically Synthesized

<400> SEQUENCE: 644

Gln Gln Tyr Asn Asn Trp Pro Pro Gly Gly Pro
1               5                   10

<210> SEQ ID NO 645
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 645

Asp Tyr Asn Tyr Pro Tyr Thr
1               5

<210> SEQ ID NO 646
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 646

Gln Gln Tyr Asn Ser Tyr Ser Leu Thr
1               5

<210> SEQ ID NO 647
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 647

Met Gln Gly Thr His Trp Pro Pro Thr Val Arg Thr
1               5                   10

<210> SEQ ID NO 648
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 648

Gln Gln Tyr Gly Ser Ser Pro Arg Tyr Thr
1               5                   10

<210> SEQ ID NO 649
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 649

Gln Gln Tyr Tyr Ser Thr Pro Phe Thr
1               5

<210> SEQ ID NO 650
<211> LENGTH: 10
<212> TYPE: PRT
<213> ORGANISM: Artificial Sequence
<220> FEATURE:
```

```
<223> OTHER INFORMATION: Chemically Synthesized

<400> SEQUENCE: 650

Gln Gln Ser Tyr Ser Thr Pro Gln Tyr Thr
1               5                   10

<210> SEQ ID NO 651
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 651

Met Gln Ala Leu Gln Thr Pro Leu Ser
1               5

<210> SEQ ID NO 652
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 652

Gln Gln Tyr Asn Ser Tyr Trp Gly Thr
1               5

<210> SEQ ID NO 653
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 653

Gln Val Trp Asp Ser Ser Ser Asp His Trp Val
1               5                   10

<210> SEQ ID NO 654
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 654

Cys Ser Tyr Ala Gly Ser Ser Thr Gly His Ala Val
1               5                   10

<210> SEQ ID NO 655
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 655

Cys Ser Tyr Ala Gly Ser Tyr Val
1               5

<210> SEQ ID NO 656
<211> LENGTH: 11
<212> TYPE: PRT
<213> ORGANISM: Artificial Sequence
<220> FEATURE:
<223> OTHER INFORMATION: Chemically Synthesized
```

<400> SEQUENCE: 656

Gln Val Trp Asp Ser Ser Asp Leu Tyr Val
1               5                   10

<210> SEQ ID NO 657
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 657

Cys Ser Tyr Ala Gly Ser Ser Thr Val Val
1               5                   10

<210> SEQ ID NO 658
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 658

Asp Pro Pro Tyr Cys Ser Gly Gly Ser Cys Tyr Tyr Tyr Gly Met Asp
1               5                   10                  15

Val

<210> SEQ ID NO 659
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 659

Asp Asn Ser Asn Tyr Phe Asp Tyr
1               5

<210> SEQ ID NO 660
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 660

Gly Gly Glu Tyr Ser Ser Ser Tyr Phe Asp Tyr
1               5                   10

<210> SEQ ID NO 661
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 661

Val Gly Thr Gly Asn Asp Ala Phe Asp Ile
1               5                   10

<210> SEQ ID NO 662
<211> LENGTH: 9
<212> TYPE: PRT
<213> ORGANISM: Artificial Sequence
<220> FEATURE:

```
<223> OTHER INFORMATION: Chemically Synthesized

<400> SEQUENCE: 662

Val Val Glu Gly Gln Leu Val Asp Tyr
1               5

<210> SEQ ID NO 663
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 663

Arg Trp Lys Gly Tyr Tyr Phe Asp Tyr
1               5

<210> SEQ ID NO 664
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 664

Gly Glu Tyr Ser Ser Ser Asp Trp Tyr Phe Asp Leu
1               5                   10

<210> SEQ ID NO 665
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 665

Gly Trp Arg Val Phe Ser Gly Ser Tyr Tyr Phe Asp Tyr
1               5                   10

<210> SEQ ID NO 666
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 666

Asp Gly Phe Gln Tyr Tyr Tyr Tyr Tyr Tyr
1               5                   10

<210> SEQ ID NO 667
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 667

Asp Gly Val Gly Ala Thr Asp Tyr
1               5

<210> SEQ ID NO 668
<211> LENGTH: 12
<212> TYPE: PRT
<213> ORGANISM: Artificial Sequence
<220> FEATURE:
<223> OTHER INFORMATION: Chemically Synthesized
```

<400> SEQUENCE: 668

Val Gln Leu Gly Ile Val Arg Trp Tyr Phe Asp Leu
1               5                   10

<210> SEQ ID NO 669
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 669

Gly Gly Ser Gly Trp Tyr Tyr Phe Asp Tyr
1               5                   10

<210> SEQ ID NO 670
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 670

Asp Gly His Ser Gly Ser Tyr Phe Asp Tyr
1               5                   10

<210> SEQ ID NO 671
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 671

Asp Trp Asp Gly Tyr Asn Asp Tyr
1               5

<210> SEQ ID NO 672
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 672

His Glu Asp Ser Gly Leu Thr Gly Asp His Tyr Phe Asp Tyr
1               5                   10

<210> SEQ ID NO 673
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 673

Gln Ser Arg Leu Gly Thr Trp Tyr Phe Asp Leu
1               5                   10

<210> SEQ ID NO 674
<211> LENGTH: 11
<212> TYPE: PRT
<213> ORGANISM: Artificial Sequence
<220> FEATURE:
<223> OTHER INFORMATION: Chemically Synthesized

```
<400> SEQUENCE: 674

Glu Glu Ser Ile Ala Ala Ala Gly Thr Asp Tyr
1               5                   10

<210> SEQ ID NO 675
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 675

Asp Pro Gly Tyr Ser Ser Ser Trp Phe Asp Tyr
1               5                   10

<210> SEQ ID NO 676
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 676

Ala Ile Ala Ala Ala Gly Asn Tyr
1               5

<210> SEQ ID NO 677
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 677

Ala Arg His Asp Tyr Ser Asn Tyr Phe Asp Tyr
1               5                   10

<210> SEQ ID NO 678
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 678

Met Gln Gly Thr His Trp Pro Arg Thr
1               5

<210> SEQ ID NO 679
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 679

Met Gln Ala Thr Gln Phe Pro Tyr Thr
1               5

<210> SEQ ID NO 680
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 680
```

```
Gln Gln Leu Asn Ser Tyr Pro Thr
1               5
```

<210> SEQ ID NO 681
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 681

```
Leu Gln His Asn Ser Tyr Pro His Thr
1               5
```

<210> SEQ ID NO 682
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 682

```
Gln Gln Leu Asn Ser Tyr Pro Phe Thr
1               5
```

<210> SEQ ID NO 683
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 683

```
Gln Gln Tyr Gly Ser Ser Pro His Asn Val Val Thr Glu Phe Thr
1               5                   10                  15
```

<210> SEQ ID NO 684
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 684

```
Gln Gln Arg Ser Asn Trp Pro Pro Leu Thr
1               5                   10
```

<210> SEQ ID NO 685
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 685

```
Cys Ser Tyr Ala Gly Ser His Val Val
1               5
```

<210> SEQ ID NO 686
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 686

```
Arg Gly Tyr Ser Ser Ser Phe Asp Tyr
1               5
```

<210> SEQ ID NO 687
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 687

```
Glu Ala Gln Ser Gly Ser Tyr Tyr Tyr
1               5
```

<210> SEQ ID NO 688
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 688

```
Arg Glu Gly Ser Gly Ser Tyr Tyr Asn Trp Tyr Phe Asp Leu
1               5                   10
```

<210> SEQ ID NO 689
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 689

```
Asp Arg Gly Tyr Asp Ser Ser Gly Tyr Tyr Ser Asp Ala Phe Asp Ile
1               5                   10                  15
```

<210> SEQ ID NO 690
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 690

```
Gln Asn Trp Gly Asp Ala Phe Asp Ile
1               5
```

<210> SEQ ID NO 691
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 691

```
Gly Ser Cys Ser Gly Gly Ser Cys Tyr Phe Asp Tyr
1               5                   10
```

<210> SEQ ID NO 692
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 692

```
Asp Arg Thr Gly Asp Leu His Tyr Tyr Tyr Gly Met Asp Val
```

```
1               5                   10
```

<210> SEQ ID NO 693
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 693

```
Asp Glu Gly Phe Gly Glu Asn Asn Trp Phe Asp Pro
1               5                   10
```

<210> SEQ ID NO 694
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 694

```
Arg Asn Trp Gly Val Ser Gly Tyr
1               5
```

<210> SEQ ID NO 695
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 695

```
Val Pro Gly Ile Gln Leu Trp Leu Lys Gly Ala Phe Asp Ile
1               5                   10
```

<210> SEQ ID NO 696
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 696

```
Ala Pro Pro Val Leu Gly Gly Glu Asn Tyr Tyr Phe Asp Tyr
1               5                   10
```

<210> SEQ ID NO 697
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 697

```
Gly Val Val Thr Gly Asp Phe Asp Tyr
1               5
```

<210> SEQ ID NO 698
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 698

```
Ala Arg Asp Ser Ser Ser Ser Trp Tyr Phe Asp Leu
1               5                   10
```

<210> SEQ ID NO 699
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 699

Asn His Tyr Ser Gly Ser Tyr Asn Tyr Trp Tyr Phe Asp Leu
1               5                   10

<210> SEQ ID NO 700
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 700

Glu Arg Gly Arg Thr Ile Ala Ala Arg Tyr Phe Asp Leu
1               5                   10

<210> SEQ ID NO 701
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 701

Asp Leu Ile Leu Val Leu Ala
1               5

<210> SEQ ID NO 702
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 702

Pro Pro Trp Phe Asp Asp Tyr Ser Asn Tyr Trp Tyr Phe Asp Leu
1               5                   10                  15

<210> SEQ ID NO 703
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 703

Gly Leu Arg Asp Gly Ala Ala Trp Tyr Phe Asp Leu
1               5                   10

<210> SEQ ID NO 704
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 704

Ala Ser Trp Pro Gly Val Trp Tyr Phe Asp Leu
1               5                   10

<210> SEQ ID NO 705
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 705

Leu Val Arg Ile Ala Ala Ala Gly Thr Glu Tyr Phe Gln His
1               5                   10

<210> SEQ ID NO 706
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 706

Gly Asn Asp Tyr Gly Asp Tyr Trp Tyr Phe Asp Leu
1               5                   10

<210> SEQ ID NO 707
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 707

Gly Ser Gly Val Tyr Gly Gly Asn Tyr Tyr Tyr Tyr Gly Met Asp Val
1               5                   10                  15

<210> SEQ ID NO 708
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 708

Gln Gln Tyr Tyr Ser Thr Pro Arg Thr
1               5

<210> SEQ ID NO 709
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 709

Gln Gln Tyr Tyr Ser Thr Pro Pro Thr
1               5

<210> SEQ ID NO 710
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 710

Gln Gln Tyr Asn Ser Tyr Pro Ile Thr
1               5

```
<210> SEQ ID NO 711
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 711

Gln Pro Tyr Asp Ser Ser Asn His Ala Val
1               5                   10

<210> SEQ ID NO 712
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 712

Cys Ser Tyr Ala Gly Ser Arg Val
1               5

<210> SEQ ID NO 713
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 713

Cys Ser Tyr Ala Gly Ser Tyr Thr Trp Ala
1               5                   10

<210> SEQ ID NO 714
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 714

Cys Ser Tyr Ala Gly Ser His Trp Val
1               5

<210> SEQ ID NO 715
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 715

Ser Ser Tyr Thr Ser Ser Ser Thr Gly Trp Val
1               5                   10

<210> SEQ ID NO 716
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 716

Leu Val Val Ile Lys Ser Tyr Tyr Tyr Gly Met Asp Val
1               5                   10

<210> SEQ ID NO 717
```

```
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 717

Asp Gly Thr Asp Tyr Tyr Asp Ser Ser Gly Tyr Tyr Trp Tyr Phe Asp
1               5                   10                  15

Leu

<210> SEQ ID NO 718
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 718

Ala Asn Tyr Gly Asp Tyr Phe Asp Tyr
1               5

<210> SEQ ID NO 719
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 719

Leu Ile Val Arg Glu Met Ala Thr Leu Tyr Gly Ser Gly Ser Tyr Gln
1               5                   10                  15

Asn Tyr Tyr

<210> SEQ ID NO 720
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 720

Asn Gly Val Tyr Ser Ser Ser Trp Tyr Trp Phe Asp Pro
1               5                   10

<210> SEQ ID NO 721
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 721

Asp Val Tyr Gly Asp Tyr Phe Asp Tyr
1               5

<210> SEQ ID NO 722
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 722

Asp Leu Gly Val Ser Gly Ser Tyr Tyr Phe Asp Tyr
1               5                   10
```

<210> SEQ ID NO 723
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 723

Gly Thr His Tyr Phe Asp Tyr
1               5

<210> SEQ ID NO 724
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 724

Glu Lys Ala Gly Thr His Tyr Phe Asp Tyr
1               5                   10

<210> SEQ ID NO 725
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 725

Asp Asp Ser Gly Ser Tyr Leu Ile Asp Tyr
1               5                   10

<210> SEQ ID NO 726
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 726

Asn Val Ala Ala Ala Gly Thr Tyr Pro Ser Ala Val Phe Tyr Tyr Tyr
1               5                   10                  15

Tyr Gly Met Asp Val
            20

<210> SEQ ID NO 727
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 727

Gly His Ser Ser Gly Tyr Tyr His Tyr Phe Asp Tyr
1               5                   10

<210> SEQ ID NO 728
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 728

```
Gly Thr Asp Asp Tyr Gly Asp Asn Arg Glu Arg Asn Tyr Phe Asp Tyr
1               5                   10                  15
```

<210> SEQ ID NO 729
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 729

```
Gln Gly Lys Ile Thr Gly Glu Gly Asn Phe Asp Tyr
1               5                   10
```

<210> SEQ ID NO 730
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 730

```
His Glu Arg Tyr Tyr Tyr Asp Ser Ser Gly Tyr Tyr Asn Trp Phe Asp
1               5                   10                  15
Pro
```

<210> SEQ ID NO 731
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 731

```
Thr Asp Thr Val Arg Thr Asp Tyr Asp Phe Trp Ser Gly Tyr Ser Tyr
1               5                   10                  15
```

<210> SEQ ID NO 732
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 732

```
Asn Ser Ile Asp Cys Ser Gly Gly Ser Cys Tyr Phe Asp Tyr
1               5                   10
```

<210> SEQ ID NO 733
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 733

```
Arg Leu His Arg Gly Ser Thr Ser Cys Tyr Asp Tyr
1               5                   10
```

<210> SEQ ID NO 734
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 734

```
Arg Leu Leu Thr Ser Ser Cys Asp Ser Gly Phe Asp Tyr
1               5                   10

<210> SEQ ID NO 735
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 735

Gly Ile Ala Ala Ala Asp Asp Ala Phe Asp Ile
1               5                   10

<210> SEQ ID NO 736
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 736

Ala Thr Lys Leu Leu Ser Phe Asp Tyr
1               5

<210> SEQ ID NO 737
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 737

Asp Gln Ser Pro Ser His Asp Ile Val Val Pro Ala Ala Ile Tyr
1               5                   10                  15

Phe Asp Tyr

<210> SEQ ID NO 738
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 738

Asp His His Tyr Glu Gly Leu Arg Leu Gly Glu Leu Ser Leu Phe Asp
1               5                   10                  15

Tyr

<210> SEQ ID NO 739
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 739

Gln Gln Tyr Tyr Ser Thr Pro Pro Tyr Thr
1               5                   10

<210> SEQ ID NO 740
<211> LENGTH: 9
<212> TYPE: PRT
<213> ORGANISM: Artificial Sequence
<220> FEATURE:
```

```
<223> OTHER INFORMATION: Chemically Synthesized

<400> SEQUENCE: 740

Tyr Ser Ala Ala Asp Asn Asn Leu Val
1               5

<210> SEQ ID NO 741
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 741

Ala Ala Trp Asp Asp Ser Leu Asn Gly Leu
1               5                   10

<210> SEQ ID NO 742
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 742

Ser Ser Tyr Thr Ser Ser Ser Thr Gly Val
1               5                   10

<210> SEQ ID NO 743
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 743

Ser Ser Tyr Thr Ser Ser Ser Thr Pro
1               5

<210> SEQ ID NO 744
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 744

Gly Thr Trp Asp Ser Ser Leu Ser Val Asn Trp Val
1               5                   10

<210> SEQ ID NO 745
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 745

Ser Ser Tyr Thr Ser Ser Ser Val Val
1               5

<210> SEQ ID NO 746
<211> LENGTH: 10
<212> TYPE: PRT
<213> ORGANISM: Artificial Sequence
<220> FEATURE:
<223> OTHER INFORMATION: Chemically Synthesized
```

```
<400> SEQUENCE: 746

Ser Ser Tyr Thr Ser Ser Ser Thr Phe Glu
1               5                   10

<210> SEQ ID NO 747
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 747

Gln Ser Tyr Asp Ser Ser Leu Ser Gly Phe Tyr Val
1               5                   10

<210> SEQ ID NO 748
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 748

Ser Ser Tyr Thr Ser Ser Ser Trp Val
1               5

<210> SEQ ID NO 749
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 749

Ser Thr Arg Thr Tyr Ser Ser Ser Trp Tyr Ala Phe Asp Ile
1               5                   10

<210> SEQ ID NO 750
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 750

Arg Arg Ile His Ser Tyr Ser Ser Leu Asp Ala Phe Asp Ile
1               5                   10

<210> SEQ ID NO 751
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 751

Glu Ala Val Trp Gly Phe Asp Tyr
1               5

<210> SEQ ID NO 752
<211> LENGTH: 9
<212> TYPE: PRT
<213> ORGANISM: Artificial Sequence
<220> FEATURE:
<223> OTHER INFORMATION: Chemically Synthesized
```

<400> SEQUENCE: 752

Gly Leu Tyr Gly Asp Tyr Phe Asp Tyr
1               5

<210> SEQ ID NO 753
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 753

Ala Gly Leu Thr Gly Val Gly Ala Phe Asp Ile
1               5                   10

<210> SEQ ID NO 754
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 754

Asp Glu Gly Tyr Leu Arg Phe Asp Tyr
1               5

<210> SEQ ID NO 755
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 755

Ala Gly Tyr Tyr Asp Ile Leu Thr Gly Tyr Tyr Tyr Phe Asp Tyr
1               5                   10                  15

<210> SEQ ID NO 756
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 756

Asp His Asp Phe Trp Ser Gly Tyr Tyr Tyr Tyr Gly Met Asp Val
1               5                   10                  15

<210> SEQ ID NO 757
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 757

Asp Pro Tyr Ser Ser Ser Tyr Tyr Phe Asp Tyr
1               5                   10

<210> SEQ ID NO 758
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 758

```
Ala Ile Asp Tyr Gly Asp Tyr Tyr Phe Asp Tyr
1               5                   10

<210> SEQ ID NO 759
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 759

Gly Gly Arg Gln Arg Gly Ser Gly Tyr Phe Asp Tyr
1               5                   10

<210> SEQ ID NO 760
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 760

His Gln Ile Asp Ser Arg Ser Thr Tyr Tyr Tyr Asp Ser Ser Gly Tyr
1               5                   10                  15

Tyr Phe Asp Tyr
            20

<210> SEQ ID NO 761
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 761

Asp Leu Gln Leu Gly Arg Tyr Tyr Phe Asp Tyr
1               5                   10

<210> SEQ ID NO 762
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 762

Ser Pro Asp Ser Ser Ser Met Ser Lys Leu Pro Tyr Phe Asp Tyr
1               5                   10                  15

<210> SEQ ID NO 763
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 763

Asp Leu Arg Glu Ala Asn Trp Asp Ala Phe Asp Ile
1               5                   10

<210> SEQ ID NO 764
<211> LENGTH: 11
<212> TYPE: PRT
<213> ORGANISM: Artificial Sequence
<220> FEATURE:
<223> OTHER INFORMATION: Chemically Synthesized
```

```
<400> SEQUENCE: 764

Tyr Ser Ser Ser Ser Phe Phe Ala Phe Asp Ile
1               5                   10

<210> SEQ ID NO 765
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 765

Gly Tyr Cys Ser Ser Thr Ser Cys Tyr Tyr Tyr Tyr Met Asp Val
1               5                   10                  15

<210> SEQ ID NO 766
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 766

Asp Arg Arg Gly Asp Leu Gly Ala Phe Asp Ile
1               5                   10

<210> SEQ ID NO 767
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 767

Asn Tyr Gly Gly Asn Lys Asn Ala Phe Asp Ile
1               5                   10

<210> SEQ ID NO 768
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 768

Ser Ile Ala Ala Arg Pro Val Asp Tyr
1               5

<210> SEQ ID NO 769
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 769

Gln Gln Tyr Asp Asn Leu Pro Leu Ser Phe Lys Val Thr
1               5                   10

<210> SEQ ID NO 770
<211> LENGTH: 9
<212> TYPE: PRT
<213> ORGANISM: Artificial Sequence
<220> FEATURE:
<223> OTHER INFORMATION: Chemically Synthesized
```

```
<400> SEQUENCE: 770

Leu Gln Asp Tyr Asn Tyr Pro Trp Thr
1               5

<210> SEQ ID NO 771
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 771

Gln Gln Tyr Tyr Ser Tyr Pro Arg Thr
1               5

<210> SEQ ID NO 772
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 772

Gln Gln Tyr Gly Ser Ser Pro Ala Lys Leu Thr
1               5                   10

<210> SEQ ID NO 773
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 773

Gln Gln Ala Asn Ser Phe Pro Leu Thr
1               5

<210> SEQ ID NO 774
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 774

Cys Ser Tyr Ala Gly Ser Ser Thr Ser Tyr Val
1               5                   10

<210> SEQ ID NO 775
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 775

Cys Ser Tyr Ala Gly Ser Ser Thr Val
1               5

<210> SEQ ID NO 776
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 776
```

```
Gly Thr Trp Asp Ser Ser Leu Ser Ala His Val
1               5                   10

<210> SEQ ID NO 777
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 777

Thr Asp His Ser Gly Ser Tyr Phe Asp Tyr
1               5                   10

<210> SEQ ID NO 778
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 778

Ser Glu Thr Asn Trp Gly Asp Asp Ala Phe Asp Ile
1               5                   10

<210> SEQ ID NO 779
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 779

Glu Ala Arg Thr Gly Ala Phe Phe Asp Tyr
1               5                   10

<210> SEQ ID NO 780
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 780

Asp Tyr Asn Phe Trp Ser Gly Tyr Tyr Thr Gly Asp Ala Phe Asp Ile
1               5                   10                  15

<210> SEQ ID NO 781
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 781

His Glu Asp Pro Asn Trp Gly Gln Pro Leu Asp Tyr
1               5                   10

<210> SEQ ID NO 782
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 782
```

Gly Val Phe Asp Asp Pro Leu Asp Tyr Gly Asp Tyr Phe Asp Tyr
1               5                   10                  15

<210> SEQ ID NO 783
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 783

Gly Leu Gly Tyr Gly Asp Tyr Val Ser Leu Tyr Phe Asp Tyr
1               5                   10

<210> SEQ ID NO 784
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 784

Ala Gln Glu Ala Met Val Ile Phe Asp Tyr
1               5                   10

<210> SEQ ID NO 785
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 785

Ala Pro Ile Thr Met Val Arg Gly Val Pro Ile Tyr Phe Asp Tyr
1               5                   10                  15

<210> SEQ ID NO 786
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 786

Leu Pro Cys Ser Ser Thr Ser Cys Tyr Ala Phe Asp Ile
1               5                   10

<210> SEQ ID NO 787
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 787

Asp Gly Ala Pro Gly Thr Gly Ala Phe Asp Ile
1               5                   10

<210> SEQ ID NO 788
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 788

Asp Gln Arg Tyr Ser Ser Ser Trp Tyr Trp Tyr Phe Asp Leu

```
<210> SEQ ID NO 789
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 789

Glu Pro Thr Gly Thr Thr Gly Thr Phe Asp Tyr
1               5                   10

<210> SEQ ID NO 790
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 790

Gly Cys Gly Ala Asp Gly Tyr
1               5

<210> SEQ ID NO 791
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 791

Thr Phe Tyr Gly Asp Tyr Phe Asp Tyr
1               5

<210> SEQ ID NO 792
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 792

Ala Asp Ser Ser Gly Trp Tyr Tyr Phe Asp Tyr
1               5                   10

<210> SEQ ID NO 793
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 793

Gly Gln Leu Trp Phe Asp Tyr
1               5

<210> SEQ ID NO 794
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 794

Ala Gly Val Val Val Thr Ala Ile Arg Ala Glu Tyr Phe Gln His
1               5                   10                  15
```

<210> SEQ ID NO 795
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 795

Asp Arg Arg Tyr Tyr Phe Asp Tyr
1               5

<210> SEQ ID NO 796
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 796

Thr Ser Ser Gly Trp Tyr Phe Asp Tyr
1               5

<210> SEQ ID NO 797
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 797

Ser Ala Arg Asp Phe Asp Tyr
1               5

<210> SEQ ID NO 798
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 798

Asp Arg Ile Gly Asp Ser Ser Tyr Tyr Phe Asp Tyr
1               5                   10

<210> SEQ ID NO 799
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 799

Pro Gly Pro Gly His Asp Ala Phe Asp Ile
1               5                   10

<210> SEQ ID NO 800
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 800

Gly Lys Ala Ala Arg Ala Phe Asp Ile
1               5

<210> SEQ ID NO 801
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 801

Asp Gly Gly Ile Ala Val Ala Asp Ala Phe Asp Ile
1               5                   10

<210> SEQ ID NO 802
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 802

Asp Leu Arg Glu Tyr Ser Ser Ser Trp Arg Phe Asp Tyr
1               5                   10

<210> SEQ ID NO 803
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 803

Gly Leu Gly Ser Tyr Tyr Phe Asp Tyr
1               5

<210> SEQ ID NO 804
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 804

Ala His Tyr Asp Ile Leu Thr Gly Tyr Tyr Ala Phe Asp Ile
1               5                   10

<210> SEQ ID NO 805
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 805

Asp Arg Ser Leu Pro Tyr Ser Ser Ser Trp Tyr Tyr Phe Asp Tyr
1               5                   10                  15

<210> SEQ ID NO 806
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 806

Gln Gln Tyr Asn Ser Tyr Ser Met Tyr Thr
1               5                   10

```
<210> SEQ ID NO 807
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 807

Gln Gln Tyr Asn Asn Tyr Ser Tyr Ser
1               5

<210> SEQ ID NO 808
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 808

Leu Gln His Asn Ser Tyr Pro Arg Thr
1               5

<210> SEQ ID NO 809
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 809

Gln Gln Tyr Tyr Ser Thr Ala Tyr Thr
1               5

<210> SEQ ID NO 810
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 810

Gln Gln Arg Ser Asn Trp Ile Thr
1               5

<210> SEQ ID NO 811
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 811

Gln Gln Arg Ser Thr Trp Pro Pro Thr
1               5

<210> SEQ ID NO 812
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 812

Ser Ser Tyr Thr Ser Ser Gly Trp Val
1               5

<210> SEQ ID NO 813
```

```
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 813

Ala Ala Trp Asp Asp Ser Leu Ser Gly Gln Val
1               5                   10

<210> SEQ ID NO 814
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 814

Ser Ser Tyr Thr Ser Ser Ser Thr Lys Val
1               5                   10

<210> SEQ ID NO 815
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 815

Gln Ala Trp Asp Ser Ser Thr Ala Val Val
1               5                   10

<210> SEQ ID NO 816
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 816

Cys Ser Tyr Ala Gly Ser Tyr Thr Phe Val
1               5                   10

<210> SEQ ID NO 817
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 817

Cys Ser Tyr Ala Gly Tyr Trp Val
1               5

<210> SEQ ID NO 818
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 818

Val Pro Ala Ser Asn Trp Asn Tyr Phe Asp Tyr
1               5                   10

<210> SEQ ID NO 819
<211> LENGTH: 8
```

```
<212> TYPE: PRT
<213> ORGANISM: Artificial Sequence
<220> FEATURE:
<223> OTHER INFORMATION: Chemically Synthesized

<400> SEQUENCE: 819

Ser Asp Trp Gly Tyr Phe Asp Tyr
1               5

<210> SEQ ID NO 820
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 820

Trp Arg Ala Ala Ala Asp Ala Phe Asp Ile
1               5                   10

<210> SEQ ID NO 821
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 821

Leu Lys Lys Ala Asn Trp Gly Ser Gly Thr His Trp Tyr Phe Asp Leu
1               5                   10                  15

<210> SEQ ID NO 822
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 822

Asp Val Ser Ser Ser Trp Tyr Phe Asp Tyr
1               5                   10

<210> SEQ ID NO 823
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 823

Arg Pro Pro Ser Ile Ala Ala Arg Tyr Tyr Tyr Tyr Met Asp Val
1               5                   10                  15

<210> SEQ ID NO 824
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 824

Gly Thr Glu Tyr Ser Ser Ser Tyr Tyr Phe Asp Tyr
1               5                   10

<210> SEQ ID NO 825
<211> LENGTH: 9
<212> TYPE: PRT
```

```
<213> ORGANISM: Artificial Sequence
<220> FEATURE:
<223> OTHER INFORMATION: Chemically Synthesized

<400> SEQUENCE: 825

Asp Arg Pro Thr Gly Asp Leu Asp Tyr
1               5

<210> SEQ ID NO 826
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 826

Asp Gly Ala Tyr Ser Ser Gly Trp Tyr Tyr Phe Asp Tyr
1               5                   10

<210> SEQ ID NO 827
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 827

Ile Leu Thr Ala Gly Val Asp Tyr
1               5

<210> SEQ ID NO 828
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 828

Asp His Val Tyr Ser Ser Ser Trp Tyr Phe Asp Tyr
1               5                   10

<210> SEQ ID NO 829
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 829

Gly Ile Arg Ala Tyr Trp Tyr Phe Asp Leu
1               5                   10

<210> SEQ ID NO 830
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 830

Ile Phe Gly Val Val Ile Tyr Tyr
1               5

<210> SEQ ID NO 831
<211> LENGTH: 14
<212> TYPE: PRT
<213> ORGANISM: Artificial Sequence
```

```
<220> FEATURE:
<223> OTHER INFORMATION: Chemically Synthesized

<400> SEQUENCE: 831

Asp Asp Arg Phe Lys Tyr Ser Ser Ser Tyr Phe Gln His
1               5                   10

<210> SEQ ID NO 832
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 832

Glu Pro Trp Phe Gly Glu Phe Tyr Phe Asp Tyr
1               5                   10

<210> SEQ ID NO 833
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 833

Asp Gln Gly Val Gly Arg Phe Asp Tyr
1               5

<210> SEQ ID NO 834
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 834

Lys Val Pro Ala Ala Gly Ile Phe Asp Tyr
1               5                   10

<210> SEQ ID NO 835
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 835

Asp Arg Arg Gly Thr Gly Phe Asp Tyr
1               5

<210> SEQ ID NO 836
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 836

Ile Ser Arg Ala Phe Asp Tyr
1               5

<210> SEQ ID NO 837
<211> LENGTH: 17
<212> TYPE: PRT
<213> ORGANISM: Artificial Sequence
<220> FEATURE:
```

-continued

<223> OTHER INFORMATION: Chemically Synthesized

<400> SEQUENCE: 837

Val Gly Pro Tyr Ser Tyr Gly Tyr Asp Tyr Ser Asn Tyr Tyr Phe Asp
1               5                   10                  15
Tyr

<210> SEQ ID NO 838
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 838

Asp His Pro Gln Tyr Tyr Phe Asp Tyr
1               5

<210> SEQ ID NO 839
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 839

Ala Asn Trp Gly Phe Tyr Tyr Phe Asp Tyr
1               5                   10

<210> SEQ ID NO 840
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 840

Gly Asp Tyr Gly Ser Gly Ser Tyr Tyr Asn Asp Tyr
1               5                   10

<210> SEQ ID NO 841
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 841

His Gly Asp Tyr Trp Phe Asp Pro
1               5

<210> SEQ ID NO 842
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 842

Ala Tyr Ser Ser Ser Ser Gly Asp Ala Phe Asp Ile
1               5                   10

<210> SEQ ID NO 843
<211> LENGTH: 9
<212> TYPE: PRT
<213> ORGANISM: Artificial Sequence

```
<220> FEATURE:
<223> OTHER INFORMATION: Chemically Synthesized

<400> SEQUENCE: 843

Gln Gln Arg Ser Thr Trp Pro Arg Thr
1               5

<210> SEQ ID NO 844
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 844

Gln Gln Ser Tyr Ser Thr Pro Pro Thr
1               5

<210> SEQ ID NO 845
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 845

Gln Gln Tyr Asn Asn Trp Leu Pro Phe Thr
1               5                   10

<210> SEQ ID NO 846
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 846

Met Ile Trp Pro Ser Asn Ala Tyr Val
1               5

<210> SEQ ID NO 847
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 847

Ser Ser Tyr Thr Ser Ser Ser Thr Leu Gly Trp Val
1               5                   10

<210> SEQ ID NO 848
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 848

Leu Leu Ser Tyr Ser Gly Ala Trp Val
1               5

<210> SEQ ID NO 849
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 849

Cys Ser Tyr Ala Gly Ser Tyr His Val Val
1               5                   10

<210> SEQ ID NO 850
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 850

Asp Arg Arg Ile Val Val Val Thr Ala Ile Asn Tyr Tyr Tyr Tyr
1               5                   10                  15

Met Asp Val

<210> SEQ ID NO 851
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 851

Glu Gly Leu Gly Asp Tyr Phe Asp Tyr
1               5

<210> SEQ ID NO 852
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 852

Gly Glu Leu Gly Pro Phe Asp Tyr
1               5

<210> SEQ ID NO 853
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 853

Gly Pro Arg Ser Phe Ala Phe Asp Ile
1               5

<210> SEQ ID NO 854
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 854

Gly Val Gly Ser Gly Tyr Tyr Tyr Phe Asp Tyr
1               5                   10

<210> SEQ ID NO 855
<211> LENGTH: 15
<212> TYPE: PRT
<213> ORGANISM: Artificial Sequence

```
<220> FEATURE:
<223> OTHER INFORMATION: Chemically Synthesized

<400> SEQUENCE: 855

Asp Leu Leu Pro Ser Arg Tyr Gly Asp Tyr Asn Trp Phe Asp Pro
1               5                   10                  15

<210> SEQ ID NO 856
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 856

Glu Arg Thr Gly Ala Phe Asp Tyr
1               5

<210> SEQ ID NO 857
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 857

Ser Thr Thr Asn Ala Val Tyr Trp Tyr Phe Asp Leu
1               5                   10

<210> SEQ ID NO 858
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 858

Gly His Leu Lys Ser Ser Tyr Ser Ser Ser Trp Tyr Ser Tyr
1               5                   10

<210> SEQ ID NO 859
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 859

Asp Thr Arg Gly Thr Gly Thr Thr Tyr Tyr Phe Asp Tyr
1               5                   10

<210> SEQ ID NO 860
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 860

Ala Pro Ala Ser His Ile Ala Ala Ala Gly Arg Ile Tyr Phe Asp Tyr
1               5                   10                  15

<210> SEQ ID NO 861
<211> LENGTH: 8
<212> TYPE: PRT
<213> ORGANISM: Artificial Sequence
<220> FEATURE:
```

<223> OTHER INFORMATION: Chemically Synthesized

<400> SEQUENCE: 861

Thr Gly Pro Tyr Tyr Phe Asp Tyr
1               5

<210> SEQ ID NO 862
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 862

Gln Val Arg Gly Trp Tyr Phe Asp Leu
1               5

<210> SEQ ID NO 863
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 863

Asp Leu Gly Ser Tyr Tyr Asp Tyr
1               5

<210> SEQ ID NO 864
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 864

Pro Leu Thr Ala Asp Tyr Trp Tyr Phe Asp Leu
1               5                   10

<210> SEQ ID NO 865
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 865

Ala Gly Thr Gly Ala Phe Asp Ile
1               5

<210> SEQ ID NO 866
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 866

Asp Tyr Gln Leu Gly Gly Ser Tyr Tyr Asp Ala Phe Asp Ile
1               5                   10

<210> SEQ ID NO 867
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 867

Ser Pro Ala Tyr Asp Cys Gly Gly Asp Cys Arg Phe Asp Tyr
1               5                   10

<210> SEQ ID NO 868
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 868

Ala Gly Thr Ala Ala Ala Gly Thr Gly Trp Phe Asp Pro
1               5                   10

<210> SEQ ID NO 869
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 869

Asp Gln Gly Tyr Tyr Tyr Gly Ser Gly Ser Tyr Leu Asp Tyr
1               5                   10

<210> SEQ ID NO 870
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 870

Gln Ala Asn Trp Gly Ser Glu Glu Ala Phe Asp Ile
1               5                   10

<210> SEQ ID NO 871
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 871

Gly Tyr Gly Asp Tyr Trp Phe Asp Pro
1               5

<210> SEQ ID NO 872
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 872

Glu Trp Val Tyr
1

<210> SEQ ID NO 873
<211> LENGTH: 10
<212> TYPE: PRT
<213> ORGANISM: Artificial Sequence
<220> FEATURE:
<223> OTHER INFORMATION: Chemically Synthesized

```
<400> SEQUENCE: 873

Ser Val Thr Gly Gly Leu Pro Met His Tyr
1               5                   10

<210> SEQ ID NO 874
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 874

Gly Val Tyr Tyr Asp Tyr Val
1               5

<210> SEQ ID NO 875
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 875

Asn Gly Arg Trp Glu Leu Pro Thr Ser Arg Phe Asn Tyr Phe Asp Tyr
1               5                   10                  15

<210> SEQ ID NO 876
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 876

Ser Lys Arg Thr Gly Glu Gly Asp Tyr
1               5

<210> SEQ ID NO 877
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 877

Asp Gly Ala Pro Thr Gly Asp Pro Ile Leu Asp Tyr
1               5                   10

<210> SEQ ID NO 878
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 878

Val Ile Ala Glu Gly Ala Thr Lys Tyr Phe Gln His
1               5                   10

<210> SEQ ID NO 879
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 879
```

```
Ile Ser Pro Asn Trp Gly Ser Gly Ala Phe Asp Ile
1               5                   10
```

<210> SEQ ID NO 880
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 880

```
Asp Phe Ser Pro Leu Tyr Asp Ser Ser Gly Tyr Tyr Phe Asp Pro
1               5                   10                  15
```

<210> SEQ ID NO 881
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 881

```
Arg Thr Gly Asp His Trp Tyr Phe Asp Leu
1               5                   10
```

<210> SEQ ID NO 882
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 882

```
Ala Ile Arg Arg Tyr Ser Gly Ser Tyr Tyr Trp Phe Asp Pro
1               5                   10
```

<210> SEQ ID NO 883
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 883

```
Gln Gln Ser Tyr Ser Thr Arg Thr
1               5
```

<210> SEQ ID NO 884
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 884

```
Gln Gln Tyr Asn Asn Trp Pro Pro Tyr Ser
1               5                   10
```

<210> SEQ ID NO 885
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 885

Gln Gln Leu Asn Ser Tyr Leu Ser Ile Thr
1               5                   10

<210> SEQ ID NO 886
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 886

Met Gln Gly Thr His Trp Trp Thr
1               5

<210> SEQ ID NO 887
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 887

Gln Gln Tyr Ala Thr Ser Leu Thr
1               5

<210> SEQ ID NO 888
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 888

Gln Gln Tyr Tyr Ser Tyr Pro Ile Thr
1               5

<210> SEQ ID NO 889
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 889

Gln Gln Tyr Gly Ser Ser Leu Leu Thr
1               5

<210> SEQ ID NO 890
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 890

Leu Gln His Gln Thr Tyr Pro Arg Thr
1               5

<210> SEQ ID NO 891
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 891

Gln Gln Tyr Gly Ser Ser Pro Val

```
1               5

<210> SEQ ID NO 892
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 892

Gln Gln Arg Ser Thr Trp Pro Leu Thr
1               5

<210> SEQ ID NO 893
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 893

Gln Ser Ala Asp Ser Ser Gly Thr Trp Val
1               5                   10

<210> SEQ ID NO 894
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 894

Cys Ser Tyr Ala Gly Ser Ser Thr His Val Val
1               5                   10

<210> SEQ ID NO 895
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 895

Met Ile Trp Ala Ser Asn Ala Trp Val
1               5

<210> SEQ ID NO 896
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 896

Gln Ala Trp Asp Ser Ser Thr Gly Val
1               5

<210> SEQ ID NO 897
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 897

Asp Phe Phe Arg Ser Ile Ala Ala Arg Pro Ser Trp Gly Pro Phe Asp
1               5                   10                  15
```

Tyr

<210> SEQ ID NO 898
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 898

Gly Ser Cys Gly Gln Thr Thr Glu Asn Trp Phe Asp Pro
1               5                   10

<210> SEQ ID NO 899
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 899

Gly Gly Tyr Cys Ser Ser Thr Ser Cys Phe Asn Tyr Gly Met Asp Val
1               5                   10                  15

<210> SEQ ID NO 900
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 900

Val Phe Trp Thr Pro Arg Tyr Asp Ser Ser Gly Tyr Tyr Tyr Phe Asp
1               5                   10                  15
Tyr

<210> SEQ ID NO 901
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 901

Asp Arg Ala Tyr Cys Gly Gly Asp Cys Tyr Ser Gly Thr Gly Gly Phe
1               5                   10                  15
Asp Pro

<210> SEQ ID NO 902
<211> LENGTH: 26
<212> TYPE: PRT
<213> ORGANISM: Artificial Sequence
<220> FEATURE:
<223> OTHER INFORMATION: Chemically Synthesized

<400> SEQUENCE: 902

Asp Ser Val Tyr Tyr Tyr Gly Ser Gly Ser Tyr Tyr Asn Glu Gly Ser
1               5                   10                  15
Thr Leu Pro Lys Tyr Asn Trp Phe Asp Pro
            20                  25

<210> SEQ ID NO 903
<211> LENGTH: 17
<212> TYPE: PRT

```
<213> ORGANISM: Artificial Sequence
<220> FEATURE:
<223> OTHER INFORMATION: Chemically Synthesized

<400> SEQUENCE: 903

Leu Leu Phe Arg Leu Thr Met Ile Val Val Thr Gly Gly Ile Asp
1               5                   10                  15

Tyr

<210> SEQ ID NO 904
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 904

Glu Pro Pro Gly Thr Thr Ser Pro Ser Leu Thr Asn Trp Phe Asp Pro
1               5                   10                  15

<210> SEQ ID NO 905
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 905

Asp Pro Phe Ile Tyr Asp Arg Asn Asp Tyr Gly Asp Tyr Gly Trp Phe
1               5                   10                  15

Asp Pro

<210> SEQ ID NO 906
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 906

Val Gly Val Glu Met Ala Thr Thr Gly Arg Cys Tyr Tyr Gly Met Asp
1               5                   10                  15

Val

<210> SEQ ID NO 907
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 907

Cys Arg Ala Ser Ser Gly Phe Gly Glu Leu Gly Asp Tyr Tyr Gly Met
1               5                   10                  15

Asp Val

<210> SEQ ID NO 908
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 908
```

```
Gly Pro Val Thr Asn Gly Tyr Tyr Phe Asp Tyr
1               5                   10
```

<210> SEQ ID NO 909
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 909

```
Asp Gln Gly Tyr Tyr Asp Ser Ser Gly Tyr Tyr Gly Phe Asp Tyr
1               5                   10                  15
```

<210> SEQ ID NO 910
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 910

```
Ala Arg Leu Gly Ala Thr Phe Asp Tyr
1               5
```

<210> SEQ ID NO 911
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 911

```
Ala Gly Gly Ala Leu Ile Pro Ala Ala Ile Asp Trp Phe Asp Pro
1               5                   10                  15
```

<210> SEQ ID NO 912
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 912

```
Asp His Ile Ser Gly Gly Ser Cys Tyr Ser Ala Phe Asp Ile
1               5                   10
```

<210> SEQ ID NO 913
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 913

```
Gly Thr Ile Phe Gly Val Val Tyr Ser Asp Tyr
1               5                   10
```

<210> SEQ ID NO 914
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 914

Pro Leu Asn Arg Ser Gly Phe Asp Tyr

```
<210> SEQ ID NO 915
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 915

Met Glu Gly Ser Tyr Tyr Tyr Asp Ser Ser Gly Tyr Pro Phe Phe Asp
1               5                   10                  15
Tyr

<210> SEQ ID NO 916
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 916

Val Pro Ala Thr Thr Trp Ile Gln Leu Trp Gly Leu Asp Tyr
1               5                   10

<210> SEQ ID NO 917
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 917

Tyr Gly Gly Asn Gly Gly Gly Leu Val Gly Ala Phe Asp Ile
1               5                   10

<210> SEQ ID NO 918
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 918

Gly Leu Arg Val Gly Tyr Val Ser Gly Ser Tyr Tyr Asn Asp Trp Phe
1               5                   10                  15
Asp Pro

<210> SEQ ID NO 919
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 919

Asp Gly Arg Glu Glu Leu Asn Ser Arg Ile Thr Met Val Arg Gly Pro
1               5                   10                  15
Phe Asp Tyr

<210> SEQ ID NO 920
<211> LENGTH: 18
<212> TYPE: PRT
<213> ORGANISM: Artificial Sequence
<220> FEATURE:
```

```
<223> OTHER INFORMATION: Chemically Synthesized

<400> SEQUENCE: 920

Val Pro Pro Leu Gly Tyr Cys Ser Gly Gly Ser Cys Leu Asn Trp Phe
1               5                   10                  15

Asp Pro

<210> SEQ ID NO 921
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 921

Glu Ile Gly Asp Ser Gly Ser Tyr Tyr Phe Asp Tyr
1               5                   10

<210> SEQ ID NO 922
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 922

Phe Gly Val Val Lys Ala Gly Asn Trp Phe Asp Pro
1               5                   10

<210> SEQ ID NO 923
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 923

Gly Gly Gln Met Asn Leu Asn Asp Gly Pro Val Leu Tyr Tyr Tyr Tyr
1               5                   10                  15

Gly Met Asp Val
            20

<210> SEQ ID NO 924
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 924

Val Asp Thr Tyr Tyr Tyr Asp Ser Ser Gly Tyr Ser Arg Tyr Tyr Phe
1               5                   10                  15

Asp Tyr

<210> SEQ ID NO 925
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 925

Val Ser Pro Lys Ile Asn Cys Ser Gly Gly Ser Cys Phe Ile Thr His
1               5                   10                  15
```

Phe Asp Tyr

<210> SEQ ID NO 926
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 926

Asp Leu Gly Asp Pro Arg Val Glu Asp Trp Phe Asp Pro
1               5                   10

<210> SEQ ID NO 927
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 927

Ala Leu Pro Tyr Cys Ser Ser Thr Ser Cys Tyr Gln Tyr Tyr Phe Asp
1               5                   10                  15

Tyr

<210> SEQ ID NO 928
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 928

Asp Gln Val Ser Tyr Gly Asp Tyr Arg Gly Tyr Tyr Phe Asp Tyr
1               5                   10                  15

<210> SEQ ID NO 929
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 929

Asp Gln Val Asp Thr Ala Met Val Leu Asp Tyr
1               5                   10

<210> SEQ ID NO 930
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 930

Leu Thr Tyr Tyr Tyr Asp Ser Ser Gly Tyr Tyr Tyr Phe Asp Tyr
1               5                   10                  15

<210> SEQ ID NO 931
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 931

```
Asp Gln Asp Ser Tyr Ser Ser Gly Trp Val Gly Leu Asp Tyr
1               5                   10
```

<210> SEQ ID NO 932
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 932

```
Gln Gln Tyr Gly Ser Ser Pro Met Tyr Thr
1               5                   10
```

<210> SEQ ID NO 933
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 933

```
Gln Gln Tyr Tyr Ser Thr Pro Tyr Thr
1               5
```

<210> SEQ ID NO 934
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 934

```
Gln Gln Tyr Gly Ser Ser Pro Phe Tyr
1               5
```

<210> SEQ ID NO 935
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 935

```
Gln Gln Arg Ser Thr Trp Pro Tyr Thr
1               5
```

<210> SEQ ID NO 936
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 936

```
Gln Gln Arg Ser Asn Trp Pro Ile Thr
1               5
```

<210> SEQ ID NO 937
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 937

```
Gln Gln Tyr Asn Asn Trp Pro Tyr Ala
```

```
1               5
```

<210> SEQ ID NO 938
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 938

```
Gly Thr Trp Asp Ser Ser Leu Ser Ala Glu Val
1               5                   10
```

<210> SEQ ID NO 939
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 939

```
Met Ile Trp Pro Ser Asn Ala Trp Val
1               5
```

<210> SEQ ID NO 940
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 940

```
Ala Trp Asp Asp Ser Leu Ser Gly Pro Ser
1               5                   10
```

<210> SEQ ID NO 941
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 941

```
Cys Ser Tyr Ala Gly Ser Ser Thr Asn Tyr Val
1               5                   10
```

<210> SEQ ID NO 942
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 942

```
Ala Gly Ser Ser Thr Leu Val Val
1               5
```

<210> SEQ ID NO 943
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 943

```
Gln Ser Tyr Asp Ser Ser Leu Ser Gly Pro Tyr Val
1               5                   10
```

```
<210> SEQ ID NO 944
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 944

Ala Gly Ser Ser Thr Tyr Val
1               5

<210> SEQ ID NO 945
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 945

Cys Ser Tyr Ala Gly Ser Tyr Thr Val
1               5

<210> SEQ ID NO 946
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 946

Ala Ala Trp Asp Asp Ser Leu Ser Gly His Val Val
1               5                   10

<210> SEQ ID NO 947
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 947

Ala His Tyr Asp Ile Leu Thr Gly Tyr Trp Phe Asp Tyr
1               5                   10

<210> SEQ ID NO 948
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 948

Ser Gly Asp Ser Ser Gly Tyr Tyr Phe Asp Tyr
1               5                   10

<210> SEQ ID NO 949
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 949

Thr Ala Gly Tyr Ser Ser Ser Trp Phe Asp Tyr
1               5                   10
```

```
<210> SEQ ID NO 950
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 950

Asp Ile Val Val Pro Ala Ala Thr Pro Gly Val Ser Gly Phe Asp
1               5                   10                  15

Tyr

<210> SEQ ID NO 951
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 951

Gly Pro Ser Val Val Met Trp Glu Leu Ser Ser Asp Ala Phe Asp Ile
1               5                   10                  15

<210> SEQ ID NO 952
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 952

Glu Trp Ala Gly Tyr Ser Ser Gly Trp Ser Asp Tyr Asn Trp Phe Asp
1               5                   10                  15

Pro

<210> SEQ ID NO 953
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 953

Ser Ala Gly Asp Trp Gly Trp Tyr Phe Asp Leu
1               5                   10

<210> SEQ ID NO 954
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 954

Val Gly Asp Tyr Ser Asn Tyr Pro Ala Asp Tyr
1               5                   10

<210> SEQ ID NO 955
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 955
```

```
Thr Tyr Ser Ser Ser Trp Leu Tyr Ile Asp Tyr
1               5                   10
```

<210> SEQ ID NO 956
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 956

```
Asp Leu Val Gly Tyr Ser Ser Trp Asn Trp Phe Asp Pro
1               5                   10
```

<210> SEQ ID NO 957
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 957

```
Asp Leu Tyr Tyr Tyr Asp Ser Ser Gly Tyr Pro Leu Gly Gly Gly Phe
1               5                   10                  15
Asp Tyr
```

<210> SEQ ID NO 958
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 958

```
Gly Thr Lys Gln Glu Leu Gly Lys Tyr Tyr Phe Asp Tyr
1               5                   10
```

<210> SEQ ID NO 959
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 959

```
Ala Gly Gln Leu Glu Pro His Tyr Phe Asp Tyr
1               5                   10
```

<210> SEQ ID NO 960
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 960

```
Gly Leu Ser Tyr Tyr Asp Ser Arg Gly Asp Tyr Phe Asp Tyr
1               5                   10
```

<210> SEQ ID NO 961
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 961

Asn Asn Gly Ala Thr Thr Trp Arg Ala Asp Tyr
1               5                   10

<210> SEQ ID NO 962
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 962

Asp Trp Gly Asp Asn Cys Ser Gly Gly Ser Cys Tyr Ser Asn Lys Val
1               5                   10                  15

Pro Asp Ala Phe Asp Ile
            20

<210> SEQ ID NO 963
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 963

Asn Glu Gly Tyr Gly Asp Tyr Leu Tyr Tyr Phe Asp Tyr
1               5                   10

<210> SEQ ID NO 964
<211> LENGTH: 24
<212> TYPE: PRT
<213> ORGANISM: Artificial Sequence
<220> FEATURE:
<223> OTHER INFORMATION: Chemically Synthesized

<400> SEQUENCE: 964

Glu Arg Val Ala Ile Gly Ile Val Gly Ala Thr Thr Ala Arg Gly Gly
1               5                   10                  15

Gln Gln Tyr Asn Trp Phe Asp Pro
            20

<210> SEQ ID NO 965
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 965

Gln Leu Leu Asn Tyr Tyr Asp Ser Ser Gly Tyr Tyr Tyr Tyr
1               5                   10

<210> SEQ ID NO 966
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 966

His Gly Ser Gly Thr Tyr Gln His Phe Asp Tyr
1               5                   10

<210> SEQ ID NO 967
<211> LENGTH: 20
<212> TYPE: PRT

```
<213> ORGANISM: Artificial Sequence
<220> FEATURE:
<223> OTHER INFORMATION: Chemically Synthesized

<400> SEQUENCE: 967

His Phe Pro Ala Ile Gly Asp Ser Ser Gly Tyr Val Gly Ala Tyr Asn
1               5                   10                  15

Trp Phe Asp Pro
            20

<210> SEQ ID NO 968
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 968

Glu Pro Asn Leu Ala Ala Ala Gly Thr Lys Lys Asn Ala Phe Asp Ile
1               5                   10                  15

<210> SEQ ID NO 969
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 969

His Phe Glu Val Gly Ala His Arg Phe Asp Pro
1               5                   10

<210> SEQ ID NO 970
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 970

Asp Gly Arg Gly Ile Ala Ala Ala Gly Thr Pro Tyr Tyr Tyr Gly Met
1               5                   10                  15

Asp Val

<210> SEQ ID NO 971
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 971

Asp Leu Thr Gly Asp Arg Gly Asn Ala Phe Asp Ile
1               5                   10

<210> SEQ ID NO 972
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 972

Asp Phe Gly Ala Ile Val Val Val Thr Asp Ala Phe Asp Ile
1               5                   10
```

<210> SEQ ID NO 973
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 973

Gly Ala Ser Asp Thr Ala Met Val Thr Tyr Tyr Tyr Gly Met Asp
1               5                   10                  15

Val

<210> SEQ ID NO 974
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 974

His Ala Pro Pro Pro Ile Ala Val Ala Gly Thr Val Ala Phe Asp Ile
1               5                   10                  15

<210> SEQ ID NO 975
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 975

Glu Val Trp Ser Gly Tyr Thr Ile Phe Gly Val Val Ile Tyr
1               5                   10

<210> SEQ ID NO 976
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 976

Thr Gly Tyr Ser Ser Gly Trp Asn Trp Phe Asp Pro
1               5                   10

<210> SEQ ID NO 977
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 977

Phe Gly Ser Ser Pro His His Ser Gly Ser Ala Val Asp Trp Phe Asp
1               5                   10                  15

Pro

<210> SEQ ID NO 978
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 978

Asp Arg Val Asp Tyr Tyr Tyr Asp Ser Ser Gly Tyr Pro Thr Asp Ala
1               5                   10                  15

Phe Asp Ile

<210> SEQ ID NO 979
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 979

Asp Pro Pro Gly Lys Gly Thr Gln Ser Phe Asp Tyr
1               5                   10

<210> SEQ ID NO 980
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 980

Ala Gly Gly Pro Leu Val Arg Tyr Ala Ala Ala Gly Tyr Trp Tyr Phe
1               5                   10                  15

Asp Leu

<210> SEQ ID NO 981
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 981

Arg Gly Thr Met Val Arg Gly Val Asn Val Gly Trp Phe Asp Pro
1               5                   10                  15

<210> SEQ ID NO 982
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 982

Asp Leu Gly Tyr Ser Tyr Gly Tyr Thr Asp Tyr
1               5                   10

<210> SEQ ID NO 983
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 983

Asp Gln Tyr Asp Ile Leu Thr Gly Phe Asp Tyr
1               5                   10

<210> SEQ ID NO 984
<211> LENGTH: 9
<212> TYPE: PRT
<213> ORGANISM: Artificial Sequence
<220> FEATURE:
<223> OTHER INFORMATION: Chemically Synthesized

```
<400> SEQUENCE: 984

Met Gln Gly Thr His Trp Pro Pro Thr
1               5

<210> SEQ ID NO 985
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 985

Gln Lys Tyr Asn Ser Ala Pro Phe Thr
1               5

<210> SEQ ID NO 986
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 986

Gln Gln Tyr Asn Asn Trp Pro Pro Val Trp Thr
1               5                   10

<210> SEQ ID NO 987
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 987

Gln Gln Tyr Asn Asn Trp Thr
1               5

<210> SEQ ID NO 988
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 988

Gln Gln Tyr Gly Ser Ser Pro Ile Thr
1               5

<210> SEQ ID NO 989
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 989

Gln Gln Tyr Asn Ser Tyr Arg Thr
1               5

<210> SEQ ID NO 990
<211> LENGTH: 7
<212> TYPE: PRT
<213> ORGANISM: Artificial Sequence
<220> FEATURE:
<223> OTHER INFORMATION: Chemically Synthesized
```

<400> SEQUENCE: 990

Gln Gln Arg Ser Asn Cys Thr
1               5

<210> SEQ ID NO 991
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 991

Gln Gln Tyr Gly Ser Ser Pro Leu Val Thr
1               5                   10

<210> SEQ ID NO 992
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 992

Gln Gln Arg Ser Asn Trp Tyr Thr
1               5

<210> SEQ ID NO 993
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 993

Val Leu Tyr Met Gly Ser Gly Val Trp Val
1               5                   10

<210> SEQ ID NO 994
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 994

Cys Ser Tyr Ala Gly Ser Tyr Thr Val Val
1               5                   10

<210> SEQ ID NO 995
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 995

Ala Ala Trp Asp Asp Ser Leu Asn Val Val
1               5                   10

<210> SEQ ID NO 996
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 996

```
Gly Ala Ser Pro Tyr Gly Gly Asn Ser Gly Ala Phe Asp Ile
1               5                   10

<210> SEQ ID NO 997
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 997

Gly Pro Asn Tyr Pro Asn Gln Ser Arg Tyr Phe Asp Leu
1               5                   10

<210> SEQ ID NO 998
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 998

Lys Thr Asp Gly Gly Gly Gly Ser Ser Ser His Phe Asp Tyr
1               5                   10

<210> SEQ ID NO 999
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 999

Asp Pro Thr Ser Val Val Met Ser Asp Ala Phe Asp Ile
1               5                   10

<210> SEQ ID NO 1000
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1000

Asp Thr Val Gly Gly Trp Leu Gly Lys Tyr Phe Gln His
1               5                   10

<210> SEQ ID NO 1001
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1001

Arg Ser Gly Ser Asn Arg Gly Leu Gly Tyr Phe Asp Tyr
1               5                   10

<210> SEQ ID NO 1002
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1002
```

Thr Asn Thr Val Val Gly Tyr Trp Tyr Phe Asp Leu
1               5                   10

<210> SEQ ID NO 1003
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1003

Asp Arg Gly Gly Asp Tyr Phe Asp Tyr
1               5

<210> SEQ ID NO 1004
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1004

Pro Gly Ser Ile Ala Ala Arg Val Leu Asp Tyr
1               5                   10

<210> SEQ ID NO 1005
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1005

His Arg Gly Ile Ala Ala Ala Gly Asp Tyr
1               5                   10

<210> SEQ ID NO 1006
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1006

His Pro Ile Gln Asp Ile Val Val Val Ala Ala Asn Trp Phe Asp
1               5                   10                  15

Pro

<210> SEQ ID NO 1007
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1007

Asp Arg Tyr Tyr Asp Ser Ser Gly Tyr Ser Asp Tyr Tyr Tyr Gly Met
1               5                   10                  15

Asp Val

<210> SEQ ID NO 1008
<211> LENGTH: 12
<212> TYPE: PRT
<213> ORGANISM: Artificial Sequence
<220> FEATURE:
<223> OTHER INFORMATION: Chemically Synthesized

```
<400> SEQUENCE: 1008

Asp Pro Gly Gly Ser Ile Ala Val Ala Gly Asp Tyr
1               5                  10

<210> SEQ ID NO 1009
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 1009

Val Gly Trp Glu Asp Asp Tyr Gly Asp Gln Gly Gly Arg Tyr Tyr Tyr
1               5                  10                  15

Tyr Gly Met Asp Val
            20

<210> SEQ ID NO 1010
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1010

Gly Ala Met Thr Thr Val Thr Thr Gly Gly Pro Ala Ala Gly Tyr Phe
1               5                  10                  15

Asp Leu

<210> SEQ ID NO 1011
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1011

Ala Gly Arg Arg Asp Gly Tyr Asn Tyr Tyr Phe Asp Tyr
1               5                  10

<210> SEQ ID NO 1012
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1012

Asp Pro His Tyr Asp Ile Leu Thr Gly Tyr Ser His Asn Trp Phe Asp
1               5                  10                  15

Pro

<210> SEQ ID NO 1013
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1013

Asp Arg Val Glu Met Ala Thr Ile Tyr Tyr Tyr Tyr Tyr Gly Met Asp
1               5                  10                  15

Val
```

<210> SEQ ID NO 1014
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1014

Asp Ala His Tyr Tyr Asp Ser Ser Gly Tyr Pro Pro Ala Tyr Tyr Phe
1               5                   10                  15

Asp Tyr

<210> SEQ ID NO 1015
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1015

Glu Gly Val Val Thr Lys Phe Pro Asp Tyr
1               5                   10

<210> SEQ ID NO 1016
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1016

Trp Gly Val Ser Asn Ser Cys Ser Ser Thr Ser Cys Tyr Ser Ser Arg
1               5                   10                  15

Leu Tyr Tyr Phe Asp Tyr
            20

<210> SEQ ID NO 1017
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1017

Asp Thr Gly His Thr Gly Asp Tyr
1               5

<210> SEQ ID NO 1018
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1018

Gly Tyr Cys Ser Ser Thr Ser Cys Tyr Arg Gly Ala Phe Asp Ile
1               5                   10                  15

<210> SEQ ID NO 1019
<211> LENGTH: 18
<212> TYPE: PRT
<213> ORGANISM: Artificial Sequence
<220> FEATURE:
<223> OTHER INFORMATION: Chemically Synthesized

```
<400> SEQUENCE: 1019

Gly Asn Val Gly Tyr Cys Thr Asn Gly Val Cys Ser Ser Ile Ser Phe
1               5                   10                  15

Asp Tyr

<210> SEQ ID NO 1020
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1020

Glu Phe Lys Arg Gly Tyr Ser Tyr Gly Tyr Trp Trp Phe Asp Pro
1               5                   10                  15

<210> SEQ ID NO 1021
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1021

Ser Thr Ile Phe Gly Val Val Ile Thr Pro Phe Asp Tyr
1               5                   10

<210> SEQ ID NO 1022
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1022

Val Gly Gly Leu Arg Pro Thr Val Thr Thr Gly Tyr Asn Trp Phe Asp
1               5                   10                  15

Pro

<210> SEQ ID NO 1023
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1023

Pro Lys Ala Asp Tyr Gly Asp Tyr Thr Pro Ala Gln Tyr Tyr Phe Asp
1               5                   10                  15

Tyr

<210> SEQ ID NO 1024
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1024

Val Thr His Pro Leu Asn Tyr Tyr Tyr Gly Met Asp Val
1               5                   10

<210> SEQ ID NO 1025
<211> LENGTH: 12
```

```
<212> TYPE: PRT
<213> ORGANISM: Artificial Sequence
<220> FEATURE:
<223> OTHER INFORMATION: Chemically Synthesized

<400> SEQUENCE: 1025

Asp Arg Gly Arg Phe Gly Glu Gly Tyr Phe Asp Tyr
1               5                   10

<210> SEQ ID NO 1026
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1026

Asp Ser Phe Pro Arg Phe Trp Ser Gly Tyr Cys Ser Phe Asp Tyr
1               5                   10                  15

<210> SEQ ID NO 1027
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1027

Asp Arg Val Val Pro His Arg Gly Thr Arg Gln Leu Asn Gly Met Asp
1               5                   10                  15

Val

<210> SEQ ID NO 1028
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1028

Asp Arg Thr Pro Thr Tyr Asp Ile Leu Thr Gly Gln Leu Asn Trp Phe
1               5                   10                  15

Asp Pro

<210> SEQ ID NO 1029
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1029

Ser Leu Asn Cys Ser Ser Thr Ser Trp Tyr Leu Pro Arg Val Gly Phe
1               5                   10                  15

Asp Tyr

<210> SEQ ID NO 1030
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1030

Val Val Ala Ala Arg Trp Asp Ile Tyr Tyr Phe Asp Tyr
```

```
1               5                  10
```

<210> SEQ ID NO 1031
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1031

```
Gly Ser Glu Lys Asn Asp Tyr Ser Asn Tyr Met Asn Trp Phe Asp Pro
1               5                   10                  15
```

<210> SEQ ID NO 1032
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1032

```
Gln Gln Tyr Asn Asn Trp Pro Pro Ser Ser Thr
1               5                   10
```

<210> SEQ ID NO 1033
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1033

```
Gln Gln Tyr Asn Asn Trp Leu Trp Thr
1               5
```

<210> SEQ ID NO 1034
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1034

```
Gln Gln Ala Asn Ser Phe Pro Trp Thr
1               5
```

<210> SEQ ID NO 1035
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1035

```
Gln Gln Tyr Asn Ser Tyr Ser His Thr
1               5
```

<210> SEQ ID NO 1036
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1036

```
Gln Gln Arg Asn Leu Val Thr
1               5
```

<210> SEQ ID NO 1037
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1037

Met Gln Ala Leu Gln Thr Leu Thr
1               5

<210> SEQ ID NO 1038
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1038

Gln Gln Ser Tyr Ser Thr Pro Gly Pro
1               5

<210> SEQ ID NO 1039
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1039

Met Gln Ala Leu Gln Thr Pro Tyr Thr
1               5

<210> SEQ ID NO 1040
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1040

Met Gln Ala Leu Gln Thr Pro Arg Thr
1               5

<210> SEQ ID NO 1041
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1041

Gln Gln Tyr Asn Ser Tyr Pro Trp Thr
1               5

<210> SEQ ID NO 1042
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1042

Leu Gln His Asn Ser Tyr Leu Phe Thr
1               5

<210> SEQ ID NO 1043
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1043

Gly Thr Trp Asp Ser Ser Leu Ser Ala His Tyr Val
1               5                   10

<210> SEQ ID NO 1044
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1044

Cys Ser Tyr Ala Gly Ser Val Val
1               5

<210> SEQ ID NO 1045
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1045

Gly Thr Trp Asp Ser Ser Leu Ser Ala Trp Val
1               5                   10

<210> SEQ ID NO 1046
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1046

Ala Ala Trp Asp Asp Ser His Tyr Val
1               5

<210> SEQ ID NO 1047
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1047

Cys Ser Tyr Ala Gly Ser Tyr Thr Leu Val
1               5                   10

<210> SEQ ID NO 1048
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1048

Ser Ser Tyr Ala Gly Ser Asn Asn Val Val
1               5                   10

```
<210> SEQ ID NO 1049
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1049

Ser Ser Tyr Thr Ser Ser Ser Ile Trp Val
1               5                   10

<210> SEQ ID NO 1050
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1050

Ser Ser Tyr Thr Ser Ser Ser Ile Pro Val Val
1               5                   10

<210> SEQ ID NO 1051
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1051

Asp Arg Tyr Val Ala Val Ala Gly Thr Val Asp Tyr
1               5                   10

<210> SEQ ID NO 1052
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1052

Ala Gly Pro Tyr Ser Ser Ser Tyr Tyr Phe Asp Tyr
1               5                   10

<210> SEQ ID NO 1053
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1053

Thr Leu Arg Gly Trp Cys Pro Asp Tyr
1               5

<210> SEQ ID NO 1054
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1054

Ala Asp Asp Tyr Ser Asn Tyr Phe Asp Tyr
1               5                   10

<210> SEQ ID NO 1055
```

```
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 1055

Asp Gly Ala Asn Gly Ala Arg Leu Gly Gly His Tyr Tyr Tyr Tyr Tyr
1               5                   10                  15

Gly Met Asp Val
            20

<210> SEQ ID NO 1056
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1056

Asp His Thr Ala Arg Gly Ala Cys Ser Ser Thr Ser Cys Tyr Ile Tyr
1               5                   10                  15

Tyr Tyr Gly Met Asp Val
            20

<210> SEQ ID NO 1057
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1057

Asp Tyr Phe Phe Gly Gln Trp Leu Ala Ala Gly Asp Ala Phe Asp Ile
1               5                   10                  15

<210> SEQ ID NO 1058
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1058

Gly Val Ala Ala Gly Ile Phe Gly Tyr
1               5

<210> SEQ ID NO 1059
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1059

Thr Tyr Phe Val Val Val Met Glu Ala Glu Tyr Phe Gln His
1               5                   10

<210> SEQ ID NO 1060
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1060
```

Asp Gly Gly Arg Gly Val Val Ala Ala Thr Leu Leu Tyr Phe Asp Tyr
1               5                   10                  15

<210> SEQ ID NO 1061
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1061

Asp Leu Ser Glu Tyr Ser Ser Ser Ser Phe Phe Arg Tyr Tyr Gly
1               5                   10                  15

Met Asp Val

<210> SEQ ID NO 1062
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1062

Asp Gly Arg Tyr Ser Ser Gly Trp Ser Tyr Phe Asp Tyr
1               5                   10

<210> SEQ ID NO 1063
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 1063

Glu Pro Pro Pro Ser Tyr Asp Ile Leu Thr Gly Ser Asn Tyr Tyr Tyr
1               5                   10                  15

Tyr Gly Met Asp Val
            20

<210> SEQ ID NO 1064
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1064

Val Ser Gly Cys Ser Ser Thr Ser Cys Phe Gly Gly Trp Phe Asp Pro
1               5                   10                  15

<210> SEQ ID NO 1065
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1065

Val Asp Thr Glu Thr Asp Asp Ser Ser Gly Tyr Ala Phe Asp Ile
1               5                   10                  15

<210> SEQ ID NO 1066
<211> LENGTH: 14
<212> TYPE: PRT
<213> ORGANISM: Artificial Sequence
<220> FEATURE:

<223> OTHER INFORMATION: Chemically Synthesized

<400> SEQUENCE: 1066

Asp Arg Cys Ser Gly Gly Ser Cys Pro Asp Ala Phe Asp Ile
1               5                   10

<210> SEQ ID NO 1067
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1067

Asp Arg Asn Gly Asp Tyr Pro Trp Tyr Phe Asp Leu
1               5                   10

<210> SEQ ID NO 1068
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1068

Gly Ala Val Val Thr Pro Gly Tyr Phe Asp Tyr
1               5                   10

<210> SEQ ID NO 1069
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1069

Ser Tyr Cys Gly Gly Asp Cys Tyr Phe Asp Tyr
1               5                   10

<210> SEQ ID NO 1070
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1070

Pro Ser Gly Asp Gly Tyr Asn Tyr Leu Glu Tyr
1               5                   10

<210> SEQ ID NO 1071
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1071

Val Gln Ser Asn Pro Leu Tyr Tyr Tyr Asp Ser Ser Gly Tyr Tyr Tyr
1               5                   10                  15

Asp Tyr

<210> SEQ ID NO 1072
<211> LENGTH: 23
<212> TYPE: PRT
<213> ORGANISM: Artificial Sequence

```
<220> FEATURE:
<223> OTHER INFORMATION: Chemically Synthesized

<400> SEQUENCE: 1072

Val Glu Pro Pro Thr Arg Val Ala His Cys Ser Ser Thr Ser Cys Tyr
1               5                   10                  15

Tyr Leu Gly Ala Phe Asp Ile
            20

<210> SEQ ID NO 1073
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1073

Gly Leu Tyr Gly Asp Tyr Val Asp Ala Phe Asp Ile
1               5                   10

<210> SEQ ID NO 1074
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 1074

His Gly Val His Leu Pro Pro Tyr Gly Ser Gly Ser Tyr Tyr Tyr Tyr
1               5                   10                  15

Tyr Gly Met Asp Val
            20

<210> SEQ ID NO 1075
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1075

Gly Lys Ile Ala Ala Ala Gly Phe Asp Tyr
1               5                   10

<210> SEQ ID NO 1076
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1076

Thr Thr Thr Val Ile Tyr Tyr Phe Asp Tyr
1               5                   10

<210> SEQ ID NO 1077
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1077

Gly Lys Tyr Gln Glu Pro Tyr Tyr Gly Asp Tyr Phe Pro Thr Arg Gly
1               5                   10                  15
```

Phe Asp Tyr

<210> SEQ ID NO 1078
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1078

Gln Gln Arg Ser Asn Leu Phe Thr
1               5

<210> SEQ ID NO 1079
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1079

Gln Gln Tyr Asn Ser Tyr Pro His Thr
1               5

<210> SEQ ID NO 1080
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1080

Gln Gln Tyr Asp Asn Leu Pro Leu Thr
1               5

<210> SEQ ID NO 1081
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1081

Gln Gln Arg Ser Asn Trp Pro Pro Ile Thr
1               5                   10

<210> SEQ ID NO 1082
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1082

Met Gln Gly Thr His Trp Pro Arg Val Thr
1               5                   10

<210> SEQ ID NO 1083
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1083

Gln Gln Arg Arg Thr Trp Ser Leu Thr
1               5

<210> SEQ ID NO 1084
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1084

Gln Gln Ser Tyr Ser Thr Pro Gln Thr
1               5

<210> SEQ ID NO 1085
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1085

Arg Ser Tyr Ala Gly Ser Ser Thr Trp Val
1               5                   10

<210> SEQ ID NO 1086
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1086

Cys Ser Tyr Ala Gly Ser Ser Thr Leu Tyr Val
1               5                   10

<210> SEQ ID NO 1087
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1087

Gln Ser Tyr Asp Ser Ser Leu Ser Val Val
1               5                   10

<210> SEQ ID NO 1088
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1088

Ser Ser Tyr Thr Ser Ser Lys Val
1               5

<210> SEQ ID NO 1089
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1089

Ser Ser Tyr Thr Ser Ser Asn Tyr Val
1               5

<210> SEQ ID NO 1090
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1090

Ser Ser Tyr Thr Ser Ser Ser Tyr Val
1               5

<210> SEQ ID NO 1091
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1091

Arg Lys Gly Ala Thr Gly Asp Trp Phe Asp Pro
1               5                   10

<210> SEQ ID NO 1092
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1092

Ser Asp Asp Ser Ser Gly Tyr Tyr Arg Ser Lys Ala Phe Asp Tyr
1               5                   10                  15

<210> SEQ ID NO 1093
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1093

Ala Pro Ser Gly Tyr Cys Ser Gly Gly Ser Cys Tyr Tyr Tyr Gly
1               5                   10                  15

Met Asp Val

<210> SEQ ID NO 1094
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1094

Leu Tyr Tyr Tyr Gly Ser Gly Ser Tyr Ser Gln Tyr Tyr Tyr Gly
1               5                   10                  15

Met Asp Val

<210> SEQ ID NO 1095
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1095

Glu Ser Asp Ile Val Val Pro Ala Ala Ser Arg Ala Ser Arg Tyr
1               5                   10                  15

Tyr Asp Tyr

<210> SEQ ID NO 1096
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1096

Val Ser Arg Asp Tyr Tyr Asp Ser Ser Gly Tyr Tyr Gly Pro Phe Ala
1               5                   10                  15

Asp Tyr

<210> SEQ ID NO 1097
<211> LENGTH: 25
<212> TYPE: PRT
<213> ORGANISM: Artificial Sequence
<220> FEATURE:
<223> OTHER INFORMATION: Chemically Synthesized

<400> SEQUENCE: 1097

Asp Ser Gly Gly Val Ala Thr Trp Gly Gln Gly Thr Leu Val Thr Val
1               5                   10                  15

Ser Ser Ala Arg Thr Ser Gln Asp Pro
            20                  25

<210> SEQ ID NO 1098
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1098

Asp Arg Arg Arg Ile Thr Met Val Arg Gly Val Thr Asn Trp Phe Asp
1               5                   10                  15

Pro

<210> SEQ ID NO 1099
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1099

Asp Met Arg Met His Tyr Gly Ser Gly Gly Tyr Trp Tyr Phe Asp Leu
1               5                   10                  15

<210> SEQ ID NO 1100
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1100

Ala Leu Ile Trp Gln Leu Ala Thr Ser Pro Leu Asp Tyr
1               5                   10

<210> SEQ ID NO 1101

```
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1101

Glu Arg Glu Pro Tyr Tyr Asp Ile Ser Asn Trp Phe Asp Pro
1               5                   10

<210> SEQ ID NO 1102
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1102

Gly Arg Val Tyr Asp Ile Leu Thr Ile Gly Ser Gly Ser Leu Tyr Ala
1               5                   10                  15

Phe Asp Ile

<210> SEQ ID NO 1103
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1103

Pro Tyr Cys Ser Gly Gly Ser Cys Tyr Ser Val Gly Ser Arg Ala Leu
1               5                   10                  15

Tyr Asn Trp Phe Asp Pro
            20

<210> SEQ ID NO 1104
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1104

Glu Ala Val Val Pro Ala Arg Ser Gly Met Asp Val
1               5                   10

<210> SEQ ID NO 1105
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1105

Asp Pro Gly Ser Gly Tyr Asp Gly Asn Asp Tyr
1               5                   10

<210> SEQ ID NO 1106
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1106

Asp Arg Gln Met Pro Gln Gly Ile Gly Ala Gln Gly Phe Asp Tyr
```

```
<210> SEQ ID NO 1107
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1107

His Ser Gly Tyr Ser Ser Ser Trp Pro Asn Val Met Asp Val
1               5                   10

<210> SEQ ID NO 1108
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1108

Gly Thr Arg Gln Asp Ser Ser Ser Trp Trp Gly His Ala Phe Asp Ile
1               5                   10                  15

<210> SEQ ID NO 1109
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1109

Glu Gly Gly Val Ser Ser Ser Trp Pro Tyr Asn Trp Phe Asp Pro
1               5                   10                  15

<210> SEQ ID NO 1110
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1110

Asp Gly Ala Ala Ala Gly Leu Arg Tyr
1               5

<210> SEQ ID NO 1111
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1111

Asp Arg Thr Gln Gln Leu Val Pro Tyr Tyr Tyr Tyr Gly Met Asp Val
1               5                   10                  15

<210> SEQ ID NO 1112
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1112

Asp Leu Leu Arg Phe Gly Glu Leu Trp Asp Tyr
1               5                   10
```

<210> SEQ ID NO 1113
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1113

Asp Val Thr Asn Gly Arg Asp Cys Ser Gly Gly Ser Cys Tyr Ser Phe
1               5                   10                  15

Asp Tyr

<210> SEQ ID NO 1114
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1114

Asp Thr His Cys Ser Ser Thr Ser Cys Tyr Ser Asp Trp Tyr Phe Asp
1               5                   10                  15

Leu

<210> SEQ ID NO 1115
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1115

Glu Gly Asp Ile Val Val Pro Ala Ala His Gly Trp Phe Asp Pro
1               5                   10                  15

<210> SEQ ID NO 1116
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1116

Pro Gly Tyr Ser Ser Ser Trp Tyr Tyr Phe Gln His
1               5                   10

<210> SEQ ID NO 1117
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1117

Gly Thr Leu Glu Thr Tyr Asp Leu Tyr Pro Arg Leu Gly Arg Gly Leu
1               5                   10                  15

Tyr Asn Trp Phe Asp Pro
            20

<210> SEQ ID NO 1118
<211> LENGTH: 18
<212> TYPE: PRT
<213> ORGANISM: Artificial Sequence
<220> FEATURE:

```
<223> OTHER INFORMATION: Chemically Synthesized

<400> SEQUENCE: 1118

Tyr Tyr Tyr Gly Ser Gly Ser Tyr Leu Gly Leu Arg Ala Leu His Phe
1               5                   10                  15

Asp Tyr

<210> SEQ ID NO 1119
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 1119

Asp Arg Val Val Val Ile Ala Glu Gly Leu Gly Tyr Tyr Tyr Tyr
1               5                   10                  15

Gly Met Asp Val
            20

<210> SEQ ID NO 1120
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1120

Gly Leu Lys Phe Gly Ala Val Arg Ser Ala Phe Asp Ile
1               5                   10

<210> SEQ ID NO 1121
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1121

Gly Cys Arg Asn Ser Ser Ser Trp Tyr Val Glu Lys Ser Asp Ala Phe
1               5                   10                  15

Asp Ile

<210> SEQ ID NO 1122
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1122

Pro Pro Tyr Tyr Tyr Asp Ser Ser Gly Tyr Tyr Leu Tyr Tyr Gly Met
1               5                   10                  15

Asp Val

<210> SEQ ID NO 1123
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1123

Gly Arg Ala Trp His Ser Tyr Gly Asp Asp Ala Phe Asp Ile
```

```
1               5                   10

<210> SEQ ID NO 1124
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1124

Gly Ser Glu Tyr Gln Leu Leu Arg Gly Trp Phe Asp Pro
1               5                   10

<210> SEQ ID NO 1125
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1125

Val Leu Pro Val Gly Ala Gly His Tyr Tyr Tyr Gly Met Asp Val
1               5                   10                  15

<210> SEQ ID NO 1126
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1126

Leu Trp Gly Leu Tyr Asn Trp Asn Tyr Phe Asp Tyr
1               5                   10

<210> SEQ ID NO 1127
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1127

Gln Gln Arg Ser Thr Trp Pro Pro Leu Thr
1               5                   10

<210> SEQ ID NO 1128
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1128

Gln Gln Tyr Tyr Asp Thr Pro Arg Ala
1               5

<210> SEQ ID NO 1129
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1129

Gln Gln Tyr Asn Asn Trp Pro Ser Tyr Thr
1               5                   10
```

<210> SEQ ID NO 1130
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1130

Met Gln Ala Leu Gln Thr Pro Trp Thr
1               5

<210> SEQ ID NO 1131
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1131

Gln Gln Tyr Asn Ser Tyr Ser Gln Trp Thr
1               5                   10

<210> SEQ ID NO 1132
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1132

Ala Gly Ser Ser Thr Tyr Asn Tyr Val
1               5

<210> SEQ ID NO 1133
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1133

Ser Ser Tyr Thr Ser Ser Ser Thr Leu
1               5

<210> SEQ ID NO 1134
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1134

Ser Ser Tyr Thr Ser Ser Ser Arg Val
1               5

<210> SEQ ID NO 1135
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1135

Gly Thr Trp Asp Ser Ser Leu Ser Thr Asn Trp Val
1               5                   10

<210> SEQ ID NO 1136
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1136

Gly Ala Tyr Tyr Gly Ser Gly Ser Tyr Tyr Lys Asp Ala Phe Asp Ile
1               5                   10                  15

<210> SEQ ID NO 1137
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1137

Ala Gly Ser Asp Ser Ser Ser Ser Ala Val Phe Asp Tyr
1               5                   10

<210> SEQ ID NO 1138
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1138

Asp Pro Arg Val Pro Gly Gly Ser Tyr Tyr Tyr Tyr Gly Met Asp Val
1               5                   10                  15

<210> SEQ ID NO 1139
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1139

Glu Pro Ala Pro Leu Gly Val Ala Gly Gly Tyr
1               5                   10

<210> SEQ ID NO 1140
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1140

Leu Pro Phe Leu Asp Leu Phe Trp Ser Gly Tyr Tyr Ala Asp Ala Phe
1               5                   10                  15

Asp Ile

<210> SEQ ID NO 1141
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1141

Val Gln Asp Asn Arg Ala Pro Asp Phe Asp Tyr
1               5                   10

```
<210> SEQ ID NO 1142
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1142

Ala Gly Gly Gly Ser Ser Ser Trp Tyr Tyr Phe Asp Tyr
1               5                   10

<210> SEQ ID NO 1143
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1143

Ser Lys Tyr Ser Ser Ser Trp Tyr Gly Asp Tyr
1               5                   10

<210> SEQ ID NO 1144
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1144

Gly Asn Arg Leu Ile Ala Ala Ala Gly Ser Tyr Tyr Tyr Gly Met
1               5                   10                  15

Asp Val

<210> SEQ ID NO 1145
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1145

Val Thr Asn Tyr Gly Ser Gly Ser Tyr Tyr Asn Gly Phe Asp Tyr
1               5                   10                  15

<210> SEQ ID NO 1146
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1146

Asp Leu Ser Asp Ser Ile Ala Ala Ala Gly Val Gly Tyr Phe Gln His
1               5                   10                  15

<210> SEQ ID NO 1147
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1147

Leu Leu Thr Val Thr Ser Tyr Phe Asp Tyr
```

```
1               5                   10
```

<210> SEQ ID NO 1148
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1148

```
Gly Pro Tyr Ser Ser Ser Trp Phe Ser Ile Asp Tyr
1               5                   10
```

<210> SEQ ID NO 1149
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1149

```
Asp Arg Val Gly Gly Ser Tyr Tyr Tyr Tyr Tyr Gly Met Asp Val
1               5                   10                  15
```

<210> SEQ ID NO 1150
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1150

```
Gly Gln Trp Glu Leu Asp Tyr
1               5
```

<210> SEQ ID NO 1151
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1151

```
Asp Arg Asn Trp Gly Phe Asp Tyr
1               5
```

<210> SEQ ID NO 1152
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1152

```
Gly Leu Leu Gly Leu Phe Asp Tyr
1               5
```

<210> SEQ ID NO 1153
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1153

```
Leu Gly Phe Gly Glu Leu Ser His Asp Tyr
1               5                   10
```

<210> SEQ ID NO 1154
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 1154

Asp Ser Met Gly Gln Ser Thr Gly Tyr Ser Tyr Gly Tyr Pro Tyr Trp
1               5                   10                  15

Tyr Phe Asp Leu
            20

<210> SEQ ID NO 1155
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1155

Cys Tyr Ser Ser Gly Trp Asp Asp Ala Phe Asp Ile
1               5                   10

<210> SEQ ID NO 1156
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1156

Pro Ser Ile Thr Met Val Arg Gly Val Ile Ile Phe Asn Trp Phe Asp
1               5                   10                  15

Pro

<210> SEQ ID NO 1157
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1157

Ser Asn Phe Gln Tyr Ser Tyr Gly Tyr Tyr
1               5                   10

<210> SEQ ID NO 1158
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1158

Asp Arg Val Lys Asp Gly Gly Ser Ser Trp Pro Asp Tyr
1               5                   10

<210> SEQ ID NO 1159
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1159

Glu Thr Gly Ile Thr Gly Thr Thr Gly Trp Phe Asp Pro
1               5                   10

<210> SEQ ID NO 1160
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1160

Val Leu Ser Gly Gly Gln Gln His Pro Ser Tyr Tyr Tyr Tyr Gly
1               5                   10                  15

Met Asp Val

<210> SEQ ID NO 1161
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1161

Gly Met Leu Phe Leu Gly Trp Tyr Tyr Phe Asp Tyr
1               5                   10

<210> SEQ ID NO 1162
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1162

Ser Ser Gly Tyr Arg His Asp Ala Phe Asp Ile
1               5                   10

<210> SEQ ID NO 1163
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1163

Val Gly Ser Trp Val Asp Tyr Trp Tyr Phe Asp Leu
1               5                   10

<210> SEQ ID NO 1164
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1164

Gly Pro Pro Asn Trp Gly Glu Gln Arg Gln Asp Asp Tyr
1               5                   10

<210> SEQ ID NO 1165
<211> LENGTH: 11
<212> TYPE: PRT
<213> ORGANISM: Artificial Sequence
<220> FEATURE:
<223> OTHER INFORMATION: Chemically Synthesized

```
<400> SEQUENCE: 1165

Asp Ser Pro Ala Ser Gly Leu Ala Phe Asp Ile
1               5                   10

<210> SEQ ID NO 1166
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1166

Gly Ala Ser Gly Ser Gly Gln Ile Gly Gly Phe Asp Tyr
1               5                   10

<210> SEQ ID NO 1167
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1167

His Tyr Tyr Tyr Asp Ser Ser Gly Tyr Tyr Ala Arg Leu Asn Ala Phe
1               5                   10                  15

Asp Ile

<210> SEQ ID NO 1168
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1168

Val Ser Leu His Ile Ala Val Ala Gly Thr Gly Pro Phe Asp Tyr
1               5                   10                  15

<210> SEQ ID NO 1169
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1169

Glu Gly Thr Gly Asp Pro Asp Ala Phe Asp Ile
1               5                   10

<210> SEQ ID NO 1170
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1170

Gly Leu Val Val Arg Cys Thr Asn Gly Val Cys Tyr Asn His Ala Phe
1               5                   10                  15

Asp Ile

<210> SEQ ID NO 1171
<211> LENGTH: 16
<212> TYPE: PRT
```

```
<213> ORGANISM: Artificial Sequence
<220> FEATURE:
<223> OTHER INFORMATION: Chemically Synthesized

<400> SEQUENCE: 1171

Asp Gln Tyr Tyr Asp Ile Leu Thr Gly Ser Ala Val Pro Phe Asp Tyr
1               5                   10                  15

<210> SEQ ID NO 1172
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1172

Val Gly Gly Asp Arg Tyr Trp Tyr Phe Asp Leu
1               5                   10

<210> SEQ ID NO 1173
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 1173

Asp Gly Gln Tyr Cys Gly Gly Asp Cys Tyr Ser Pro Tyr Tyr Tyr Tyr
1               5                   10                  15

Tyr Gly Met Asp Val
            20

<210> SEQ ID NO 1174
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1174

Gln Gln Arg Ser Asn Trp Trp
1               5

<210> SEQ ID NO 1175
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1175

Gln Gln Ser Tyr Ser Thr Leu Thr
1               5

<210> SEQ ID NO 1176
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1176

Gln Gln Ser Tyr Ser Thr Trp Thr
1               5

<210> SEQ ID NO 1177
```

```
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1177

Gln Gln Leu Asn Ser Tyr Pro Pro Ile Thr
1               5                   10

<210> SEQ ID NO 1178
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1178

Gln Gln Ser Tyr Ser Thr Pro Pro Ile Thr
1               5                   10

<210> SEQ ID NO 1179
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1179

Met Gln Gly Thr His Trp Pro Tyr Thr
1               5

<210> SEQ ID NO 1180
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1180

Gln Gln Arg Ser Asn Trp Pro Pro Val Thr
1               5                   10

<210> SEQ ID NO 1181
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1181

Gln Ser Tyr Asp Ser Ser Leu Ser Gly His Val Val
1               5                   10

<210> SEQ ID NO 1182
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1182

Ala Trp Asp Asp Ser Leu Ser Gly Trp Val
1               5                   10

<210> SEQ ID NO 1183
<211> LENGTH: 12
```

<212> TYPE: PRT
<213> ORGANISM: Artificial Sequence
<220> FEATURE:
<223> OTHER INFORMATION: Chemically Synthesized

<400> SEQUENCE: 1183

Gln Ser Tyr Asp Ser Ser Leu Ser Gly Asp Val Val
1               5                   10

<210> SEQ ID NO 1184
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1184

Gly Thr Trp Asp Ser Ser Leu Ser Ala Arg Tyr Val
1               5                   10

<210> SEQ ID NO 1185
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1185

Gln Ser Tyr Asp Ser Ser Asn His Trp Val
1               5                   10

<210> SEQ ID NO 1186
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1186

Glu Met Gly Met Ala Ala Gly Tyr Ser Tyr Gly Phe Asp Tyr
1               5                   10

<210> SEQ ID NO 1187
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1187

Asp Arg Gly Glu Phe Asp Tyr
1               5

<210> SEQ ID NO 1188
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1188

Gly Arg Gly Ile Thr Gly Thr Asn Tyr Phe Asp Tyr
1               5                   10

<210> SEQ ID NO 1189
<211> LENGTH: 11
<212> TYPE: PRT

```
<213> ORGANISM: Artificial Sequence
<220> FEATURE:
<223> OTHER INFORMATION: Chemically Synthesized

<400> SEQUENCE: 1189

Asp Ser Ser Val Val Ala Ala Arg Phe Asp Tyr
1               5                   10

<210> SEQ ID NO 1190
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1190

Glu Gly Thr Gly Phe Asp Tyr
1               5

<210> SEQ ID NO 1191
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1191

Asp Leu Arg Glu Tyr Lys Gly Asp Trp Phe Asp Pro
1               5                   10

<210> SEQ ID NO 1192
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1192

Asp Gly Ala Tyr Tyr Tyr Gly Ser Gly Ser Ser Thr Phe Asp Tyr
1               5                   10                  15

<210> SEQ ID NO 1193
<211> LENGTH: 23
<212> TYPE: PRT
<213> ORGANISM: Artificial Sequence
<220> FEATURE:
<223> OTHER INFORMATION: Chemically Synthesized

<400> SEQUENCE: 1193

Gly Arg Arg Asn Phe Ser Arg Gly Asp Tyr Tyr Asp Ser Ser Gly Tyr
1               5                   10                  15

Tyr Thr Thr Pro Phe Asp Tyr
                20

<210> SEQ ID NO 1194
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1194

Asp Lys Thr Gly Ala Ser Arg Leu Gly Tyr Cys Thr Asn Gly Val Cys
1               5                   10                  15

Pro Asp Ala Phe Asp Ile
                20
```

<210> SEQ ID NO 1195
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1195

Asp Ser Gly Tyr Ser Ser Gly Trp Ser His Asp Ala Phe Asp Ile
1               5                   10                  15

<210> SEQ ID NO 1196
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1196

Asp Trp Pro Gly Ala Ala Ala Gly Leu Asp Tyr
1               5                   10

<210> SEQ ID NO 1197
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1197

Gly Leu Phe Ile Thr Met Ile Val Val Gly Asp Ala Phe Asp Ile
1               5                   10                  15

<210> SEQ ID NO 1198
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1198

Asp Lys Ile Val Val Pro Ala Ala Met Gly Gly Asn Tyr Phe Asp
1               5                   10                  15

Tyr

<210> SEQ ID NO 1199
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1199

Glu Arg Trp Glu Leu Arg Thr Asp Ala Phe Asp Ile
1               5                   10

<210> SEQ ID NO 1200
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 1200

Asp Gly Ala Gly Val Val Val Ala Ala Thr Leu Leu Asp Asp Ala

Phe Asp Ile

<210> SEQ ID NO 1201
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1201

Ile Ser Ser Ile Ala Ala Leu Pro Asp Tyr
1               5                   10

<210> SEQ ID NO 1202
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1202

Lys Asn Trp Gly Gly Cys Tyr Ala Phe Asp Ile
1               5                   10

<210> SEQ ID NO 1203
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1203

Leu Asn Gly Leu Gly Ala Phe Asp Ile
1               5

<210> SEQ ID NO 1204
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1204

Asp Ile Arg Phe Leu Glu Trp Phe Asp Tyr
1               5                   10

<210> SEQ ID NO 1205
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1205

Asp Thr Ala Gly Gly Glu Leu Leu Pro Tyr Tyr Phe Asp Tyr
1               5                   10

<210> SEQ ID NO 1206
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1206

Leu Leu Val Gly Arg Gly Leu Gln Lys His Tyr Tyr Phe Asp Tyr
1               5                   10                  15

<210> SEQ ID NO 1207
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1207

Gly Arg Ala Ala Gly Gly Ile Asp Tyr
1               5

<210> SEQ ID NO 1208
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1208

Ile Ile Thr Met Val Arg Gly Val Ile Ile Thr Tyr Asn Trp Phe Asp
1               5                   10                  15

Pro

<210> SEQ ID NO 1209
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1209

Gly Asn Trp Asp Gly Gly Leu Phe His Tyr
1               5                   10

<210> SEQ ID NO 1210
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1210

Pro Gly Tyr Ser Ser Gly Trp Asp Tyr Trp Tyr Phe Asp Leu
1               5                   10

<210> SEQ ID NO 1211
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1211

Glu Asp Ile Val Gly Ala Ile Arg Arg Ala Phe Asp Ile
1               5                   10

<210> SEQ ID NO 1212
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1212

Asp Gly Gly Ser Tyr Ser Ala Phe Asp Ile
1               5                   10

<210> SEQ ID NO 1213
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 1213

Asp Leu Ser Pro Asn Leu Ile Ala Ala Arg Asp Ala Ile Asp Tyr
1               5                   10                  15

<210> SEQ ID NO 1214
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1214

Gly Leu Gly Arg Ala Thr Ser Tyr Gly Asp Ala Phe Asp Ile
1               5                   10

<210> SEQ ID NO 1215
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 1215

Asp Arg Pro Val Asp Tyr
1               5

<210> SEQ ID NO 1216
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1216

Gln Gln Tyr Asn Asn Trp Pro Leu Tyr Ser
1               5                   10

<210> SEQ ID NO 1217
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1217

Gln Gln Tyr Gly Ser Ser Pro Pro Phe Thr
1               5                   10

<210> SEQ ID NO 1218
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1218

```
Gln Gln Tyr Asn Ser Tyr Ser Pro Leu Thr
1               5                   10

<210> SEQ ID NO 1219
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1219

Gln Gln Tyr Gly Ser Ser Leu Phe Thr
1               5

<210> SEQ ID NO 1220
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1220

Gln Gln Tyr Asn Ser Tyr Ser Pro Asn Ser
1               5                   10

<210> SEQ ID NO 1221
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1221

Met Gln Ala Thr Gln Phe Pro Arg Thr
1               5

<210> SEQ ID NO 1222
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1222

Gln Gln Tyr Tyr Ser Tyr Pro Leu Phe Thr
1               5                   10

<210> SEQ ID NO 1223
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1223

Val Leu Tyr Met Gly Ser Gly Ile Trp Val
1               5                   10

<210> SEQ ID NO 1224
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1224

Gly Arg Gln Val Gly Gly Gly Trp Lys Asp Ala Phe Asp Ile
```

```
<210> SEQ ID NO 1225
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1225

Gly Leu Trp Ser Glu Gly Val Tyr Tyr Phe Asp Tyr
1               5                   10

<210> SEQ ID NO 1226
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1226

His Gly Gly Ser Gln Pro Gly Ile Val Gly Ala Thr Leu Ala Phe Asp
1               5                   10                  15

Ile

<210> SEQ ID NO 1227
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1227

Gly Thr Gly Thr Val Thr Thr Asn Trp Phe Asp Pro
1               5                   10

<210> SEQ ID NO 1228
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1228

Asp Arg Leu His Tyr Tyr Tyr Tyr Met Asp Val
1               5                   10

<210> SEQ ID NO 1229
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1229

Gly Glu Gly Val Leu Gly Tyr
1               5

<210> SEQ ID NO 1230
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 1230
```

Ser Gln Phe Leu Arg Glu Met Ala Thr Ile Arg Asn Leu Thr Thr Asp
1               5                   10                  15

Asp Tyr

<210> SEQ ID NO 1231
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1231

Glu Gly Ala Ala Ala Gly Thr Ser Tyr Tyr Phe Asp Tyr
1               5                   10

<210> SEQ ID NO 1232
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1232

Asp Gly Leu Gly Ile Arg Gly Val Ala Asp Tyr
1               5                   10

<210> SEQ ID NO 1233
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1233

His Gly Ser Arg Pro Val Thr Thr Tyr Asp Tyr
1               5                   10

<210> SEQ ID NO 1234
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1234

Ser Gly Thr Gly Ala Phe Asp Ile
1               5

<210> SEQ ID NO 1235
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1235

Val Phe Leu Gly Ser Val Arg Glu Leu Leu Ala Glu Tyr Phe Gln His
1               5                   10                  15

<210> SEQ ID NO 1236
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1236

```
Ala Trp Gly Ser Asp Ala Phe Asp Ile
1               5
```

<210> SEQ ID NO 1237
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1237

```
Ser Glu Glu Lys Ala Pro Pro Ala
1               5
```

<210> SEQ ID NO 1238
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1238

```
Thr Ile Ser Asp Ala Phe Asp Ile
1               5
```

<210> SEQ ID NO 1239
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1239

```
Asp Glu Gly His Ser Gly Ser Tyr Phe Asp Tyr
1               5                   10
```

<210> SEQ ID NO 1240
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1240

```
Asp Pro Gly Asp Ala Phe Asp Ile
1               5
```

<210> SEQ ID NO 1241
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 1241

```
Lys Arg Gly Val Phe Asp Tyr
1               5
```

<210> SEQ ID NO 1242
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 1242

Asp Ser Pro Ile Glu Tyr Ser Ser Ser Gly Pro Tyr Tyr Tyr Tyr
1               5                   10                  15

Tyr Tyr Gly Met Asp Val
            20

<210> SEQ ID NO 1243
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 1243

Glu Gly Gly Asp Ser Gly Ser Tyr Tyr Phe Asp Tyr
1               5                   10

<210> SEQ ID NO 1244
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 1244

Ala Ser Ala Arg Ile Val Val Val Ile Thr Asn Val Asp Tyr
1               5                   10

<210> SEQ ID NO 1245
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1245

Met Gln Ser Ile Gln Leu Pro Leu Thr
1               5

<210> SEQ ID NO 1246
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1246

Lys Arg Tyr Gly Asn Ser Pro Tyr Thr
1               5

<210> SEQ ID NO 1247
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1247

Gln Gln Tyr Asn Ser Tyr Pro Arg Thr
1               5

<210> SEQ ID NO 1248
<211> LENGTH: 10
<212> TYPE: PRT
<213> ORGANISM: Artificial Sequence
<220> FEATURE:
<223> OTHER INFORMATION: Chemically Synthesized

```
<400> SEQUENCE: 1248

Gln Gln Arg Ser Thr Trp Pro Pro Phe Thr
1               5                   10

<210> SEQ ID NO 1249
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1249

Gln Gln Leu Asn Ser Tyr Pro Tyr Thr
1               5

<210> SEQ ID NO 1250
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1250

Gln Gln Tyr Asp Asn Leu Pro Pro Leu Phe Thr
1               5                   10

<210> SEQ ID NO 1251
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1251

Gln Gln Arg Ser Asn Trp Pro Arg Leu Thr
1               5                   10

<210> SEQ ID NO 1252
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 1252

Gln Val Trp Asp Ser Ser Thr Val Val
1               5

<210> SEQ ID NO 1253
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 1253

Ala Ala Trp Asp Asp Ser Leu Asn Val Trp Val
1               5                   10
```